(12) United States Patent
Brodeur et al.

(10) Patent No.: US 7,914,794 B2
(45) Date of Patent: Mar. 29, 2011

(54) GROUP B STREPTOCOCCUS ANTIGENS

(75) Inventors: Bernard R. Brodeur, Sillery (CA);
Clément Rioux, Ville de Cap rouge (CA); Martine Boyer, Beauport (CA); Isabelle Charlebois, St-Nicolas (CA); Josée Hamel, Sillery (CA); Denis Martin, St-Augustin-de-Desmaures (CA)

(73) Assignee: ID Biomedical Corporation, Laval (CA)

( * ) Notice: Subject to any disclaimer, the term of this patent is extended or adjusted under 35 U.S.C. 154(b) by 1833 days.

(21) Appl. No.: 10/340,792

(22) Filed: Jan. 13, 2003

(65) Prior Publication Data

US 2003/0228323 A1 Dec. 11, 2003

Related U.S. Application Data

(63) Continuation of application No. 09/252,088, filed on Feb. 18, 1999, now abandoned, which is a continuation of application No. 60/075,425, filed on Feb. 20, 1998.

(51) Int. Cl.
*A61K 39/09* (2006.01)
(52) U.S. Cl. .................................. 424/190.1; 424/237.1
(58) Field of Classification Search .................... None
See application file for complete search history.

(56) References Cited

U.S. PATENT DOCUMENTS

| | | | |
|---|---|---|---|
| 5,225,331 A | 7/1993 | Lacroix et al. | 435/7.34 |
| 5,302,386 A | 4/1994 | Kasper et al. | 424/92 |
| 5,472,696 A | 12/1995 | Boyle et al. | 424/244.1 |
| 5,595,740 A | 1/1997 | Brady | 424/190.1 |
| 5,648,241 A | 7/1997 | Michel et al. | 435/69.3 |
| 5,679,768 A | 10/1997 | Briles et al. | 530/300 |
| 5,721,339 A | 2/1998 | Boyle et al. | 530/350 |
| 5,843,713 A * | 12/1998 | Yoshida et al. | 435/69.1 |
| 5,869,064 A | 2/1999 | Lindahl et al. | 424/244.1 |
| 5,908,629 A * | 6/1999 | Michel et al. | 424/197.11 |
| 6,248,329 B1 * | 6/2001 | Chandrashekar et al. | 424/191.1 |
| 6,420,135 B1 * | 7/2002 | Kunsch et al. | 435/69.1 |
| 2007/0275004 A1 | 11/2007 | Rioux et al. | 424/190.1 |

FOREIGN PATENT DOCUMENTS

| | | |
|---|---|---|
| EP | 1054971 B1 | 12/2006 |
| WO | WO 94/21685 | 9/1994 |
| WO | 98/18930 A2 | 5/1998 |
| WO | WO98/18931 | 5/1998 |
| WO | 99/42588 A2 | 8/1999 |
| WO | WO 00/06736 | 2/2000 |
| WO | 01/32882 A2 | 5/2001 |
| WO | 03/068813 A2 | 8/2003 |

OTHER PUBLICATIONS

Bowie et al (Science, 1990, 247:1306-1310).*
Burgess et al (J. of Cell Bio. 111:2129-2138, 1990).*
Lazar et al. (Molecular and Cellular Biology, 1988, 8:1247-1252).*
Bork (Genome Research, 2000,10:398-400).*
Ellis, Chapter 29 of Vaccines, Plotkin, et al. (eds) WB Saunders, Philadelphia, 1988, pp. 568-574.*
Kil et al. (Infect. Immun., 62:2440-2449, 1994).*
UniProtKB/TrEMBL entry Q54524, http://ca.expasy.org/cgi-bin/niceprot.pl/printable?ac=Q54524, accessed Aug. 14, 2006.*
Colman, Res. Immunol., 145:33-36, 1994.*
Abaza et al., J. Prot. Chem., 11:433-444, 1992.*
Blythe et al., Prot. Sci., 14:246-248, 2005.*
Accession No. JH0633, seq. in Legros et al., *Gene* 112(2):247-250, 1992, sequence alignment only.
Accession No. S53362, Guyonnet-Duperat et al., *Biochem J.* 305:211-19, 1995, sequence alignment only.
Baltimore, R., et al., "Antigenic specificity of opsonophagocytic antibodies in rabbit anti-sera to group B *Streptococci*," *Journal of Immunology* 118(2):673-78, Feb. 1977.
Carberry-Goh, et al., "Streptococcal Genetics," *American Society of Microbiology*, Washington, D.C., pp. 22-24, 1987.
Ferrieri, P., et al., "Surface-localized protein antigens of group B *Streptococci*," *Reviews of Infectious Diseases* 10 (Suppl 2):S363-6, Jul.-Aug. 1988.
GenBank Database Accession No. AF026542, Oct. 15, 1997.
GenBank Database Accession No. AF062533, Feb. 11, 1999.
GenBank Database Accession No. L23843, Jan. 4, 1994.
GenBank Database Accession No. V52136, Oct. 23, 1998.
Heard, S., et al., "New phenotypic typing scheme for group B *Streptococci*," *Journal of Clinical Pathology* 46(2):145-8, Feb. 1993.
Kil, K., et al., "Cloning and sequence analysis of a gene encoding a 67-kilodalton myosin-cross-reactive antigen of *Streptococcus pyogenes* reveals its similarity with class II major histocompatibility antigens," *Infection and Immunity* 62(6):2440-9, Jun. 1994.
Lachenauer, C., et al., "A protective surface protein from type V group B *Streptococci* shares N-terminal sequence homology with the alpha C protein," *Infection and Immunity* 64(10):4255-60, Oct. 1996.
Lachenauer, C., et al., "Cloning and expression in *Escherichia coli* of a protective surface protein from type V group B *Streptococci*," *Advances in Experimental Medicine and Biology* 418:615-8, Dec. 1997.
Lancefield, R., et al., "Multiple mouse-protective antibodies directed against group B *Streptococci*. Special reference to antibodies effective against protein antigens," *Journal of Experimental Medicine* 142(1):165-79, Jul. 1, 1975.
Linden, V., "Mouse-protective effect of rabbit anti-R-protein antibodies against group B *Streptococci* type II carrying R-protein. Lack of effect on type III carrying R-protein," *Acta Pathol. Microbial. Immunol. Scand.* [B] 91(2):145-51, Apr. 1983.
Maeland, J., et al., "*Streptococcus agalactiae* beta gene and gene product variations," *Journal of Medical Microbiology* 46(12):999-1005, Dec. 1997.

(Continued)

Primary Examiner — N. M Minnifield
Assistant Examiner — Brian J Gangle
(74) Attorney, Agent, or Firm — Seed IP Law Group PLLC

(57) ABSTRACT

Group B *streptococcus* (GBS) proteins and polynucleotides encoding them are disclosed. Said proteins are antigenic and therefore useful vaccine components for the prophylaxis or therapy of streptococcus infection in animals. Also disclosed are recombinant methods of producing the protein antigens as well as diagnostic assays for detecting streptococcus bacterial infection.

15 Claims, 40 Drawing Sheets

OTHER PUBLICATIONS

Michel, J., et al., "Cloned alpha and beta C-protein antigens of group B *Streptococci* elicit protective immunity," *Infection and Immunity* 59(6):2023-8, Jun. 1991.

Michel, J., et al., "Genetics and Molecular Biology of *Streptococci, Lactococci and Enterococci*," *American Society for Microbiology*, pp. 214-218, 1991.

Michel, J., et al., "Large, identical, tandem repeating units in the C protein alpha antigen gene, bca, of group B *Streptococci*," *Proceedings of the National Academy of Science USA* 89(21):10060-4, Nov. 1, 1992.

Pincus, S., et al., "Group B streptococcal opacity variants," *Journal of Bacteriology* 174(11):3739-49, Jun. 1992.

Salasia, S., et al., "Phase variation in *Streptococci* of serological group B. Characteristic properties of isolates from human and bovine infection," *APMIS* 102(12):925-30, Dec. 1994.

Sequence Alignment for SEQ ID No. 16, of US Pat. T,344,199, Hofler et al., filed Jul. 1997.

SPTREMBL Accession No. Q54524, Nov. 1, 1994.

Swiss-Prot. Accession No. Q54524, EMBL Accession No. U09352, Nov. 1996.

Wastfelt, M., et al., "Identification of a family of streptococcal surface proteins with extremely repetitive structure," *Journal of Biological Chemistry* 271(31):18892-7, Aug. 2, 1996.

Gravekamp et al., "Variation in repeat number within the alpha C protein of group B *Streptococci* alters antigenicity and protective epitopes," *Infection and Immunity* 64(9):3576-83, 1996.

Baltimore, R., et al., "Mouse protection test for group B *Streptococcus* type III," *Journal of Infectious Disease* 140(1):81-8, Jul. 1979.

Brodeur, B., et al., "Identification of group B streptococcal Sip protein, which elicits cross-protective immunity," *Infection and Immunity* 68(10):5610-8, Oct. 2000.

Kasper, D., et al., "Immune response to type III group B streptococcal polysaccharido-tetanus toxoid conjugate vaccine," *Journal of Clinical Investigation* 98(10):2308-14, Nov. 15, 1996.

Kogan, G., et al., "Structural and immunochemical characterization of the type VIII group B *Streptococcus* capsular polysaccharide," *Journal of Biological Chemistry* 271(15):8786-90, Apr. 12, 1996.

Larsson, C., et al., "Experimental vaccination against group B *Streptococcus*, an encapsulated bacterium, with highly purified preparations of cell surface proteins Rib and alpha," *Infection and Immunity* 64(9):3518-23, Sep. 1996.

Larsson, C., et al., "Protection against experimental infection with group B *Streptococcus* by immunization with a bivalent protein vaccine," *Vaccine*, 17(5):454-8, Feb. 5, 1999.

Madoff, L., et al., "Maternal immunization of mice with group B streptococcal type III polysaccharide-beta C protein conjugate elicits protective antibody to multiple serotypes," *Journal of Clinical Investigation* 94(1):286-92, Jul. 1994.

Martin, D., et al., "Protection from group B streptococcal infection in neonatal mice by maternal immunization with recombinant Sip protein," *Infection and Immunity* 70(9):4897-901, Sep. 2002.

Noya, F., et al., "Prevention of group B streptococcal infection," *Infectious Disease Clinics of North America* 6(1):41-55, Mar. 1992.

Paoletti, L., et al., "Neonatal mouse protection against infection with multiple group B streptococcal (GBS) serotypes by maternal immunization with a tetravalent GBS polysaccharide-tetanus toxoid conjugate vaccine," *Infection and Immunity* 62(8):3236-43, Aug. 1994.

Park, Hee-Myung, et al., "Identification of Lactoferrin-binding Proteins in *Streptococcus dysgalactiae* subsp. *Dysgalactiae* and *Streptococcus agalactiae* Isolated from Cows with Mastitis," *FEMS Microbiology Letters*, 207:87 90, 2002.

Reinscheid, D., et al., "Identification and molecular analysis of PcsB, a protein required for cell wall separation of group B *Streptococcus*," *Journal of Bacteriology* 183(4):1175-83, Feb. 2001.

Rioux, S., et al., "Localization of surface immunogenic protein on group B *Streptococcus*,"*Infection and Immunity* 69(8):5162-5, Aug. 2001.

Schuchat, A., "Epidemiology of group B streptococcal disease in the United States: shifting paradigms," *Clinical Microbiology Reviews* 11(3):497-513, Jul. 1998.

Schuchat, A., et al., "Prevention of Perinatal Group B Streptococcal Disease: A Public Health Perspective," *Morbidity and Mortality Weekly Report*, 45(RR-7):1-24, May 31, 1996.

Stalhammar-Carlemalm, M., et al., "Protein rib: a novel group B streptococcal cell surface protein that confers protective immunity and is expressed by most strains causing invasive infections," *Journal of Experimental Medicine* 177(6):1593-603, Jun. 1, 1993.

Jameson et al., "The antigenic index: a novel algorithm for predicting antigenic determinants," *Computer Application Bioscience* 4(1):181-186, 1988.

Kolaskar et al., "A semi-empirical method for prediction of antigenic determinants on protein antigens," *FEBS* 276(1,2): 172-174, 1990.

Lipman et al., "Monoclonal Versus Polyclonal Antibodies: Distinguishing Characteristics, Applications, and Information Resources," *ILAR Journal* 46(3):258-268, 2005.

Maione et al., "Identification of a Universal Group B *Streptococcus* Vaccine by Multiple Genome Screen," *Science* 309:148-150, 2005.

Menéndez-Arias et al., "A BASIC microcomputer program for prediction of B and T cell epitopes in proteins," *Comput. Appl. Biosci.* 6(2):101-105, 1990.

Nakai et al., "PSORT: a program for detecting sorting signals in proteins and predicting their subcellular localization," *TIBS* 24:34-35, 1999.

Roitt et al., *Immunology*, 4th Edition, 1998, pp. 7.7-7.8, Mosby, London.

Thornton et al., "Location of 'continuous' antigenic determinants in the protruding regions of proteins," *EMBO Journal* 5(2):409-413, 1986.

Wan et al., "Epitope Map for a Growth Hormone Receptor Agonist Monoclonal Antibody, MAb 263," *Molecular Endocrinology* 17(11):2240-2250, 2003.

GenBank Database Accession No. Q93GJ8, Dec. 1, 2001.

Hopp, "Retrospective: 12 Years of Antigenic Determinant Predictions, and More," *Peptide Research* 6(4):183-190, 1993.

Hofmann et al., "On the theoretical prediction of protein antigenic determinants from amino acid sequences," *Biomed. Biochim. Acta* 46(11):855-866, 1987.

\* cited by examiner

| | | | | | |
|---|---|---|---|---|---|
| TATCTGGCAA | AGAGCCAGCT | AATCGTTTTA | GTTGGGCTAA | AAATAAATTA | TTAATCAATG | 60 |
| S G K | E P A | N R F S | W A K | N K L | L I N G | |
| ----> | | | | | | |
| GATTCATTGC | AACTCTAGCA | GCAACTATCT | TATTTTTGC | AGTTCAATTC | ATAGGTCTTA | 120 |
| F I A | T L A | A T I L | F F A | V Q F | I G L K | |
| AACCAGATTA | CCCTGGAAAA | ACCTACTTTA | TTATCCTATT | GACAGCATGG | ACTTTGATGG | 180 |
| P D Y | P G K | T Y F I | I L L | T A W | T L M A | |
| CATTAGTAAC | TGCTTTAGTG | GGATGGGATA | ATAGGTATGG | TTCCTTCTTG | TCGTTATTAA | 240 |
| L V T | A L V | G W D N | R Y G | S F L | S L L I | |
| TATTATTATT | CCAGCTTGGT | TCAAGCGCAG | GAACTTACCC | AATAGAATTG | AGTCCTAAGT | 300 |
| L L F | Q L G | S S A G | T Y P | I E L | S P K F | |
| TCTTTCAAAC | AATTCAACCA | TTTTTACCGA | TGACTTACTC | TGTTTCAGGA | TTAAGAGAGA | 360 |
| F Q T | I Q P | F L P M | T Y S | V S G | L R E T | |
| CCATCTCGTT | GACGGGAGAC | GTTAACCATC | AATGGAGAAT | GCTAGTAATC | TTTTTAGTAT | 420 |
| I S L | T G D | V N H Q | W R M | L V I | F L V S | |
| CATCGATGAT | ACTTGCTCTT | CTTATTTATC | GTAAACAAGA | AGATTAATAG | AAAGTATCTA | 480 |
| S M I | L A L | L I Y R | K Q E | D | | |
| GTGATAGACT | AACAGTATGA | TATGGTATGT | CAAAGTATTT | AGGAGGAGAA | GATATGTCTA | 540 |
| | | | | | M S T | |
| | | | | | ┃----> | |
| CTTTAACAAT | AATTATTGCA | ACATTAACTG | CTTTGGAACA | TTTTTATATT | ATGTATTTGG | 600 |
| L T I | I I A | T L T A | L E H | F Y I | M Y L E | |
| AGACGTTAGC | CACCCAGTCA | AATATGACTG | GGAAGATTTT | TAGTATGTCT | AAAGAAGAGT | 660 |
| T L A | T Q S | N M T G | K I F | S M S | K E E L | |
| TGTCATATTT | ACCCGTTATT | AAACTTTTTA | AGAATCAAGG | TGTATACAAC | GGCTTGATTG | 720 |
| S Y L | P V I | K L F K | N Q G | V Y N | G L I G | |
| GCCTATTCCT | CCTTTATGGG | TTATATATTT | CACAGAATCA | AGAAATTGTA | GCTGTTTTTT | 780 |
| L F L | L Y G | L Y I S | Q N Q | E I V | A V F L | |
| TAATCAATGT | ATTGCTAGTT | GCTATTTATG | GTGCTTTGAC | AGTTGATAAA | AAAATCTTAT | 840 |
| I N V | L L V | A I Y G | A L T | V D K | K I L L | |
| TAAAACAGGG | TGGTTTACCT | ATATTAGCTC | TTTTAACATT | CTTATTTTAA | TACTACTTAG | 900 |
| K Q G | G L P | I L A L | L T F | L F | | |
| CCGTTCGATT | TAGTTGAACG | GCTTTTAGTA | ATCATTTTTT | TCTCATAATA | CAGGTAGTTT | 960 |
| AAGTAATTTG | TCTTTAAAAA | TAGTATAATA | TAACTACGAA | TTCAAAGAGA | GGTGACTTTG | 1020 |
| ATTATGACTG | AGAACTGGTT | ACATACTAAA | GATGGTTCAG | ATATTTATTA | TCGTGTCGTT | 1080 |
| M T E | N W L | H T K | D G S D | I Y Y | R V V | |
| ┃----> | | | | | | |
| GGTCAAGGTC | AACCGATTGT | TTTTTTACAT | GGCAATAGCT | TAAGTAGTCG | CTATTTTGAT | 1140 |
| G Q G Q | P I V | F L H | G N S L | S S R | Y F D | |
| AAGCAAATAG | CATATTTTTC | TAAGTATTAC | CAAGTTATTG | TTATGGATAG | TAGAGGGCAT | 1200 |
| K Q I A | Y F S | K Y Y | Q V I V | M D S | R G H | |
| GGCAAAAGTC | ATGCAAAGCT | AAATACCATT | AGTTTCAGGC | AAATAGCAGT | TGACTTAAAG | 1260 |
| G K S H | A K L | N T I | S F R Q | I A V | D L K | |

*FIG. 1a (1)*

```
GATATCTTAG TTCATTTAGA GATTGATAAA GTTATATTGG TAGGCCATAG CGATGGTGCC    1320
 D  I  L  V  H  L  E  I  D  K  V  I  L  V  G  H  S  D  G  A

AATTTAGCTT TAGTTTTTCA AACGATGTTT CCAGGTATGG TTAGAGGGCT TTTGCTTAAT    1380
 N  L  A  L  V  F  Q  T  M  F  P  G  M  V  R  G  L  L  N

TCAGGGAACC TGACTATTCA TGGTCAGCGA TGGTGGGATA TTCTTTTAGT AAGGATTGCC    1440
 S  G  N  L  T  I  H  G  Q  R  W  W  D  I  L  L  V  R  I  A

TATAAATTCC TTCACTATTT AGGGAAACTC TTTCCGTATA TGAGGCAAAA AGCTCAAGTT    1500
 Y  K  F  L  H  Y  L  G  K  L  F  P  Y  M  R  Q  K  A  Q  V

ATTTCGCTTA TGTTGGAGGA TTTGAAGATT AGTCCAGCTG ATTTACAGCA TGTGTCAACT    1560
 I  S  L  M  L  E  D  L  K  I  S  P  A  D  L  Q  H  V  S  T

CCTGTAATGG TTTTGGTTGG AAATAAGGAC ATAATTAAGT TAAATCATTC TAAGAAACTT    1620
 P  V  M  V  L  V  G  N  K  D  I  I  K  L  N  H  S  K  K  L

GCTTCTTATT TTCCAAGGGG GGAGTTTTAT TCTTTAGTTG GCTTTGGGCA TCACATTATT    1680
 A  S  Y  F  P  R  G  E  F  Y  S  L  V  G  F  G  H  H  I  I

AAGCAAGATT CCCATGTTTT TAATATTATT GCAAAAAAGT TTATCAACGA TACGTTGAAA    1740
 K  Q  D  S  H  V  F  N  I  I  A  K  K  F  I  N  D  T  L  K

GGAGAAATTG TTGAAAAAGC TAATTGAAAA AGTCAAATCA CTGACTTCTG TGATTAAAAT    1800
 G  E  I  V  E  K  A  N

TGTATTTTTT ATATCTGTTT TAGTGCTTAT TATTGTTGAA ATGATTCATT TGAAACGAAC    1860
                                            M  I  H  L  K  R  T
                                            |----->

TATTTCTGTT GAGCAACTAA AGAGTGTTTT TGGGCAATTA TCTCCAATGA ATCTTTTCTT    1920
 I  S  V  E  Q  L  K  S  V  F  G  Q  L  S  P  M  N  L  F  L

AATTATCCTT GTGGGGGTTA TCGCTGTCTT ACCGACAACC GGATATGACT TTGTACTGAA    1980
 I  I  L  V  G  V  I  A  V  L  P  T  T  G  Y  D  F  V  L  N

TGGACTTTTA CGTACAGATA AAAGCAAAAG GTATATTTTA CAGACTAGTT GGTGTATCAA    2040
 G  L  L  R  T  D  K  S  K  R  Y  I  L  Q  T  S  W  C  I  N

CACTTTTAAT AACTTGTCAG GATTCGGTGG CTTAATCGAT ATTGGGTTGC GCATGGCTTT    2100
 T  F  N  N  L  S  G  F  G  G  L  I  D  I  G  L  R  M  A  F

TTATGGTAAA AAAGGTCAAG AGAAGAGTGA CCTAAGAGAA GTGACTCGTT TTTTACCCTA    2160
 Y  G  K  K  G  Q  E  K  S  D  L  R  E  V  T  R  F  L  P  Y

TCTTATTTCT GGTCTGTCAT TTATTAGTGT GATTGCCTTA ATCATGAGCC ATATTTTTCA    2220
 L  I  S  G  L  S  F  I  S  V  I  A  L  I  M  S  H  I  F  H

TGCCAAAGCT AGTGTTGATT ACTATTATTT GGTATTAATT GGTGCTAGTA TGTATTTTCC    2280
 A  K  A  S  V  D  Y  Y  Y  L  V  L  I  G  A  S  M  Y  F  P

TGTTATTTAT TGGATTTCTG GTCATAAAGG AAGCCATTAT TTCGGAGATA TGCCATCTAG    2340
 V  I  Y  W  I  S  G  H  K  G  S  H  Y  F  G  D  M  P  S  S

TACTCGTATA AAATTAGGTG TTGTTTCTTT TTTTGAATGG GGATGTGCGG CCGCAGCATT    2400
 T  R  I  K  L  G  V  V  S  F  F  E  W  G  C  A  A  A  A  F

TATAATTATC GGTTATTTAA TGGGCATTCA TCTACCAGTT TATAAAATTT TACCACTATT    2460
 I  I  I  G  Y  L  M  G  I  H  L  P  V  Y  K  I  L  P  L  F
```

*FIG. 1a (2)*

```
TTGTATTGGT TGTGCCGTCG GGATTGTATC CCTTATTCCC GGTGGATTAG GAAGTTTTGA    2520
 C  I  G  C   A  V  G  I  V  S   L  I  P  G    G  L  G  S    F  E

ATTAGTTCTA TTTACAGGGT TTGCTGCCGA GGGACTACCT AAAGAAACTG TGGTTGCATG    2580
 L  V  L  F   T  G  F   A  A  E   G  L  P  K    E  T  V  V   A  W

GTTATTACTT TATCGTTTAG CCTACTATAT TATTCCATTC TTTGCAGGTA TCTATTTCTT    2640
 L  L  L  Y   R  L  A   Y  Y  I   I  P  F  F    A  G  I  Y    F  F

TATCCATTAT TTAGGTAGTC AAATAAATCA ACGTTATGAA AATGTCCCGA AAGAGTTAGT    2700
 I  H  Y  L   G  S  Q   I  N  Q   R  Y  E  N    V  P  K  E   L  V

ATCAACTGTT CTACAAACCA TGGTGAGCCA TTTGATGCGT ATTTTAGGTG CATTCTTAAT    2760
 S  T  V  L   Q  T  M   V  S  H   L  M  R  I    L  G  A  F    L  I
                                      |---->

ATTTTCAACA GCATTTTTTG AAAATATTAC TTATATTATG TGGTTGCAGA AGCTAGGCTT    2820
 F  S  T  A    F  F  E    N  I  T   Y  I  M   W  L  Q  K    L  G  L

GGACCCATTA CAAGAACAAA TGTTATGGCA GTTTCCAGGT TTATTGCTGG GGGTTTGTTT    2880
 D  P  L  Q    E  Q  M   L  W  Q   F  P  G  L    L  L  G  V   C  F

TATTCTCTTA GCTAGAACTA TTGATCAAAA AGTGAAAAAT GCTTTTCCAA TTGCTATTAT    2940
 I  L  L  A    R  T  I   D  Q  K   V  K  N  A    F  P  I  A   I  I

CTGGATTACT TTGACATTGT TTTATCTTAA TTTAGGTCAT ATTAGTTGGC GACTATCTTT    3000
 W  I  T  L    T  L  F   Y  L  N   L  G  H  I.   S  W  R  L   S  F

CTGGTTTATT TTACTATTGT TAGGCTTATT AGTCATTAAG CCAACTCTCT ATAAAAAACA    3060
 W  F  I  L    L  L  G   L  L  V   I  K  P  T    L  Y  K  K   Q

ATTTATTTAT AGCTGGGAAG AGCGTATTAA GGATGGAATC ATTATCGTTA GTTTAATGGG    3120
 F  I  Y  S    W  E  E   R  I  K   D  G  I  I    I  V  S  L   M  G

AGTTCTATTT TATATTGCAG GACTACTATT CCCTATCAGG GCTCATATTA CAGGTGGTAG    3180
 V  L  F  Y    I  A  G   L  L  F   P  I  R  A    H  I  T  G   G  S

TATTGAACGC CTGCATTATA TCATAGCATG GGAGCCGATA GCATTGGCTA CGTTGATTCT    3240
 I  E  R  L    H  Y  I   I  A  W   E  P  I  A    L  A  T  L   I  L

TACTCTCGTT TATTTATGTT TGGTTAAGAT TTTACAAGGA AAATCTTGTC AGATTGGTGA    3300
 T  L  V  Y    L  C  L   V  K  I   L  Q  G  K    S  C  Q  I   G  D

TGTGTTCAAT GTGGATCGTT ATAAAAAACT ACTTCAAGCT TACGGTGGTT CTTCGGATAG    3360
 V  F  N  V    D  R  Y   K  K  L   L  Q  A  Y    G  G  S  D   S

CGGTTTAGCC TTTTTAAATG ATAAAAGGCT CTACTGGTAC AAAAAAAATG GAGAAGATTG    3420
 G  L  A  F    L  N  D   K  R  L   Y  W  Y  Q    K  N  G  E   D  C

CGTTGCGTTC CAATTTGTAA TTGTCAATAA TAAATGTCTT ATTATGGGGG AACCAGCCGG    3480
 V  A  F  Q    F  V  I   V  N  N   K  C  L  I    M  G  E  P   A  G

TGATGACACT TATATTCGTG AAGCTATTGA ATCGTTTATT GATGATGCTG ATAAGCTAGA    3540
 D  D  T  Y    I  R  E   A  I  E   S  F  I  D    D  A  D  K   L  D

CTATGACCTT GTTTTTTACA GTATTGGACA GAAGTTGACA CTACTTTTAC ATGAGTATGG    3600
 Y  D  L  V    F  Y  S   I  G  Q   K  L  T  L    L  L  H  E   Y  G

TTTTGACTTT ATGAAAGTTG GTGAGGATGC TTTAGTTAAT TTAGAAACGT TTACTCTTAA    3660
 F  D  F  M    K  V  G   E  D  A   L  V  N  L    E  T  F  T   L  K
```

*FIG. 1a (3)*

| | |
|---|---|
| AGGGAATAAG TACAAACCTT TCAGAAATGC CCTAAATAGA GTTGAAAAGG ATGGTTTCTA<br> G  N  K  Y   K  P  F   R  N  A   L  N  R   V  E  K   D  G   F  Y | 3720 |
| TTTCGAAGTT GTACAATCGC CACATAGTCA AGAGCTACTA AATAGTTTGG AAGAGATTTC<br> F  E   V  V   Q  S   P   H   S  Q   E   L  L   N   S   L  E   E   I   S | 3780 |
| TAATACTTGG TTAGAAGGAC GTCCTGAAAA AGGTTTCTCA CTAGGATATT TTAATAAAGA<br> N  T  W   L   E   G   R   P    E   K    G   F   S    L   G   Y    F   N   K   D | 3840 |
| TTATTTCCAA CAAGCCCCAA TAGCTTTGGT AAAAAATGCT GAACACGAAG TTGTTGCTTT<br> Y  F   Q   Q    A   P    I    A    L   V    K    N   A   E    H   E   V    V    A   F | 3900 |
| TGCTAATATT ATGCCAAACT ATGAAAAGAG TATTATCTCT ATTGATTTAA TGCGTCACGA<br> A  N   I   M    P   N    Y    E    K   S    I    I    S    I    D    L   M    R    H   D | 3960 |
| TAAACAGAAA ATTCCGAATG GCGTTATGGA TTTCCTCTTT TTATCATTAT TCTCTTATTA<br> K  Q   K   I    P   N    G    V    M   D    F    L    F    L    S    L    F    S    Y    Y | 4020 |
| TCAAGAGAAG GGATACCACT ATTTTGATTT GGGGATGGCA CCTTTATCAG GAGTTGGTCG<br> Q  E   K   G    Y   H    Y    F    D   L    G    M    A    P    L    S    G    V    G    R | 4080 |
| CGTTGAAACA AGTTTTGCTA AAGAGAGAAT GGCGTATCTT GTCTATCATT TCGGTAGTCA<br> V  E   T   S    F   A    K    E    R   M    A    Y    L    V    Y    H    F    G    S    H | 4140 |
| TTTCTACTCA TTTAATGGTT TACACAAGTA TAAGAAGAAG TTTACACCAT TGTGGTCGGA<br> F  Y   S   F    N   G    L    H    K   Y    K    K    K    F    T    P    L    W    S    E | 4200 |
| ACGTTATATT TCTTGTTCTC GTTCGTCCTG GTTAATTTGT GCTATTTGTG CCCTATTAAT<br> R  Y   I   S    C   S    R    S     S   W    L     I    C    A     I    C    A     L     L    M | 4260 |
| GGAAGATAGT AAAATTAAGA TTGTTAAATA AGCTTTATTT GGCAATTAAA AAGAGCATGT<br> E  D   S   K    I   K    I    V    K | 4320 |
| CATGCGACAT GCTCTTTTTA AATCATTTAA TACCATTGAT TGCTTGAATC TACTTTATAA | 4380 |
| TATGATGTGC TTTTAAATAT TGTTTAGCTA CTGTAGCTGC TGATTTATGC TTTACAGCTA | 4440 |
| CTTGGTAGTT CATTTCTTGC ATTTCTTTTT CAGTGATATG ACCAGCAAGT TTATTGAGAG | 4500 |
| CTTTTTTTAC TTGA   (SEQ ID NO:1) | 4514 |

[clone1-dna/aa]

FIG. 1a (4)

| | | | | |
|---|---|---|---|---|
| SGKEPANRFS | WAKNKLLING | FIATLAATIL | FFAVQFIGLK | PDYPGKTYFI | 50
| ILLTAWTLMA | LVTALVGWDN | RYGSFLSLLI | LLFQLGSSAG | TYPIELSPKF | 100
| FQTIQPFLPM | TYSVSGLRET | ISLTGDVNHQ | WRMLVIFLVS | SMILALLIYR | 150
| KQED | (SEQ ID NO:2) | | | | 154

FIG. 1b

| | | | | |
|---|---|---|---|---|
| MSTLTIIIAT | LTALEHFYIM | YLETLATQSN | MTGKIFSMSK | EELSYLPVIK | 50
| LFKNQGVYNG | LIGLFLLYGL | YISQNQEIVA | VFLINVLLVA | IYGALTVDKK | 100
| ILLKQGGLPI | LALLTFLF | (SEQ ID NO:3) | | | 118

FIG. 1c

| | | | | |
|---|---|---|---|---|
| MTENWLHTKD | GSDIYYRVVG | QGQPIVFLHG | NSLSSRYFDK | QIAYFSKYYQ | 50
| VIVMDSRGHG | KSHAKLNTIS | FRQIAVDLKD | ILVHLEIDKV | ILVGHSDGAN | 100
| LALVFQTMFP | GMVRGLLLNS | GNLTIHGQRW | WDILLVRIAY | KFLHYLGKLF | 150
| PYMRQKAQVI | SLMLEDLKIS | PADLQHVSTP | VMVLVGNKDI | IKLNHSKKLA | 200
| SYFPRGEFYS | LVGFGHHIIK | QDSHVFNIIA | KKFINDTLKG | EIVEKAN | 247
| (SEQ ID NO:4) | | | | |

FIG. 1d

```
MIHLKRTISV  EQLKSVFGQL  SPMNLFLIIL  VGVIAVLPTT  GYDFVLNGLL   50
RTDKSKRYIL  QTSWCINTFN  NLSGFGGLID  IGLRMAFYGK  KGQEKSDLRE  100
VTRFLPYLIS  GLSFISVIAL  IMSHIFHAKA  SVDYYYLVLI  GASMYFPVIY  150
WISGHKGSHY  FGDMPSSTRI  KLGVVSFFEW  GCAAAAFIII  GYLMGIHLPV  200
YKILPLFCIG  CAVGIVSLIP  GGLGSFELVL  FTGFAAEGLP  KETVVAWLLL  250
YRLAYYIIPF  FAGIYFFIHY  LGSQINQRYE  NVPKELVSTV  LQTMVSHLMR  300
ILGAFLIFST  AFFENITYIM  WLQKLGLDPL  QEQMLWQFPG  LLLGVCFILL  350
ARTIDQKVKN  AFPIAIIWIT  LTLFYLNLGH  ISWRLSFWFI  LLLLGLLVIK  400
PTLYKKQFIY  SWEERIKDGI  IIVSLMGVLF  YIAGLLFPIR  AHITGGSIER  450
LHYIIAWEPI  ALATLILTLV  YLCLVKILQG  KSCQIGDVFN  VDRYKKLLQA  500
YGGSSDSGLA  FLNDKRLYWY  QKNGEDCVAF  QFVIVNNKCL  IMGEPAGDDT  550
YIREAIESFI  DDADKLDYDL  VFYSIGQKLT  LLLHEYGFDF  MKVGEDALVN  600
LETFTLKGNK  YKPFRNALNR  VEKDGFYFEV  VQSPHSQELL  NSLEEISNTW  650
LEGRPEKGFS  LGYFNKDYFQ  QAPIALVKNA  EHEVVAFANI  MPNYEKSIIS  700
IDLMRHDKQK  IPNGVMDFLF  LSLFSYYQEK  GYHYFDLGMA  PLSGVGRVET  750
SFAKERMAYL  VYHFGSHFYS  FNGLHKYKKK  FTPLWSERYI  SCSRSSWLIC  800
AICALLMEDS  KIKIVK      (SEQ ID NO:5)                      816
```

*FIG. 1e*

```
MRILGAFLIF  STAFFENITY  IMWLQKLGLD  PLQEQMLWQF  PGLLLGVCFI   50
LLARTIDQKV  KNAFPIAIIW  ITLTLFYLNL  GHISWRLSFW  FILLLLGLLV  100
IKPTLYKKQF  IYSWEERIKD  GIIIVSLMGV  LFYIAGLLFP  IRAHITGGSI  150
ERLHYIIAWE  PIALATLILT  LVYLCLVKIL  QGKSCQIGDV  FNVDRYKKLL  200
QAYGGSSDSG  LAFLNDKRLY  WYQKNGEDCV  AFQFVIVNNK  CLIMGEPAGD  250
DTYIREAIES  FIDDADKLDY  DLVFYSIGQK  LTLLLHEYGF  DFMKVGEDAL  300
VNLETFTLKG  NKYKPFRNAL  NRVEKDGFYF  EVVQSPHSQE  LLNSLEEISN  350
TWLEGRPEKG  FSLGYFNKDY  FQQAPIALVK  NAEHEVVAFA  NIMPNYEKSI  400
ISIDLMRHDK  QKIPNGVMDF  LFLSLFSYYQ  EKGYHYFDLG  MAPLSGVGRV  450
ETSFAKERMA  YLVYHFGSHF  YSFNGLHKYK  KKFTPLWSER  YISCSRSSWL  500
ICAICALLME  DSKIKIVK    (SEQ ID NO:6)                      518
```

*FIG. 1f*

```
AATTTTGATA TCGAAACAAC AACTTTTGAG GCAATGAAAA AGCACGCGTC ATTATTGGAG        60
 N  F  D  I  E  T  T   T  F  E   A  M  K  K   H  A  S   L  L  E
---->
AAAATATCTG TTGAGCGTTC TTTTATTGAA TTTGATAAAC TTCTATTAGC ACCTTATTGG       120
 K  I  S  V  E  R  S  F  I  E   F  D  K  L   L  L  A   P  Y  W

CGTAAAGGAA TGCTGGCACT AATAGATAGT CATGCTTTTA ATTATCTACC ATGCTTAAAA       180
 R  K  G  M  L  A  L   I  D  S   H  A  F  N  Y  L  P   C  L  K

AATAGGGAAT TACAATTAAG CGCCTTTTTG TCCCAGTTAG ATAAAGATTT TTTATTTGAG       240
 N  R  E  L  Q  L  S  A  F  L   S  Q  L  D   K  D  F   L  F  E

ACATCAGAAC AAGCTTGGGC ATCACTCATC TTGAGTATGG AAGTTGAACA CACAAAGACT       300
 T  S  E  Q  A  W  A   S  L  I  L  S  M  E   V  E  H   T  K  T

TTTTTAAAAA AATGGAAGAC ATCAACTCAC TTTCAAAAAG ATGTTGAGCA TATAGTGGAT       360
 F  L  K  K  W  K  T   S  T  H   F  Q  K  D   V  E  H  I  V  D

GTTTATCGTA TTCGTGAACA AATGGGATTG GCTAAAGAAC ATCTTTATCG TTATGGAAAA       420
 V  Y  R  I  R  E  Q   M  G  L   A  K  E  H   L  Y  R   Y  G  K

ACTATAATAA AACAAGCGGA AGGTATTCGC AAAGCAAGAG GCTTGATGGT TGATTTCGAA       480
 T  I  I  K  Q  A  E   G  I  R   K  A  R  G   L  M  V   D  F  E

AAAATAGAAC AACTAGATAG TGAGTTAGCA ATCCATGATA GGCATGAGAT AGTTGTCAAT       540
 K  I  E  Q  L  D  S   E  L  A   I  H  D  R   H  E  I   V  V  N

GGTGGCACCT TAATCAAGAA ATTAGGAATA AAACCTGGTC CACAGATGGG AGATATTATC       600
 G  G  T  L  I  K  K   L  G  I   K  P  G  P   Q  M  G   D  I  I

TCTCAAATTG AATTAGCCAT TGTTTTAGGA CAACTGATTA ATGAAGAAGA GGCTATTTTA       660
 S  Q  I  E  L  A  I   V  L  G   Q  L  I  N   E  E  E   A  I  L

CATTTTGTTA AGCAGTACTT GATGGATTAG AGAGGATTAT ATGAGCGATT TTTTAGTAGA       720
 H  F  V  K  Q  Y  L   M  D                   M  S  D  F  L  V  D
                                               |---->
TGGATTGACT AAGTCGGTTG GTGATAAGAC GGTCTTTAGT AATGTTTCAT TTATCATCCA       780
 G  L  T  K  S  V  G   D  K  T   V  F  S  N   V  S  F   I  I  H

TAGTTTAGAC CGTATTGGGA TTATTGGTGT CAATGGAACT GGAAAGACAA CACTATTAGA       840
 S  L  D  R  I  G  I   I  G  V   N  G  T  G   K  T  T   L  L  D

TGTTATTTCG GGTGAATTAG GTTTTGATGG TGATCGTTCC CCTTTTTCAT CAGCTAATGA       900
 V  I  S  G  E  L  G   F  D  G   D  R  S  P   F  S  S   A  N  D

TTATAAGATT GCTTATTTAA AACAAGAACC AGACTTTGAT GATTCTCAGA CAATTTTGGA       960
 Y  K  I  A  Y  L  K   Q  E  P   D  F  D  D   S  Q  T   I  L  D

CACCGTACTT TCTTCTGACT TAAGAGAGAT GGCTTTAATT AAAGAATATG AATTATTGCT      1020
 T  V  L  S  S  D  L   R  E  M   A  L  I  K   E  Y  E   L  L  L

TAATCACTAC GAAGAAAGTA AGCAATCACG TCTAGAGAAA GTAATGGCAG AAATGGATTC      1080
 N  H  Y  E  E  S  K   Q  S  R   L  E  K  V   M  A  E   M  D  S

TTTAGATGCT TGGTCTATTG AGAGCGAAGT CAAAACAGTA TTATCCAAAT TAGGTATTAC      1140
 L  D  A  W  S  I  E   S  E  V   K  T  V  L   S  K  L   G  I  T

TGATTTGCAG TTGTCGGTTG GTGAATTATC AGGAGGATTA CGAAGACGTG TTCAATTAGC      1200
 D  L  Q  L  S  V  G   E  L  S   G  G  L  R   R  R  V   Q  L  A
```

*FIG. 2a (1)*

```
GCAAGTATTA TTAAATGATG CAGATTTATT GCTCTTAGAC GAACCTACTA ACCACTTAGA    1260
 Q  V  L    L  N  D  A   D  L  L    L  L  D    E  P  T     N  H  L  D

TATTGACACT ATTGCATGGT TAACGAATTT TTTGAAAAAT AGTAAAAAGA CAGTGCTTTT    1320
 I  D  T    I  A  W  L  T  N  F    L  K  N    S  K  K  T  V  L  F

TATAACTCAT GATCGTTATT TTCTAGACAA TGTTGCAACA CGTATTTTTG AATTAGATAA    1380
 I  T  H    D  R  Y  F  L  D  N    V  A  T    R  I  F  E  L  D  K

GGCACAGATT ACAGAATATC AAGGCAATTA TCAGGATTAT GTCCGACTTC GTGCAGAACA    1440
 A  Q  I    T  E  Y  Q  G  N  Y    Q  D  Y    V  R  L    R  A  E  Q

AGACGAGCGT GATGCTGCTA GTTTACATAA AAAGAAACAG CTTTATAAAC AGGAACTAGC    1500
 D  E  R    D  A  A  S  L  H  K    K  K  Q    L  Y  K  Q  E  L  A

TTGGATGCGT ACTCAGCCAC AAGCTCGTGC AACGAAACAA CAGGCTCGTA TTAATCGTTT    1560
 W  M  R    T  Q  P  Q  A  R  A    T  K  Q    Q  A  R  I  N  R  F

TCAAAATCTA AAAAACGATT TACACCAAAC AAGCGATACA AGCGATTTGG AAATGACATT    1620
 Q  N  L    K  N  D  L  H  Q  T    S  D  T    S  D  L  E  M  T  F

TGAAACAAGT CGAATTGGGA AAAAGGTTAT TAATTTTGAA AATGTCTCTT TTTCTTACCC    1680
 E  T  S    R  I  G  K  K  V  I    N  F  E    N  V  S  F  S  Y  P

AGATAAATCT ATCTTGAAAG ACTTTAATTT GTTAATTCAA AATAAAGACC GTATTGGCAT    1740
 D  K  S    I  L  K  D  F  N  L    L  I  Q    N  K  D  R  I  G  I

CGTTGGAGAT AATGGTGTTG GAAAGTCAAC CTTACTTAAT TTAATTGTTC AAGATTTACA    1800
 V  G  D    N  G  V  G  K  S  T    L  L  N    L  I  V  Q  D  L  Q

GCCGGATTCG GGTAATGTCT CTATTGGTGA AACGATACGT GTAGGTTACT TTTCACAACA    1860
 P  D  S    G  N  V  S  I  G  E    T  I  R    V  G  Y  F  S  Q  Q

ACTTCATAAT ATGGATGGCT CAAAACGTGT TATTAATTAT TTGCAAGAGG TTGCAGATGA    1920
 L  H  N    M  D  G  S  K  R  V    I  N  Y    L  Q  E  V  A  D  E

GGTTAAAACT AGTGTCGGTA CAACAAGTGT GACAGAACTA TTGGAACAAT TTCTCTTTCC    1980
 V  K  T    S  V  G  T  T  S  V    T  E  L    L  E  Q  F  L  F  P

ACGTTCGACA CATGGAACAC AAATTGCAAA ATTATCAGGT GGTGAGAAAA AAAGACTTTA    2040
 R  S  T    H  G  T  Q  I  A  K    L  S  G    G  E  K  K  R  L  Y

CCTTTTAAAA ATCCTGATTG AAAAGCCTAA TGTGTTACTA CTTGATGAGC CGACAAATGA    2100
 L  L  K    I  L  I  E  K  P  N    V  L  L    D  E  P  T  N  D

CTTAGATATT GCTACATTAA CTGTTCTTGA AAATTTTTTA CAAGGCTTTG GTGGTCCTGT    2160
 L  D  I    A  T  L  T  V  L  E    N  F  L    Q  G  F  G  G  P  V

GATTACAGTT AGTCACGATC GTTACTTTTT AGATAAAGTG GCTAATAAAA TTATTGCGTT    2220
 I  T  V    S  H  D  R  Y  F  L    D  K  V    A  N  K  I  I  A  F

TGAAGATAAC GATATCCGTG AATTTTTTGG TAATTATACT GATTATTTAG ATGAAAAAGC    2280
 E  D  N    D  I  R  E  F  F  G    N  Y  T    D  Y  L  D  E  K  A

ATTTAATGAG CAAAATAATG AAGTTATCAG TAAAAAAGAG AGTACCAAGA CAAGTCGTGA    2340
 F  N  E    Q  N  N  E  V  I  S    K  K  E    S  T  K  T  S  R  E

AAAGCAAAGT CGTAAAAGAA TGTCTTACTT TGAAAAACAA GAATGGGCGA CAATTGAAGA    2400
 K  Q  S    R  K  R  M  S  Y  F    E  K  Q    E  W  A  T  I  E  D

CGATATTATG ATATTGGAAA ATACTATCAC TCGTATAGAA AATGATATGC AAACATGTGG    2460
```

```
      D   I   M       I   L   E   N       T   I   T       R   I   E       N   D   M   Q       T   C   G
TAGTGATTTT ACAAGGTTAT CTGATTTACA AAAGGAATTA GATGCAAAAA ATGAAGCACT         2520
 S   D   F       T   R   L   S       D   L   Q       K   E   L       D   A   K   N       E   A   L

TCTAGAAAAG TATGACCGTT ATGAGTACCT TAGTGAGTTA GACACATGAT TATCCGTCCG         2580
 L   E   K       Y   D   R   Y       E   Y   L       S   E   L       D   T   M   I       I   R   P
                                                                                 |---->
ATTATTAAAA ATGATGACCA AGCAGTTGCA CAATTAATTC GACAAAGTTT ACGCGCCTAT         2640
 I   I   K   N       D   D   Q       A   V   A       Q   L   I   R       Q   S   L       R   A   Y

GATTTAGATA AACCTGATAC AGCATATTCA GACCCTCACT TAGATCATTT GACCTCATAC         2700
 D   L   D   K       P   D   T       A   Y   S       D   P   H   L       D   H   L       T   S   Y

TACGAAAAAA TAGAGAAGTC AGGATTCTTT GTCATTGAGG AGAGAGATGA GATTATTGGC         2760
 Y   E   K   I       E   K   S       G   F   F       V   I   E   E       R   D   E       I   I   G

TGTGGCGGCT TTGGTCCGCT GAAAAATCTA ATTGCAGAGA TGCAGAAGGT GTACATTGCA         2820
 C   G   G   F       G   P   L       K   N   L       I   A   E   M       Q   K   V       Y   I   A

GAACGTTTCC GTGGTAAGGG GCTTGCTACT GATTTAGTGA AAATGATTGA AGTAGAAGCT         2880
 E   R   F   R       G   K   G       L   A   T       D   L   V   K       M   I   E       V   E   A

CGAAAAATTG GGTATAGACA ACTTTATTTA GAGACAGCCA GTACTTTGAG TAGGGCAACT         2940
 R   K   I   G       Y   R   Q       L   Y   L       E   T   A   S       T   L   S       R   A   T

GCGGTTTATA AGCATATGGG ATATTGTGCC TTATCGCAAC CAATAGCAAA TGATCAAGGT         3000
 A   V   Y   K       H   M   G       Y   C   A       L   S   Q   P       I   A   N       D   Q   G

CATACAGCTA TGGATATTTG GATGATTAAA GATTTATAAG TTGAAAGTGG ATTAGTGAAC         3060
 H   T   A   M       D   I   W       M   I   K       D   L

ATGGATTAAT TATTTTGAGA TAAGAGGAAA GAAAAGGAGA CATATATGGC ATATATTTGG         3120
                                                       M   A       Y   I   W
                                                       |---->
TCTTATTTGA AAAGGTACCC CAATTGGTTA TGGCTTGATT TACTAGGAGC TATGCTTTTT         3180
 S   Y   L   K       R   Y   P       N   W   L       W   L   D   L       L   G   A       M   L   F

GTGACGGTTA TCCTAGGAAT GCCCACAGCC TTAGCGGGTA TGATTGATAA TGGCGTTACA         3240
 V   T   V   I       L   G   M       P   T   A       L   A   G   M       I   D   N       G   V   T

AAAGGTGATC GGACTGGAGT TTATCTGTGG ACGTTCATCA TGTTTATATT TGTTGTACTA         3300
 K   G   D   R       T   G   V       Y   L   W       T   F   I   M       F   I   F       V   V   L

GGTATTATTG GGCGTATTAC GATGGCTTAC GCATCTAGTC GCTTAACGAC AACAATGATT         3360
 G   I   I   G       R   I   T       M   A   Y       A   S   S   R       L   T   T       T   M   I

AGAGATATGC GTAATGATAT GTATGCTAAG CTTCAAGAAT ACTCCCATCA TGAATATGAA         3420
 R   D   M   R       N   D   M       Y   A   K       L   Q   E   Y       S   H   H       E   Y   E

CAGATAGGTG TATCTTCACT AGTGACACGT ATGACAAGCG ATACTTTTGT TTTGATGCAA         3480
 Q   I   G   V       S   S   L       V   T   R       M   T   S   D       T   F   V       L   M   Q

TTTGCTGAAA TGTCTTTACG TTTAGGCCTA GTAACTCCTA TGGTAATGAT TTTTAGCGTG         3540
 F   A   E   M       S   L   R       L   G   L       V   T   P   M       V   M   I       F   S   V

GTTATGATAC TAATTACGAG TCCATCTTTG GCTTGGCTTG TAGCGGTTGC GATGCCTCTT         3600
 V   M   I   L       I   T   S       P   S   L       A   W   L   V       A   V   A       M   P   L

TTGGTAGGAG TCGTTTTATA TGTAGCTATA AAAACAAAAC CTTTATCTGA AAGACAACAG         3660
 L   V   G   V       V   L   Y       V   A   I       K   T   K   P       L   S   E       R   Q   Q
```

*FIG. 2a (3)*

```
ACTATGCTTG ATAAAATCAA TCAATATGTT CGTGAAAATT TAACAGGGTT ACGCGTTGTT   3720
 T  M  L  D  K  I  N  Q  Y  V  R  E  N  L  T  G  L  R  V  V

AGAGCCTTTG CAAGAGAGAA TTTTCAATCA CAAAAATTTC AAGTCGCTAA CCAACGTTAC   3780
 R  A  F  A  R  E  N  F  Q  S  Q  K  F  Q  V  A  N  Q  R  Y

ACAGATACTT CAACTGGTCT TTTTAAATTA ACAGGGCTAA CAGAACCACT TTTCGTTCAA   3840
 T  D  T  S  T  G  L  F  K  L  T  G  L  T  E  P  L  F  V  Q

ATTATTATTG CAATGATTGT GGCTATCGTT TGGTTTGCTT TGGATCCCTT ACAAAGAGGT   3900
 I  I  I  A  M  I  V  A  I  V  W  F  A  L  D  P  L  Q  R  G

GCTATTAAAA TAGGGGATTT AGTTGCTTTT ATCGAATATA GCTTCCATGC TCTCTTTTCA   3960
 A  I  K  I  G  D  L  V  A  F  I  E  Y  S  F  H  A  L  F  S

TTTTTGCTAT TTGCCAATCT TTTTACTATG TATCCTCGTA TGGTGGTATC AAGCCATCGT   4020
 F  L  L  F  A  N  L  F  T  M  Y  P  R  M  V  V  S  S  H  R

ATTAGAGAGG TGATGGATAT GCCAATCTCT ATCAATCCTA ATGCCGAAGG TGTTACGGAT   4080
 I  R  E  V  M  D  M  P  I  S  I  N  P  N  A  E  G  V  T  D

ACGAAACTTA AAGGGCATTT AGAATTTGAT AATGTAACAT TCGCTTATCC AGGAGAAACA   4140
 T  K  L  K  G  H  L  E  F  D  N  V  T  F  A  Y  P  G  E  T

GAGAGTCCCG TTTTGCATGA TATTTCTTTT AAAGCTAAGC CTGGAGAAAC AATTGCTTTT   4200
 E  S  P  V  L  H  D  I  S  F  K  A  K  P  G  E  T  I  A  F

ATTGGTTCAA CAGGTTCAGG AAAATCTTCT CTTGTTAATT TGATTCCACG TTTTTATGAT   4260
 I  G  S  T  G  S  G  K  S  S  L  V  N  L  I  P  R  F  Y  D

GTGACACTTG GAAAAATCTT AGTAGATGGA GTTGATGTAA GAGATTATAA CCTTAAATCA   4320
 V  T  L  G  K  I  L  V  D  G  V  D  V  R  D  Y  N  L  K  S

CTTCGCCAAA AGATTGGATT TATCCCCCAA AAAGCTCTTT TATTTACAGG GACAATAGGA   4380
 L  R  Q  K  I  G  F  I  P  Q  K  A  L  L  F  T  G  T  I  G

GAGAATTTAA AATATGGAAA AGCTGATGCT ACTATTGATG ATCTTAGACA AGCGGTTGAT   4440
 E  N  L  K  Y  G  K  A  D  A  T  I  D  D  L  R  Q  A  V  D

ATTTCTCAAG CTAAAGAGTT TATTGAGAGT CACCAAGAAG CCTTTGAAAC GCATTTAGCT   4500
 I  S  Q  A  K  E  F  I  E  S  H  Q  E  A  F  E  T  H  L  A

GAAGGTGGGA GCAATCTTTC TGGGGGTCAA AAACAACGGT TATCTATTGC TAGGGCTGTT   4560
 E  G  G  S  N  L  S  G  G  Q  K  Q  R  L  S  I  A  R  A  V

GTTAAAGATC CAGATTTATA TATTTTTGAT GATTCATTTT CTGCTCTCGA TTATAAGACA   4620
 V  K  D  P  D  L  Y  I  F  D  D  S  F  S  A  L  D  Y  K  T

GACGCTACTT TAAGAGCGCG TCTAAAAGAA GTAACCGGTG ATTCTACAGT TTTGATAGTT   4680
 D  A  T  L  R  A  R  L  K  E  V  T  G  D  S  T  V  L  I  V

GCTCAAAGGG TGGGTACGAT TATGGATGCT GATCAGATTA TTGTCCTTGA TGAAGGCGAA   4740
 A  Q  R  V  G  T  I  M  D  A  D  Q  I  I  V  L  D  E  G  E

ATTGTCGGTC GTGGTACCCA CGCTCAATTA ATAGAAAATA ATGCTATTTA TCGTGAAATC   4800
 I  V  G  R  G  T  H  A  Q  L  I  E  N  N  A  I  Y  R  E  I

GCTGAGTCAC AACTGAAGAA CCAAAACTTA TCAGAAGGAG AGTGATTGTA TGAGAAAAAA   4860
 A  E  S  Q  L  K  N  Q  N  L  S  E  G  E        M  R  K  K
                                                 |---->
```

*FIG. 2a (4)*

```
ATCTGTTTTT TTGAGATTAT GGTCTTACCT AACTCGCTAC AAAGCTACTC TTTTCTTAGC    4920
 S  V  F    L  R  L  W    S  Y  L    T  R  Y    K  A  T  L    F  L  A

GATTTTTTTG AAAGTTTTAT CTAGTTTTAT GAGTGTTCTG GAGCCTTTTA TTTTAGGGTT    4980
 I  F  L    K  V  L  S    S  F  M    S  V  L    E  P  F  I    L  G  L

AGCGATAACA GAGTTGACTG CTAACCTTGT TGATATGGCT AAGGGAGTTT CTGGGGCAGA    5040
 A  I  T    E  L  T  A    N  L  V    D  M  A    K  G  V  S    G  A  E

ATTGAACGTT CCTTATATTG CTGGTATTTT GATTATTTAT TTTTTCAGAG GTGTTTTCTA    5100
 L  N  V    P  Y  I  A    G  I  L    I  I  Y    F  F  R  G    V  F  Y

TGAATTAGGT TCTTATGGCT CAAATT   (SEQ ID NO:7)                         5126
 E  L  G    S  Y  G  S    N
```

*FIG. 2a (5)*

```
NFDIETTTFE AMKKHASLLE KISVERSFIE FDKLLLAPYW RKGMLALIDS    50
HAFNYLPCLK NRELQLSAFL SQLDKDFLFE TSEQAWASLI LSMEVEHTKT   100
FLKKWKTSTH FQKDVEHIVD VYRIREQMGL AKEHLYRYGK TIIKQAEGIR   150
KARGLMVDFE KIEQLDSELA IHDRHEIVVN GGTLIKKLGI KPGPQMGDII   200
SQIELAIVLG QLINEEEAIL HFVKQYLMD   (SEQ ID NO:8)          229
```

FIG. 2b

```
MSDFLVDGLT KSVGDKTVFS NVSFIIHSLD RIGIIGVNGT GKTTLLDVIS    50
GELGFDGDRS PFSSANDYKI AYLKQEPDFD DSQTILDTVL SSDLREMALI   100
KEYELLLNHY EESKQSRLEK VMAEMDSLDA WSIESEVKTV LSKLGITDLQ   150
LSVGELSGGL RRRVQLAQVL LNDADLLLLD EPTNHLDIDT IAWLTNFLKN   200
SKKTVLFITH DRYFLDNVAT RIFELDKAQI TEYQGNYQDY VRLRAEQDER   250
DAASLHKKKQ LYKQELAWMR TQPQARATKQ QARINRFQNL KNDLHQTSDT   300
SDLEMTFETS RIGKKVINFE NVSFSYPDKS ILKDFNLLIQ NKDRIGIVGD   350
NGVGKSTLLN LIVQDLQPDS GNVSIGETIR VGYFSQQLHN MDGSKRVINY   400
LQEVADEVKT SVGTTSVTEL LEQFLFPRST HGTQIAKLSG GEKKRLYLLK   450
ILIEKPNVLL LDEPTNDLDI ATLTVLENFL QGFGGPVITV SHDRYFLDKV   500
ANKIIAFEDN DIREFFGNYT DYLDEKAFNE QNNEVISKKE STKTSREKQS   550
RKRMSYFEKQ EWATIEDDIM ILENTITRIE NDMQTCGSDF TRLSDLQKEL   600
DAKNEALLEK YDRYEYLSEL DT   (SEQ ID NO:9)                 622
```

FIG. 2c

```
MIIRPIIKND DQAVAQLIRQ SLRAYDLDKP DTAYSDPHLD HLTSYYEKIE    50
KSGFFVIEER DEIIGCGGFG PLKNLIAEMQ KVYIAERFRG KGLATDLVKM   100
IEVEARKIGY RQLYLETAST LSRATAVYKH MGYCALSQPI ANDQGHTAMD   150
IWMIKDL   (SEQ ID NO:10)                                 157
```

FIG. 2d

```
MAYIWSYLKR YPNWLWLDLL GAMLFVTVIL GMPTALAGMI DNGVTKGDRT     50
GVYLWTFIMF IFVVLGIIGR ITMAYASSRL TTTMIRDMRN DMYAKLQEYS    100
HHEYEQIGVS SLVTRMTSDT FVLMQFAEMS LRLGLVTPMV MIFSVVMILI    150
TSPSLAWLVA VAMPLLVGVV LYVAIKTKPL SERQQTMLDK INQYVRENLT    200
GLRVVRAFAR ENFQSQKFQV ANQRYTDTST GLFKLTGLTE PLFVQIIIAM    250
IVAIVWFALD PLQRGAIKIG DLVAFIEYSF HALFSLLFA  NLFTMYPRMV    300
VSSHRIREVM DMPISINPNA EGVTDTKLKG HLEFDNVTFA YPGETESPVL    350
HDISFKAKPG ETIAFIGSTG SGKSSLVNLI PRFYDVTLGK ILVDGVDVRD    400
YNLKSLRQKI GFIPQKALLF TGTIGENLKY GKADATIDDL RQAVDISQAK    450
EFIESHQEAF ETHLAEGGSN LSGGQKQRLS IARAVVKDPD LYIFDDSFSA    500
LDYKTDATLR ARLKEVTGDS TVLIVAQRVG TIMDADQIIV LDEGEIVGRG    550
THAQLIENNA IYREIAESQL KNQNLSEGE  (SEQ ID NO:11)          579
```

*FIG. 2e*

```
MRKKSVFLRL WSYLTRYKAT LFLAIFLKVL SSFMSVLEPF ILGLAITELT     50
ANLVDMAKGV SGAELNVPYI AGILIIYFFR GVFYELGSYG SN             92
(SEQ ID NO:12)
```

*FIG. 2f*

```
AATTTGGAAG TGCTCTATCA ACAGTTGAAG TAAAGGAGAT TATTAGTGAA GAAAACATAT    60
  F  G  S   A  L  S    T  V  E    K  I  I    S  E  E    N  I  W
         ---->
GGTTATATCG GCTCAGTTGC TGCCATTTTA CTAGCTACTC ATATTGGAAG TTACCAACTT   120
 L  Y  R   L  S  C    H  F  T    S  Y  S    Y  W  K    L  P  T  W
GGTAAGCATC ATATGGGTCT AGCAACAAAG GACAATCAGA TTGCCTATAT TGATGACAGC   180
             M  G  L  A  T  K    D  N  Q  I  A  Y  I  D  D  S
                |---->
AAAGGTAAGG CAAAAGCCCC TAAAACAAAC AAAACGATGG ATCAAATCAG TGCTGAAGAA   240
 K  G  K   A  K  A  P  K  T  N   K  T  M  D  Q  I  S   A  E  E
GGCATCTCTG CTGAACAGAT CGTAGTCAAA ATTACTGACC AAGGCTATGT GACCTCACAC   300
 G  I  S  A  E  Q  I   V  V  K    I  T  D  Q  G  Y  V  T  S  H
GGTGACCATT ATCATTTTTA CAATGGGAAA GTTCCTTATG ATGCGATTAT TAGTGAAGAG   360
G  D  H  Y  H  F  Y   N  G  K    V  P  Y  D  A  I  I   S  E  E
TTGTTGATGA CGGATCCTAA TTACCGTTTT AAACAATCAG ACGTTATCAA TGAAATCTTA   420
 L  L  M   T  D  P  N  Y  R  F   K  Q  S  D  V  I  N   E  I  L
       |---->
GACGGTTACG TTATTAAAGT CAATGGCAAC TATTATGTTT ACCTCAAGCC AGGTAGTAAG   480
 D  G  Y  V  I  K  V   N  G  N   Y  Y  V  Y  L  K  P   G  S  K
CGCAAAAACA TTCGAACCAA ACAACAAATT GCTGAGCAAG TAGCCAAAGG AACTAAAGAA   540
 R  K  N  I  R  T  K   Q  Q  I   A  E  Q  V  A  K  G   T  K  E
GCTAAAGAAA AAGGTTTAGC TCAAGTGGCC CATCTCAGTA AAGAAGAAGT TGCGGCAGTC   600
 A  K  E  K  G  L  A   Q  V  A   H  L  S  K  E  E  V   A  A  V
AATGAAGCAA AAAGACAAGG ACGCTATACT ACAGACGATG GCTATATTTT TAGTCCGACA   660
N  E  A  K  R  Q  G    R  Y  T   T  D  D  G  Y  I  F   S  P  T
GATATCATTG ATGATTTAGG AGATGCTTAT TTAGTACCTC ATGGTAATCA CTATCATTAT   720
 D  I  I  D  D  L  G   D  A  Y   L  V  P  H  G  N  H   Y  H  Y
ATTCCTAAAA AGGATTTGTC TCCAAGTGAG CTAGCTGCTG CACAAGCCTA CTGGAGTCAA   780
 I  P  K  K  D  L  S   P  S  E   L  A  A  A  Q  A  Y   W  S  Q
AAACAAGGTC GAGGTGCTAG ACCGTCTGAT TACCGCCCGA CACCAGCCCC AGGTCGTAGG   840
 K  Q  G  R  G  A  R   P  S  D   Y  R  P  T  P  A  P   G  R  R
AAAGCCCCAA TTCCTGATGT GACGCCTAAC CCTGGACAAG GTCATCAGCC AGATAACGGT   900
 K  A  P  I  P  D  V   T  P  N   P  G  Q  G  H  Q  P   D  N  G
GGCTATCATC CAGCGCCTCC TAGGCCAAAT GATGCGTCAC AAAACAAACA CCAAAGAGAT   960
 G  Y  H  P  A  P  P   R  P  N   D  A  S  Q  N  K  H   Q  R  D
GAGTTTAAAG GAAAAACCTT TAAGGAACTT TTAGATCAAC TACACCGTCT TGATTTGAAA  1020
 E  F  K  G  K  T  F   K  E  L   L  D  Q  L  H  R  L   D  L  K
TACCGTCATG TGGAAGAAGA TGGGTTGATT TTTGAACCGA CTCAAGTGAT CAAATCAAAC  1080
 Y  R  H  V  E  E  D   G  L  I   F  E  P  T  Q  V  I   K  S  N
GCTTTTGGGT ATGTGGTGCC TCATGGAGAT CATTATCATA TTATCCCAAG AAGTCAGTTA  1140
 A  F  G  Y  V  V  P   H  G  D   H  Y  H  I  I  P  R   S  Q  L
TCACCTCTTG AAATGGAATT AGCAGATCGA TACTTAGCTG GCCAAACTGA GGACAATGAC  1200
 S  P  L  E  M  E  L   A  D  R   Y  L  A  G  Q  T  E   D  N  D
TCAGGTTCAG AGCACTCAAA ACCATCAGAT AAAGAAGTGA CACATACCTT TCTTGGTCAT  1260
```

FIG. 3a (1)

```
          S  G  S  E      H  S  K      P  S  D      K  E  V  T      H  T  F      L  G  H
CGCATCAAAG CTTACGGAAA AGGCTTAGAT GGTAAACCAT ATGATACGAG TGATGCTTAT  1320
 R  I  K  A  Y  G  K   G  L  D   G  K  P  Y    D  T  S     D  A  Y

GTTTTTAGTA AAGAATCCAT TCATTCAGTG GATAAATCAG GAGTTACAGC TAAACACGGA  1380
 V  F  S  K  E  S  I   H  S  V   D  K  S  G    V  T  A     K  H  G

GATCATTTCC ACTATATAGG ATTTGGAGAA CTTGAACAAT ATGAGTTGGA TGAGGTCGCT  1440
 D  H  F  H  Y  I  G   F  G  E   L  E  Q  Y    E  L  D     E  V  A

AACTGGGTGA AAGCAAAAGG TCAAGCTGAT GAGCTTGCTG CTGCTTTGGA TCAGGAACAA  1500
 N  W  V  K  A  K  G   Q  A  D   E  L  A  A    A  L  D     Q  E  Q

GGCAAAGAAA AACCACTCTT TGACACTAAA AAAGTGAGTC GCAAAGTAAC AAAAGATGGT  1560
 G  K  E  K  P  L  F   D  T  K   K  V  S  R    K  V  T     K  D  G

AAAGTGGGCT ATATGATGCC AAAAGATGGT AAGGACTATT TCTATGCTCG TGATCAACTT  1620
 K  V  G  Y  M  M  P   K  D  G   K  D  Y  F    Y  A  R     D  Q  L

GATTTGACTC AGATTGCCTT TGCCGAACAA GAACTAATGC TTAAAGATAA GAAGCATTAC  1680
 D  L  T  Q  I  A  F   A  E  Q   E  L  M  L    K  D  K     K  H  Y

CGTTATGACA TTGTTGACAC AGGTATTGAG CCACGACTTG CTGTAGATGT GTCAAGTCTG  1740
 R  Y  D  I  V  D  T   G  I  E   P  R  L  A    V  D  V     S  S  L

CCGATGCATG CTGGTAATGC TACTTACGAT ACTGGAAGTT CGTTTGTTAT CCCACATATT  1800
 P  M  H  A  G  N  A   T  Y  D   T  G  S  S    F  V  I     P  H  I

GATCATATCC ATGTCGTTCC GTATTCATGG TTGACGCGCG ATCAGATTGC AACAGTCAAG  1860
 D  H  I  H  V  V  P   Y  S  W   L  T  R  D    Q  I  A     T  V  K

TATGTGATGC AACACCCCGA AGTTCGTCCG GATGTATGGT CTAAGCCAGG GCATGAAGAG  1920
 Y  V  M  Q  H  P  E   V  R  P   D  V  W  S    K  P  G     H  E  E

TCAGGTTCGG TCATTCCAAA TGTTACGCCT CTTGATAAAC GTGCTGGTAT GCCAAACTGG  1980
 S  G  S  V  I  P  N   V  T  P   L  D  K  R    A  G  M     P  N  W

CAAATTATCC ATTCTGCTGA AGAAGTTCAA AAAGCCCTAG CAGAAGGTCG TTTTGCAACA  2040
 Q  I  I  H  S  A  E   E  V  Q   K  A  L  A    E  G  R     F  A  T

CCAGACGGCT ATATTTTCGA TCCACGAGAT GTTTTGGCCA AAGAAACTTT TGTATGGAAA  2100
 P  D  G  Y  I  F  D   P  R  D   V  L  A  K    E  T  F     V  W  K

GATGGCTCCT TTAGCATCCC AAGAGCAGAT GGCAGTTCAT TGAGAACCAT TAATAAATCT  2160
 D  G  S  F  S  I  P   R  A  D   G  S  S  L    R  T  I     N  K  S

GATCTATCCC AAGCTGAGTG GCAACAAGCT CAAGAGTTAT TGGCAAAGAA AAATACTGGT  2220
 D  L  S  Q  A  E  W   Q  Q  A   Q  E  L  L    A  K  K     N  T  G

GATGCTACTG ATACGGATAA ACCCAAAGAA AAGCAACAGG CAGATAAGAG CAATGAAAAC  2280
 D  A  T  D  T  D  K   P  K  E   K  Q  Q  A    D  K  S     N  E  N

CAACAGCCAA GTGAAGCCAG TAAAGAAGAA AAAGAATCAG ATGACTTTAT AGACAGTTTA  2340
 Q  Q  P  S  E  A  S   K  E  E   K  E  S  D    D  F  I     D  S  L

CCAGACTATG GTCTAGATAG AGCAACCCTA GAAGATCATA TCAATCAATT AGCACAAAAA  2400
 P  D  Y  G  L  D  R   A  T  L   E  D  H  I    N  Q  L     A  Q  K

GCTAATATCG ATCCTAAGTA TCTCATTTTC CAACCAGAAG GTGTCCAATT TTATAATAAA  2460
 A  N  I  D  P  K  Y   L  I  F   Q  P  E  G    V  Q  F     Y  N  K
```

*FIG. 3a (2)*

```
AATGGTGAAT TGGTAACTTA TGATATCAAG ACACTTCAAC AAATAAACCC TTAACCAAAA  2520
 N  G  E  L  V  T  Y  D  I  K  T  L  Q  Q  I  N  P

GAAGATCTCA TTGTTAAAGC ACTGCTTTGT CAAAGCAAGT TACGGTGATT TTGAAGTCAT  2580

TCTATGTAAC GAGTAGTGAT AAAAGTTGGA TAATAGCGGT TTTCTTTTGC AAAGAAATGG  2640

TATCCATGTT AGAATAGTAA AAAAGAGGA GGATTCTTGG ACTAATGTCA AATAAGTAGA  2700

CAGAAAACTG TGTTATTTTA TTGCGTTAAA ATAATTTTCT TCTTTCTGAT TAGGGGTTAG  2760
         . K  I  A  N  F  Y  N  E  E  K  Q  N  P  T  L

TCCTAGATTA GCCGTATGTG GGTTGTAATT GTTATAAAAA TTCTCAATGT ATTCAAAGCA  2820
 G  L  N  A  T  H  P  N  Y  N  N  Y  F  N  E  I  Y  E  F  C

GTCTAATTGA ACCTGTTTGA TATTTTGATA ATGTTTTCGG TTGATTTGTC TATGCTTTAA  2880
 D  L  Q  V  Q  K  I  N  Q  Y  H  K  R  N  I  Q  R  H  K  L

ATACTTGAAA AATGCTTCAG TTACGGCATT ATCATAAGGA TATCCAGGAT TAGAAAAAGA  2940
 Y  K  F  F  A  E  T  V  A  N  D  Y  P  Y  G  P  N  S  F

ATGCATGATA TTGGCACTGC ACCCTAATAG TGAGACGCAA GAAAAACACT TTTAGGCAAT  3000
 H  M                                                     A  I
<----|
CAGTTTTCTG TACTGTACAG GCGACTGGTC GTTTAATCTC TGTTGAATTC TAGTTTCATT  3060
 L  K  R  Y  Q  V  P  S  Q  D  N  L  R  Q  Q  I  R  T  E  N

ATAAAATGTA ATGTAATTTT TAACAATATT TGTTATACTA TCTTTGTTGT ATTTTCTCCT  3120
 Y  F  T  I  Y  N  K  V  I  N  T  I  S  D  K  N  Y  K  R  R

ATTATGGAAA TAAAAGGTTT CAGTCTTTAG GACGGTGTGA AACCATTCAA TACAGGCATT  3180
 N  H  F  Y  F  T  E  T  K  L  V  T  H  F  W  E  I  C  A  N

ATCTGCAGGT GTTCCTTTTC GAGACATTGA GCGGATAATG TCTTTTTCCG TGCAAGCCTG  3240
 D  A  P  T  G  K  R  S  M  S  R  I  I  D  K  E  T  C  A  Q

GTAGTAAGCC ATAGAAGTAT ACACTGAGCC TTGGTCACTG TGTAAGATTG CTCCTTTATT  3300
    Y  Y  A  M
          <----|
TAGGCAATTT TAACTGATTA AGGGTGTCTA GTACAAAATC CGTGTCCTGA CAATCTGAGA  3360
 K  P  L  K  L  Q  N  L  T  D  L  V  F  D  T  D  Q  C  D  S

TAGTGTAAGC TATAATTTCT CGGTTATAGA GATTCATAAT TGATGAGAGA TACAATTTAC  3420
 I  T  Y  A  I  I  E  R  N  Y  L  N  M  I  S  S  L  Y  L  K

AGTTACCGAA ATATAGGTAG GTAATATCTG TTACGAGCTT TTCCTTAGGC TTATCGGCAT  3480
 C  N  G  F  Y  L  Y  T  I  D  T  V  L  K  E  K  P  K  D  A

GGAAATCCCG ACTCAATTTA TTATCTGTTA AATAATAAGC TTTACCCAAA TTGGGAACTT  3540
 H  G  D  R  S  L  K  N  D  T  L  Y  Y  A  K  G  L  N  P  V

TCTTGGTACG TGTCCGACAA AGCCAGCCAT TATTTTTCAT GATACGATAG ACTTTCTTTG  3600
 K  K  T  R  T  R  C  L  W  G  N  N  K  M  I  R  Y  V  K  K

TATTAACAGT CAATCCGTGG ATTTTTTTGA GCAATCGTGT AATGGTACGA TAGCCATAAA  3660
 T  N  V  T  L  G  H  I  K  K  L  L  R  T  I  T  R  Y  G  Y

TAAAGTGATT CTCCATACAG AGCTGTTCAA TTAATTCAAT AAGGTCATCT TTTTTTGCGG  3720
 I  F  H  N  E  M
             <----|
```

*FIG. 3a (3)*

```
CTTCTCATAC TCCTTTTTCC AACGGTAATA GGTCGACCGC TTGACCTTAA AACAGTCTAG  3780

AATGAAAACT ATCGGGTAGT TGTTTTTATA GTCTTCCACA AGCTTGATAA GACTTACTTT  3840
                                                         . K
ATCGATTTCC TTATCAAGCC TCGATACTTT TTTAAGAGGT CAACCTGTAA TTGTAATTGT  3900
 I  S  K    R  I  L  G    R  Y  K    K  L  L    D  V  Q  L    Q  L  Q

TCCACTTCAG ACAGATGTTC CAAGCCTTTA CCGTAGGTAT ATTGCTTGCC AACACCTTGA  3960
 E  V  E    S  L  H  E    L  G  K    G  Y  T    Y  Q  K  G    V  G  Q

TGAAAACGAT AAAGCTCCTC GTTTCGTAC  CATTTCATCC AAGTATAGAT TGACTATTA   4020
 H  F  R    Y  L  E  E    N  E  Y    W  K  M    W  T  Y  I    Q  S  N

TTTTTGATGC CTAAAGTCTC CATAATAACT CTGTTAGACT TGCCTGCTTT CTTCATATCG  4080
 N  K  I    G  L  T  E    M  I  V    R  N  S    K  G  A  K    K  M  D

ATGCAAGCCA GCTTAGTTTC CCATGAATAT GCTTTTTTAA CCATAATAAA ACATTCCTGT  4140
 I  C  A    L  K  T  E    W  S  Y    A  K  K    V  M
                                              <----|
TTCTAGTTTA CTAAATTTCA ACAGGAGTGT TTTTCTTTTG TCTCATTTTA GGGATTCAGT  4200

GCCTATTGTT GTCATCAATT ATTTTTCTAA ATTCCCCGGA CTTAAATTGT GACCCTTGGT  4260

CGGAATGAAA GAGAAGTGTT CCTTCAATCT TTCTTTTATT AAGTGAAAAG GCAACACTTT  4320

TCTGTACAAC ATTTATAAAG TGTTTTTCTA GGCAATTAAT CTTTTAGTCA TTGGTGTTTG  4380
                                 . A  I  L    R  K  T    M  P  T  Q

GTAGTTGAGA CTACCATGAA TGCGGTGGTA ATTCCACCAA TGAACATAGT CTTTAGTCTT  4440
 Y  N  L    S  G  H    I  R  H  Y    N  W  W    H  V  Y    D  K  T  K

AAGAGCTAGT TCTTCCAGCA ATTGAAAGGT TTCTTGATAA ACAAATTCAA TTTTGAAAGC  4500
 L  A  L    E  E  L    Q  F  T    E  Q  Y    V  F  E    I  K  F  A

ACGATACGTA CTTTCAGCTA CGGCATTGTC ATAAGGATAA CCAGCCTGAC TAAGCGAACG  4560
 R  Y  T    S  E  A    V  A  N  D    Y  P  Y    G  A  Q    S  L  S  R

TGTGATTCCA AAGGCTTCCA ATATTTCATC AATTAACTGA TTATCAAACT CTTTGCCACG  4620
 T  I  G    F  A  E    L  I  E  D    I  L  Q    N  D  F    E  K  G  R

ATCTGAATGG AACATCTTGA CTTTGGTCAG GGCGTAAGGG ATGCTTTGTA TGGCTTGCTT  4680
 D  S  H    F  M  K    V  K  T  L    A  Y  P    I  S  Q    I  A  Q  K

AACGAGTTCA GCGGTCTTGT GCCAACCAAG AGACAGGCCG ATGATTTCAC GGTTGTATAG  4740
 V  L  E    A  T  K    H  W  G  L    S  L  G    I  I  E    R  N  Y  L

GTCAATGATG AGGCAAACAT AAGCCCAACG ATTGCCTACA CGAACATAGG TTAAGTCAGT  4800
 D  I  I    L  C  V    Y  A  W  R    N  G  V    R  V  Y    T  L  D  T

GACTAAGGCT TGTAGTGGTC TTTCTTGCTT AAATTGCCTG TCTAAGTGG TGGGAATAGG   4860
 V  L  A    Q  L  P    R  E  Q  K    F  Q  R    D  L  H    N  P  I  P

GGCTTCATTC TTGCCTCTAG AATGTGGTTT GAAGGTGGCT TTCTGATAAA CAGAAACCAA  4920
 A  E  N    K  G  R    S  H  P  K    F  T  A    K  Q  Y    V  S  V  L

ATTGAGTCGC TTCATAATGC GTCGAATCCG ACGACGTGAA AGTGTGATAC CTTCGTTATT  4980
 N  L  R    K  M  I    R  R  I  R    R  R  S    L  T  I    G  E  N  N

CAAGCATATT TTGATTTTTC TGGATCCGTA TCTAGACTCG CTATCGAGAA AAATTCTTTT  5040
 L  C  I    K  I  K    R  S  G  Y    R  S  E    S  D  L    F  I  R  K
```

*FIG. 3a (4)*

```
AATAGTTTCT TCAAACTCCG TTTCAGATAC TGACTCCACG GCTTGATAGT AATAACTTGA    5100
  I  T  E   E  F  E    T  E  S  V   S  E  V    A  Q  Y    Y  Y  S  S

GTGTGGCATA TTCAGCCAGC GACACATCTT TGAAATGCTG TATTTATCCT TATTAGCAGT    5160
 H  P  M    N  L  W    R  C  M    K  S  I  S   Y  K  D    K  N  A  T

GATTATTTCC CTTTTTGTGC CATAATCACC GCTGCTTGCT TTAGGATATC TAATT         5215
  I  I  E   R  K  T    G  Y  D  G   S  S  A    K  P  Y    R  I
(SEQ ID NO:13)                                          <----|
```

FIG. 3a (5)

```
FGSALSTVEV KEIISEENIW LYRLSCCHFT SYSYWKLPTW                           40
(SEQ ID NO:14)
```

FIG. 3b

```
MGLATKDNQI AYIDDSKGKA KAPKTNKTMD QISAEEGISA EQIVVKITDQ                50
GYVTSHGDHY HFYNGKVPYD AIISEELLMT DPNYRFKQSD VINEILDGYV               100
IKVNGNYYVY LKPGSKRKNI RTKQQIAEQV AKGTKEAKEK GLAQVAHLSK               150
EEVAAVNEAK RQGRYTTDDG YIFSPTDIID DLGDAYLVPH GNHYHYIPKK               200
DLSPSELAAA QAYWSQKQGR GARPSDYRPT PAPGRRKAPI PDVTPNPGQG               250
HQPDNGGYHP APPRPNDASQ NKHQRDEFKG KTFKELLDQL HRLDLKYRHV               300
EEDGLIFEPT QVIKSNAFGY VVPHGDHYHI IPRSQLSPLE MELADRYLAG               350
QTEDNDSGSE HSKPSDKEVT HTFLGHRIKA YGKGLDGKPY DTSDAYVFSK               400
ESIHSVDKSG VTAKHGDHFH YIGFGELEQY ELDEVANWVK AKGQADELAA               450
ALDQEQGKEK PLFDTKKVSR KVTKDGKVGY MMPKDGKDYF YARDQLDLTQ               500
IAFAEQELML KDKKHYRYDI VDTGIEPRLA VDVSSLPMHA GNATYDTGSS               550
FVIPHIDHIH VVPYSWLTRD QIATVKYVMQ HPEVRPDVWS KPGHEESGSV               600
IPNVTPLDKR AGMPNWQIIH SAEEVQKALA EGRFATPDGY IFDPRDVLAK               650
ETFVWKDGSF SIPRADGSSL RTINKSDLSQ AEWQQAQELL AKKNTGDATD               700
TDKPKEKQQA DKSNENQQPS EASKEEKESD DFIDSLPDYG LDRATLEDHI               750
NQLAQKANID PKYLIFQPEG VQFYNKNGEL VTYDIKTLQQ INP                      793
(SEQ ID NO:15)
```

FIG. 3c

```
MTDPNYRFKQ  SDVINEILDG  YVIKVNGNYY  VYLKPGSKRK  NIRTKQQIAE   50
QVAKGTKEAK  EKGLAQVAHL  SKEEVAAVNE  AKRQGRYTTD  DGYIFSPTDI  100
IDDLGDAYLV  PHGNHYHYIP  KKDLSPSELA  AAQAYWSQKQ  GRGARPSDYR  150
PTPAPGRRKA  PIPDVTPNPG  QGHQPDNGGY  HPAPPRPNDA  SQNKHQRDEF  200
KGKTFKELLD  QLHRLDLKYR  HVEEDGLIFE  PTQVIKSNAF  GYVVPHGDHY  250
HIIPRSQLSP  LEMELADRYL  AGQTEDNDSG  SEHSKPSDKE  VTHTFLGHRI  300
KAYGKGLDGK  PYDTSDAYVF  SKESIHSVDK  SGVTAKHGDH  FHYIGFGELE  350
QYELDEVANW  VKAKGQADEL  AAALDQEQGK  EKPLFDTKKV  SRKVTKDGKV  400
GYMMPKDGKD  YFYARDQLDL  TQIAFAEQEL  MLKDKKHYRY  DIVDTGIEPR  450
LAVDVSSLPM  HAGNATYDTG  SSFVIPHIDH  IHVVPYSWLT  RDQIATVKYV  500
MQHPEVRPDV  WSKPGHEESG  SVIPNVTPLD  KRAGMPNWQI  IHSAEEVQKA  550
LAEGRFATPD  GYIFDPRDVL  AKETFVWKDG  SFSIPRADGS  SLRTINKSDL  600
SQAEWQQAQE  LLAKKNTGDA  TDTDKPKEKQ  QADKSNENQQ  PSEASKEEKE  650
SDDFIDSLPD  YGLDRATLED  HINQLAQKAN  IDPKYLIFQP  EGVQFYNKNG  700
ELVTYDIKTL  QQINP       (SEQ ID NO:16)                     715
```

FIG. 3d

```
MHSFSNPGYP  YDNAVTEAFF  KYLKHRQINR  KHYQNIKQVQ  LDCFEYIENF   50
YNNYNPHTAN  LGLTPNQKEE  NYFNAIK    (SEQ ID NO:17)           77
```

FIG. 3e

```
MAYYQACTEK  DIIRSMSRKG  TPADNACIEW  FHTVLKTETF  YFHNRRKYNK   50
DSITNIVKNY  ITFYNETRIQ  QRLNDQSPVQ  YRKLIA    (SEQ ID NO:18) 86
```

FIG. 3f

```
MENHFIYGYR  TITRLLKKIH  GLTVNTKKVY  RIMKNNGWLC  RTRTKKVPNL   50
GKAYYLTDNK  LSRDFHADKP  KEKLVTDITY  LYFGNCKLYL  SSIMNLYNRE  100
IIAYTISDCQ  DTDFVLDTLN  QLKLPK    (SEQ ID NO:19)            126
```

FIG. 3g

MVKKAYSWET KLACIDMKKA GKSNRVIMET LGIKNNSQIY TWMKWYENEE  50
LYRFHQGVGK QYTYGKGLEH LSEVEQLQLQ VDLLKKYRGL IRKSIK      96
(SEQ ID NO:20)

*FIG. 3h*

IRYPKASSGD YGTKREIITA NKDKYSISKM CRWLNMPHSS YYYQAVESVS  50
ETEFEETIKR IFLDSESRYG SRKIKICLNN EGITLSRRRI RRIMKRLNLV 100
SVYQKATFKP HSRGKNEAPI PNHLDRQFKQ ERPLQALVTD LTYVRVGNRW 150
AYVCLIIDLY NREIIGLSLG WHKTAELVKQ AIQSIPYALT KVKMFHSDRG 200
KEFDNQLIDE ILEAFGITRS LSQAGYPYDN AVAESTYRAF KIEFVYQETF 250
QLLEELALKT KDYVHWWNYH RIHGSLNYQT PMTKRLIA (SEQ ID NO:21)288

*FIG. 3i*

```
AATTTGAAAG CAGAATTATC TGTAGAAGAT GAGCAATATA CAGCAACAGT TTATGGTAAA   60
 N  L  K  A  E  L  S  V  E  D  E  Q  Y  T  A  T  V  Y  G  K
---->
TCTGCTCATG GTTCAACACC ACAAGAAGGT GTTAATGGGG CGACTTATTT AGCTCTTTAT  120
 S  A  H  G  S  T  P  Q  E  G  V  N  G  A  T  Y  L  A  L  Y
CTAAGTCAAT TTGATTTTGA AGGTCCTGCT CGTGCTTTCT TAGATGTTAC AGCCAACATT  180
 L  S  Q  F  D  F  E  G  P  A  R  A  F  L  D  V  T  A  N  I
ATTCACGAAG ACTTCTCAGG TGAAAAACTT GGAGTAGCTT ATGAAGATGA CTGTATGGGA  240
 I  H  E  D  F  S  G  E  K  L  G  V  A  Y  E  D  D  C  M  G
CCATTGAGCA TGAATGCAGG TGTCTTCCAG TTTGATGAAA CTAATGATGA TAATACTATC  300
 P  L  S  M  N  A  G  V  F  Q  F  D  E  T  N  D  D  N  T  I
GCTCTTAATT TCCGTTACCC ACAAGGGACA GATGCTAAAA CTATCCAAAC TAAGCTTGAG  360
 A  L  N  F  R  Y  P  Q  G  T  D  A  K  T  I  Q  T  K  L  E
AAACTTAACG GAGTTGAAAA AGTGACTCTT TCTGACCATG AACACACACC ACACTATGTA  420
 K  L  N  G  V  E  K  V  T  L  S  D  H  E  H  T  P  H  Y  V
CCTATGGACG ATGAATTAGT ATCAACCTTA CTAGCTGTCT ATGAAAAGCA AACTGGTCTT  480
 P  M  D  D  E  L  V  S  T  L  L  A  V  Y  E  K  Q  T  G  L
AAAGGACATG AACAGGTTAT TGGTGGTGGG ACATTTGGTC GCTTACTTGA ACGGGGTGTT  540
 K  G  H  E  Q  V  I  G  G  G  T  F  G  R  L  L  E  R  G  V
GCATACGGTG CCATGTTCCC AGGAGATGAA AACACTATGC ATCAAGCTAA TGAGTACATG  600
 A  Y  G  A  M  F  P  G  D  E  N  T  M  H  Q  A  N  E  Y  M
CCTTTAGAAA ATATTTTCCG TTCGGCTGCT ATCTACGCAG AAGCTATCTA TGAATTAATC  660
```

AAATAAAATA ATCCTTAAAC TAAATATGTG ATCAATGATA AAGGGTGGTG AAGACATGAA      720
 K  .

AGTGTCTTTG CCTCTTTTCA TAAGGTTAGA TTTGGAGACT TTATGACTGA CTTGGAAAAA      780
                                               M   T   D       L   E   K
                                               |---->

ATTATTAAAG CAATAAAAAG TGATTCACAG AATCAAAATT ATACAGAAAA TGGTATTGAT      840
 I   I   K       I   K   S       D   S   Q       N   Q   N   Y       T   E   N       G   I   D

CCTTTGTTTG CTGCTCCTAA AACAGCTAGG ATCAATATTG TTGGCCAAGC ACCTGGTTTA      900
 P   L   F   A       A   P   K       T   A   R       I   N   I   V       G   Q   A       P   G   L

AAAACTCAAG AAGCAAGACT CTATTGGAAA GATAAATCTG GAGATCGTCT ACGCCAGTGG      960
 K   T   Q   E       A   R   L       Y   W   K       D   K   S       G   D   R   L       R   Q   W

CTTGGAGTTG ATGAAGAGAC ATTTTACCAT TCTGGAAAAT TTGCTGTTTT ACCTTTAGAT      1020
 L   G   V   D       E   E   T       F   Y   H       S   G   K   F       A   V   L       P   L   D

TTTTATTACC CAGGCAAAGG AAAATCAGGA GATTTACCCC CTAGAAAAGG TTTTGCGGAG      1080
 F   Y   Y   P       G   K   G       K   S   G       D   L   P   P       R   K   G       F   A   E

AAATGGCACC CTCTTATTTT AAAAGAAATG CCTAATGTTC AATTGACCTT GCTAGTTGGT      1140
 K   W   H   P       L   I   L       K   E   M       P   N   V   Q       L   T   L       L   V   G

CAGTATGCTC AGAAATATTA TCTTGGAAGC TCCGCACATA AAAATCTAAC AGAAACAGTT      1200
 Q   Y   A   Q       K   Y   Y       L   G   S       S   A   H   K       N   L   T       E   T   V

AAAGCTTACA AAGACTATCT ACCCGATTAT TTACCCCTGG TTCACCCATC ACCGCGAAAT      1260
 K   A   Y   K       D   Y   L       P   D   Y       L   P   L   V       H   P   S       P   R   N

CAAATTTGGC TAAAGAAGAA TCCATGGTTT GAAAAAGATC TAATCGTTGA TTTACAAAAG      1320
 Q   I   W   L       K   K   N       P   W   F       E   K   D       L   I   V   D       L   Q   K

ATAGTAGCAG ATATTTTAAA AGATTAAGGA TAGGAGTTGG TATGAGAGAT AATCATCTAC      1380
 I   V   A   D       I   L   K       D   .                               M   R   D       N   H   L   H
                                                                          |---->

ACACGTATTT TTCCTATGAT TGTCAAACGG CATTTGAGGA CTATATTAAT GGTTTTACAG      1440
  T   Y   F       S   Y   D       C   Q   T   A       F   E   D       Y   I   N       G   F   T   G

GTGAATTTAT CACGACAGAA CATTTTGATT TATCAAATCC TTACACCGGT CAAGACGATG      1500
  E   F   I       T   T   E       H   F   D   L       S   N   P       Y   T   G       Q   D   D   V

TTCCTGATTA TAGTGCTTAT TGTCAAAAAA TAGATTATCT TAATCAGAAA TATGGAAATC      1560
  P   D   Y       S   A   Y       C   Q   K   I       D   Y   L       N   Q   K       Y   G   N   R

GATTTAAAAA AGGAATTGAA ATCGGTTATT TTAAAGATAG GGAATCAGAT ATTTTAGATT      1620
  F   K   K       G   I   E       I   G   Y   F       K   D   R       E   S   D       I   L   D   Y

ATTTAAAAAA TAAAGAATTT GATTTAAAAC TATTGTCAAT CCATCATAAT GGTAGGTATG      1680
  L   K   N       K   E   F       D   L   K   L       L   S   I       H   H   N       G   R   Y   D

ATTATCTGCA AGAAGAAGCT CTGAAAGTAC AACAAAGGG AGCTTTTAGC AGATTACTTT      1740
  Y   L   Q       E   E   A       L   K   V   P       T   K   G       A   F   S       R   L   L   .

AATCGTATGG AATTTGCCAT AGGCCGTGTG GAAGCGCACG TTTTAGCTCA CTTTGATTAT      1800

GGTTTTCGTA AGTTAAACTT AGATGTAGAA GATTTAAAAC CGTTTGAAAC GCAATTGAAG      1860

CGCATTTTCA TAAAGATGTT ATCTAAGGGG TTAGCTTTTG AACTAAATAC CAAATCCCTT      1920
```

*FIG. 4a (2)*

```
TATCTATATG GGAATGAAAA ACTTTATCGC TATGCTTTAG AGATACTCAA ACAGCTTGGT  1980

TGTAAACAAT ACTCTATAGG CTCTGACGGT CATATTCCTG AACATTTTTG TTATGAATTT  2040

GATAGACTTC AAGGTCTGCT AAAGGACTAT CAAATTGATG AAAATCATTT GATATGAGGA  2100

AATTTTTGAT AAAAAAGCTA GGCAATATTG CTTAGCTTTT TTGTAATGCT ATTGATAGTT  2160

TTAGTGAAAA TTTCAAAAAA ATAAAGAAAT CATTTACTTG TTGCAAGCGC TTGCGTAAAT  2220

TGTTATGATT TTATTGGTAA CAATTCATTA AAAAAGGAGA ATGATATGAA AGAAAAAGAC  2280
                                                    M  K  R  K  D
                                                    |----->
TTATTTGGTG ATAAACAAAC TCAATACACG ATTAGAAAGT TAAGTGTTGG AGTAGCTTCA  2340
L  F  G  D  K  Q  T  Q  Y  T  I  R  K  L  S  V  G  V  A  S

GTTACAACAG GGTATGTAT TTTTCTTCAT AGTCCACAGG TATTTGCTGA AGAAGTAAGT  2400
V  T  T  G  V  C  I  F  L  H  S  P  Q  V  F  A  E  E  V  S

GTTTCTCCTG CAACTACAGC GATTGCAGAG TCGAATATTA ATCAGGTTGA CAACCAACAA  2460
V  S  P  A  T  T  A  I  A  E  S  N  I  N  Q  V  D  N  Q  Q

TCTACTAATT TAAAAGATGA CATAAACTCA AACTCTGAGA CGGTTGTGAC ACCCTCAGAT  2520
S  T  N  L  K  D  D  I  N  S  N  S  E  T  V  V  T  P  S  D

ATGCCGGATA CCAAGCAATT AGTATCAGAT GAAACTGACA CTCAAAAGGG AGTGACAGAG  2580
M  P  D  T  K  Q  L  V  S  D  E  T  D  T  Q  K  G  V  T  E

CCGGATAAGG CGACAAGCCT GCTTGAAGAA AATAAAGGTC CTGTTTCAGA TAAAAATACC  2640
P  D  K  A  T  S  L  L  E  E  N  K  G  P  V  S  D  K  N  T

TTAGATTTAA AAGTAGCACC ATCTACATTG CAAAATACTC CCGACAAAAC TTCTCAAGCT  2700
L  D  L  K  V  A  P  S  T  L  Q  N  T  P  D  K  T  S  Q  A

ATAGGTGCTC CAAGCCCTAC CTTGAAAGTA GCTAATCAAG CTCCACGGAT TGAAAATGGT  2760
I  G  A  P  S  P  T  L  K  V  A  N  Q  A  P  R  I  E  N  G

TACTTTAGGC TACATCTTAA AGAATTGCCT CAAGGTCATC CTGTAGAAAG CACTGGACTT  2820
Y  F  R  L  H  L  K  E  L  P  Q  G  H  P  V  E  S  T  G  L

TGGATATGGG GAGATGTTGA TCAACCGTCT AGTAATTGGC CAAATGGTGC TATCCCTATG  2880
W  I  W  G  D  V  D  Q  P  S  S  N  W  P  N  G  A  I  P  M

ACTGATGCTA AGAAAGATGA TTACGGTTAT TATGTTGATT TTAAATTATC TGAAAAACAA  2940
T  D  A  K  K  D  D  Y  G  Y  Y  V  D  F  K  L  S  E  K  Q

CGAAAACAAA TATCTTTTTT AATTAATAAC AAAGCAGGGA CAAATTTAAG CGGCGATCAT  3000
R  K  Q  I  S  F  L  I  N  N  K  A  G  T  N  L  S  G  D  H

CATATTCCAT TATTACGACC TGAGATGAAC CAAGTTTGGA TTGATGAAAA GTACGGTATA  3060
H  I  P  L  L  R  P  E  M  N  Q  V  W  I  D  E  K  Y  G  I

CATACTTATC AACCCCTCAA AGAAGGGTAT GTCCGTATTA ACTATTTGAG TTCCTCTAGT  3120
H  T  Y  Q  P  L  K  E  G  Y  V  R  I  N  Y  L  S  S  S

AACTATGACC ACTTATCAGC ATGGCTCTTT AAAGATGTTG CAACCCCYTC AACAACTTGG  3180
N  Y  D  H  L  S  A  W  L  F  K  D  V  A  T  P  S  T  T  W

CCAGATGGTA GTAATTTTGT GAATCAAGGA CTATATGGAA GGTATATTGA TGTATCACTA  3240
P  D  G  S  N  F  V  N  Q  G  L  Y  G  R  Y  I  D  V  S  L
```

*FIG. 4a (3)*

```
AAAACTAACG CCAAAGAGAT TGGTTTTCTA ATCTTAGATG AAAGTAAGAC AGGAGATGCA   3300
 K  T  N  A   K  E  I   G  F  L    I  L  D  E   S  K  T   G  D  A

GTGAAAGTTC AACCCAACGA CTATGTTTTT AGAGATTTAG CTAACCATAA CCAAATTTTT   3360
 V  K  V  Q   P  N  D   Y  V  F   R  D  L  A   N  H  N   Q  I  F

GTAAAAGATA AGGATCCAAA GGTTTATAAT AATCCTTATT ACATTGATCA AGTGCAGCTA   3420
 V  K  D  K   D  P  K   V  Y  N   N  P  Y  Y   I  D  Q   V  Q  L

AAGGATGCCC AACAAATTGA TTTAACAAGT ATTCAAGCAA GTTTTACAAC TCTAGATGGG   3480
 K  D  A  Q   Q  I  D   L  T  S   I  Q  A  S   F  T  T   L  D  G

GTAGATAAAA CTGAAATTTT AAAAGAATTG AAAGTGACTG ATAAAAATCA AAATGCTATA   3540
 V  D  K  T   E  I  L   K  E  L   K  V  T  D   K  N  Q   N  A  I

CAAATTTCTG ATATCACTCT CGATACTAGT AAATCTCTTT TAATAATCAA AGGCGACTTT   3600
 Q  I  S  D   I  T  L   D  T  S   K  S  L  L   I  I  K   G  D  F

AATCCTAAAC AAGGTCATTT CAACATATCT TATAATGGTA ACAATGTCAT GACAAGGCAA   3660
 N  P  K  Q   G  H  F   N  I  S   Y  N  G  N   N  V  M   T  R  Q

TCTTGGGAAT TTAAAGACCA ACTTTATGCT TATAGTGGAA ATTTAGGTGC AGTTCTCAAT   3720
 S  W  E  F   K  D  Q   L  Y  A   Y  S  G  N   L  G  A   V  L  N

CAAGATGGTT CAAAAGTTGA AGCCAGCCTC TGGTCACCGA GTGCTGATAG TGTCACTATG   3780
 Q  D  G  S   K  V  E   A  S  L   W  S  P  S   A  D  S   V  T  M

ATTATTTATG ACAAAGATAA CCAAAACAGG GTTGTAGCGA CTACCCCCCT TGTGAAAAAT   3840
 I  I  Y  D   K  D  N   Q  N  R   V  V  A  T   T  P  L   V  K  N

AATAAAGGTG TTTGGCAGAC GATACTTGAT ACTAAATTAG GTATTAAAAA CTATACTGGT   3900
 N  K  G  V   W  Q  T   I  L  D   T  K  L  G   I  K  N   Y  T  G

TACTATTATC TTTACGAAAT AAAAAGAGGT AAGGATAAGG TTAAGATTTT AGATCCTTAT   3960
 Y  Y  Y  L   Y  E  I   K  R  G   K  D  K  V   K  I  L   D  P  Y

GCAAAGTCAT TAGCAGAGTG GGATAGTAAT ACTGTTAATG ATGATATTAA AACGGCTAAA   4020
 A  K  S  L   A  E  W   D  S  N   T  V  N  D   D  I  K   T  A  K

GCAGCTTTTG TAAATCCAAG TCAACTTGGA CCTCAAAATT TAAGTTTTGC TAAAATTGCT   4080
 A  A  F  V   N  P  S   Q  L  G   P  Q  N  L   S  F  A   K  I  A

AATTTTAAAG GAAGACAAGA TGCTGTTATA TACGAAGCAC ATGTAAGAGA CTTCACTTCT   4140
 N  F  K  G   R  Q  D   A  V  I   Y  E  A  H   V  R  D   F  T  S

GATCGATCTT TGGATGGAAA ATTAAAAAAT CAATTTGGTA CCTTTGCAGC CTTTTCAGAG   4200
 D  R  S  L   D  G  K   L  K  N   Q  F  G  T   F  A  A   F  S  E

AAACTAGATT ATTTACAAAA ATTAGGAGTT ACACACATTC AGCTTTTACC GGTATTGAGT   4260
 K  L  D  Y   L  Q  K   L  G  V   T  H  I  Q   L  L  P   V  L  S

TATTTTTATG TTAATGAAAT GGATAAGTCA CGCTCAACAG CTTACACTTC CTCAGACAAT   4320
 Y  F  Y  V   N  E  M   D  K  S   R  S  T  A   Y  T  S   S  D  N

AATTACAATT GGGGCTATGA CCCACAGAGC TATTTTGCTC TTTCTGGGAT GTATTCAGAG   4380
 N  Y  N  W   G  Y  D   P  Q  S   Y  F  A  L   S  G  M   Y  S  E

AAACCAAAAG ATCCATCAGC ACGTATCGCC GAATTAAAAC AATTAATACA TGATATTCAT   4440
 K  P  K  D   P  S  A   R  I  A   E  L  K  Q   L  I  H   D  I  H
```

*FIG. 4a (4)*

```
AAACGTGGCA TGGGGGTTAT ACTTGATGTC GTCTATAATC ACACTGCAAA AACTTATCTC   4500
 K  R  G  M  G  V  I   L  D  V    V  Y  N  H   T  A  K    T  Y  L

TTTGAGGATA TAGAACCTAA TTATTATCAC TTTATGAATG AAGATGGTTC ACCAAGAGAA   4560
 F  E  D  I  E  P  N   Y  Y  H    F  M  N  E   D  G  S    P  R  E

AGTTTTGGAG GGGGACGTTT AGGAACCACT CATGCAATGA GTCGTCGTGT TTTGGTTGAT   4620
 S  F  G  G  G  R  L   G  T  T    H  A  M  S   R  R  V    L  V  D

TCCATTAAAT ATCTTACAAG TGAATTTAAA GTTGATGGTT TCCGTTTTGA TATGATGGGA   4680
 S  I  K  Y  L  T  S   E  F  K    V  D  G  F   R  F  D    M  M  G

GATCATGATG CGGCTGCGAT TGAATTAGCT TATAAAGAAG CTAAAGCTAT TAATCCTAAT   4740
 D  H  D  A  A  A  I   E  L  A    Y  K  E  A   K  A  I    N  P  N

ATGATTATGA TTGGTGAGGG CTGGAGAACA TTCCAAGGCG ATCAAGGTCA GCCGGTTAAA   4800
 M  I  M  I  G  E  G   W  R  T    F  Q  G  D   Q  G  Q    P  V  K

CCAGCTGACC AAGATTGGAT GAAGTCAACC GATACAGTTG GCGTCTTTTC AGATGATATT   4860
 P  A  D  Q  D  W  M   K  S  T    D  T  V  G   V  F  S    D  D  I

CGTAATAGCT TGAAATCTGG TTTTCCAAAT GAAGGTACTC CAGCTTTCAT CACAGGTGGC   4920
 R  N  S  L  K  S  G   F  P  N    E  G  T  P   A  F  I    T  G  G

CCACAATCTT TACAAGGTAT TTTTAAAAAT ATCAAAGCAC AACCTGGGAA TTTTGAAGCA   4980
 P  Q  S  L  Q  G  I   F  K  N    I  K  A  Q   P  G  N    F  E  A

GATTCGCCAG GAGATGTGGT GCAGTATATT GCTGCACATG ATAACCTTAC CTTGCATGAT   5040
 D  S  P  G  D  V  V   Q  Y  I    A  A  H  D   N  L  T    L  H  D

GTGATTGCAA AATCAATT       (SEQ ID NO:22)                           5058
 V  I  A  K  S  I .
```

*FIG. 4a (5)*

```
NLKAELSVED EQYTATVYGK SAHGSTPQEG VNGATYLALY LSQFDFEGPA    50
RAFLDVTANI IHEDFSGEKL GVAYEDDCMG PLSMNAGVFQ FDETNDDNTI   100
ALNFRYPQGT DAKTIQTKLE KLNGVEKVTL SDHEHTPHYV PMDDELVSTL   150
LAVYEKQTGL KGHEQVIGGG TFGRLLERGV AYGAMFPGDE NTMHQANEYM   200
PLENIFRSAA IYAEAIYELI K    (SEQ ID NO:23)                221
```

*FIG. 4b*

```
MTDLEKIIKA IKSDSQNQNY TENGIDPLFA APKTARINIV GQAPGLKTQE    50
ARLYWKDKSG DRLRQWLGVD EETFYHSGKF AVLPLDFYYP GKGKSGDLPP   100
RKGFAEKWHP LILKEMPNVQ LTLLVGQYAQ KYYLGSSAHK NLTETVKAYK   150
DYLPDYLPLV HPSPRNQIWL KKNPWFEKDL IVDLQKIVAD ILKD         194
(SEQ ID NO:24)
```

*FIG. 4c*

```
MRDNHLHTYF  SYDCQTAFED  YINGFTGEFI  TTEHFDLSNP  YTGQDDVPDY   50
SAYCQKIDYL  NQKYGNRFKK  GIEIGYFKDR  ESDILDYLKN  KEFDLKLLSI  100
HHNGRYDYLQ  EEALKVPTKG  AFSRLL  (SEQ ID NO:25)              126
```

*FIG. 4d*

```
MKRKDLFGDK  QTQYTIRKLS  VGVASVTTGV  CIFLHSPQVF  AEEVSVSPAT   50
TAIAESNINQ  VDNQQSTNLK  DDINSNSETV  VTPSDMPDTK  QLVSDETDTQ  100
KGVTEPDKAT  SLLEENKGPV  SDKNTLDLKV  APSTLQNTPD  KTSQAIGAPS  150
PTLKVANQAP  RIENGYFRLH  LKELPQGHPV  ESTGLWIWGD  VDQPSSNWPN  200
GAIPMTDAKK  DDYGYYVDFK  LSEKQRKQIS  FLINNKAGTN  LSGDHHIPLL  250
RPEMNQVWID  EKYGIHTYQP  LKEGYVRINY  LSSSSNYDHL  SAWLFKDVAT  300
PSTTWPDGSN  FVNQGLYGRY  IDVSLKTNAK  EIGFLILDES  KTGDAVKVQP  350
NDYVFRDLAN  HNQIFVKDKD  PKVYNNPYYI  DQVQLKDAQQ  IDLTSIQASF  400
TTLDGVDKTE  ILKELKVTDK  NQNAIQISDI  TLDTSKSLLI  IKGDFNPKQG  450
HFNISYNGNN  VMTRQSWEFK  DQLYAYSGNL  GAVLNQDGSK  VEASLWSPSA  500
DSVTMIIYDK  DNQNRVVATT  PLVKNNKGVW  QTILDTKLGI  KNYTGYYYLY  550
EIKRGKDKVK  ILDPYAKSLA  EWDSNTVNDD  IKTAKAAFVN  PSQLGPQNLS  600
FAKIANFKGR  QDAVIYEAHV  RDFTSDRSLD  GKLKNQFGTF  AAFSEKLDYL  650
QKLGVTHIQL  LPVLSYFYVN  EMDKSRSTAY  TSSDNNYNWG  YDPQSYFALS  700
GMYSEKPKDP  SARIAELKQL  IHDIHKRGMG  VILDVVYNHT  AKTYLFEDIE  750
PNYYHFMNED  GSPRESFGGG  RLGTTHAMSR  RVLVDSIKYL  TSEFKVDGFR  800
FDMMGDHDAA  AIELAYKEAK  AINPNMIMIG  EGWRTFQGDQ  GQPVKPADQD  850
WMKSTDTVGV  FSDDIRNSLK  SGFPNEGTPA  FITGGPQSLQ  GIFKNIKAQP  900
GNFEADSPGD  VVQYIAAHDN  LTLHDVIAKS  I  (SEQ ID NO:26)      931
```

*FIG. 4e*

```
AATTCAAAGT TTGACAGAAG GTCAACTTCG TTCTGATATC CCTGAGTTCC GTGCTGGTGA    60
 I  Q  S    L  T  E  G   Q  L  R    S  D  I    P  E  F  R   A  G  D
 ---->
TACTGTACGT GTTCACGCTA AAGTTGTTGA AGGTACTCGC GAACGTATTC AGATCTTTGA   120
 T  V  R   V  H  A  K   V  V  E    G  T  R   E  R  I    Q  I  F  E
AGGTGTTGTT ATCTCACGTA AAGGTCAAGG AATCTCAGAA ATGTACACAG TACGTAAAAT   180
 G  V  V    I  S  R  K   G  Q  G    I  S  E   M  Y  T  V   R  K  I
TTCTGGTGGT ATCGGTGTAG AGCGTACATT CCCAATTCAC ACTCCTCGTG TTGATAAAAT   240
 S  G  G    I  G  V  E   R  T  F    P  I  H    T  P  R  V   D  K  I
CGAAGTTGTT CGTTATGGTA AAGTACGTCG TGCTAAACTT TACTACTTAC GCGCATTGCA   300
 E  V  V    R  Y  G  K   V  R  R    A  K  L    Y  Y  L  R   A  L  Q
AGGTAAAGCT GCACGTATTA AAGAAATCCG TCGTTAATTT TGATGATCAG ATTTTAAAAA   360
TGCTTGGTTG TTTGAGGATA GTAACTATGT TTTAAAACTG ACAACCAAG ACGTAAAAAA    420
TCTGCCTGTG GGCAGTTTTT TTACTAGGTC CCCTTAGTTC AATGGATATA ACAACTCCCT   480
                                                .  H  I  Y   C  S  G
CCTAAGGAGT AATTGCTGGT TCGATTCCGG CAGGGGACAT ATTCATTGCA TGTAAATAGC   540
 G  L  S    Y  N  S  T   R  N  R    C  P  V    Y  E  N  C   T  F  L
GGTTTAGAGC TATTTTGCCC CAAATTTCTC TGATTAAGTT TATCGTTCCT ATCTTTTGT    600
 P  K  S    S  N  Q  G   L  N  R    Q  N  L    K  D  N  R   D  K  Q
TCTTGTAATT GATGTGCGTA AACTTCTAAA GTGATATTTA AATTCTCGTG ATCTAAAACT   660
 E  Q  L    Q  H  A  Y   V  E  L    T  I  N    L  N  E  H   D  L  V
TGAGAGATGG AAATTAGATA GCTTGCAAAT GTATGCCTGA GAGAGTGCAC TCGTACCTCG   720
 Q  S  I    S  I  L  Y   S  A  F    T  H  R    L  S  H  V   R  V  E
CGACCAGTTA TTTTTCGGAT AGTTTTATTG ACTGCATTAT TTGAAAGTTT GTCGAATAAT   780
 R  G  T    I  K  R  I   T  K  N    V  A  N    N  S  L  K   D  F  L
CTGTCGTTTT TATTTTTTGT AAAATTCATGC AAAAAAAATA ATGTATCATT GTCAATTGGT   840
 R  D  N    K  N  K  T   F  E  H    L  F  F    L  T  D  N   D  I  P
ATATTTCTGA TACTACTTTT GTTTTTTGTT GGCAGGTATC TTTGGTTGAA ATGATAATCC   900
 I  N  R    I  S  S  K   N  K  T    P  L  Y    R  Q  N  F   H  Y  D
CAAGTTTTAT TAATTGATAA ATATTTGTTA GTGTAATCAA TATCATTAAC TGTTAAACCT   960
 W  T  K    N  I  S  L   Y  K  N    T  Y  D    I  D  N  V   T  L  G
AAACATTCAG CGAAGCGCAT GCCAGTTTTA GCGATGAGGT ATAACGCTGC ATACGATTGA   1020
 L  C  E    A  F  R  M
            <----|
TGTTGTGATT TTTCTTTACA AATTTTTATC AAGCGTAAGT ATTCATTGGT TTCAAGAAAT   1080
TTTATCTCTA TTTACGCCCC TTATTTTTTG CTTTAACCTT AGTGAATAAA CAAAAATTTT   1140
TTTCTATATA TCCCTCGTGA ACAGCCATGG ATACGCAGGC TTTTACATGT ATGTTAAAAC   1200
GCTTTACTGT ATCTTGCACA TGCGTTTGAC TATAATGATT TATGACTTGT TGATATTTAG   1260
```

*FIG. 5a (1)*

```
TGGAAGTAAT ATTGCAAAGT AATATATTTC CTATTATATG TTTATACGAT ATTCGATATT    1320
CCCACCCGTT GTCGCGTTTA CGGAAATACG CCATTGATAT ACTCCACATT AGCTAAAGAA    1380
CAGGGTGTTC AAGGCTACCT TGATGGAAAA GGCTCTCTTA GAGATATTTG TAAATGGTAT    1440
GATATCTCAA GTCGCTCTGT TCTCCAAAAG TGGATAAAAC GGTATACTAG TGGTGAAGAC    1500
TTGAAAGCCA CTAGTAGAGG ATATAGCCGT ATGAAACAAG GAAGGCAAGC CACATTTGAA    1560
GAACGTGTAG AGATTGTTAA CTACACCATT GCCCATGGGA AAGACTATCA AGCAGCTATT    1620
GAGAAGTTTG GTGTTTCCTA CCAACAAATT TATTCTTGGG TGCGTAAGCT TGAGAAGAAT    1680
GGCTCACAAG GTTTGGTTGA TAGACGTGTG AAAGGGTTGG AGAGTAGGCC TGATTTAACC    1740
GAGATTGAGC AACTTTAACT CAAGATTAAA CAATTGGAGG AACGTAATCG TCTCTTAGAA    1800
ATCGAGGTTA GTTTACTAAA AAAGTTAGAA GACATCAAAC GAGGAAACAG ACGGTAAGAC    1860
TAGGTAAGCA TTTAGCGGAG TTCCAAGTAA TCAAGAATTA TTACGATGAG GAATCTAATG    1920
TGCCTATTCA GGCCTTATGC CAACTCTTGA AGGGGTCTCG TTCAGGCTAT TACAAGTGGC    1980
TCAATCGTCA AAAAACAGAT TTTGAGACAA AAAATACAAA GCTAATGGCT AAAATCAAGG    2040
AACTTCGTAG ACTCTACAAT GGTATCTTAG GTTATCGCCG TATGACAACA TTTATTAATC    2100
GTCAACTTGG GACAACTTAA AACAAGAAAC GGATTCGTTG ATTGATGAAC ATTCTGGGGA    2160
TTAGTTCAGT CATTCGTCGT GTTAGCCATG CTTGTACAAA AGCTGGTGAC AGATTTTACG    2220
AAGAAAATAT TCTTAATCGT GAATTTACAG CCACAGCTCA TAACCAGAAA TGGTGCACAG    2280
ATGTCACCTA TCTTCAATAC GGTCTGGGAG CTAAAGCTTA TCTCAGTGCG ATTAAAGACC    2340
TGTATAACGG TTCTATTATC GCTTATGAGA TTAGTCACAA CAATGAAATC CACTTGTTAT    2400
GAAGACCATT AAAAAGGGGC TAGAGCTCAA TCCAGGAGCC ACACCTATCA TCCATAGCGA    2460
TTGAGGTAGT CAATATACTT CCAAAGAATA CCGTTATATC ATACAACAAG CTGGTCTGAC    2520
CTTATCCATG TCCCGGATTG GCAAATGTAT TGATAATGCA CCAACTGAAA GTTTCTTTGG    2580
GTTTTTCAAG ACTGAGTCTT ACCACCTTAA GAAATACAAC TCTTATGATG AGTTGGTCAA    2640
TGATGTGGCA CGTTATATCG AATTCTACAA CACACAACGT TATCAATCAA AATTAAACAA    2700
CCTGACTCCT CTAGAATTCA GGAATCAGGT TGCATAACTT ATCTTTTATT ATTTGACTGT    2760
CTACTTGACA GGGAGCCGTT CAGATTGCTT AACCTTTCTA AATTTGCTAA AATAGCTACA    2820
AGAAAACGAG CCATTTAATG CTTATTCTT ATACTGTCTT GCCTCACGCT CTCCTCGACC    2880
AAAAATTGAG CGTGAGGCTT TTGTTTCAT TAAACGATGA TATTTCCATA TTCATCAGTT    2940
TGTTTTCCGA GAGCCATCAA AGCTTCGATA AGGTCGATAA TTCCAGGAAT AAAGGTAATA    3000
CTAAAAATAA TATATAAAAA AACCTGGCCT ATTTTTCCTG CGTAAAATTT ATGCGCTCCA    3060
ATGCCGCCCA AAAGAACGTT AATAAAACAT AAACTACTAT GTTAGCATAA GACTTTATTT    3120
```

*FIG. 5a (2)*

```
TTACAACTGA ATTTCATATA AATGGATTAG AGTAAGGGAT AAAAGAAATT AGCATAGCTC   3180

TTTTGAAAAT AAAAAAATTA ATATAATATG GAAAAAATTT TATTTCATAA ACGTTTCATA   3240

AAAGGTATGT AATCTAGTAT TTAGGCAACA CTATTTTGTC ACTGGTGTCT AGTAACTTAT   3300

AGATTGATAA TTTTACTAGT AAACGTAATT CTTCGCTTTA AGAGTTAAAT GTCTATTTAT   3360

TGTAAGCTAA ATTGGGAGGT GAACTTATGT AAAATTAGAT AGGTACTGTC AAGTACGGGA   3420

TGATTATTGA AACAGCCAGT ATGCATCATA AAATCTGTAT TGCTTAATAA CTATTTCCTT   3480

AACCAGACAT CAGTTCATTG TTTATCATCG CTACCCTAAG TCTAGTTTTT TCAATAGAGC   3540

ATTAGGTAGT TTTTGATAAT AAAACTATAT AAACATGAGA ATTAGATTTC GTATTGCATT   3600

CTTCATAATG AGTTATTTGA GATTTTCCTT TGAATAAATA GATACGAAAT TCAGTAACTT   3660

CATATATAAA CGGCTCTATC ATTGAGATAG TTTGTCAAAT GAAGAAATTT TTAATGGAAA   3720

TAGTTTTAAA AACATTAGTT GTAGGCGATG TAAAAATATT AATCCAGTGG ATGCAATAGT   3780

TGCGGAGTAA AAATAGAGAG GAGTAATTAG GAAGTGATAA AAAATGCTAT AGCATATATT   3840

ACCAGAAAAA AAAATAGAAC ACTTATTATA TTTGCTATTT TAACAATTGT TCTTTCTTGC   3900

TTGTATTCAT GTTTAACAAT AATGAAATCA AGTAATGAAA TAGAAAAGGC TTTATATGAA   3960
                                    M  K  S   S  N  E    E  K  A   L  Y  E
                                    |---->

AGTTCTAATT CTTCAATATC AATTACAAAA AAAGATGGTA AATATTTTAA TATTAATCAA   4020
 S  S  N  S   S  I  S   I  T  K    K  D  G  K    Y  F  N    I  N  Q

TTTAAGAATA TTGAAAAAAT AAAAGAGGTT GAAGAAAAAA TATTTCAATA TGATGGATTA   4080
 F  K  N  I   I  E  K   I  K  E   V   E  E  K  I    F  Q  Y    D  G  L

GCAAAATTGA AAGATCTTAA AGTAGTTAGT GGTGAGCAAA GTATAAATAG AGAAGATTTA   4140
 A  K  L  K    D  L  K    V  V  S    G  E  Q  S    I  N  R    E  D  L

TCTGACGAAT TTAAAAATGT TGTTTCACTA GAAGCTACAA GTAATACTAA AAGAAATCTT   4200
 S  D  E  F   K  N  V    V  S  L    E  A  T  S    N  T  K  R    N  L

TTATTTAGTA GTGGAGTATT TAGTTTTAAA GAAGGAAAAA ATATAGAAGA AAATGATAAG   4260
 L  F  S  S    G  V  F    S  F  K    E  G  K    N  I  E  E    N  D  K

AATTCAATTC TTGTTCATGA AGAATTTGCT AAACAAAACA AACTAAAATT GGGTGATGAA   4320
 N  S  I  L    V  H  E    E  F  A    K  Q  N  K    L  K  L    G  D  E

ATTGATCTTG AATTACTAGA TACGGAAAAA AGTGGAAAAA TAAAAAGTCA TAAATTTAAA   4380
 I  D  L  E    L  L  D    T  E  K    S  G  K  I    K  S  H    K  F  K

ATTATAGGAA TCTTTTCTGG TAAAAAACAG GAAACATATA CAGGATTATC ATCTGATTTT   4440
 I  I  G  I    F  S  G    K  K  Q    E  T  Y  T    G  L  S    S  D  F

AGCGAAAATA TGGTTTTTGT AGATTATTCA ACTAGCCAAG AAATATTAAA TAAATCAGAG   4500
 S  E  N  M    V  F  V    D  Y  S    T  S  Q  E    I  L  N    K  S  E

AATAATAGAA TTGCAAATAA AATTTTAATG TATTCTGGTA GTTTAGAATC TACAGAGCTT   4560
 N  N  R  I    A  N  K    I  L  M    Y  S  G  S    L  E  S    T  E  L

GCCTTAAAACA AATTGAAAGA CTTTAAAATT GATAAGTCAA AGTATTCTAT TAAGAAAGAT   4620
```

*FIG. 5a (3)*

```
                A  L  N  K   L  K  D  F  K  I    D  K  S  K  Y    S  I  K  K  D
AATAAAGCAT TCGAAGAGTC TTTAGAGTCA GTGAGTGGAA TAAAACATAT AATTAAAATA  4680
 N  K  A  F   E  E  S  L  E  S    V  S  G  I  K    H  I  K  I

ATGACTTATT CGATTATGTT AGGTGGAATA GTTGTTCTTT CATTAATCTT GATTCTATGG  4740
 M  T  Y  S   I  M  L  G  G  I    V  V  L  S  L    I  L  I  L  W

TTAAGAGAAA GAATTATGA AATAGGTATA TTTTTATCTA TTGGAACAAC TAAGATACAA   4800
 L  R  E  R   I  Y  E  I  G  I    F  L  S  I  G    T  T  K  I  Q

ATTATAAGGC AATTTATATT TGAGTTAATA TTCATATCAA TACCAAGTAT AATATCCTCC  4860
 I  I  R  Q   F  I  F  E  L  I    F  I  S  I  P    S  I  I  S  S

TTATTTTTAG GGAATCTACT ATTAAAAGTA ATTGTAGAAG GATTTATTAA CTCAGAGAAC  4920
 L  F  L  G   N  L  L  L  K  V    I  V  E  G  F    I  N  S  E  N

TCAATGATTT TCGGTGGAAG TTTAATAAAT AAAAGCAGTT TTATGTTAAA CATAACAACA  4980
 S  M  I  F   G  G  S  L  I  N    K  S  S  F  M    L  N  I  T  T

CTTGCAGAAA GTTATTTAAT ATTAATAAGT ATTATTGTTT TATCAGTTGT AATGGCCTCT  5040
 L  A  E  S   Y  L  I  L  I  S    I  I  V  L  S    V  V  M  A  S

TCATTAATAT TATTTAAGAA ACCACAAGAA ATATTATCAA AAATAAGTTA GGAGCAAATA  5100
 S  L  I  L   F  K  K  P  Q  E    I  L  S  K  I    S  .

ATGGATATAT TAGAAATAAA GAATGTAAAT TACAGTTACG CAAATTCTAA AGAAAAAGTT  5160
 M  D  I  L   E  I  K  N  V  N    Y  S  Y  A  N    S  K  E  K  V
 |----->
TTGTCAGGAG TAAATCAAAA ATTTGAACTT GGAAAGTTTT ATGCGATAGT AGGGAAGTCA  5220
 L  S  G  V   N  Q  K  F  E  L    G  K  F  Y  A    I  V  G  K  S

GGAACAGGAA AATCCACACT TCTTTCCTTA CTTGCAGGAC TTGATAAAGT TCAAACAGGA  5280
 G  T  G  K   S  T  L  L  S  L    L  A  G  L  D    K  V  Q  T  G

AAAATCTTGT TTAAGAATGA AGATATAGAA AAGAAAGGAT ATAGTAATCA CAGAAAAAAT  5340
 K  I  L  F   K  N  E  D  I  E    K  K  G  Y  S    N  H  R  K  N

AATATATCTT TGGTATTTCA AAATTATAAT TTAATAGATT ATTTATCGCC GATTGAAAAT  5400
 N  I  S  L   V  F  Q  N  Y  N    L  I  D  Y  L    S  P  I  E  N

ATTAGACTAG TAAATAAATC AGTAGATGAG AGTATCTTGT TCGAATTAGG TTTAGATAAA  5460
 I  R  L  V   N  K  S  V  D  E    S  I  L  F  E    L  G  L  D  K

AAACAAATAA AAAGAAATGT TATGAAATTA TCTGGTGGTC AGCAACAAAG GGTAGCTATT  5520
 K  Q  I  K   R  N  V  M  K  L    S  G  G  Q  Q    Q  R  V  A  I

GCTAGGGCAC TGGTATCAGA TGCCCCAATA ATACTAGCTG ATGAGCCTAC CGGTAACCTA  5580
 A  R  A  L   V  S  D  A  P  I    I  L  A  D  E    P  T  G  N  L

GACAGTGTTA CTGCTGGAGA AATAATT    (SEQ ID NO:27)                   5607
 D  S  V  T   A  G  E  I  I  .
```

*FIG. 5a (4)*

```
IQSLTEGQLR  SDIPEFRAGD  TVRVHAKVVE  GTRERIQIFE  GVVISRKGQG    50
ISEMYTVRKI  SGGIGVERTF  PIHTPRVDKI  EVVRYGKVRR  AKLYYLRALQ   100
GKAARIKEIR  R    (SEQ ID NO:28)                              111
```

FIG. 5b

```
MRFAECLGLT  VNDIDYTNKY  LSINKTWDYH  FNQRYLPTKN  KSSIRNIPID    50
NDTLFFLHEF  TKNKNDRLFD  KLSNNAVNKT  IRKITGREVR  VHSLRHTFAS   100
YLISISQVLD  HENLNITLEV  YAHQLQEQKD  RNDKLNQRNL  GQNSSKPLFT   150
CNEYVPCRNR  TSNYSLGGSC  YIH    (SEQ ID NO:29)                173
```

FIG. 5c

```
MKSSNEIEKA  LYESSNSSIS  ITKKDGKYFN  INQFKNIEKI  KEVEEKIFQY    50
DGLAKLKDLK  VVSGEQSINR  EDLSDEFKNV  VSLEATSNTK  RNLLFSSGVF   100
SFKEGKNIEE  NDKNSILVHE  EFAKQNKLKL  GDEIDLELLD  TEKSGKIKSH   150
KFKIIGIFSG  KKQETYTGLS  SDFSENMVFV  DYSTSQEILN  KSENNRIANK   200
ILMYSGSLES  TELALNKLKD  FKIDKSKYSI  KKDNKAFEES  LESVSGIKHI   250
IKIMTYSIML  GGIVVLSLIL  ILWLRERIYE  IGIFLSIGTT  KIQIIRQFIF   300
ELIFISIPSI  ISSLFLGNLL  LKVIVEGFIN  SENSMIFGGS  LINKSSFMLN   350
ITTLAESYLI  LISIIVLSVV  MASSLILFKK  PQEILSKIS               389
(SEQ ID NO:30)
```

FIG. 5d

```
MDILEIKNVN  YSYANSKEKV  LSGVNQKFEL  GKFYAIVGKS  GTGKSTLLSL    50
LAGLDKVQTG  KILFKNEDIE  KKGYSNHRKN  NISLVFQNYN  LIDYLSPIEN   100
IRLVNKSVDE  SILFELGLDK  KQIKRNVMKL  SGGQQQRVAI  ARALVSDAPI   150
ILADEPTGNL  DSVTAGEII    (SEQ ID NO:31)                     169
```

FIG. 5e

| | | | | | | |
|---|---|---|---|---|---|---|
| CATATGACAA | TATTTTTCAA | AGTCTACATC | ACTTACTCGC | CTGTCGTGGA | AAATCTGGCA | 60 |
| ATACATTAAT | CGACCAATTA | GTTGCTGATG | GTTTACTTCA | TGCAGATAAT | CACTACCATT | 120 |
| TTTTCAATGG | GAAGTCTCTG | GCCACTTTCA | ATACTAACCA | ATTGATTCGC | GAAGTTGTCT | 180 |
| ATGTTGAAAT | ATCCTTAGAT | ACTATGTCTA | GTGGTGAACA | TGATTTAGTA | AAAGTTAACA | 240 |
| TTATCAGACC | CACTACCGAG | CATACTATCC | CCACGATGAT | GACAGCTAGC | CCCTATCATC | 300 |
| AAGGTATCAA | TGATCCTGCC | GCAGACCAAA | AAACATACCA | AATGGAGGGT | GCGCTAGCAG | 360 |
| TTAAACAGCC | TAAACACATA | CAAGTTGACA | CAAAACCATT | TAAAGAAGAA | GTAAAACATC | 420 |
| CTTCAAAATT | ACCCATCAGC | CCTGCAACTG | AAAGCTTCAC | ACACATTGAC | AGTTATAGTC | 480 |
| TCAATGACTA | TTTTCTTTCT | CGTGGTTTTG | CTAATATATA | CGTTTCAGGT | GTGGGTACTG | 540 |
| CTGGCTCTAC | GGGTTTCATG | ACCAGTGGGG | ATTACCAACA | AATACAAAGC | TTTAAAGCAG | 600 |
| TCATTGATTG | GTTAAATGGT | AAGGTTACTG | CATTCACAAG | TCATAAACGA | GATAAACAAG | 660 |
| TCAAGGCTGA | TTGGTCAAAC | GGCCTTGTAG | CAACCACAGG | TAAATCTTAT | CTCGGTACCA | 720 |
| TGTCAACTGG | TTTAGCAACA | ACTGGCGTTG | AGGGGCTGAA | AGTCATTATC | GCTGAAGCCG | 780 |
| CAATCTCCAC | ATGGTATGAT | TATTATCGAG | AAAATGGGCT | TGTGTGTAGT | CCAGGCGGCT | 840 |
| ACCCCGGTGA | AGATTTAGAC | GTTTTAACAG | AATTAACATA | CTCACGAAAC | CTCTTAGCTG | 900 |
| GTGATTACAT | CAAAAACAAC | GATTGCTATC | AAGCATTGTT | AAATGAACAA | TCAAAAGCAA | 960 |
| TTGACCGTCA | AAGTGGGGAT | TACAACCAAT | ACTGGCATGA | CCGTAATTAC | CTAACTCACG | 1020 |
| TCAATAATGT | CAAAAGTCGA | GTAGTTTACA | CTCATGGACT | ACAGGATTGG | AATGTTAAGC | 1080 |
| CAAGACATGT | CTACAAAGTT | TTCAATGCAT | TGCCTCAAAC | CATCAAAAAA | CACCTTTTTT | 1140 |
| TACATCAAGG | TCAACATGTG | TATATGCATA | ATTGGCAGTC | GATTGATTTT | CGTGAAAGCA | 1200 |
| TGAATGCCTT | ACTAAGCCAA | GAACTACTTG | GCATTGACAA | TCATTTCCAA | TTAGAAGAGG | 1260 |
| TCATTTGGCA | AGATAATACT | ACTGAGCAAA | CTTGGCAAGT | TTTAGATGCT | TTCGGAGGAA | 1320 |
| ACCATCAAGA | GCAAATTGGT | TTAGGTGATA | GTAAAAAACT | TATTGATAAC | CATTATGACA | 1380 |
| AAGAAGCCTT | TGATACTTAT | TGTAAAGACT | TCAATGTGTT | CAAAAATGAT | CTTTTCAAGG | 1440 |
| GAAATAATAA | AACCAATCAA | ATCACTATTA | ATCTTCCTCT | AAAGAAAAAT | TATCTCCTGA | 1500 |
| ATGGACAGTG | CAAACTCCAT | CTACGTGTTA | AAACTAGTGA | CAAAAAGGCC | ATTTTATCAG | 1560 |
| CCCAAATCTT | AGACTATGGT | CCTAAAAAAC | GATTCAAAGA | TACACCAACC | ATCAAATTCT | 1620 |
| TAAACAGCCT | TGATAATGGT | AAAAATTTTG | CCAGAGAAGC | TTTACGTGAA | CTCCCGTTTA | 1680 |
| CTAAAGATCA | TTATCGTGTC | ATCAGTAAAG | GTGTCTTGAA | CCTTCAAAAT | CGTACAGACT | 1740 |
| TACTTACAAT | TGAGGCTATC | GAGCCAGAAC | AATGGTTTGA | TATCGAGTTT | AGCCTCCAAC | 1800 |
| CAAGTATATA | TCAATTGAGT | AAAGGTGATA | ATCTAAGGAT | TATCCTTTAT | ACAACTGATT | 1860 |
| TTGAACATAC | CATTCGAGAT | AATGCTAGTT | ACTCTATAAC | AGTAGATTTG | AGTCAATCTT | 1920 |
| ATTTAACTAT | CCCAACTAAT | CAAGGAAATT | AACTTATGAA | ACTTCTTACT | AAAGAACGGT | 1980 |
| TTGATGATTC | TCAACACTTT | TGGTACCAGA | TCAATTTATT | ACAAGAGAGT | AACTTCGGAG | 2040 |
| CAGTTTTTGA | CCATGATAAT | AAAAACATTC | CACAGGTTGT | TGCAACTATT | GTTGATGATT | 2100 |
| TACAAGGTTC | CGGAAGTTCG | AATCATTTCT | GGTATTTTGG | CAATACTACT | GATACTTCCA | 2160 |
| TCCTTATGAT | TGCTCATTTA | AATCGAAAAT | TCTATATTCA | GGTTAATTTA | AAGGACTTTG | 2220 |
| ACTTTGCACT | CAATTTAATA | GCTATAAATA | ATTGGAAGAG | TCTCCTCCAA | ACTCAACTTG | 2280 |
| AAGCTCTAAA | CGATACCCTA | GCAATATTTC | AATAAATAAG | GTAGAATGGA | GTGACAAAGC | 2340 |
| AACGCGAGGG | AGACTGATTA | ATGTCATCTT | ATTGGAATAA | CTATCCTGAA | CTTAAAAAAA | 2400 |

*FIG. 6a (1)*

```
ATATTGATGA AACCAATCAA CTAATTCAAG AAAGAATACA GGTCAGAAAT AAAGATATTG  2460
AAGCGGCGCT AAGCCAACTC ACAGCTGCGG GAGGAAAACA GCTCAGACCA GCATTCTTTT  2520
ACCTTTTTTC TCAACTTGGT AATAAGGAGA ATCAAGATAC TCAGCAACTA AAGAAAATCG  2580
CTGCTTCTTT AGAAATCCTT CACGTTGCTA CATTAATCCA TGATGATGTC ATTGATGACT  2640
CACCACTAAG ACGTGGAAAT ATGACCATTC AAAGCAAGTT TGGCAAAGAC ATCGCAGTTT  2700
ATACTGGGGA TTTACTTTTC ACAGTCTTTT TCGATCTTAT TTAGAATCT ATGACTGATA  2760
CACCATTTAT GAGGATTAAT GCAAAATCTA TGCGTAAAAT TCTCATGGGA GAATTGGACC  2820
AGATGCACCT TCGTTACAAT CAACAACAAG GTATCCATCA CTATTTACGT GCGATTTCAG  2880
GTAAGACAGC CGAACTCTTT AAATTAGCTA GCAAAGAAGG AGCTTACTTT GGTGGTGCAG  2940
AGAAGGAGGT TGTTCGTCTA GCAGGCCATA TCGGCTTTAA CATTGGTATG ACATTCCAAA  3000
TTTTGGATGA TATCCTGGAT TATACTGCAG ATAAAAAAAC ATTTAATAAG CCTGTCTTAG  3060
AGGATTTAAC ACAAGGCGTT TACAGCCTTC CTCTACTTCT TGCCATTGAA GAAAATCCTG  3120
ATATTTTCAA ACCTATTTTA GATAAAAAAA CAGATATGGC TACTGAAGAC ATGGAAAAAA  3180
TTGCTTATCT CGTCGTTTCC CATAGAGGTG TTGACAAAGC TCGCCATCTA GCTCGTAAAT  3240
TTACTGAGAA AGCTATTAGT GACATAAATA AGCTACCCCA GAACTCTGCA AAAAAACAGT  3300
TGCTACAATT AACTAATTAC CTTTTAAAAC GCAAAATTTA AATAATAAAA AAACATTCCA  3360
CAATGCTAGA AAAGCAGTTA GGGAATGTTT TTTTATTATC ATTTATTTAT CGCACCTATC  3420
AATCATCATA GATCACCATC ATCAGCGGCT TCAGCTGAC GGTAACGTTG ACTACTTTGA  3480
GACAATTCTT GAGGAGAACC TTCCAACTCT AATTGCCCAT TTTCTATAAA TAAGATACGA  3540
TCAGCATGTT CAATACCTTT TAAGTGATGT GTAATCCAAA CTAAGGTCTT ACCTTCCAAT  3600
TCTTTCATAA ATACCCTTAG TAAGGCTTGT TCAGTAATAG GATCAAGTCC AACAGTTGGC  3660
TCATCTAAGA TAACAATTGG GACATCTTTT AGTAAGATTC TAGCCAAAGC AATTCTATGC  3720
CTTTCGCCAC CTGAAAACCT AAGTCCAGCT TCATCAACCA TTGTATAGAG ACCATCTGAT  3780
AAATCAGTGA CCATCTCTTT CAATCCAACT CGTTCAAGAA CTTTCCATAC ATCTTCTTCA  3840
CTAGCATCTT GGTTTCCAAT GCGAATGTTA TTTAGCAGGG TTGTATTAAA AAGGTAGGGC  3900
GCTTGTTGTA TCACTCCAAT ATAGTTAGAA ATGCAATCAC CAACTATTGA AACATCAGCA  3960
CCGCCTAGGG TAATCTTCCC TTGACTTGCT TTCAAGTCGC CACGAAGTAG ACTAGCTAAG  4020
GTACTCTTGC CAGAACCACT CCGCCCTAAA ATAGCAATTT TTTCTCCTTC TTTAATATCC  4080
AAATCTAAAT GATGCAAAAC CCATTTCTCT TGTGGCTTAT ACTGGAAACT TAAATTCTTG  4140
ACGGAAAAAT CATATGGCTT ATTAGGCAAT T  (SEQ ID NO:32)                4171
```

*FIG. 6a (2)*

| | | | | |
|---|---|---|---|---|
| YDNIFQSLHH | LLACRGKSGN | TLIDQLVADG | LLHADNHYHF | FNGKSLATFN | 50 |
| TNQLIREVVY | VEISLDTMSS | GEHDLVKVNI | IRPTTEHTIP | TMMTASPYHQ | 100 |
| GINDPAADQK | TYQMEGALAV | KQPKHIQVDT | KPFKEEVKHP | SKLPISPATE | 150 |
| SFTHIDSYSL | NDYFLSRGFA | NIYVSGVGTA | GSTGFMTSGD | YQQIQSFKAV | 200 |
| IDWLNGKVTA | FTSHKRDKQV | KADWSNGLVA | TTGKSYLGTM | STGLATTGVE | 250 |
| GLKVIIAEAA | ISTWYDYYRE | NGLVCSPGGY | PGEDLDVLTE | LTYSRNLLAG | 300 |
| DYIKNNDCYQ | ALLNEQSKAI | DRQSGDYNQY | WHDRNYLTHV | NNVKSRVVYT | 350 |
| HGLQDWNVKP | RHVYKVFNAL | PQTIKKHLFL | HQGQHVYMHN | WQSIDFRESM | 400 |
| NALLSQELLG | IDNHFQLEEV | IWQDNTTEQT | WQVLDAFGGN | HQEQIGLGDS | 450 |
| KKLIDNHYDK | EAFDTYCKDF | NVFKNDLFKG | NNKTNQITIN | LPLKKNYLLN | 500 |
| GQCKLHLRVK | TSDKKAILSA | QILDYGPKKR | FKDTPTIKFL | NSLDNGKNFA | 550 |
| REALRELPFT | KDHYRVISKG | VLNLQNRTDL | LTIEAIEPEQ | WFDIEFSLQP | 600 |
| SIYQLSKGDN | LRIILYTTDF | EHTIRDNASY | SITVDLSQSY | LTIPTNQGN | 649 |
| (SEQ ID NO:33) | | | | | |

FIG. 6b

| | | | | |
|---|---|---|---|---|
| MKLLTKERFD | DSQHFWYQIN | LLQESNFGAV | FDHDNKNIPQ | VVATIVDDLQ | 50 |
| GSGSSNHFWY | FGNTTDTSIL | MIAHLNRKFY | IQVNLKDFDF | ALNLIAINNW | 100 |
| KSLLQTQLEA | LNDTLAIFQ | (SEQ ID NO:34) | | | 119 |

FIG. 6c

| | | | | |
|---|---|---|---|---|
| MSSYWNNYPE | LKKNIDETNQ | LIQERIQVRN | KDIEAALSQL | TAAGGKQLRP | 50 |
| AFFYLFSQLG | NKENQDTQQL | KKIAASLEIL | HVATLIHDDV | IDDSPLRRGN | 100 |
| MTIQSKFGKD | IAVYTGDLLF | TVFFDLILES | MTDTPFMRIN | AKSMRKILMG | 150 |
| ELDQMHLRYN | QQQGIHHYLR | AISGKTAELF | KLASKEGAYF | GGAEKEVVRL | 200 |
| AGHIGFNIGM | TFQILDDILD | YTADKKTFNK | PVLEDLTQGV | YSLPLLLAIE | 250 |
| ENPDIFKPIL | DKKTDMATED | MEKIAYLVVS | HRGVDKARHL | ARKFTEKAIS | 300 |
| DINKLPQNSA | KKQLLQLTNY | LLKRKI | (SEQ ID NO:35) | | 326 |

FIG. 6d

```
LPNKPYDFSV KNLSFQYKPQ EKWVLHHLDL DIKEGEKIAI LGRSGSGKST   50
LASLLRGDLK ASQGKITLGG ADVSIVGDCI SNYIGVIQQA PYLFNTTLLN  100
NIRIGNQDAS EEDVWKVLER VGLKEMVTDL SDGLYTMVDE AGLRFSGGER  150
HRIALARILL KDVPIVILDE PTVGLDPITE QALLRVFMKE LEGKTLVWIT  200
HHLKGIEHAD RILFIENGQL ELEGSPQELS QSSQRYRQLK AADDGDL     247
(SEQ ID NO:36)
```

*FIG. 6e*

```
AATTCTATTT GGAGGTTTTT CTTGAATAAA TGGTTAGTTA AGGCAAGTTC CTTAGTTGTT    60
TTAGGTGGTA TGGTTTTATC TGCGGGTTCC CGAGTTTTAG CGGATACTTA TGTCCGTCCA   120
ATTGATAATG GTAGAATTAC AACAGGTTTC AATGGTTATC CTGGACATTG TGGGGTGGAT   180
TATGCTGTTC CGACTGGAAC GATTATTAGG GCAGTGGCAG ATGGTACTGT GAAATTTGCA   240
GGAGCTGGAG CCAACTTTTC TTGGATGACA GACTTAGCAG GAAATTGTGT CATGATTCAA   300
CATGCGGATG GAATGCATAG TGGTTACGCT CATATGTCAC GTGTGGTGGC TAGGACTGGG   360
GAAAAAGTCA ACAAGGAGA TATCATCGGT TACGTAGGAG CAACTGGTAT GGCGACGGGA   420
CCTCACCTTC ATTTTGAATT TTTACCAGCT AACCCTAATT TTCAAAATGG TTTCCATGGA   480
CGTATCAATC AACGTCACT AATTGCTAAC GTTGCGACCT TTAGTGGAAA AACGCAAGCA   540
TCAGCTCCAA GCATTAAGCC ATTACAATCA GCTCCTGTAC AGAATCAATC TAGTAAATTA   600
AAAGTGTATC GAGTAGATGA ATTACAAAAG GTTAATGGTG TTTGGTTAGT CAAAAATAAC   660
ACCCTAACGC CGACTGGGTT TGATTGGAAC GATAATGGTA TACCAGCATC AGAAATTGAT   720
GAGGTTGATG CTAATGGTAA TTTGACAGCT GACCAGGTTC TTCAAAAAGG TGGTTACTTT   780
ATCTTTAATC CTAAAACTCT TAAGACTGTA GAAAAACCCA TCCAAGGAAC AGCTGGTTTA   840
ACTTGGGCTA AGACACGCTT TGCTAATGGT AGTTCAGTTT GGCTTCGCGT TGACAACAGT   900
CAAGAACTGC TTTACAAATA GTTTGAGGTA TTGATTCATT GTTTTAAATG ACAGTTTTGT   960
TACTAACTAA GTACAATTTC TTTAAACCGT CTGAAAATAA TTTTATAGTC CAGTAAAGTG  1020
TGATATTATA GTCTCGGACT AATAAAAAGG AAATAGGAAT TGAAGCAATG AAAATGAATA  1080
AAAAGGTACT ATTGACATCG ACAATGGCAG CTTCGCTATT ATCAGTCGCA AGTGTTCAAG  1140
CACAAGAAAC AGATACGACG TGGACAGCAC GTACTGTTTC AGAGGTAAAG GCTGATTTGG  1200
TAAAGCAAGA CAATAAATCA TCATATACTG TGAAATATGG TGATACACTA AGCGTTATTT  1260
CAGAAGCAAT GTCAATTGAT ATGAATGTCT TAGCAAAAAT TAATAACATT GCAGATATCA  1320
ATCTTATTTA TCCTGAGACA ACACTGACAG TAACTTACGA TCAGAAGAGT CATACTGCCA  1380
CTTCAATGAA AATAGAAACA CCAGCAACAA ATGCTGCTGG TCAAACAACA GCTACTGTGG  1440
ATTTGAAAAC CAATCAAGTT TCTGTTGCAG ACCAAAAAGT TTCTCTCAAT ACAATTTCGG  1500
AAGGTATGAC ACCAGAAGCA GCAACAACGA TTGTTTCGCC AATGAAGACA TATTCTTCTG  1560
CGCCAGCTTT GAAATCAAAA GAAGTATTAG CACAAGAGCA AGCTGTTAGT CAAGCAGCAG  1620
CTAATGAACA GGTATCAACA GCTCCTGTGA AGTCGATTAC TTCAGAAGTT CCAGCAGCTA  1680
AAGAGGAAGT TAAACCAACT CAGACGTCAG TCAGTCAGTC AACAACAGTA TCACCAGCTT  1740
CTGTTGCCGC TGAAACACCA GCTCCAGTAG CTAAAGTAGC ACCGGTAAGA ACTGTAGCAG  1800
CCCCTAGAGT GGCAAGTGTT AAAGTAGTCA CTCCTAAAGT AGAAACTGGT GCATCACCAG  1860
AGCATGTATC AGCTCCAGCA GTTCCTGTGA CTACGACTTC AACAGCTACA GACAGTAAGT  1920
TACAAGCGAC TGAAGTTAAG AGCGTTCCGG TAGCACAAAA AGCTCCAACA GCAACACCGG  1980
TAGCACAACC AGCTTCAACA ACAAATGCAG TAGCTGCACA TCCTGAAAAT GCAGGGCTCC  2040
AACCTCATGT TGCAGCTTAT AAAGAAAAAG TAGCGTCAAC TTATGGAGTT AATGAATTCA  2100
GTACATACCG TGCAGGTGAT CCAGGTGATC ATGGTAAAGG TTTAGCAGTC GACTTTATTG  2160
TAGGTAAAAA CCAAGCACTT GGTAATGAAG TTGCACAGTA CTCTACACAA AATATGGCAG  2220
CAAATAACAT TCATATGTT ATCTGGCAAC AAAAGTTTTA CTCAAATACA AATAGTATTT  2280
ATGGACCTGC TAATACTTGG AATGCAATGC CAGATCGTGG TGGCGTTACT GCCAACCATT  2340
ATGACCATGT TCACGTATCA TTTAACAAAT AATATAAAAA AGGAAGCTAT TTGGCTTCTT  2400
```

*FIG. 7a (1)*

```
TTTTATATGC CTTGAATAGA CTTTCAAGGT TCTTATCTAA TTTTTATTAA ATTGAGGAGA  2460
TTAAGCTATA AGTCTGAAAC TACTTTCACG TTAACCGTGA CTAAATCAAA ACGTTAAAAC  2520
TAAAATCTAA GTCTGTAAAG ATTATTGAAA ACGCTTTAAA AACAGATATA ATAAGGTTTG  2580
TAGATATCTA AAATTAAAAA AGATAAGGAA GTGAGAATAT GCCACATCTA AGTAAAGAAG  2640
CTTTTAAAAA GCAAATAAAA AATGGCATTA TTGTGTCATG TCAAGCTTTG CCTGGGGAGC  2700
CTCTTTATAC TGAAAGTGGA GGTGTTATGC CTCTTTTAGC TTTGGCAGCT CAAGAAGCAG  2760
GAGCGGTTGG TATAAGAGCC AATAGTGTCC GCGACATTAA GGAAATTCAA GAAGTTACTA  2820
ATTTACCTAT CATCGGCATT ATTAAACGTG AATATCCTCC ACAAGAACCA TTTATCACTG  2880
CTACGATGAC AGAGGTGGAT CAATTAGCTA GTTTAGATAT TGCAGTAATA GCCTTAGATT  2940
GTACACTTAG AGAGCGTCAT GATGGTTTGA GTGTAGCTGA GTTTATTCAA AAGATAAAAG  3000
GGAAATATCC TGAACAGTTG CTAATGGCTG ATATAAGTAC TTTTGAAGAA GGTAAAAATG  3060
CTTTTGAAGC AGGAGTTGAT TTTGTGGGTA CAACTCTATC TGGATACACA GATTACAGCC  3120
GCCAAGAAGA AGGACCGGAT ATAGAACTCC TTAATAAGCT TGTCAAGCC GGTATAGATG   3180
TGATTGCGGA AGGTAAAATT CATACTCCTA AGCAAGCTAA TGAAATTAAT CATATAGGTG  3240
TTGCAGGAAT TGTAGTTGGT GGTGCTATCA CTAGACCAAA AGAAATAGCG GAGCGTTTCA  3300
TCTCAGGACT TAGTTAAAAG TGTTACTCAA AAATCAAAAT CAAATAAAA AAGGGGAATA   3360
GTTATGAGTA TCAAAAAAAG TGTGATTGGT TTTTGCCTCG GAGCTGCAGC ATTATCAATG  3420
TTTGCTTGTG TAGACAGTAG TCAATCTGTT ATGGCTGCCG AGAAGGATAA AGTCGAAATT  3480
(SEQ ID NO:37)
```

FIG. 7a (2)

```
NSIWRFFLNK WLVKASSLVV LGGMVLSAGS RVLADTYVRP IDNGRITTGF   50
NGYPGHCGVD YAVPTGTIIR AVADGTVKFA GAGANFSWMT DLAGNCVMIQ  100
HADGMHSGYA HMSRVVARTG EKVKQGDIIG YVGATGMATG PHLHFEFLPA  150
NPNFQNGFHG RINPTSLIAN VATFSGKTQA SAPSIKPLQS APVQNQSSKL  200
KVYRVDELQK VNGVWLVKNN TLTPTGFDWN DNGIPASEID EVDANGNLTA  250
DQVLQKGGYF IFNPKTLKTV EKPIQGTAGL TWAKTRFANG SSVWLRVDNS  300
QELLYK    (SEQ ID NO:38)                                306
```

FIG. 7b

| | | | | | |
|---|---|---|---|---|---|
| MKMNKKVLLT | STMAASLLSV | ASVQAQETDT | TWTARTVSEV | KADLVKQDNK | 50 |
| SSYTVKYGDT | LSVISEAMSI | DMNVLAKINN | IADINLIYPE | TTLTVTYDQK | 100 |
| SHTATSMKIE | TPATNAAGQT | TATVDLKTNQ | VSVADQKVSL | NTISEGMTPE | 150 |
| AATTIVSPMK | TYSSAPALKS | KEVLAQEQAV | SQAAANEQVS | TAPVKSITSE | 200 |
| VPAAKEEVKP | TQTSVSQSTT | VSPASVAAET | PAPVAKVAPV | RTVAAPRVAS | 250 |
| VKVVTPKVET | GASPEHVSAP | AVPVTTTSTA | TDSKLQATEV | KSVPVAQKAP | 300 |
| TATPVAQPAS | TTNAVAAHPE | NAGLQPHVAA | YKEKVASTYG | VNEFSTYRAG | 350 |
| DPGDHGKGLA | VDFIVGKNQA | LGNEVAQYST | QNMAANNISY | VIWQQKFYSN | 400 |
| TNSIYGPANT | WNAMPDRGGV | TANHYDHVHV | SFNK | (SEQ ID NO:39) | 434 |

*FIG. 7c*

| | | | | | |
|---|---|---|---|---|---|
| MPHLSKEAFK | KQIKNGIIVS | CQALPGEPLY | TESGGVMPLL | ALAAQEAGAV | 50 |
| GIRANSVRDI | KEIQEVTNLP | IIGIIKREYP | PQEPFITATM | TEVDQLASLD | 100 |
| IAVIALDCTL | RERHDGLSVA | EFIQKIKGKY | PEQLLMADIS | TFEEGKNAFE | 150 |
| AGVDFVGTTL | SGYTDYXRQE | EGPDIELLNK | LCQAGIDVIA | EGKIHTPKQA | 200 |
| NEINHIGVAG | IVVGGAITRP | KEIAERFISG | LS | (SEQ ID NO:40) | 232 |

*FIG. 7d*

| | | | |
|---|---|---|---|
| MSIKKSVIGF | CLGAAALSMF | ACVDSSQSVM | AAEKDKVEI | 39 |

(SEQ ID NO:41)

*FIG. 7e*

```
ATGAAAATGA ATAAAAAGGT ACTATTGACA TCGACAATGG CAGCTTCGCT      50
ATTATCAGTC GCAAGTGTTC AAGCACAAGA AACAGATACG ACGTGGACAG     100
CACGTACTGT TTCAGAGGTA AAGGCTGATT TGGTAAAGCA AGACAATAAA     150
TCATCATATA CTGTGAAATA TGGTGATACA CTAAGCGTTA TTTCAGAAGC     200
AATGTCAATT GATATGAATG TCTTAGCAAA AATTAATAAC ATTGCAGATA     250
TCAATCTTAT TTATCCTGAG ACAACACTGA CAGTAACTTA CGATCAGAAG     300
AGTCATACTG CCACTTCAAT GAAAATAGAA ACACCAGCAA CAAATGCTGC     350
TGGTCAAACA ACAGCTACTG TGGATTTGAA AACCAATCAA GTTTCTGTTG     400
CAGACCAAAA AGTTTCTCTC AATACAATTT CGGAAGGTAT GACACCAGAA     450
GCAGCAACAA CGATTGTTTC GCCAATGAAG ACATATTCTT CTGCGCCAGC     500
TTTGAAATCA AAAGAAGTAT TAGCACAAGA GCAAGCTGTT AGTCAAGCAG     550
CAGCTAATGA ACAGGTATCA ACAGCTCCTG TGAAGTCGAT TACTTCAGAA     600
GTTCCAGCAG CTAAAGAGGA AGTTAAACCA ACTCAGACGT CAGTCAGTCA     650
GTCAACAACA GTATCACCAG CTTCTGTTGC CGCTGAAACA CCAGCTCCAG     700
TAGCTAAAGT AGCACCGGTA AGAACTGTAG CAGCCCCTAG AGTGGCAAGT     750
GTTAAAGTAG TCACTCCTAA AGTAGAAACT GGTGCATCAC CAGAGCATGT     800
ATCAGCTCCA GCAGTTCCTG TGACTACGAC TTCAACAGCT ACAGACAGTA     850
AGTTACAAGC GACTGAAGTT AAGAGCGTTC CGGTAGCACA AAAAGCTCCA     900
ACAGCAACAC CGGTAGCACA ACCAGCTTCA ACAACAAATG CAGTAGCTGC     950
ACATCCTGAA AATGCAGGGC TCCAACCTCA TGTTGCAGCT TATAAAGAAA    1000
AAGTAGCGTC AACTTATGGA GTTAATGAAT TCAGTACATA CCGTGCAGGT    1050
GATCCAGGTG ATCATGGTAA AGGTTTAGCA GTCGACTTTA TTGTAGGTAA    1100
AAACCAAGCA CTTGGTAATG AAGTTGCACA GTACTCTACA CAAAATATGG    1150
CAGCAAATAA CATTTCATAT GTTATCTGGC AACAAAAGTT TTACTCAAAT    1200
ACAAATAGTA TTTATGGACC TGCTAATACT TGGAATGCAA TGCCAGATCG    1250
TGGTGGCGTT ACTGCCAACC ATTATGACCA TGTTCACGTA TCATTTAACA    1300
AATAA                                                     1305
```

(SEQ ID NO:42)

FIG. 8

```
CAAGAAACAG ATACGACGTG GACAGCACGT ACTGTTTCAG AGGTAAAGGC   50
TGATTTGGTA AAGCAAGACA ATAAATCATC ATATACTGTG AAATATGGTG  100
ATACACTAAG CGTTATTTCA GAAGCAATGT CAATTGATAT GAATGTCTTA  150
GCAAAAATTA ATAACATTGC AGATATCAAT CTTATTTATC CTGAGACAAC  200
ACTGACAGTA ACTTACGATC AGAAGAGTCA TACTGCCACT TCAATGAAAA  250
TAGAAACACC AGCAACAAAT GCTGCTGGTC AAACAACAGC TACTGTGGAT  300
TTGAAAACCA ATCAAGTTTC TGTTGCAGAC CAAAAAGTTT CTCTCAATAC  350
AATTTCGGAA GGTATGACAC CAGAAGCAGC AACAACGATT GTTTCGCCAA  400
TGAAGACATA TTCTTCTGCG CCAGCTTTGA AATCAAAAGA AGTATTAGCA  450
CAAGAGCAAG CTGTTAGTCA AGCAGCAGCT AATGAACAGG TATCAACAGC  500
TCCTGTGAAG TCGATTACTT CAGAAGTTCC AGCAGCTAAA GAGGAAGTTA  550
AACCAACTCA GACGTCAGTC AGTCAGTCAA CAACAGTATC ACCAGCTTCT  600
GTTGCCGCTG AAACACCAGC TCCAGTAGCT AAAGTAGCAC CGGTAAGAAC  650
TGTAGCAGCC CCTAGAGTGG CAAGTGTTAA AGTAGTCACT CCTAAAGTAG  700
AAACTGGTGC ATCACCAGAG CATGTATCAG CTCCAGCAGT TCCTGTGACT  750
ACGACTTCAA CAGCTACAGA CAGTAAGTTA CAAGCGACTG AAGTTAAGAG  800
CGTTCCGGTA GCACAAAAAG CTCCAACAGC AACACCGGTA GCACAACCAG  850
CTTCAACAAC AAATGCAGTA GCTGCACATC CTGAAAATGC AGGGCTCCAA  900
CCTCATGTTG CAGCTTATAA AGAAAAAGTA GCGTCAACTT ATGGAGTTAA  950
TGAATTCAGT ACATACCGTG CAGGTGATCC AGGTGATCAT GGTAAAGGTT 1000
TAGCAGTCGA CTTTATTGTA GGTAAAAACC AAGCACTTGG TAATGAAGTT 1050
GCACAGTACT CTACACAAAA TATGGCAGCA AATAACATTT CATATGTTAT 1100
CTGGCAACAA AAGTTTTACT CAAATACAAA TAGTATTTAT GGACCTGCTA 1150
ATACTTGGAA TGCAATGCCA GATCGTGGTG GCGTTACTGC CAACCATTAT 1200
GACCATGTTC ACGTATCATT TAACAAATAA   (SEQ ID NO:43)     1230
```

FIG. 9a

```
QETDTTWTAR TVSEVKADLV KQDNKSSYTV KYGDTLSVIS EAMSIDMNVL   50
AKINNIADIN LIYPETTLTV TYDQKSHTAT SMKIETPATN AAGQTTATVD  100
LKTNQVSVAD QKVSLNTISE GMTPEAATTI VSPMKTYSSA PALKSKEVLA  150
QEQAVSQAAA NEQVSTAPVK SITSEVPAAK EEVKPTQTSV SQSTTVSPAS  200
VAAETPAPVA KVAPVRTVAA PRVASVKVVT PKVETGASPE HVSAPAVPVT  250
TTSTATDSKL QATEVKSVPV AQKAPTATPV AQPASTTNAV AAHPENAGLQ  300
PHVAAYKEKV ASTYGVNEFS TYRAGDPGDH GKGLAVDFIV GKNQALGNEV  350
AQYSTQNMAA NNISYVIWQQ KFYSNTNSIY GPANTWNAMP DRGGVTANHY  400
DHVHVSFNK   (SEQ ID NO:44)                              409
```

FIG. 9b

GROUP B STREPTOCOCCUS ANTIGENS

CROSS-REFERENCES TO RELATED APPLICATIONS

This application is a continuation of U.S. application Ser. No. 09/252,088, filed Feb. 18, 1999, now abandoned, which application claims the benefit of U.S. Provisional Application No. 60/075,425, filed Feb. 20, 1998, all of which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 484112_418C1_SEQUENCE_LISTING.txt. The text file is 140 KB, was created on Feb. 11, 2008, and is being submitted electronically via EFS-Web.

FIELD OF THE INVENTION

The present invention is related to antigens, more particularly protein antigens of group B *streptococcus* (GBS) bacterial pathogen which are useful as vaccine components for therapy and/or prophylaxis.

BACKGROUND OF THE INVENTION

*Streptococcus* are gram (+) bacteria that are differentiated by group specific carbohydrate antigens A through O found on their cell surface. *Streptococcus* groups are further distinguished by type-specific capsular polysaccharide antigens. Several serotypes have been identified for the Group B *streptococcus* (GBS): Ia, Ib, II, III, IV, V, VI, VII and VIII. GBS also contains antigenic proteins known as "C-proteins" (alpha, beta, gamma and delta), some of which have been cloned.

Although GBS is a common component of the normal human vaginal and colonic flora this pathogen has long been recognized as a major cause of neonatal sepsis and meningitis, late-onset meningitis in infants, postpartum endometritis as well as mastitis in dairy herds. Expectant mothers exposed to GBS are at risk of postpartum infection and may transfer the infection to their baby as the child passes through the birth canal. Although the organism is sensitive to antibiotics, the high attack rate and rapid onset of sepsis in neonates and meningitis in infants results in high morbidity and mortality.

To find a vaccine that will protect individuals from GBS infection, researches have turned to the type-specific antigens. Unfortunately these polysaccharides have proven to be poorly immunogenic in humans and are restricted to the particular serotype from which the polysaccharide originates. Further, capsular polysaccharide elicit a T cell independent response i.e. no IgG production. Consequently capsular polysaccharide antigens are unsuitable as a vaccine component for protection against GBS infection.

Others have focused on the C-protein beta antigen which demonstrated immunogenic properties in mice and rabbit models. This protein was found to be unsuitable as a human vaccine because of its undesirable property of interacting with high affinity and in a non-immunogenic manner with the Fc region of human IgA. The C-protein alpha antigen is rare in type III serotypes of GBS which is the serotype responsible for most GBS mediated conditions and is therefore of little use as a vaccine component.

Therefore there remains an unmet need for GBS antigens that may be used as vaccine components for the prophylaxis and/or therapy of GBS infection.

SUMMARY OF THE INVENTION

According to one aspect, the present invention provides an isolated polynucleotide encoding a polypeptide having at least 70% identity to a second polypeptide comprising a sequence selected from the group consisting of:
SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO:10, SEQ ID NO:11, SEQ ID NO:12, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:33, SEQ ID NO:34, SEQ ID NO:35, SEQ ID NO:36, SEQ ID NO:38, SEQ ID NO:39, SEQ ID NO:40, SEQ ID NO:41 and SEQ ID NO:44 or fragments, analogs or derivatives thereof.

In other aspects, there is provided vectors comprising polynucleotides of the invention operably linked to an expression control region, as well as host cells transfected with said vectors and methods of producing polypeptides comprising culturing said host cells under conditions suitable for expression.

In yet another aspect, there is provided novel polypeptides encoded by polynucleotides of the invention.

BRIEF DESCRIPTION OF THE DRAWINGS

FIG. 1*a* (1)-1*a* (4) is the DNA sequence of clone 1 (SEQ ID NO:1) with corresponding amino acid sequences for open reading frames (SEQ ID NO:2; SEQ ID NO:3; SEQ ID NO:4; SEQ ID NO:5; SEQ ID NO:6).
FIG. 1*b* is the amino acid sequence SEQ ID NO: 2.
FIG. 1*c* is the amino acid sequence SEQ ID NO: 3.
FIG. 1*d* is the amino acid sequence SEQ ID NO: 4.
FIG. 1*e* is the amino acid sequence SEQ ID NO: 5.
FIG. 1*f* is the amino acid sequence SEQ ID NO: 6.
FIG. 2*a* (1)-2*a* (5) is the DNA sequence of clone 2 (SEQ ID NO:7) with corresponding amino acid sequences for open reading frames (SEQ ID NO:8; SEQ ID NO:9; SEQ ID NO:10; SEQ ID NO:11; SEQ ID NO:12).
FIG. 2*b* is the amino acid sequence SEQ ID NO: 8.
FIG. 2*c* is the amino acid sequence SEQ ID NO: 9.
FIG. 2*d* is the amino acid sequence SEQ ID NO:10.
FIG. 2*e* is the amino acid sequence SEQ ID NO:11.
FIG. 2*f* is the amino acid sequence SEQ ID NO:12.
FIG. 3*a* (1)-3*a* (5) is the DNA sequence of clone 3 (SEQ ID NO:13) with corresponding amino acid sequences for open reading frames SEQ ID NO:14; SEQ ID NO:15; SEQ ID NO:16; SEQ ID NO:46 (which in reverse order is SEQ ID NO:17); SEQ ID NO:47; (which in reverse order is SEQ ID NO:18); SEQ ID NO:48 (which in reverse order is SEQ ID NO:19); SEQ ID NO:49 (which in reverse order is SEQ ID NO:20); SEQ ID NO:50 (which in reverse order is SEQ ID NO:21).
FIG. 3*b* is the amino acid sequence SEQ ID NO:14.
FIG. 3*c* is the amino acid sequence SEQ ID NO:15.
FIG. 3*d* is the amino acid sequence SEQ ID NO:16.
FIG. 3*e* is the amino acid sequence SEQ ID NO:17.
FIG. 3*f* is the amino acid sequence SEQ ID NO:18.

FIG. 3g is the amino acid sequence SEQ ID NO:19.
FIG. 3h is the amino acid sequence SEQ ID NO:20.
FIG. 3i is the amino acid sequence SEQ ID NO:21.
FIG. 4a(1)-4a(5) is the DNA sequence of clone 4 (SEQ ID NO:22) with corresponding amino acid sequences for open reading frames (SEQ ID NO:23; SEQ ID NO:24; SEQ ID NO:25; SEQ ID NO:26).
FIG. 4b is the amino acid sequence SEQ ID NO:23.
FIG. 4c is the amino acid sequence SEQ ID NO:24.
FIG. 4d is the amino acid sequence SEQ ID NO:25.
FIG. 4e is the amino acid sequence SEQ ID NO:26.
FIG. 5a(1)-5a(4) is the DNA sequence of clone 5 (SEQ ID NO:27) with corresponding amino acid sequences for open reading frames (SEQ ID NO:28; SEQ ID NO:51 (which in reverse order is SEQ ID NO:29); SEQ ID NO:30; SEQ ID NO:31).
FIG. 5b is the amino acid sequence SEQ ID NO:28.
FIG. 5c is the amino acid sequence SEQ ID NO:29.
FIG. 5d is the amino acid sequence SEQ ID NO:30.
FIG. 5e is the amino acid sequence SEQ ID NO:31.
FIG. 6a(1)-6a(2) is the DNA sequence of clone 6 (SEQ ID NO:32).
FIG. 6b is the amino acid sequence SEQ ID NO:33.
FIG. 6c is the amino acid sequence SEQ ID NO:34.
FIG. 6d is the amino acid sequence SEQ ID NO:35.
FIG. 6e is the amino acid sequence SEQ ID NO:36.
FIG. 7a(1)-7a(2) is the DNA sequence of clone 7 (SEQ ID NO:37).
FIG. 7b is the amino acid sequence SEQ ID NO:38.
FIG. 7c is the amino acid sequence SEQ ID NO:39.
FIG. 7d is the amino acid sequence SEQ ID NO:41.
FIG. 7e is the amino acid sequence SEQ ID NO:41.
FIG. 8 is the DNA sequence of a part of clone 7 including a signal sequence (SEQ ID NO:42).
FIG. 9a is the DNA sequence of a part of clone 7 without a signal sequence (SEQ ID NO:43).
FIG. 9b is the amino acid sequence (SEQ ID NO:44).

DETAILED DESCRIPTION OF THE INVENTION

Figure 10:
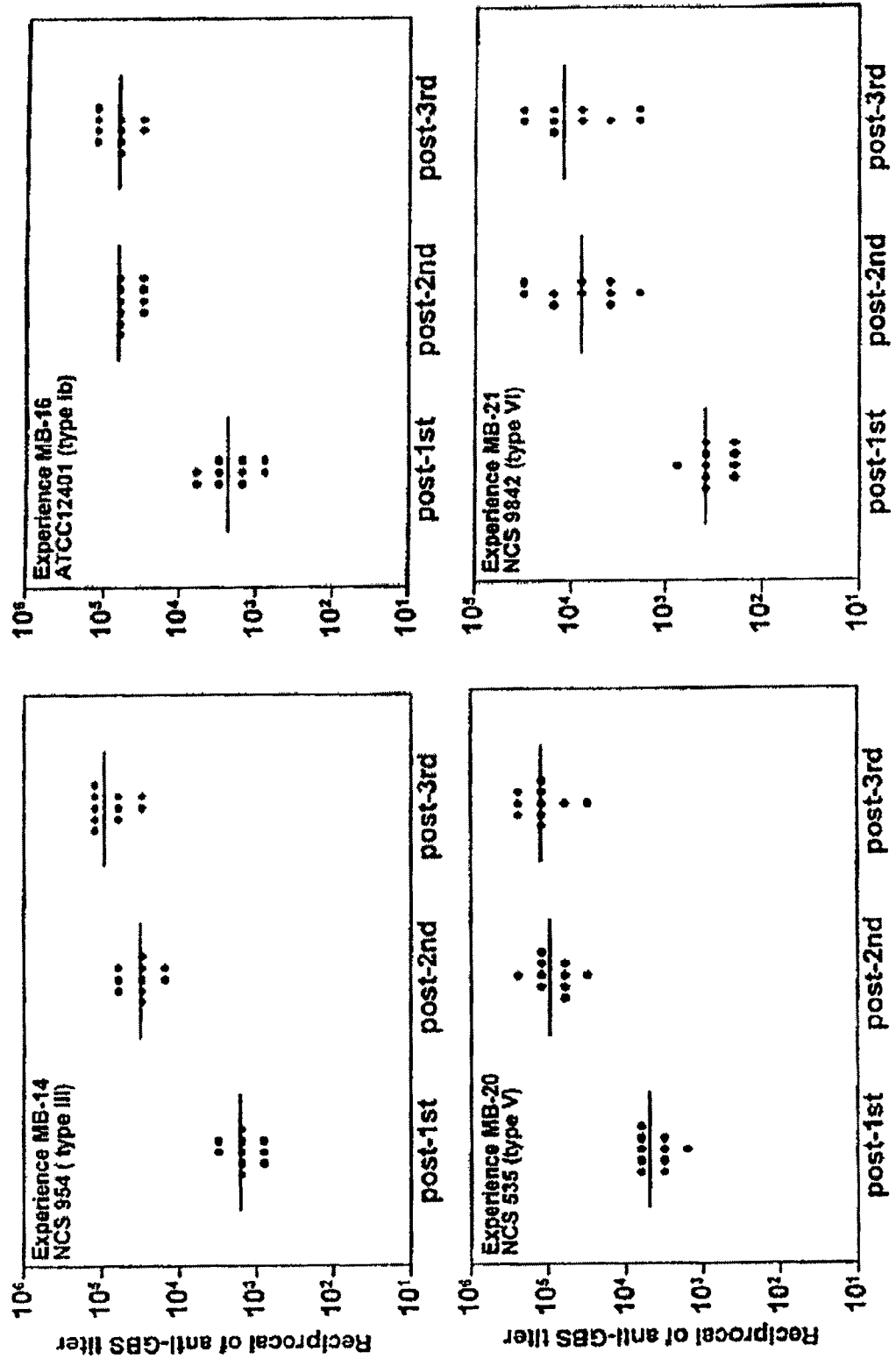
FIG. 10 represents the distribution of anti-GBS ELISA titers in sera from CD-1 mice immunized with recombinant GBS protein corresponding to the SEQ ID NO:39.

The present invention relates to novel antigenic polypeptides of group B *streptococcus* (GBS) characterized by the amino acid sequence selected from the group consisting of:
SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO:10, SEQ ID NO:11, SEQ ID NO:12, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:33, SEQ ID NO:34, SEQ ID NO:35, SEQ ID NO:36, SEQ ID NO:38, SEQ ID NO:39, SEQ ID NO:40, SEQ ID NO:41 and SEQ ID NO:44 or fragments, analogs or derivatives thereof.

A preferred embodiment of the invention includes SEQ ID NO: 39 and SEQ ID NO:44.

A further preferred embodiment of the invention is SEQ ID NO: 39.

A further preferred embodiment of the invention is SEQ ID NO: 44.

As used herein, "fragments", "derivatives" or "analogs" of the polypeptides of the invention include those polypeptides in which one or more of the amino acid residues are substituted with a conserved or non-conserved amino acid residue (preferably conserved) and which may be natural or unnatural.

The terms <<fragments>>, <<derivatives>> or <<analogues>> of polypeptides of the present invention also include polypeptides which are modified by addition, deletion, substitution of amino acids provided that the polypeptides retain the capacity to induce an immune response.

By the term <<conserved amino acid>> is meant a substitution of one or more amino acids for another in which the antigenic determinant (including its secondary structure and hydropathic nature) of a given antigen is completely or partially conserved in spite of the substitution.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

Preferably, derivatives and analogs of polypeptides of the invention will have about 70% identity with those sequences illustrated in the figures or fragments thereof. That is, 70% of the residues are the same. More preferably polypeptides will have greater than 95% homology. In another preferred embodiment, derivatives and analogs of polypeptides of the invention will have fewer than about 20 amino acid residue substitutions, modifications or deletions and more preferably less than 10. Preferred substitutions are those known in the art as conserved i.e. the substituted residues share physical or chemical properties such as hydrophobicity, size, charge or functional groups.

Furthermore, in those situations where amino acid regions are found to be polymorphic, it may be desirable to vary one or more particular amino acids to more effectively mimic the different epitopes of the different GBS strains.

Also included are polypeptides which have fused thereto other compounds which alter the polypeptides biological or pharmacological properties i.e. polyethylene glycol (PEG) to increase half-life; leader or secretory amino acid sequences for ease of purification; prepro- and pro-sequences; and (poly)saccharides.

Moreover, the polypeptides of the present invention can be modified by terminal —NH$_2$ acylation (eg. by acetylation, or thioglycolic acid amidation, terminal carbosy amidation, e.g. with ammonia or methylamine) to provide stability, increased hydrophobicity for linking or binding to a support or other molecule.

Also contemplated are hetero and homo polypeptide multimers of the polypeptide fragments, analogues and derivatives. These polymeric forms include, for example, one or more polypeptides that have been cross-linked with cross-linkers such as avidin/biotin, gluteraldehyde or dimethylsuperimidate. Such polymeric forms also include polypeptides containing two or more tandem or inverted contiguous sequences, produced from multicistronic mRNAs generated by recombinant DNA technology.

Preferably, a fragment, analog or derivative of a polypeptide of the invention will comprise at least one antigenic region i.e. at least one epitope.

In order to achieve the formation of antigenic polymers (i.e. synthetic multimers), polypeptides may be utilized having bishaloacetyl groups, nitroarylhalides, or the like, where the reagents being specific for thio groups. Therefore, the link between two mercapto groups of the different peptides may be a single bond or may be composed of a linking group of at least two, typically at least four, and not more than 16, but usually not more than about 14 carbon atoms.

In a particular embodiment, polypeptide fragments, analogs and derivatives of the invention do not contain a methionine (Met) starting residue. Preferably, polypeptides will not incorporate a leader or secretory sequence (signal sequence). The signal portion of a polypeptide of the invention may be determined according to established molecular biological techniques. In general, the polypeptide of interest may be isolated from a GBS culture and subsequently sequenced to determine the initial residue of the mature protein and therefor the sequence of the mature polypeptide.

According to another aspect, there is provided vaccine compositions comprising one or more GBS polypeptides of the invention in admixture with a pharmaceutically acceptable carrier diluent or adjuvant.

Suitable adjuvants include oils i.e. Freund's complete or incomplete adjuvant; salts i.e. $AlK(SO_4)_2$, $AlNa(SO_4)_2$, $AlNH_4(SO_4)_2$, $Al(OH)_3$, $AlPO_4$, silica, kaolin; saponin derivative; carbon polynucleotides i.e. poly IC and poly AU and also detoxified cholera toxin (CTB)and *E. coli* heat labile toxin for induction of mucosal immunity. Preferred adjuvants include QuilA™ (an adjuvant containing saponins from the bark of Quillaja saponaria, Alhydrogel™ (an aluminum hydroxide (hydrate alumina) adjuvant) and Adjuphos™ (an Aluminum phosphate adjuvant). Vaccines of the invention may be administered parenterally by injection, rapid infusion, nasopharyngeal absorption, dermoabsorption, or bucal or oral.

Vaccine compositions of the invention are used for the treatment or prophylaxis of *streptococcus* infection and/or diseases and symptoms mediated by *streptococcus* infection, in particular group A *streptococcus* (*pyogenes*), group B *streptococcus* (GBS or *agalactiae*), *dysgalactiae*, *uberis*, *nocardia* as well as *Staphylococcus aureus*. General information about *Streptococcus* is available in Manual of Clinical Microbiology by P. R. Murray et al. (1995, 6$^{th}$ Edition, ASM Press, Washington, D.C.) which is herein incorporated by reference. More particularly group B *streptococcus*, *agalactiae*. In a particular embodiment vaccines are administered to those individuals at risk of GBS infection such as pregnant women and infants for sepsis, meningitis and pneumonia as well as immunocompromised individuals such as those with diabetes, liver disease or cancer. Vaccines may also have veterinary applications such as for the treatment of mastitis in cattle which is mediated by the above mentioned bacteria as well as *E. coli*.

The vaccine of the present invention can also be used for the manufacture of a medicament used for the treatment or prophylaxis of *streptococcus* infection and/or diseases and symptoms mediated by *streptococcus* infection, in particular group A *streptococcus* (*pyogenes*), group B *streptococcus* (GBS or *agalactiae*), *dysgalactiae*, *uberis*, *nocardia* as well as *Staphylococcus aureus*. More particularly group B *streptococcus*, *agalactiae*.

Vaccine compositions are preferably in unit dosage form of about 0.001 to 100 µg/kg (antigen/body weight) and more preferably 0.01 to 10 µg/kg and most preferably 0.1 to 1 µg/kg 1 to 3 times with an interval of about 1 to 12 weeks intervals between immunizations, and more preferably 1 to 6 weeks.

According to another aspect, there is provided polynucleotides encoding polypeptides of group B *streptococcus* (GBS) characterized by the amino acid sequence selected from the group consisting of:
SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO:10, SEQ ID NO:11, SEQ ID NO:12, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:23, SEQ ID NO:24, SEQ ID NO:25, SEQ ID NO:26, SEQ ID NO:28, SEQ ID NO:29, SEQ ID NO:30, SEQ ID NO:31, SEQ ID NO:33, SEQ ID NO:34, SEQ ID NO:35, SEQ ID NO:36, SEQ ID NO:38, SEQ ID NO:39, SEQ ID NO:40, SEQ ID NO:41 and SEQ ID NO:44 or fragments, analogs or derivatives thereof.

Preferred polynucleotides are those illustrated in FIGS. 1*a* (SEQ. ID NO: 1), 2*a* (SEQ ID NO: 7), 3*a* (SEQ ID NO: 13), 4*a* (SEQ ID NO: 22), 5*a* (SEQ ID NO: 27), 6*a* (SEQ ID NO: 32), 7*a* (SEQ ID NO: 37), 8 (SEQ ID NO: 42) and 9 (SEQ ID NO: 43) which correspond to the open reading frames, encoding polypeptides of the invention.

Preferred polynucleotides are those illustrated in FIGS. 1*a* (SEQ ID NO: 1), 2*a* (SEQ ID NO: 7), 3*a* (SEQ ID NO: 13), 4*a* (SEQ ID NO: 22), 5*a* (SEQ ID NO: 27), 6*a* (SEQ ID NO: 32), 7*a* (SEQ ID NO: 37), 8 (SEQ ID NO: 42) and 9(SEQ ID NO: 43) and fragments, analogues and derivatives thereof.

More preferred polynucleotides of the invention are those illustrated in FIGS. 7 (SEQ ID NO: 37), 8 (SEQ ID NO 42) and 9 (SEQ ID NO: 43).

Most preferred polynucleotides of the invention are those illustrated in FIGS. 8 (SEQ ID NO 42) and 9 (SEQ ID NO: 43).

It will be appreciated that the polynucleotide sequences illustrated in the figures may be altered with degenerate codons yet still encode the polypeptides of the invention.

Due to the degeneracy of nucleotide coding sequences, other polynucleotide sequences which encode for substantially the same polypeptides of the present invention may be used in the practice of the present invention. These include but are not limited to nucleotide sequences which are altered by the substitution of different codons that encode the same amino acid residue within the sequence, thus producing a silent change.

Accordingly the present invention further provides polynucleotides which hybridize to the polynucleotide sequences herein above described (or the complement sequences thereof) having 50% and preferably at least 70% identity between sequences. More preferably polynucleotides are hybridizable under stringent conditions i.e. having at least 95% identity and most preferably more than 97% identity.

By capable of hybridizing under stringent conditions is meant annealing of a nucleic acid molecule to at least a region of a second nucleic acid sequence (whether as cDNA, mRNA, or genomic DNA) or to its complementary strand under standard conditions, e.g. high temperature and/or low salt content, which tend to disfavor hybridization of noncomplementary nucleotide sequences. A suitable protocol is described in Maniatis T. et al., Molecular cloning A Laboratory Manual, Cold Springs Harbor Laboratory, 1982, which is herein incorporated by reference.

In a further aspect, polynucleotides encoding polypeptides of the invention, or fragments, analogs or derivatives thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

According to another aspect, there is provided a process for producing polypeptides of the invention by recombinant techniques by expressing a polynucleotide encoding said polypeptide in a host cell and recovering the expressed polypeptide product. Alternatively, the polypeptides can be produced according to established synthetic chemical techniques i.e. solution phase or solid phase synthesis of oligopeptides which are ligated to produce the full polypeptide (block ligation).

For recombinant production, host cells are transfected with vectors which encode the polypeptide, and then cultured in a nutrient media modified as appropriate for activating promoters, selecting transformants or amplifying the genes. Suitable vectors are those that are viable and replicable in the chosen host and include chromosomal, non-chromosomal and synthetic DNA sequences e.g. bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgarno sequence)., and optionally an operator (control element). One can select individual components of the expression control region that are appropriate for a given host and vector according to established molecular biology principles (Sambrook et al, Molecular Cloning: A Laboratory Manual, 2nd ed., Cold Spring Harbor, N.Y., 1989 incorporated herein by reference). Suitable promoters include but are not limited to LTR or SV40 promoter, E. coli lac, tac or trp promoters and the phage lambda $P_L$ promoter. Vectors will preferably incorporate an origin of replication as well as selection markers i.e. ampicillin resistance gene. Suitable bacterial vectors include pET, pQE70, pQE60, pQE-9, pbs, pD10 phagescript, psiX174, pbluescript SK, pbsks, pNH8A, pNH16a, pNH18A, pNH46A, ptrc99a, pKK223-3, pKK233-3, pDR540, pRIT5 and eukaryotic vectors pBlueBacIII, pWLNEO, pSV2CAT, pOG44, pXT1, pSG, pSVK3, pBPV, pMSG and pSVL. Host cells may be bacterial i.e. *E. coli, Bacillus subtilis, Streptomyces*; fungal i.e. *Aspergillus niger, Aspergillus nidulins*; yeast i.e. Saccharomyces or eukaryotic i.e. CHO, COS.

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide i.e. using ammonium sulfate or ethanol precipitation, acid extraction, anion or cation exchange chromatography, phosphocellulose chromatography, hydrophobic interaction chromatography, hydroxylapatite chromatography and lectin chromatography. Final purification may be achieved using HPLC.

The polypeptide may be expressed with or without a leader or secretion sequence. In the former case the leader may be removed using post-translational processing (see U.S. Pat. Nos. 4,431,739; 4,425,437; and 4,338,397 incorporated herein by reference) or be chemically removed subsequent to purifying the expressed polypeptide.

According to a further aspect, the GBS polypeptides of the invention may be used in a diagnostic test for *streptococcus* infection in particular GBS infection. Several diagnostic methods are possible, for example detecting *streptococcus* organism in a biological sample, the following procedure may be followed:
a) obtaining a biological sample from a patient;
b) incubating an antibody or fragment thereof reactive with a GBS polypeptide of the invention with the biological sample to form a mixture; and
c) detecting specifically bound antibody or bound fragment in the mixture which indicates the presence of *streptococcus*.

Alternatively, a method for the detection of antibody specific to a *streptococcus* antigen in a biological sample containing or suspected of containing said antibody may be performed as follows:
a) isolating a biological sample from a patient;
b) incubating one or more GBS polypeptides of the invention or fragments thereof with the biological sample to form a mixture; and
c) detecting specifically bound antigen or bound fragment in the mixture which indicates the presence of-antibody specific to *streptococcus*.

One of skill in the art will recognize that this diagnostic test may take several forms, including an immunological test such as an enzyme-linked immunosorbent assay (ELISA), a radioimmunoassay or a latex agglutination assay, essentially to determine whether antibodies specific for the protein are present in an organism.

The DNA sequences encoding polypeptides of the invention may also be used to design DNA probes for use in detecting the presence of *streptococcus* in a biological sample suspected of containing such bacteria. The detection method of this invention comprises:
a) isolating the biological sample from a patient;
b) incubating one or more DNA probes having a DNA sequence encoding a polypeptide of the invention or fragments thereof with the biological sample to form a mixture; and
c) detecting specifically bound DNA probe in the mixture which indicates the presence of *streptococcus* bacteria.

The DNA probes of this invention may also be used for detecting circulating *streptococcus* i.e. GBS nucleic acids in a sample, for example using a polymerase chain reaction, as a method of diagnosing *streptococcus* infections. The probe may be synthesized using conventional techniques and may be immobilized on a solid phase, or may be labeled with a detectable label. A preferred DNA probe for this application is an oligomer having a sequence complementary to at least about 6 contiguous nucleotides of the GBS polypeptides of the invention.

Another diagnostic method for the detection-of *streptococcus* in a patient comprises:
a) labeling an antibody reactive with a polypeptide of the invention or fragment thereof with a detectable label;
b) administering the labeled antibody or labeled fragment to the patient; and
c) detecting specifically bound labeled antibody or labeled fragment in the patient which indicates the presence of *streptococcus*.

A further aspect of the invention is the use of the GBS polypeptides of the invention as immunogens for the production of specific antibodies for the diagnosis and in particular the treatment of *streptococcus* infection. Suitable antibodies may be determined using appropriate screening methods, for example by measuring the ability of a particular antibody to passively protect against *streptococcus* infection in a test model. One example of an animal model is the mouse model described in the examples herein. The antibody may be a whole antibody or an antigen-binding fragment thereof and may in general belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which were produced using molecular biology techniques. The antibody or antibody fragments may be polyclonal, or preferably monoclonal. It may be specific for a number of epitopes associated with the GBS polypeptides but is preferably specific for one.

EXAMPLE 1

Murine Model of Lethal Group B Streptococcus (GBS) Infection

The mouse model of GBS infection is described in detail in Lancefield et al (J Exp Med 142:165-179,1975 which is herein incorporated by reference). GBS strain C388/90 (Clinical isolate obtained in 1990 from the cephalorachidian fluid of a patient suffering from meningitis, Children's Hospital of Eastern Ontario, Ottawa, Canada) and NCS246 (National Center for Streptococcus, Provincial Laboratory of Public Health for Northern Alberta, Edmonton, Canada) were respectively serotyped as type Ia/c and type II/R.

To increase their virulence, the GBS strains C388/90 (serotype Ia/c) and NCS 246 (serotype II/R) were serially passaged through mice as described previously (Lancefield et al. J Exp Med 142:165-179, 1975). Briefly, the increase of virulence was monitored using intraperitoneal inoculations of serial dilutions of a subculture in Todd-Hewitt broth obtained from either the blood or spleen of infected mice. After the last passage, infected blood samples were used to inoculate Todd-Hewitt broth. After an incubation of 2 hours at 37° C. with 7% $CO_2$ glycerol at a final concentration of 10% (v/v) was added to the culture. The culture was then aliquoted and stored at −80° C. for use in GBS challenge experiments. The number of cfu of GBS present in these frozen samples was determined. The bacterial concentration necessary to kill 100% (LD100) of the 18 weeks old mice were determined to be $3.5 \times 10^5$ and $1 \times 10^5$ respectively for GBS strain C388/90 and NCS246, which corresponded to a significant increase in virulence for both strains. Indeed, the LD100 recorded before the passages for these two strains was higher than $10^9$ cfu.

In a bacterial challenge, a freshly thawed aliquot of a virulent GBS strain was adjusted to the appropriate bacterial concentration using Todd-Hewitt broth and 1 ml was injected intraperitoneally to each female CD-1 mouse. The mice used for the passive protection experiments were 6 to 8 weeks old, while the ones used for the active protection experiments were approximately 18 weeks old at the time of the challenge. All inocula were verified by colony counts. Animals were observed for any sign of infection four times daily for the first 48 h after challenge and then daily for the next 12 days. At the end of that period, blood samples were obtained from the survivors and frozen at −20° C. The spleen obtained from each mouse that survived the challenge was cultured in order to identify any remaining GBS.

EXAMPLE 2

Immunization and Protection in Mice With Formaldehyde Killed Whole GBS Cells Formaldehyde killed GBS whole cells were prepared according to the procedures described in Lancefield et al (J Exp Med 142:165-179,1975 which is herein incorporated by reference). Briefly, an overnight culture on sheep blood agar plates (Quelab Laboratories, Montreal, Canada) of a GBS strain was washed twice in PBS buffer (phosphate bufferedsaline, pH 7.2), adjusted to approximately $3 \times 10^9$ cfu/mL and incubated overnight in PBS containing 0.3% (v/v) formaldehyde. The killed GBS suspension was washed with PBS and kept frozen at −80° C.

Female CD-1 mice, 6 to 8 weeks old (Charles River, St-Constant, Québec, Canada), were injected subcutaneously three times at two weeks interval with 0.1 ml of formaldehyde killed cells of GBS strain C388/90 (~$6 \times 10^7$ GBS) or 0.1 ml of PBS for the control group. On the day before the immunization, Alhydrogel™ (Superfos Biosector, Frederikssund, Denmark) at a final concentration of 0.14 mg or 0.21.mg of Al, was added to these preparations and incubated overnight at 4° C. with agitation. Serum samples were obtained from each mouse before the beginning of the immunization protocol and two weeks after the last injection. The sera were frozen at −20° C.

Eight mice in each control group injected with PBS and the group immunized with formaldehyde killed whole cells GBS strain C388/90 (Ia/c) were challenged with $1.5 \times 10^4$ cfu of GBS strain C388/90 (Ia/c) one week after the third injection. All mice immunized with the formaldehyde killed GBS whole cells survived the homologous challenge while, within 5 days after the challenge, only 4 out of the 8 mice injected with PBS survived from the infection. In order to increase the mortality rate in the control groups, the bacterial suspension had to be adjusted according to the age of the mice at the time of the bacterial challenge. In subsequent challenge experiments, when mice were older than 15 weeks, the bacterial inoculum was increased to concentrations between $3.0 \times 10^5$ and $2.5 \times 10^6$ cfu.

TABLE 1

Immunization of CD1 mice with formaldehyde killed whole cells of GBS and subsequent homologous challenge [strain C388/90 (Ia/c)] and heterologous challenge [strain NCS246 (II/R)]

| | number of living mice 14 days after the bacterial challenge (% Survival) | |
|---|---|---|
| antigenic preparations used for immunization[1] | homologous challenge: strain C388/90 (Ia/c) | heterologous challenge: strain NCS246 (II/R) |
| 1st infection | | |
| formaldehyde killed cells of GBS strain C388/90 (Ia/c)[2] | 8/8 (100)[3] | n.d.[5] |
| control PBS | 4/8 (50) | n.d. |
| 2nd infection | | |
| formaldehyde killed cells of GES strain C388/90 (Ia/c) | 6/6 (100)[4] | 0/6 (0)[6] |
| control PBS | 2/6 (33) | 0/6 (0) |

[1]alhydrogel ™ at a final concentration of 0.14 mg or 0.21 mg of Al was used;
[2]approximately $6 \times 10^7$ cfu;
[3]intraperitoneal challenge with 1 mL Todd-Hewitt culture medium containing GBS C388/90 (Ia/c) suspension adjusted to $1.5 \times 10^4$ cfu;
[4]intraperitoneal challenge with 1 mL Todd-Hewitt culture medium containing GBS C388/90 (Ia/c) suspension adjusted to $2.1 \times 10^6$ cfu;
[5]not done;
[6]intraperitoneal challenge with 1 mL Todd-Hewitt culture medium containing GBS NCS246 (II/R) suspension adjusted to $1.2 \times 10^5$ cfu.

In another experiment, one group of 12 mice corresponding to a control group was injected with PBS, while a second group of 12 mice was immunized with formaldehyde killed whole cells of GBS strain C388/90 (Ia/c). Six mice from each of these two groups were challenged with 2.1×10⁶ cfu of the GBS strain C388/90 (Ia/c) (Table I). As the first challenge experiment, all mice immunized with the GBS strain C388/90 (Ia/c) survived the homologous challenge. Only two out of the 6 mice injected with PBS survived the infection.

The remaining 6 mice in both groups were then used one week later to verify whether this antigenic preparation could confer cross protection against strain NCS246 (II/R) which produce a serologically distinct capsule. None of the mice infected with this second GBS strain survived the infection. The later result suggested that most of the protective immune response induced by formaldehyde killed strain C388/90 is directed against the capsular polysaccharide and that it could be restricted to strains of that particular serotype. These results clearly indicated that this particular model of infection can be efficiently used to study the protection conferred by vaccination.

EXAMPLE 3

Immunization of Rabbit With Formaldehyde Killed Whole GBS Cells and Passive Protection in Mice A New Zealand rabbit (2.5 kg, Charles River, St-Constant, Québec, Canada) was immunized with formaldehyde killed cells of GBS strain C388/90 (Ia/c) to obtain hyperimmune serum. This rabbit was injected subcutaneously three times at three weeks interval with approximately 1.5×10⁹ cfu of formaldehyde killed whole cells of GBS strain C388/90 (Ia/c). Freund's complete adjuvant (Gibco BRL Life Technologies, Grand Island, N.Y.) was used as the adjuvant for the first immunization, while Freund's incomplete adjuvant (Gibco BRL) was used for the following two injections. Serum samples were obtained before the beginning of the immunization protocol and two weeks after the last injection. The sera were frozen at −20° C.

The ability of this particular rabbit hyperimmune serum to passively protect mice against a lethal infection with GBS was also evaluated. Intraperitoneal injection of mice with either 15 or 25 μL of hyperimmune rabbit serum 18 hours before the challenge protected 4 out of 5 mice (80%) against the infection. Comparatively, survival rates lower than 20% were recorded for mice in the control group injected with PBS or serum obtained from a rabbit immunized with meningococcal outer membrane preparation. This result clearly indicates that the immunization of another animal species with killed GBS cells can induce the production of antibodies that can passively protect mice. This reagent will also be used to characterize clones.

TABLE 2

Passive protection of CD-1 mice conferred by rabbit serum obtained after immunization with formaldehyde killed group B whole *streptococci* (strain C388/90 (Ia/c)) antigenic preparation

| groups | number of living mice 14 days after the bacterial challenge with GBS strain C388/90 (Ia/c)² | % survival |
|---|---|---|
| rabbit hyperimmune serum² -25 μl | 4/5 | 80 |
| rabbit hyperimmune serum¹ -15 μl | 4/5 | 80 |

TABLE 2-continued

Passive protection of CD-1 mice conferred by rabbit serum obtained after immunization with formaldehyde killed group B whole *streptococci* (strain C388/90 (Ia/c)) antigenic preparation

| groups | number of living mice 14 days after the bacterial challenge with GBS strain C388/90 (Ia/c)² | % survival |
|---|---|---|
| control rabbit serum -25 μl | 1/5 | 20 |
| control PBS | 1/10 | 10 |

¹Freund's complete adjuvant was used for first immunization, and Freund's incomplete adjuvant for the following two injections;
²intraperitoneal challenge with 1 ml Todd-Hewitt culture medium containing GBS C388/90 (Ia/c) suspension adjusted to 2 × 10⁴ cfu.

EXAMPLE 4

Recombinant Production of His.Tag-GBS Fusion Protein

The coding region of a GBS gene was amplified by PCR (DNA Thermal Cycler GeneAmp PCR system 2400 Perkin Elmer, San Jose, Calif.) from the genomic DNA of GBS strain C388/90 (Ia/c) using the oligos that contained base extensions for the addition of the restriction sites BglII (AGATCT) and HindIII (AAGCTT), respectively. The PCR product was purified from agarose gel using a QIAEX® II gel extraction kit from QIAGEN® (Chatsworth, Calif.), digested with the restriction enzymes BglII and HindIII (Pharmacia Canada Inc Baie d'Urfe, Canada), and extracted with phenol:chloroform before ethanol precipitation. The pET-32b(+) vector (Novagen, Madison, Wis.) containing the thioredoxin-His.Tag sequence was digested with the restriction enzymes BglII and HindIII, extracted with phenol:chloroform, and then ethanol precipitated. The BglII-HindIII genomic DNA fragment was ligated to the BglII-HindIII pET-32b(+) vector to create the coding sequence for thioredoxin-His.Tag-GBS fusion protein whose gene was under control of the T7 promoter. The ligated products were transformed into *E. coli* strain XLI Blue MRF' (Δ(mcrA)183Δ (mcrCB-hsdSMR-mrr) 173 endA1 supE44 thi-1 recA1 gyrA96 relA1. lac [F' proAB lacI$^q$ΔM15Tn10 (Tet$^r$)]$^c$) (Stratagene, La Jolla, Calif.) according to the method of Simanis (Hanahan, D. DNA Cloning, 1985, D. M. Glover (ed.), pp. 109-135 which is herein incorporated by reference). The recombinant pET plasmid was purified using a QIAGEN® kit (QIAGEN, Chatsworth, Calif.) and the nucleotide sequence of the DNA insert was verified by DNA sequencing (Taq Dye Deoxy Terminator Cycle Sequencing kit, ABI, Foster City, Calif.). The recombinant pET plasmid was transformed by electroporation (Gene Pulser II apparatus, BIO-RAD Labs, Mississauga, Canada) into *E. coli* strain AD494 (DE3) (Δara⁻leu797 ΔlacX74 ΔphoA PvuII phoR ΔmalF3 F' [lac⁺ (lacI$^q$) pro] trxB::Kan (DE3)) (Novagen, Madison, Wis.). In this strain of *E. coli*, the T7 promoter controlling expression of the fusion protein, is specifically recognized by the T7 RNA polymerase (present on the λDE3 prophage) whose gene is under the control of the lac promoter which is inducible by isopropyl-β-D-thio-galactopyranoside (IPTG).

The transformant AD494(DE3)/rpET was grown at 37° C. with agitation at 250 rpm in LB broth (peptone 10 g/L, Yeast extract 5 g/L, NaCl 10 g/L) containing 100 μg of ampicillin (Sigma-Aldrich Canada Ltd., Oakville, Canada) per mL until the A₆₀₀ reached a value of 0.6. In order to induce the production of the thioredoxin-His.Tag-GBS fusion protein, the cells were incubated for 2 additional hours in the presence of IPTG at a final concentration of 1 mM. The bacterial cells were harvested by centrifugation.

The recombinant fusion protein produced by AD494 (DE3)/rpET32 upon IPTG induction for 2 h was partially obtained as insoluble inclusion bodies which were purified from endogenous *E. coli* proteins by the isolation of insoluble aggregates (Gerlach, G. F. et al 1992, Infect. Immun. 60:892). Induced cells from a 500 mL culture were resuspended in 20 mL of 25% sucrose-50 mM Tris-HCl buffer (pH 8.0) and frozen at −70° C. Lysis of cells in thawed suspension was achieved by the addition of 5 mL of a solution of lysozyme (10 mg/mL) in 250 mM Tris-HCl buffer (pH 8.0) followed by an incubation of 10 to 15 min on ice, and the addition of 150 mL of detergent mix (5 parts of 20 mM Tris-HCl buffer [pH 7.4]-300 mM NaCl-2% deoxycholic acid-2% Nonidet® P-40 (nonyphenylpolyethylene glycol) and 4 parts of 100 mM Tris-HCl buffer [pH 8]-50 mM EDTA-2% Triton® X-100 (octyl phenol ethoxylate)) followed by 5 min incubation on ice. Upon sonication, protein aggregates were harvested by centrifugation for 30 min at 35,000×g and a sample of the soluble cellular fraction was kept. The aggregated proteins were solubilized in 6M guanidine hydrochloride. The presence of the fusion protein in both the soluble and insoluble fractions was shown by Western Blot analysis using the serum of a mouse injected with formaldehyde killed cells of GBS strain C388/90 (Ia/c) that survived a bacterial challenge with the corresponding GBS strain.

The purification of the fusion protein from the soluble fraction of IPTG-induced AD494(DE3)/rpET was done by affinity chromatography based on the properties of the His.Tag sequence (6 consecutive histidine residues) to bind to divalent cations ($Ni^{2+}$) immobilized on the His.Bind metal chelation resin (Novagen, Madison, Wis.). The purification method used are those described in the pET system Manual, 6th Edition (Novagen, Madison, Wis.) which is herein incorporated by reference. Briefly, the pelleted cells obtained from a 100 mL culture induced with IPTG was resuspended in 4 mL of Binding buffer (5 mM imidazole-500 mM NaCl-20 mM Tris-HCl pH 7.9), sonicated, and spun at 39,000×g for 20 min to remove debris. The supernatant was filtered (0.45 μm pore size membrane) and deposited on a column of His.Bind resin equilibrated in Binding buffer. The column was then washed with 10 column volumes of Binding buffer followed by 6 column volumes of Wash buffer (20 mM imidazole-500 mM NaCl-20 mM Tris-HCl pH 7.9). The thioredoxin-His.Tag-GBS fusion protein was eluted with Elute buffer (1M imidazole-500 mM NaCl-20 mM Tris-HCl pH 7.9). The removal of the salt and imidazole from the sample was done by dialysis against 3×1 liter PBS at 4° C.

The quantities of fusion protein obtained from either the soluble or insoluble cytoplasmic fractions of *E. coli* were estimated by Coomassie staining of a sodium dodecyl sulfate (SDS)-polyacrylamide gel with serial dilutions of these proteins and a bovine serum albumin standard (Pierce Chemical Co. Rockford, Ill.).

EXAMPLE 5

Recombinant Production of GBS Protein Under Control of Lambda PL Promoter

The DNA coding region of a GBS protein was inserted downstream of the promoter $\lambda P_L$ into the translation vector pURV22. This plasmid was derived from p629 (George et al, 1987, Bio/Technology 5:600) from which the coding region for a portion of the herpes simplex virus type I (HSV-I) glycoprotein (gD-1) was removed and the ampicillin resistance gene replaced by a kanamycin cassette obtained from the plasmid vector pUC4 K (Pharmacia Biotech Canada Inc., Baie D'Urfe, Canada). The vector contained a cassette of the bacteriophage. λ cI857 temperature sensitive repressor gene from which the functional $P_R$ promoter had been deleted. The inactivation of the cI857 repressor by temperature increase from the ranges of 30-37° C. to 37-42° C. resulted in the induction of the gene under the control of λ $P_L$. The translation of the gene was controlled by the ribosome binding site cro followed downstream by a BglII restriction site (AGATCT) and the ATG: ACTAAGGAGGTTAGATCTATG (SEQ ID NO:45).

Restriction enzymes and T4 DNA ligase were used according to suppliers (Pharmacia Biotech Canada Inc., Baie D'Urfe, Canada; and New England Biolabs Ltd., Mississauga, Canada). Agarose gel electrophoresis of DNA fragments was performed as described by Sambrook et al. (Molecular cloning A laboratory Manual, 1989, Cold Spring Harbor Laboratory Press, N.Y which is herein incorporated by reference) Chromosomal DNA of the GBS bacteria was prepared according to procedures described in Jayarao et al (J. Clin. Microbiol., 1991, 29:2774 which is herein incorporated by reference). DNA amplification reactions by polymerase chain reaction (PCR) were made using DNA Thermal Cycler GeneAmp® PCR system 2400 (Perkin Elmer, San Jose, Calif.). Plasmids used for DNA sequencing were purified using plasmid kits from QIAGEN (Chatsworth, Calif.). DNA fragments were purified from agarose gels using QIAEX II gel extraction kits from QIAGEN (Chatsworth, Calif.). Plasmid transformations were carried out by the method described by Hanahan (*DNA Cloning*, Glover (ed.) pp, 109-135, 1985 which is herein incorporated by reference). The sequencing of genomic DNA inserts in plasmids was done using synthetic oligonucleotides which were synthesized by oligonucleotide synthesizer model 394 (the Perkin-Elmer Corp., Applied Biosystems Div. (ABI), Foster City, Calif.). The sequencing reactions were carried out by PCR using the Taq Dye Deoxy Terminator Cycle Sequencing kit (ABI, Foster City, Calif.) and DNA electrophoresis was performed on automated DNA sequencer 373A (ABI, Foster City, Calif.). The assembly of the DNA sequence was performed using the program Sequencer 3.0 (Gene Codes Corporation, Ann Arbor, Mich.). Analysis of the DNA sequences and their predicted polypeptides was performed with the program Gene Works® version 2.45 (Intelligenetics, Inc., Mountain View Calif.).

The coding region of the GBS gene was amplified by PCR from GBS strain C388/90 (Ia/c) genomic DNA using oligos that contained base extensions for the addition of restriction sites BglII (AGATCT) and XbaI(TCTAGA), respectively. The PCR product was purified from agarose gel using a QIAEX II gel extraction kit from QIAGEN (Chatsworth, Calif.), digested with the restriction enzymes BglII and XbaI, and extracted with phenol:chloroform before ethanol precipitation. The pURV22 vector was digested with the restriction enzymes BglII and XbaI, extracted with phenol:chloroform, and ethanol precipitated. The BglII-XbaI genomic DNA fragment was ligated to the BglII-XbaI pURV22 vector in which the GBS gene was under the control of the λPL promoter. The ligated products were transformed into *E. coli* strain XLI Blue MRF' (Δ(mcrA)183Δ(mcrCB-hsdSMR-mrr)173 endA1 supE44 thi-1 recA1 gyrA96 relA1 lac[F' proAB laCI$^q$ZΔM15 Tn10 (Tet$^r$)]$^c$) (Stratagene, La Jolla Calif.) according to the methods described in Hanahan, supra. Transformants harboring plasmids with the insert were identified by analysis of lysed cells submitted to electrophoresis on agarose gel (Sambrook et al, supra). The recombinant pURV22 plasmid was purified using a QIAGEN kit (QIAGEN, Chatsworth, Calif.) and the nucleotide sequence of the DNA insert was verified by DNA sequencing.

The transformant XLI Blue MRF'/rpURV22 was grown at 34° C. with agitation at 250 rpm in LB broth containing 50%g of kanamycin per mL until the $A_{00}$ reached a value of 0.6. In order to induce the production of the fusion protein, the cells were incubated for 4 additional hours at 39° C. The bacterial cells were harvested by centrifugation resuspended in sample buffer, boiled for 10 min and kept at −20° C.

EXAMPLE 6

Subcloning GBS Protein Gene in CMV Plasmid pCMV-GH

The DNA coding region of a GBS protein was inserted in phase downstream of the human growth hormone (hGH) gene which was under the transcriptional control of the cytomegalovirus (CMV) promoter in the plasmid vector pCMV-GH (Tang et al, Nature, 1992, 356:152). The CMV promoter is non functional in *E. coli* cells but active upon administration of the plasmid in eukaryotic cells. The vector also incorporated the ampicillin resistance gene.

The coding region of the gene was amplified by PCR from genomic DNA of GBS strain C388/90 (Ia/c) using the oligos that contained base extensions for the addition of the restriction sites BglII (AGATCT) and HindIII (AAGCTT). The PCR product was purified from agarose gel using a QIAEX II gel extraction kit from QIAGEN (Chatsworth, Calif.), digested with the restriction enzymes BglII and HindIII, and extracted with phenol:chloroform before ethanol precipitation. The pCMV-GH vector (Laboratory of Dr. Stephen A. Johnston, Department of Biochemistry, The University of Texas, Dallas, Tex.) containing the human growth hormone to create fusion proteins was digested with the restriction enzymes BamHI and HindIII, extracted with phenol:chloroform, and ethanol precipitated. The 1.3-kb BglII-HindIII genomic DNA fragment was ligated to the BamHI-HindIII pCMV-GH vector to create the hGH-GBS fusion protein under the control of the CMV promoter. The ligated products were transformed into *E. coli* strain DH5α [φ80 lacZ ΔM15 endA1 recA1 hsdR17 ($^r$K$^{-m}$K$^+$) supE44 thi-1λ$^-$ gyrA96 relA1 Δ(lacZYA-argF)U169] (Gibco BRL, Gaithersburg, Md.) according to the methods described by Hanahan, supra. Transformants harboring plasmids with the insert were identified by analysis of lysed cells submitted to electrophoresis on agarose gel (Sambrook, J. et al, supra). The recombinant pCMV plasmid was purified using a QIAGEN kit (QIAGEN, Chatsworth, Calif.) and the nucleotide sequence of the DNA insert was verified by DNA sequencing.

EXAMPLE 7

Immunological Activity of GBS Protein to GBS Challenge

Four groups of 12 female CD-1 mice (Charles River, St-Constant, Quebec, Canada) of 6 to 8 weeks were injected subcutaneously three times at three week intervals with 0.1 mL of the following antigenic preparations: formaldehyde killed cells of GBS strain C388/90 (~6×10$^7$ cfu), 20 μg of thioredoxin-His.Tag-GBS fusion protein obtained from the insoluble (inclusion bodies) or 20 μg of the fusion protein, affinity-purified (nickel column), from the soluble cytoplasmic fraction in *E. coli*, or 20 μg of affinity purified (nickel column) thioredoxin-His.Tag control polypeptide. 20 μg of QuilA™ (Cedarlane Laboratories Ltd, Hornby, Canada) was added to each antigenic preparation as the adjuvant. Serum samples were obtained from each mouse before immunization (PB) and on days 20 (TB1), 41 (TB2) and 54 (TB3) during the immunization protocols. Sera were frozen at −20° C.

An increase of the ELISA titers was recorded after each injection of the fusion protein indicating a good primary response and a boost of the specific humoral immune response after each of the second and third administration. At the end of the immunization period, the means of reciprocal ELISA titers was 456,145 for the group immunized with 20%g of fusion protein obtained from inclusion bodies compared to 290,133 for the group of mice immunized with the protein from soluble fraction in *E. coli*. The latter result suggests that the protein obtained from inclusion bodies could be more immunogenic than the soluble protein. Analysis of mice sera in ELISA using the affinity purified thioredoxin-His.Tag to coat plates showed that negligible antibody titers are made against the thioredoxin-His.Tag portion of the fusion protein. The reactivity of the sera from mice injected with the recombinant fusion protein was also tested by ELISA against formaldehyde killed whole cells of GBS strain C388/90. The antibodies induced by immunization with recombinant fusion protein also recognized their specific epitopes on GBS cells indicating that their conformation is close enough to the native *streptococcal* protein to induce cross-reactive antibodies.

To verify whether the immune response induced by immunization could protect against GBS infection, mice were challenged with 3.5×10$^5$ cfu of GBS strains C338/90(Ia/c) and 1.2×10$^5$ cfu of strain NCS246 (II/R) the results of which are illustrated in tables 3 and 4 respectively. Mice immunized with control thioredoxin-His.Tag peptide were not protected against challenge with either GBS strain while those immunized with formaldehyde killed C388/90 whole cells only provided protection against homologous challenge. The thioredoxin-His.Tag-GBS fusion protein of the invention protected mice from challenge with both GBS strains. Blood and spleen culture of these mice did not reveal the presence of any GBS.

TABLE 3

Survival from GBS strain C388/90 (Ia/c) challenge[1]

| immunizing agent | no. mice surviving challenge | % survival |
|---|---|---|
| thioredoxin-His.Tag[2] | 1/6 | 17 |
| formaldehyde killed C388/90 cells[3] | 6/6 | 100 |
| thioredoxin-His.Tag-GBS fusion (inclusion body preparation)[4] | 6/6 | 100 |
| thioredoxin-His.Tag-GBs fusion (cytoplasmic fraction)[4] | 6/6 | 100 |

[1]intraperitoneal administration with 1 ml Todd Hewitt culture medium adjusted to 3.5 × 10$^5$ cfu;
[2]20 μg administered; posterior legs paralyzed in surviving mouse; GBS detected in blood and spleen;
[3]6 × 10$^7$ cfu administered;
[4]20 μg administered.

TABLE 4

Survival from GBS strain NCS246 (II/R) challenge[1]

| immunizing agent | no. mice surviving challenge | % survival |
|---|---|---|
| thioredoxin-His.Tag[2] | 0/6 | 0 |
| formaldehyde killed C388/90 cells[3] | 2/6 | 34 |

TABLE 4-continued

Survival from GBS strain NCS246 (II/R) challenge[1]

| immunizing agent | no. mice surviving challenge | % survival |
|---|---|---|
| thioredoxin-His.Tag-GBS fusion (inclusion body preparation)[2] | 5/5[4] | 100 |
| thioredoxin-His.Tag-GBS fusion (cytoplasmic fraction)[2] | 6/6 | 100 |

[1]intraperitoneal administration with 1 ml Todd-Hewitt culture medium containing GBS NCS246(II/R) suspension adjusted to $1.2 \times 10^5$ cfu.
[2]20 μg administered;
[3]$6 \times 10^7$ cfu administered;
[4]one mouse died during immunization.

EXAMPLE 8

Immunization With Recombinant GBS Protein Confers Protection Against Experimental GBS Infection This example illustrates the protection of mice against fatal GBS infection by immunization with the recombinant protein corresponding to the SEQ ID NO:39.

Groups of 10 female CD-1 mice (Charles River) were immunized subcutaneously three times at three-week intervals with 20 μg of recombinant protein purified from *E. coli* strain BLR (Novagen®) harboring the recombinant pURV22 plasmid vector containing the GBS gene corresponding to SEQ ID NO:42 in presence of 20 μg of QuilA™ adjuvant (Cedarlane Laboratories Ltd/Hornby, Canada) or, as control, with QuilA™ adjuvant alone in ?BS. Blood samples were collected from the orbital sinus on day 1, 22 and 43 prior to each immunization and fourteen days (day 57) following the third injection. One week later the mice were challenged with approximately $10^4$ to $10^6$ CFU of various virulent GBS strains. Samples of the GBS challenge inoculum were plated on TSA/5% sheep blood agar plates to determine the CFU and to verify the challenge dose. Deaths were recorded for a period of 14 days and on day 14 post-challenge, the surviving mice were sacrificed and blood and spleen were tested for the presence of GBS organisms. The survival data are shown in table 5.

Prechallenge sera were analyzed for the presence of antibodies reactive with GBS by standard immunoassays. Elisa and immunoblot analyses indicated that immunization with recombinant GBS protein produced in *E. coli* elicited antibodies reactive with both, recombinant and native GBS protein. Antibody responses to GBS are described in Example 9.

TABLE 5

Ability of recombinant GBS protein corresponding to SEQ ID NO: 39 to elicit protection against 8 diverse CBS challenge strains

| Immunogen | Challenge strain Designation | Type | No. alive:No. dead[1] | |
|---|---|---|---|---|
| rGBS protein | C388/90 | Ia/c | 8:2 | (P < 0.0001) |
| none | | | 0:10 | |
| rGBS protein | NCS 246 | II/R | 10:0 | (P = 0.0012) |
| none | | | 3:7 | |
| rGBS protein | ATCC12401 | Ib | 10:0 | (P = 0.001) |
| none | | | 3:7 | |
| rGBS protein | NCS 535 | V | 10:0 | (P = 0.01) |
| none | | | 5:5 | |
| rGBS protein | NCS 9842 | VI | 10:0 | (P < 0.0001) |
| none | | | 0:10 | |
| rGBS protein NCS 915-F[3] | NCS 915 | III | 7:3 1:9 | (P = 0.0007)[2] |
| none | | | 4:6 | |
| rGBS protein NCS 954-F | NCS 954 | III/R | 7:3 4:6 | (P = 0.002) |
| none | | | 1:9 | |
| rGBS protein COH1-F | COH1 | III | 4:6 3:7 | (P = 0.0004) |
| none | | | 0:10 | |

[1]Groups of 10 mice per group were used, the number of mice surviving to infection and the number of dead mice are indicated. The survival curves corresponding to recombinant GBS protein-immunized animals were compared to the survival curves corresponding to mock-immunized animals using the log-rank test for nonparametric analysis.
[2]Comparison analysis to NCS915-F-immunized animals.
[3]Animals were immunized with formaldehyde-killed GBS in presence of QuilA ™ adjuvant.

All hemocultures from surviving mice were negative at day 14 post-challenge. Spleen cultures from surviving mice were negative except for few mice from experiment MB-11.

EXAMPLE 9

Vaccination With the Recombinant GBS Protein Elicits an Immune Response to GBS

Groups of 10 female CD-1 mice were immunized subcutaneously with recombinant GBS protein corresponding to SEQ ID NO:39 as described in Example 8. In order to assess the antibody response to native GBS protein, sera from blood samples collected prior each immunization and fourteen days after the third immunization were tested for antibody reactive with GBS cells by ELISA using plates coated with formaldehyde-killed GBS cells from type III strain NCS 954, type Ib strain ATCC12401, type V strain NCS 535 or type VI strain NCS 9842. The specificity of the raised antibodies for GBS protein was confirmed by Western blot analyses to GBS cell extracts and purified recombinant antigens. The results shown in FIG. 10 clearly demonstrate that animals respond strongly to recombinant GBS protein used as immunogens with median reciprocal antibody titers varying between 12000 and 128000, for sera collected after the third immunization, depending of the coating antigen. All preimmune sera were negative when tested at a dilution of 1:100. GBS-reactive antibodies were detectable in the sera of each animal after a single injection of recombinant GBS protein.

EXAMPLE 10

Antigenic Conservation of the GBS Protein of the Present Invention

Monoclonal antibodies (MAbs) specific to the GBS protein of the present invention were used to demonstrate that this surface antigen is produced by all GBS and that it is also antigenically highly conserved.

A collection of 68 GBS isolates was used to evaluate the reactivity of the GBS-specific MAbs. These strains were obtained from the National Center for *Streptococcus*, Provincial Laboratory of Public Health for Northern Alberta, Canada; Centre Hospitalier Universitaire de Quebec, Pavillon CHUL, Quebec, Canada; American Type Culture Collection, USA; Laboratoire de Sante Publique du Quebec, Canada; and Dept. of Infectious Disease, Children's Hospital and Medical Center, Seattle, USA. All eight Mabs were tested against the following panel of strains: 6 isolates of serotype Ia or Ia/c, 3 isolates of serotype Ib, 4 isolates of serotype II, 14 isolates of serotype III, 2 isolates of serotype IV, 2 isolates of serotype V, 2 isolates of serotype VI, 2 isolates of serotype VII, 1 isolate of serotype VIII, 10 isolates that were not serotyped and 3 bovine *S. agalactiae* strains. MAb 3A2 was also reacted with additional GBS: 9 isolates of serotype Ia/c and 10 isolates of serotype V. The strains were grown overnight on blood agar plates at 37° C. in an atmosphere of 5% $CO_2$. Cultures were stored at −70° C. in heart infusion broth with 20% (v/v) glycerol.

To obtain the GBS protein-specific MAbs, mice were immunized three times at three-week intervals with 20 μg of purified recombinant GBS protein (SEQ ID NO:44) in the presence of 20% QuilA™ adjuvant. Hybridoma cell lines were generated by fusion of spleen cells recovered from immunized mice with the nonsecreting SP2/O myeloma cell line as described previously (Hamel, J. et al. 1987. J. Med. Microbiol. 23:163-170 which is herein incorporated by reference). Hybrid clone supernatants were tested for specific antibody production by ELISA using formaldehyde inactivated GBS and purified recombinant GBS protein (SEQ ID NO:39 or 44) as coating antigen, as previously described (Hamel, J. et al. 1987. J. Med. Microbiol. 23:163-170). Specific hybrid were cloned by limiting dilutions, expanded, and frozen in liquid nitrogen. Production of recombinant GBS protein was presented in Examples 4 & 5. Purified recombinant GBS protein or formaldehyde inactivated GBS were resolved by electrophoresis by using the discontinuous buffer system of Laemmli as recommended by the manufacturer and then transfer onto nitrocellulose membrane for Western immunoblotting as described previously (Martin et al. 1992. Infect. Immun. 60:2718-2725 which is herein incorporated by reference).

Western immunoblotting experiments clearly indicated that all eight MAbs recognized a protein band that corresponded to the purified recombinant GBS protein (SEQ ID NO:39). These MAbs also reacted with a protein band present in every GBS isolates tested so far. The reactivity of these GBS-specific MAbs are presented in Table 6. Each MAb reacted well with all 46 GBS. In addition, these MAbs also recognized the 3 *S. agalactiae* strains of bovine origin that were tested. MAb 3A2 also recognized nineteen GBS; 9 isolates of serotype Ia/c and 10 of serotype V. The other MAbs were not tested against these additional strains.

These results demonstrated that the GBS protein (SEQ ID NO:39) was produced by all the 65 GBS and the three 3 *S. agalactiae* strains of bovine origin that were tested so far.

More importantly, these results clearly demonstrated that the epitopes recognized by these eight GBS-specific MAbs were widely distributed and conserved among GBS. These results also indicated that these epitopes were not restricted to serologically related isolates since representatives of all known GBS serotypes including the major disease causing groups were tested.

In conclusion, the data presented in this example clearly demonstrated that the GBS protein of the present invention is produced by all GBS and that it is antigenically highly conserved.

TABLE 6

Reactivity of eight GBS protein-specific MAbs with different *S. agalactiae* strains as evaluated by Western immunoblots.

Number of each serotype of *s. agalactiae* strains recognized by the MAbs.

| Mabs | Ia or Ia/c (6) | Ib (3) | II (4) | III (4) | IV (2) | V (2) | VI (2) | VII (2) | VIII (1) | NT (10)[2] | TOTAL (26) | Bovine (3) |
|---|---|---|---|---|---|---|---|---|---|---|---|---|
| 3A2[1] | 6 | 3 | 4 | 4 | 2 | 2 | 2 | 2 | 1 | 10 | 46 | 3 |
| 5A12 | 6 | 3 | 4 | 4 | 2 | 2 | 2 | 2 | 1 | 10 | 46 | 3 |
| 6G11 | 6 | 3 | 4 | 4 | 2 | 2 | 2 | 2 | 1 | 10 | 46 | 2 |
| 8B9 | 6 | 3 | 4 | 4 | 2 | 2 | 2 | 2 | 1 | 10 | 46 | 3 |
| 8E11 | 6 | 3 | 4 | 4 | 2 | 2 | 2 | 2 | 1 | 10 | 46 | 3 |
| 12B12 | 6 | 3 | 4 | 4 | 2 | 2 | 2 | 2 | 1 | 10 | 46 | 3 |
| 18F11 | 6 | 3 | 4 | 4 | 2 | 2 | 2 | 2 | 1 | 10 | 46 | 3 |
| 20G2 | 6 | 3 | 4 | 4 | 2 | 2 | 2 | 2 | 1 | 10 | 46 | 3 |

[1]Nine additional strains of serotype Ia/c and 10 strains of serotype V were recognized by MAb 3A2.
[2]These strains were not serotyped

SEQUENCE LISTING

<160> NUMBER OF SEQ ID NOS: 51

<210> SEQ ID NO 1
<211> LENGTH: 4514
<212> TYPE: DNA
<213> ORGANISM: Group B Streptococcus

<400> SEQUENCE: 1

```
tatctggcaa agagccagct aatcgtttta gttgggctaa aaataaatta ttaatcaatg      60
gattcattgc aactctagca gcaactatct tattttttgc agttcaattc ataggtctta     120
```

```
aaccagatta ccctggaaaa acctacttta ttatcctatt gacagcatgg actttgatgg    180
cattagtaac tgctttagtg ggatgggata ataggtatgg ttccttcttg tcgttattaa    240
tattattatt ccagcttggt tcaagcgcag gaacttaccc aatagaattg agtcctaagt    300
tctttcaaac aattcaacca tttttaccga tgacttactc tgtttcagga ttaagagaga    360
ccatctcgtt gacgggagac gttaaccatc aatggagaat gctagtaatc ttttagtat     420 catcgatgat acttgctctt cttatttatc gtaaacaaga agattaatag aaagtatcta    480
gtgatagact aacagtatga tatggtatgt caaagtattt aggaggagaa gatatgtcta    540
ctttaacaat aattattgca acattaactg ctttggaaca ttttatatt atgtatttgg      600 agacgttagc cacccagtca aatatgactg ggaagatttt tagtatgtct aaagaagagt    660
tgtcatattt acccgttatt aaactttta agaatcaagg tgtatacaac ggcttgattg      720
gcctattcct cctttatggg ttatatattt cacagaatca agaaattgta gctgtttttt     780
taatcaatgt attgctagtt gctatttatg gtgctttgac agttgataaa aaaatcttat    840
taaaacaggg tggtttacct atattagctc ttttaacatt cttattttaa tactacttag    900
ccgttcgatt tagttgaacg gcttttagta atcatttttt tctcataata caggtagttt    960
aagtaatttg tctttaaaaa tagtataata taactacgaa ttcaaagaga ggtgactttg    1020
attatgactg agaactggtt acatactaaa gatggttcag atatttatta tcgtgtcgtt   1080
ggtcaaggtc aaccgattgt ttttttacat ggcaatagct taagtagtcg ctattttgat   1140
aagcaaatag catattttc taagtattac caagttattg ttatggatag tagagggcat    1200
ggcaaaagtc atgcaaagct aaataccatt agtttcaggc aaatagcagt tgacttaaag   1260
gatatcttag ttcatttaga gattgataaa gttatattgg taggccatag cgatggtgcc   1320
aatttagctt tagttttttca aacgatgttt ccaggtatgg ttagagggct tttgcttaat   1380
tcagggaacc tgactattca tggtcagcga tggtgggata ttcttttagt aaggattgcc   1440
tataaattcc ttcactattt agggaaactc ttttccgtata tgaggcaaaa agctcaagtt   1500
atttcgctta tgttggagga tttgaagatt agtccagctg atttacagca tgtgtcaact   1560
cctgtaatgg ttttggttgg aaataaggac ataattaagt taaatcattc taagaaactt   1620
gcttcttatt ttccaagggg ggagttttat tctttagttg gctttgggca tcacattatt   1680
aagcaagatt cccatgtttt taatattatt gcaaaaagt ttatcaacga tacgttgaaa    1740
ggagaaattg ttgaaaaagc taattgaaaa agtcaaatca ctgacttctg tgattaaaat   1800
tgtatttttt atatctgttt tagtgcttat tattgttgaa atgattcatt tgaaacgaac   1860
tatttctgtt gagcaactaa agagtgtttt tgggcaatta tctccaatga atcttttctt   1920
aattatcctt gtgggggtta tcgctgtctt accgacaacc ggatatgact ttgtactgaa   1980
tggactttta cgtacagata aaagcaaaag gtatatttta cagactagtt ggtgtatcaa   2040 cactttaat aacttgtcag gattcggtgg cttaatcgat attgggttgc gcatggcttt   2100
ttatggtaaa aaaggtcaag agaagagtga cctaagagaa gtgactcgtt ttttacccta   2160
tcttatttct ggtctgtcat ttattagtgt gattgcctta atcatgagcc atattttca    2220 tgccaaagct agtgttgatt actattattt ggtattaatt ggtgctagta tgtattttcc   2280
tgttatttat tggatttctg gtcataaagg aagccattat ttcggagata tgccatctag   2340
tactcgtata aaattaggtg ttgttctctt ttttgaatgg ggatgtgcgg ccgcagcatt   2400
tataattatc ggttatttaa tgggcattca tctaccagtt tataaatttt taccactatt   2460
ttgtattggt tgtgccgtcg ggattgtatc ccttattccc ggtggattag aagttttga   2520
```

```
attagttcta tttacagggt tgctgccga gggactacct aaagaaactg tggttgcatg    2580
gttattactt tatcgtttag cctactatat tattccattc tttgcaggta tctatttctt    2640
tatccattat ttaggtagtc aaataaatca acgttatgaa aatgtcccga aagagttagt    2700
atcaactgtt ctacaaacca tggtgagcca tttgatgcgt attttaggtg cattcttaat    2760
attttcaaca gcattttttg aaaatattac ttatattatg tggttgcaga agctaggctt    2820
ggacccatta caagaacaaa tgttatggca gtttccaggt ttattgctgg gggtttgttt    2880
tattctctta gctagaacta ttgatcaaaa agtgaaaaat gcttttccaa ttgctattat    2940
ctggattact ttgacattgt tttatcttaa tttaggtcat attagttggc gactatcttt    3000
ctggtttatt ttactattgt taggcttatt agtcattaag ccaactctct ataaaaaaca    3060
atttatttat agctgggaag agcgtattaa ggatggaatc attatcgtta gtttaatggg    3120 agttctatt tatattgcag gactactatt ccctatcagg gctcatatta caggtggtag    3180
tattgaacgc ctgcattata tcatagcatg ggagccgata gcattggcta cgttgattct    3240
tactctcgtt tatttatgtt tggttaagat tttacaagga aaatcttgtc agattggtga    3300
tgtgttcaat gtggatcgtt ataaaaaact acttcaagct tacggtggtt cttcggatag    3360
cggtttagcc ttttttaaatg ataaaaggct ctactggtac caaaaaaatg gagaagattg    3420
cgttgcgttc caatttgtaa ttgtcaataa taaatgtctt attatggggg aaccagccgg    3480
tgatgacact tatattcgtg aagctattga atcgtttatt gatgatgctg ataagctaga    3540
ctatgacctt gttttttaca gtattggaca gaagttgaca ctacttttac atgagtatgg    3600
ttttgacttt atgaaagttg gtgaggatgc tttagttaat ttagaaacgt ttactcttaa    3660
agggaataag tacaaacctt tcagaaatgc cctaaataga gttgaaaagg atggtttcta    3720
tttcgaagtt gtacaatcgc cacatagtca agagctacta aatagtttgg aagagatttc    3780
taatacttgg ttagaaggac gtcctgaaaa aggtttctca ctaggatatt ttaataaaga    3840
ttatttccaa caagccccaa tagctttggt aaaaaatgct gaacacgaag ttgttgcttt    3900
tgctaatatt atgccaaact atgaaaagag tattatctct attgatttaa tgcgtcacga    3960
taaacagaaa attccgaatg gcgttatgga tttcctcttt ttatcattat tctcttatta    4020
tcaagagaag ggataccact attttgattt ggggatggca cctttatcag gagttggtcg    4080
cgttgaaaca gtttttgcta aagagagaat ggcgtatctt gtctatcatt tcggtagtca    4140
tttctactca tttaatggtt tacacaagta taagaagaag tttacaccat gtggtcgga    4200 acgttatatt tcttgttctc gttcgtcctg gttaatttgt gctatttgtg ccctattaat    4260
ggaagatagt aaaattaaga ttgttaaata agctttattt ggcaattaaa aagagcatgt    4320
catgcgacat gctcttttta aatcatttaa taccattgat tgcttgaatc tactttataa    4380
tatgatgtgc ttttaaatat tgtttagcta ctgtagctgc tgatttatgc tttacagcta    4440
cttggtagtt catttcttgc atttcttttt cagtgatatg accagcaagt ttattgagag    4500 cttttttttac ttga                                                     4514
```

<210> SEQ ID NO 2
<211> LENGTH: 154
<212> TYPE: PRT
<213> ORGANISM: Group B streptococcus

```
<400> SEQUENCE: 2

Ser Gly Lys Glu Pro Ala Asn Arg Phe Ser Trp Ala Lys Asn Lys Leu
 1               5                  10                  15

Leu Ile Asn Gly Phe Ile Ala Thr Leu Ala Ala Thr Ile Leu Phe Phe
             20                  25                  30

Ala Val Gln Phe Ile Gly Leu Lys Pro Asp Tyr Pro Gly Lys Thr Tyr
         35                  40                  45

Phe Ile Ile Leu Leu Thr Ala Trp Thr Leu Met Ala Leu Val Thr Ala
     50                  55                  60

Leu Val Gly Trp Asp Asn Arg Tyr Gly Ser Phe Leu Ser Leu Leu Ile
65                  70                  75                  80

Leu Leu Phe Gln Leu Gly Ser Ser Ala Gly Thr Tyr Pro Ile Glu Leu
                 85                  90                  95

Ser Pro Lys Phe Phe Gln Thr Ile Gln Pro Phe Leu Pro Met Thr Tyr
            100                 105                 110

Ser Val Ser Gly Leu Arg Glu Thr Ile Ser Leu Thr Gly Asp Val Asn
            115                 120                 125

His Gln Trp Arg Met Leu Val Ile Phe Leu Val Ser Ser Met Ile Leu
        130                 135                 140

Ala Leu Leu Ile Tyr Arg Lys Gln Glu Asp
145                 150

<210> SEQ ID NO 3
<211> LENGTH: 118
<212> TYPE: PRT
<213> ORGANISM: Group B streptococcus

<400> SEQUENCE: 3

Met Ser Thr Leu Thr Ile Ile Ala Thr Leu Thr Ala Leu Glu His
 1               5                  10                  15

Phe Tyr Ile Met Tyr Leu Glu Thr Leu Ala Thr Gln Ser Asn Met Thr
             20                  25                  30

Gly Lys Ile Phe Ser Met Ser Lys Glu Glu Leu Ser Tyr Leu Pro Val
         35                  40                  45

Ile Lys Leu Phe Lys Asn Gln Gly Val Tyr Asn Gly Leu Ile Gly Leu
     50                  55                  60

Phe Leu Leu Tyr Gly Leu Tyr Ile Ser Gln Asn Gln Glu Ile Val Ala
65                  70                  75                  80

Val Phe Leu Ile Asn Val Leu Leu Val Ala Ile Tyr Gly Ala Leu Thr
                 85                  90                  95

Val Asp Lys Lys Ile Leu Leu Lys Gln Gly Gly Leu Pro Ile Leu Ala
            100                 105                 110

Leu Leu Thr Phe Leu Phe
        115

<210> SEQ ID NO 4
<211> LENGTH: 247
<212> TYPE: PRT
<213> ORGANISM: Group B streptococcus

<400> SEQUENCE: 4

Met Thr Glu Asn Trp Leu His Thr Lys Asp Gly Ser Asp Ile Tyr Tyr
 1               5                  10                  15

Arg Val Val Gly Gln Gly Gln Pro Ile Val Phe Leu His Gly Asn Ser
             20                  25                  30

Leu Ser Ser Arg Tyr Phe Asp Lys Gln Ile Ala Tyr Phe Ser Lys Tyr
         35                  40                  45
```

```
Tyr Gln Val Ile Val Met Asp Ser Arg Gly His Gly Lys Ser His Ala
 50                  55                  60

Lys Leu Asn Thr Ile Ser Phe Arg Gln Ile Ala Val Asp Leu Lys Asp
 65                  70                  75                  80

Ile Leu Val His Leu Glu Ile Asp Lys Val Ile Leu Val Gly His Ser
                 85                  90                  95

Asp Gly Ala Asn Leu Ala Leu Val Phe Gln Thr Met Phe Pro Gly Met
                100                 105                 110

Val Arg Gly Leu Leu Asn Ser Gly Asn Leu Thr Ile His Gly Gln
                115                 120                 125

Arg Trp Trp Asp Ile Leu Leu Val Arg Ile Ala Tyr Lys Phe Leu His
            130                 135                 140

Tyr Leu Gly Lys Leu Phe Pro Tyr Met Arg Gln Lys Ala Gln Val Ile
145                 150                 155                 160

Ser Leu Met Leu Glu Asp Leu Lys Ile Ser Pro Ala Asp Leu Gln His
                165                 170                 175

Val Ser Thr Pro Val Met Val Leu Val Gly Asn Lys Asp Ile Ile Lys
                180                 185                 190

Leu Asn His Ser Lys Lys Leu Ala Ser Tyr Phe Pro Arg Gly Glu Phe
            195                 200                 205

Tyr Ser Leu Val Gly Phe Gly His His Ile Ile Lys Gln Asp Ser His
            210                 215                 220

Val Phe Asn Ile Ile Ala Lys Lys Phe Ile Asn Asp Thr Leu Lys Gly
225                 230                 235                 240

Glu Ile Val Glu Lys Ala Asn
                245

<210> SEQ ID NO 5
<211> LENGTH: 816
<212> TYPE: PRT
<213> ORGANISM: Group B streptococcus

<400> SEQUENCE: 5

Met Ile His Leu Lys Arg Thr Ile Ser Val Glu Gln Leu Lys Ser Val
  1               5                  10                  15

Phe Gly Gln Leu Ser Pro Met Asn Leu Phe Leu Ile Ile Leu Val Gly
                 20                  25                  30

Val Ile Ala Val Leu Pro Thr Thr Gly Tyr Asp Phe Val Leu Asn Gly
             35                  40                  45

Leu Leu Arg Thr Asp Lys Ser Lys Arg Tyr Ile Leu Gln Thr Ser Trp
 50                  55                  60

Cys Ile Asn Thr Phe Asn Asn Leu Ser Gly Phe Gly Gly Leu Ile Asp
 65                  70                  75                  80

Ile Gly Leu Arg Met Ala Phe Tyr Gly Lys Lys Gly Gln Glu Lys Ser
                 85                  90                  95

Asp Leu Arg Glu Val Thr Arg Phe Leu Pro Tyr Leu Ile Ser Gly Leu
                100                 105                 110

Ser Phe Ile Ser Val Ile Ala Leu Ile Met Ser His Ile Phe His Ala
            115                 120                 125

Lys Ala Ser Val Asp Tyr Tyr Leu Val Leu Ile Gly Ala Ser Met
            130                 135                 140

Tyr Phe Pro Val Ile Tyr Trp Ile Ser Gly His Lys Gly Ser His Tyr
145                 150                 155                 160

Phe Gly Asp Met Pro Ser Ser Thr Arg Ile Lys Leu Gly Val Val Ser
                165                 170                 175
```

-continued

```
Phe Phe Glu Trp Gly Cys Ala Ala Ala Phe Ile Ile Gly Tyr
            180                 185                 190

Leu Met Gly Ile His Leu Pro Val Tyr Lys Ile Leu Pro Leu Phe Cys
        195                 200                 205

Ile Gly Cys Ala Val Gly Ile Val Ser Leu Ile Pro Gly Gly Leu Gly
    210                 215                 220

Ser Phe Glu Leu Val Leu Phe Thr Gly Phe Ala Ala Glu Gly Leu Pro
225                 230                 235                 240

Lys Glu Thr Val Val Ala Trp Leu Leu Leu Tyr Arg Leu Ala Tyr Tyr
                245                 250                 255

Ile Ile Pro Phe Phe Ala Gly Ile Tyr Phe Phe Ile His Tyr Leu Gly
            260                 265                 270

Ser Gln Ile Asn Gln Arg Tyr Glu Asn Val Pro Lys Glu Leu Val Ser
        275                 280                 285

Thr Val Leu Gln Thr Met Val Ser His Leu Met Arg Ile Leu Gly Ala
    290                 295                 300

Phe Leu Ile Phe Ser Thr Ala Phe Phe Glu Asn Ile Thr Tyr Ile Met
305                 310                 315                 320

Trp Leu Gln Lys Leu Gly Leu Asp Pro Leu Gln Glu Gln Met Leu Trp
                325                 330                 335

Gln Phe Pro Gly Leu Leu Leu Gly Val Cys Phe Ile Leu Leu Ala Arg
            340                 345                 350

Thr Ile Asp Gln Lys Val Lys Asn Ala Phe Pro Ile Ala Ile Ile Trp
        355                 360                 365

Ile Thr Leu Thr Leu Phe Tyr Leu Asn Leu Gly His Ile Ser Trp Arg
    370                 375                 380

Leu Ser Phe Trp Phe Ile Leu Leu Leu Gly Leu Leu Val Ile Lys
385                 390                 395                 400

Pro Thr Leu Tyr Lys Lys Gln Phe Ile Tyr Ser Trp Glu Glu Arg Ile
                405                 410                 415

Lys Asp Gly Ile Ile Ile Val Ser Leu Met Gly Val Leu Phe Tyr Ile
            420                 425                 430

Ala Gly Leu Leu Phe Pro Ile Arg Ala His Ile Thr Gly Gly Ser Ile
        435                 440                 445

Glu Arg Leu His Tyr Ile Ile Ala Trp Glu Pro Ile Ala Leu Ala Thr
    450                 455                 460

Leu Ile Leu Thr Leu Val Tyr Leu Cys Leu Val Lys Ile Leu Gln Gly
465                 470                 475                 480

Lys Ser Cys Gln Ile Gly Asp Val Phe Asn Val Asp Arg Tyr Lys Lys
                485                 490                 495

Leu Leu Gln Ala Tyr Gly Gly Ser Ser Asp Ser Gly Leu Ala Phe Leu
            500                 505                 510

Asn Asp Lys Arg Leu Tyr Trp Tyr Gln Lys Asn Gly Glu Asp Cys Val
        515                 520                 525

Ala Phe Gln Phe Val Ile Val Asn Asn Lys Cys Leu Ile Met Gly Glu
    530                 535                 540

Pro Ala Gly Asp Asp Thr Tyr Ile Arg Glu Ala Ile Glu Ser Phe Ile
545                 550                 555                 560

Asp Asp Ala Asp Lys Leu Asp Tyr Asp Leu Val Phe Tyr Ser Ile Gly
                565                 570                 575

Gln Lys Leu Thr Leu Leu Leu His Glu Tyr Gly Phe Asp Phe Met Lys
            580                 585                 590

Val Gly Glu Asp Ala Leu Val Asn Leu Glu Thr Phe Thr Leu Lys Gly
        595                 600                 605
```

```
Asn Lys Tyr Lys Pro Phe Arg Asn Ala Leu Asn Arg Val Glu Lys Asp
        610                 615                 620

Gly Phe Tyr Phe Glu Val Val Gln Ser Pro His Ser Gln Glu Leu Leu
625                 630                 635                 640

Asn Ser Leu Glu Glu Ile Ser Asn Thr Trp Leu Glu Gly Arg Pro Glu
                645                 650                 655

Lys Gly Phe Ser Leu Gly Tyr Phe Asn Lys Asp Tyr Phe Gln Gln Ala
                660                 665                 670

Pro Ile Ala Leu Val Lys Asn Ala Glu His Glu Val Val Ala Phe Ala
        675                 680                 685

Asn Ile Met Pro Asn Tyr Glu Lys Ser Ile Ile Ser Ile Asp Leu Met
        690                 695                 700

Arg His Asp Lys Gln Lys Ile Pro Asn Gly Val Met Asp Phe Leu Phe
705                 710                 715                 720

Leu Ser Leu Phe Ser Tyr Tyr Gln Glu Lys Gly Tyr His Tyr Phe Asp
                725                 730                 735

Leu Gly Met Ala Pro Leu Ser Gly Val Gly Arg Val Glu Thr Ser Phe
                740                 745                 750

Ala Lys Glu Arg Met Ala Tyr Leu Val Tyr His Phe Gly Ser His Phe
        755                 760                 765

Tyr Ser Phe Asn Gly Leu His Lys Tyr Lys Lys Phe Thr Pro Leu
        770                 775                 780

Trp Ser Glu Arg Tyr Ile Ser Cys Ser Arg Ser Ser Trp Leu Ile Cys
785                 790                 795                 800

Ala Ile Cys Ala Leu Leu Met Glu Asp Ser Lys Ile Lys Ile Val Lys
                805                 810                 815

<210> SEQ ID NO 6
<211> LENGTH: 518
<212> TYPE: PRT
<213> ORGANISM: Group B streptococcus

<400> SEQUENCE: 6

Met Arg Ile Leu Gly Ala Phe Leu Ile Phe Ser Thr Ala Phe Phe Glu
1               5                   10                  15

Asn Ile Thr Tyr Ile Met Trp Leu Gln Lys Leu Gly Leu Asp Pro Leu
                20                  25                  30

Gln Glu Gln Met Leu Trp Gln Phe Pro Gly Leu Leu Leu Gly Val Cys
            35                  40                  45

Phe Ile Leu Leu Ala Arg Thr Ile Asp Gln Lys Val Lys Asn Ala Phe
        50                  55                  60

Pro Ile Ala Ile Ile Trp Ile Thr Leu Thr Leu Phe Tyr Leu Asn Leu
65              70                  75                  80

Gly His Ile Ser Trp Arg Leu Ser Phe Trp Phe Ile Leu Leu Leu Leu
                85                  90                  95

Gly Leu Leu Val Ile Lys Pro Thr Leu Tyr Lys Lys Gln Phe Ile Tyr
                100                 105                 110

Ser Trp Glu Glu Arg Ile Lys Asp Gly Ile Ile Val Ser Leu Met
            115                 120                 125

Gly Val Leu Phe Tyr Ile Ala Gly Leu Leu Phe Pro Ile Arg Ala His
        130                 135                 140

Ile Thr Gly Gly Ser Ile Glu Arg Leu His Tyr Ile Ile Ala Trp Glu
145                 150                 155                 160

Pro Ile Ala Leu Ala Thr Leu Ile Leu Thr Leu Val Tyr Leu Cys Leu
                165                 170                 175
```

```
Val Lys Ile Leu Gln Gly Lys Ser Cys Gln Ile Gly Asp Val Phe Asn
            180                 185                 190

Val Asp Arg Tyr Lys Lys Leu Leu Gln Ala Tyr Gly Ser Ser Asp
            195                 200                 205

Ser Gly Leu Ala Phe Leu Asn Asp Lys Arg Leu Tyr Trp Tyr Gln Lys
    210                 215                 220

Asn Gly Glu Asp Cys Val Ala Phe Gln Phe Val Ile Val Asn Asn Lys
225                 230                 235                 240

Cys Leu Ile Met Gly Glu Pro Ala Gly Asp Asp Thr Tyr Ile Arg Glu
                245                 250                 255

Ala Ile Glu Ser Phe Ile Asp Asp Ala Asp Lys Leu Asp Tyr Asp Leu
            260                 265                 270

Val Phe Tyr Ser Ile Gly Gln Lys Leu Thr Leu Leu Leu His Glu Tyr
            275                 280                 285

Gly Phe Asp Phe Met Lys Val Gly Glu Asp Ala Leu Val Asn Leu Glu
            290                 295                 300

Thr Phe Thr Leu Lys Gly Asn Lys Tyr Lys Pro Phe Arg Asn Ala Leu
305                 310                 315                 320

Asn Arg Val Glu Lys Asp Gly Phe Tyr Phe Glu Val Val Gln Ser Pro
                325                 330                 335

His Ser Gln Glu Leu Leu Asn Ser Leu Glu Glu Ile Ser Asn Thr Trp
            340                 345                 350

Leu Glu Gly Arg Pro Glu Lys Gly Phe Ser Leu Gly Tyr Phe Asn Lys
            355                 360                 365

Asp Tyr Phe Gln Gln Ala Pro Ile Ala Leu Val Lys Asn Ala Glu His
            370                 375                 380

Glu Val Val Ala Phe Ala Asn Ile Met Pro Asn Tyr Glu Lys Ser Ile
385                 390                 395                 400

Ile Ser Ile Asp Leu Met Arg His Asp Lys Gln Lys Ile Pro Asn Gly
                405                 410                 415

Val Met Asp Phe Leu Phe Leu Ser Leu Phe Ser Tyr Tyr Gln Glu Lys
            420                 425                 430

Gly Tyr His Tyr Phe Asp Leu Gly Met Ala Pro Leu Ser Gly Val Gly
            435                 440                 445

Arg Val Glu Thr Ser Phe Ala Lys Glu Arg Met Ala Tyr Leu Val Tyr
            450                 455                 460

His Phe Gly Ser His Phe Tyr Ser Phe Asn Gly Leu His Lys Tyr Lys
465                 470                 475                 480

Lys Lys Phe Thr Pro Leu Trp Ser Glu Arg Tyr Ile Ser Cys Ser Arg
                485                 490                 495

Ser Ser Trp Leu Ile Cys Ala Ile Cys Ala Leu Leu Met Glu Asp Ser
            500                 505                 510

Lys Ile Lys Ile Val Lys
            515

<210> SEQ ID NO 7
<211> LENGTH: 5126
<212> TYPE: DNA
<213> ORGANISM: Group B streptococcus

<400> SEQUENCE: 7
aattttgata tcgaaacaac aactttgag gcaatgaaaa agcacgcgtc attattggag      60
aaaatatctg ttgagcgttc ttttattgaa tttgataaac ttctattagc accttattgg    120
cgtaaaggaa tgctggcact aatagatagt catgctttta attatctacc atgcttaaaa    180
```

```
aatagggaat tacaattaag cgccttttig tcccagttag ataaagattt tttatttgag    240
acatcagaac aagcttgggc atcactcatc ttgagtatgg aagttgaaca cacaaagact    300
tttttaaaaa aatggaagac atcaactcac tttcaaaaag atgttgagca tatagtggat    360
gtttatcgta ttcgtgaaca aatgggattg gctaaagaac atctttatcg ttatggaaaa    420
actataataa aacaagcgga aggtattcgc aaagcaagag gcttgatggt tgatttcgaa    480
aaaatagaac aactagatag tgagttagca atccatgata ggcatgagat agttgtcaat    540
ggtggcacct taatcaagaa attaggaata aaacctggtc cacagatggg agatattatc    600
tctcaaattg aattagccat tgttttagga caactgatta tgaagaaga ggctatttta     660 cattttgtta agcagtactt gatggattag agaggattat atgagcgatt ttttagtaga    720
tggattgact aagtcggttg gtgataagac ggtctttagt aatgtttcat ttatcatcca    780
tagtttagac cgtattggga ttattggtgt caatggaact ggaaagacaa cactattaga    840
tgttatttcg ggtgaattag gttttgatgg tgatcgttcc ccttttttcat cagctaatga   900 ttataagatt gcttatttaa aacaagaacc agactttgat gattctcaga caattttgga    960
caccgtactt tcttctgact taagagagat ggctttaatt aaagaatatg aattattgct   1020
taatcactac gaagaaagta agcaatcacg tctagagaaa gtaatggcag aaatggattc   1080
tttagatgct tggtctattg agagcgaagt caaaacagta ttatccaaat taggtattac   1140
tgatttgcag ttgtcggttg gtgaattatc aggaggatta cgaagacgtg ttcaattagc   1200
gcaagtatta ttaaatgatg cagatttatt gctcttagac gaacctacta accacttaga   1260
tattgacact attgcatggt taacgaattt tttgaaaaat agtaaaaaga cagtgctttt   1320
tataactcat gatcgttatt ttctagacaa tgttgcaaca cgtattttg aattagataa    1380 ggcacagatt acagaatatc aaggcaatta tcaggattat gtccgacttc gtgcagaaca   1440
agacgagcgt gatgctgcta gtttacataa aaagaaacag ctttataaac aggaactagc   1500
ttggatgcgt actcagccac aagctcgtgc aacgaaacaa caggctcgta ttaatcgttt   1560
tcaaaatcta aaaaacgatt tacaccaaac aagcgataca agcgatttgg aaatgacatt   1620
tgaaacaagt cgaattggga aaaaggttat taattttgaa aatgtctctt tttcttaccc   1680
agataaatct atcttgaaag actttaattt gttaattcaa aataaagacc gtattggcat   1740
cgttggagat aatggtgttg gaaagtcaac cttacttaat ttaattgttc aagatttaca   1800
gccggattcg ggtaatgtct ctattggtga acgatacgt gtaggttact tttcacaaca    1860
acttcataat atggatggct caaaacgtgt tattaattat ttgcaagagg ttgcagatga   1920
ggttaaaact agtgtcggta caacaagtgt gacagaacta ttggaacaat ttctctttcc   1980
acgttcgaca catggaacac aaattgcaaa attatcaggt ggtgagaaaa aaagacttta   2040
ccttttaaaa atcctgattg aaaagcctaa tgtgttacta cttgatgagc cgacaaatga   2100
cttagatatt gctacattaa ctgttcttga aaattttta caaggctttg gtggtcctgt    2160
gattacagtt agtcacgatc gttactttt agataaagtg gctaataaaa ttattgcgtt    2220
tgaagataac gatatccgtg aatttttgg taattatact gattatttag atgaaaaagc    2280
atttaatgag caaataatg aagttatcag taaaaaagag agtaccaaga caagtcgtga    2340
aaagcaaagt cgtaaaagaa tgtcttactt tgaaaaacaa gaatgggcga caattgaaga   2400
cgatattatg atattggaaa atactatcac tcgtatagaa aatgatatgc aaacatgtgg   2460
tagtgatttt acaaggttat ctgatttaca aaaggaatta gatgcaaaaa atgaagcact   2520
tctagaaaag tatgaccgtt atgagtacct tagtgagtta gacacatgat tatccgtccg   2580
```

```
attattaaaa atgatgacca agcagttgca caattaattc gacaaagttt acgcgcctat      2640
gatttagata aacctgatac agcatattca gaccctcact tagatcattt gacctcatac      2700
tacgaaaaaa tagagaagtc aggattcttt gtcattgagg agagagatga gattattggc      2760
tgtggcggct ttggtccgct gaaaaatcta attgcagaga tgcagaaggt gtacattgca      2820
gaacgtttcc gtggtaaggg gcttgctact gatttagtga aaatgattga agtagaagct      2880
cgaaaaattg ggtatagaca actttattta gagacagcca gtactttgag tagggcaact      2940
gcggtttata agcatatggg atattgtgcc ttatcgcaac caatagcaaa tgatcaaggt      3000
catacagcta tggatatttg gatgattaaa gatttataag ttgaaagtgg attagtgaac      3060
atggattaat tattttgaga taagaggaaa gaaaaggaga catatatggc atatatttgg      3120
tcttatttga aaaggtaccc caattggtta tggcttgatt tactaggagc tatgcttttt      3180
gtgacggtta tcctaggaat gcccacagcc ttagcgggta tgattgataa tggcgttaca      3240
aaaggtgatc ggactggagt ttatctgtgg acgttcatca tgtttatatt tgttgtacta      3300
ggtattattg ggcgtattac gatggcttac gcatctagtc gcttaacgac aacaatgatt      3360
agagatatgc gtaatgatat gtatgctaag cttcaagaat actcccatca tgaatatgaa      3420
cagataggtg tatcttcact agtgacacgt atgacaagcg atacttttgt tttgatgcaa      3480
tttgctgaaa tgtctttacg tttaggccta gtaactccta tggtaatgat ttttagcgtg      3540
gttatgatac taattacgag tccatctttg gcttggcttg tagcggttgc gatgcctctt      3600
ttggtaggag tcgttttata tgtagctata aaaacaaaac ctttatctga agacaacag       3660 actatgcttg ataaaatcaa tcaatatgtt cgtgaaaatt taacagggtt acgcgttgtt      3720
agagcctttg caagagagaa ttttcaatca caaaaatttc aagtcgctaa ccaacgttac      3780
acagatactt caactggtct ttttaaatta acagggctaa cagaaccact tttcgttcaa      3840
attattattg caatgattgt ggctatcgtt tggtttgctt tggatccctt acaaagaggt      3900
gctattaaaa taggggattt agttgctttt atcgaatata gcttccatgc tctcttttca      3960 ttttgctat ttgccaatct ttttactatg tatcctcgta tggtggtatc aagccatcgt      4020
attagagagg tgatggatat gccaatctct atcaatccta atgccgaagg tgttacggat      4080
acgaaactta aagggcattt agaatttgat aatgtaacat cgcttatcc aggagaaaca      4140 gagagtcccg ttttgcatga tatttctttt aaagctaagc ctggagaaac aattgctttt      4200
attggttcaa caggttcagg aaaatcttct cttgttaatt tgattccacg ttttatgat       4260 gtgacacttg gaaaaatctt agtagatgga gttgatgtaa gagattataa ccttaaatca      4320
cttcgccaaa agattggatt tatcccccaa aaagctcttt tatttacagg gacaatagga      4380
gagaatttaa aatatggaaa agctgatgct actattgatg atcttagaca agcggttgat      4440
atttctcaag ctaaagagtt tattgagagt caccaagaag cctttgaaac gcatttagct      4500
gaaggtggga gcaatctttc tgggggtcaa aacaacggt  tatctattgc tagggctgtt      4560
gttaaagatc cagatttata tattttgat gattcatttt ctgctctcga ttataagaca       4620
gacgctactt taagagcgcg tctaaaagaa gtaaccggtg attctacagt tttgatagtt      4680
gctcaaaggg tgggtacgat tatggatgct gatcagatta ttgtccttga tgaaggcgaa      4740
attgtcggtc gtggtaccca cgctcaatta atagaaaata tgctatttta tcgtgaaatc      4800
gctgagtcac aactgaagaa ccaaaactta tcagaaggag agtgattgta tgagaaaaaa      4860
atctgttttt ttgagattat ggtcttacct aactcgctac aaagctactc ttttcttagc      4920 gattttttg aaagttttat ctagtttat gagtgttctg gagcctttta ttttagggtt        4980
```

```
agcgataaca gagttgactg ctaaccttgt tgatatggct aagggagttt ctggggcaga    5040
attgaacgtt ccttatattg ctggtatttt gattatttat tttttcagag gtgttttcta    5100
tgaattaggt tcttatggct caaatt                                          5126
```

<210> SEQ ID NO 8
<211> LENGTH: 229
<212> TYPE: PRT
<213> ORGANISM: Group B streptococcus

<400> SEQUENCE: 8

```
Asn Phe Asp Ile Glu Thr Thr Phe Glu Ala Met Lys Lys His Ala
  1               5                  10                  15

Ser Leu Leu Glu Lys Ile Ser Val Glu Arg Ser Phe Ile Glu Phe Asp
             20                  25                  30

Lys Leu Leu Leu Ala Pro Tyr Trp Arg Lys Gly Met Leu Ala Leu Ile
         35                  40                  45

Asp Ser His Ala Phe Asn Tyr Leu Pro Cys Leu Lys Asn Arg Glu Leu
     50                  55                  60

Gln Leu Ser Ala Phe Leu Ser Gln Leu Asp Lys Asp Phe Leu Phe Glu
 65                  70                  75                  80

Thr Ser Glu Gln Ala Trp Ala Ser Leu Ile Leu Ser Met Glu Val Glu
                 85                  90                  95

His Thr Lys Thr Phe Leu Lys Lys Trp Lys Thr Ser Thr His Phe Gln
            100                 105                 110

Lys Asp Val Glu His Ile Val Asp Val Tyr Arg Ile Arg Glu Gln Met
        115                 120                 125

Gly Leu Ala Lys Glu His Leu Tyr Arg Tyr Gly Lys Thr Ile Ile Lys
    130                 135                 140

Gln Ala Glu Gly Ile Arg Lys Ala Arg Gly Leu Met Val Asp Phe Glu
145                 150                 155                 160

Lys Ile Glu Gln Leu Asp Ser Glu Leu Ala Ile His Asp Arg His Glu
                165                 170                 175

Ile Val Val Asn Gly Gly Thr Leu Ile Lys Lys Leu Gly Ile Lys Pro
            180                 185                 190

Gly Pro Gln Met Gly Asp Ile Ile Ser Gln Ile Glu Leu Ala Ile Val
        195                 200                 205

Leu Gly Gln Leu Ile Asn Glu Glu Glu Ala Ile Leu His Phe Val Lys
    210                 215                 220

Gln Tyr Leu Met Asp
225
```

<210> SEQ ID NO 9
<211> LENGTH: 622
<212> TYPE: PRT
<213> ORGANISM: Group B streptococcus

<400> SEQUENCE: 9

```
Met Ser Asp Phe Leu Val Asp Gly Leu Thr Lys Ser Val Gly Asp Lys
  1               5                  10                  15

Thr Val Phe Ser Asn Val Ser Phe Ile Ile His Ser Leu Asp Arg Ile
             20                  25                  30

Gly Ile Ile Gly Val Asn Gly Thr Gly Lys Thr Thr Leu Leu Asp Val
         35                  40                  45

Ile Ser Gly Glu Leu Gly Phe Asp Gly Asp Arg Ser Pro Phe Ser Ser
     50                  55                  60
```

-continued

```
Ala Asn Asp Tyr Lys Ile Ala Tyr Leu Lys Gln Glu Pro Asp Phe Asp
 65                  70                  75                  80

Asp Ser Gln Thr Ile Leu Asp Thr Val Leu Ser Ser Asp Leu Arg Glu
                 85                  90                  95

Met Ala Leu Ile Lys Glu Tyr Glu Leu Leu Asn His Tyr Glu Glu
            100                 105                 110

Ser Lys Gln Ser Arg Leu Glu Lys Val Met Ala Glu Met Asp Ser Leu
            115                 120                 125

Asp Ala Trp Ser Ile Glu Ser Glu Val Lys Thr Val Leu Ser Lys Leu
130                 135                 140

Gly Ile Thr Asp Leu Gln Leu Ser Val Gly Leu Ser Gly Gly Leu
145                 150                 155                 160

Arg Arg Arg Val Gln Leu Ala Gln Val Leu Leu Asn Asp Ala Asp Leu
                165                 170                 175

Leu Leu Leu Asp Glu Pro Thr Asn His Leu Asp Ile Asp Thr Ile Ala
                180                 185                 190

Trp Leu Thr Asn Phe Leu Lys Asn Ser Lys Lys Thr Val Leu Phe Ile
            195                 200                 205

Thr His Asp Arg Tyr Phe Leu Asp Asn Val Ala Thr Arg Ile Phe Glu
210                 215                 220

Leu Asp Lys Ala Gln Ile Thr Glu Tyr Gln Gly Asn Tyr Gln Asp Tyr
225                 230                 235                 240

Val Arg Leu Arg Ala Glu Gln Asp Glu Arg Asp Ala Ala Ser Leu His
                245                 250                 255

Lys Lys Lys Gln Leu Tyr Lys Gln Glu Leu Ala Trp Met Arg Thr Gln
            260                 265                 270

Pro Gln Ala Arg Ala Thr Lys Gln Gln Ala Arg Ile Asn Arg Phe Gln
            275                 280                 285

Asn Leu Lys Asn Asp Leu His Gln Thr Ser Asp Thr Ser Asp Leu Glu
            290                 295                 300

Met Thr Phe Glu Thr Ser Arg Ile Gly Lys Lys Val Ile Asn Phe Glu
305                 310                 315                 320

Asn Val Ser Phe Ser Tyr Pro Asp Lys Ser Ile Leu Lys Asp Phe Asn
                325                 330                 335

Leu Leu Ile Gln Asn Lys Asp Arg Ile Gly Ile Val Gly Asp Asn Gly
            340                 345                 350

Val Gly Lys Ser Thr Leu Leu Asn Leu Ile Val Gln Asp Leu Gln Pro
            355                 360                 365

Asp Ser Gly Asn Val Ser Ile Gly Glu Thr Ile Arg Val Gly Tyr Phe
370                 375                 380

Ser Gln Gln Leu His Asn Met Asp Gly Ser Lys Arg Val Ile Asn Tyr
385                 390                 395                 400

Leu Gln Glu Val Ala Asp Glu Val Lys Thr Ser Val Gly Thr Thr Ser
                405                 410                 415

Val Thr Glu Leu Leu Glu Gln Phe Leu Phe Pro Arg Ser Thr His Gly
            420                 425                 430

Thr Gln Ile Ala Lys Leu Ser Gly Gly Glu Lys Lys Arg Leu Tyr Leu
            435                 440                 445

Leu Lys Ile Leu Ile Glu Lys Pro Asn Val Leu Leu Leu Asp Glu Pro
450                 455                 460

Thr Asn Asp Leu Asp Ile Ala Thr Leu Thr Val Leu Glu Asn Phe Leu
465                 470                 475                 480

Gln Gly Phe Gly Gly Pro Val Ile Thr Val Ser His Asp Arg Tyr Phe
                485                 490                 495
```

```
Leu Asp Lys Val Ala Asn Lys Ile Ile Ala Phe Glu Asp Asn Asp Ile
            500                 505                 510

Arg Glu Phe Phe Gly Asn Tyr Thr Asp Tyr Leu Asp Glu Lys Ala Phe
            515                 520                 525

Asn Glu Gln Asn Glu Val Ile Ser Lys Lys Glu Ser Thr Lys Thr
            530                 535                 540

Ser Arg Glu Lys Gln Ser Arg Lys Arg Met Ser Tyr Phe Glu Lys Gln
545                 550                 555                 560

Glu Trp Ala Thr Ile Glu Asp Asp Ile Met Ile Leu Glu Asn Thr Ile
                565                 570                 575

Thr Arg Ile Glu Asn Asp Met Gln Thr Cys Gly Ser Asp Phe Thr Arg
            580                 585                 590

Leu Ser Asp Leu Gln Lys Glu Leu Asp Ala Lys Asn Glu Ala Leu Leu
            595                 600                 605

Glu Lys Tyr Asp Arg Tyr Glu Tyr Leu Ser Glu Leu Asp Thr
            610                 615                 620

<210> SEQ ID NO 10
<211> LENGTH: 157
<212> TYPE: PRT
<213> ORGANISM: Group B streptococcus

<400> SEQUENCE: 10

Met Ile Ile Arg Pro Ile Ile Lys Asn Asp Asp Gln Ala Val Ala Gln
  1               5                  10                  15

Leu Ile Arg Gln Ser Leu Arg Ala Tyr Asp Leu Asp Lys Pro Asp Thr
             20                  25                  30

Ala Tyr Ser Asp Pro His Leu Asp His Leu Thr Ser Tyr Tyr Glu Lys
         35                  40                  45

Ile Glu Lys Ser Gly Phe Phe Val Ile Glu Glu Arg Asp Glu Ile Ile
     50                  55                  60

Gly Cys Gly Gly Phe Gly Pro Leu Lys Asn Leu Ile Ala Glu Met Gln
 65                  70                  75                  80

Lys Val Tyr Ile Ala Glu Arg Phe Arg Gly Lys Gly Leu Ala Thr Asp
                 85                  90                  95

Leu Val Lys Met Ile Glu Val Glu Ala Arg Lys Ile Gly Tyr Arg Gln
            100                 105                 110

Leu Tyr Leu Glu Thr Ala Ser Thr Leu Ser Arg Ala Thr Ala Val Tyr
        115                 120                 125

Lys His Met Gly Tyr Cys Ala Leu Ser Gln Pro Ile Ala Asn Asp Gln
    130                 135                 140

Gly His Thr Ala Met Asp Ile Trp Met Ile Lys Asp Leu
145                 150                 155

<210> SEQ ID NO 11
<211> LENGTH: 579
<212> TYPE: PRT
<213> ORGANISM: Group B streptococcus

<400> SEQUENCE: 11

Met Ala Tyr Ile Trp Ser Tyr Leu Lys Arg Tyr Pro Asn Trp Leu Trp
  1               5                  10                  15

Leu Asp Leu Leu Gly Ala Met Leu Phe Val Thr Val Ile Leu Gly Met
             20                  25                  30

Pro Thr Ala Leu Ala Gly Met Ile Asp Asn Gly Val Thr Lys Gly Asp
         35                  40                  45
```

```
Arg Thr Gly Val Tyr Leu Trp Thr Phe Ile Met Phe Ile Phe Val Val
 50                  55                  60

Leu Gly Ile Ile Gly Arg Ile Thr Met Ala Tyr Ala Ser Ser Arg Leu
 65                  70                  75                  80

Thr Thr Thr Met Ile Arg Asp Met Arg Asn Asp Met Tyr Ala Lys Leu
                 85                  90                  95

Gln Glu Tyr Ser His His Glu Tyr Glu Gln Ile Gly Val Ser Ser Leu
            100                 105                 110

Val Thr Arg Met Thr Ser Asp Thr Phe Val Leu Met Gln Phe Ala Glu
            115                 120                 125

Met Ser Leu Arg Leu Gly Leu Val Thr Pro Met Val Met Ile Phe Ser
130                 135                 140

Val Val Met Ile Leu Ile Thr Ser Pro Ser Leu Ala Trp Leu Val Ala
145                 150                 155                 160

Val Ala Met Pro Leu Leu Val Gly Val Val Leu Tyr Val Ala Ile Lys
                165                 170                 175

Thr Lys Pro Leu Ser Glu Arg Gln Gln Thr Met Leu Asp Lys Ile Asn
                180                 185                 190

Gln Tyr Val Arg Glu Asn Leu Thr Gly Leu Arg Val Val Arg Ala Phe
            195                 200                 205

Ala Arg Glu Asn Phe Gln Ser Gln Lys Phe Gln Val Ala Asn Gln Arg
210                 215                 220

Tyr Thr Asp Thr Ser Thr Gly Leu Phe Lys Leu Thr Gly Leu Thr Glu
225                 230                 235                 240

Pro Leu Phe Val Gln Ile Ile Ala Met Ile Val Ala Ile Val Trp
                245                 250                 255

Phe Ala Leu Asp Pro Leu Gln Arg Gly Ala Ile Lys Ile Gly Asp Leu
                260                 265                 270

Val Ala Phe Ile Glu Tyr Ser Phe His Ala Leu Phe Ser Phe Leu Leu
            275                 280                 285

Phe Ala Asn Leu Phe Thr Met Tyr Pro Arg Met Val Val Ser Ser His
290                 295                 300

Arg Ile Arg Glu Val Met Asp Met Pro Ile Ser Ile Asn Pro Asn Ala
305                 310                 315                 320

Glu Gly Val Thr Asp Thr Lys Leu Lys Gly His Leu Glu Phe Asp Asn
                325                 330                 335

Val Thr Phe Ala Tyr Pro Gly Glu Thr Glu Ser Pro Val Leu His Asp
                340                 345                 350

Ile Ser Phe Lys Ala Lys Pro Gly Glu Thr Ile Ala Phe Ile Gly Ser
                355                 360                 365

Thr Gly Ser Gly Lys Ser Ser Leu Val Asn Leu Ile Pro Arg Phe Tyr
            370                 375                 380

Asp Val Thr Leu Gly Lys Ile Leu Val Asp Gly Val Asp Val Arg Asp
385                 390                 395                 400

Tyr Asn Leu Lys Ser Leu Arg Gln Lys Ile Gly Phe Ile Pro Gln Lys
                405                 410                 415

Ala Leu Leu Phe Thr Gly Thr Ile Gly Glu Asn Leu Lys Tyr Gly Lys
                420                 425                 430

Ala Asp Ala Thr Ile Asp Asp Leu Arg Gln Ala Val Asp Ile Ser Gln
            435                 440                 445

Ala Lys Glu Phe Ile Glu Ser His Gln Glu Ala Phe Glu Thr His Leu
            450                 455                 460

Ala Glu Gly Gly Ser Asn Leu Ser Gly Gly Gln Lys Gln Arg Leu Ser
465                 470                 475                 480
```

```
Ile Ala Arg Ala Val Val Lys Asp Pro Asp Leu Tyr Ile Phe Asp Asp
                485                 490                 495

Ser Phe Ser Ala Leu Asp Tyr Lys Thr Asp Ala Thr Leu Arg Ala Arg
            500                 505                 510

Leu Lys Glu Val Thr Gly Asp Ser Thr Val Leu Ile Val Ala Gln Arg
        515                 520                 525

Val Gly Thr Ile Met Asp Ala Asp Gln Ile Ile Val Leu Asp Glu Gly
    530                 535                 540

Glu Ile Val Gly Arg Gly Thr His Ala Gln Leu Ile Glu Asn Asn Ala
545                 550                 555                 560

Ile Tyr Arg Glu Ile Ala Glu Ser Gln Leu Lys Asn Gln Asn Leu Ser
                565                 570                 575

Glu Gly Glu

<210> SEQ ID NO 12
<211> LENGTH: 92
<212> TYPE: PRT
<213> ORGANISM: Group B streptococcus

<400> SEQUENCE: 12

Met Arg Lys Lys Ser Val Phe Leu Arg Leu Trp Ser Tyr Leu Thr Arg
1               5                   10                  15

Tyr Lys Ala Thr Leu Phe Leu Ala Ile Phe Leu Lys Val Leu Ser Ser
            20                  25                  30

Phe Met Ser Val Leu Glu Pro Phe Ile Leu Gly Leu Ala Ile Thr Glu
        35                  40                  45

Leu Thr Ala Asn Leu Val Asp Met Ala Lys Gly Val Ser Gly Ala Glu
    50                  55                  60

Leu Asn Val Pro Tyr Ile Ala Gly Ile Leu Ile Ile Tyr Phe Phe Arg
65                  70                  75                  80

Gly Val Phe Tyr Glu Leu Gly Ser Tyr Gly Ser Asn
                85                  90

<210> SEQ ID NO 13
<211> LENGTH: 5215
<212> TYPE: DNA
<213> ORGANISM: Group B streptococcus

<400> SEQUENCE: 13
aatttggaag tgctctatca acagttgaag taaaggagat tattagtgaa gaaaacatat      60
ggttatatcg gctcagttgc tgccatttta ctagctactc atattggaag ttaccaactt     120
ggtaagcatc atatgggtct agcaacaaag acaatcaga ttgcctatat tgatgacagc      180
aaaggtaagg caaagccccc taaaacaaac aaaacgatgg atcaaatcag tgctgaagaa     240
ggcatctctg ctgaacagat cgtagtcaaa attactgacc aaggctatgt gacctcacac     300
ggtgaccatt atcattttta caatgggaaa gttccttatg atgcgattat tagtgaagag     360
ttgttgatga cggatcctaa ttaccgtttt aaacaatcag acgttatcaa tgaaatctta     420
gacggttacg ttattaaagt caatggcaac tattatgttt acctcaagcc aggtagtaag     480
cgcaaaaaca ttcgaaccaa acaacaaatt gctgagcaag tagccaaagg aactaaagaa     540 gctaagaaa aaggtttagc tcaagtggcc catctcagta agaagaagt tgcggcagtc      600 aatgaagcaa aagacaagg acgctatact cagacgatg gctatatttt tagtccgaca      660
gatatcattg atgattagg agatgcttat ttagtacctc atggtaatca ctatcattat     720
attcctaaaa aggatttgtc tccaagtgag ctagctgctg cacaagccta ctggagtcaa     780
```

```
aaacaaggtc gaggtgctag accgtctgat taccgcccga caccagcccc aggtcgtagg      840
aaagccccaa ttcctgatgt gacgcctaac cctggacaag gtcatcagcc agataacggt      900
ggctatcatc cagcgcctcc taggccaaat gatgcgtcac aaaacaaaca ccaaagagat      960
gagtttaaag gaaaaacctt taaggaactt ttagatcaac tacaccgtct tgatttgaaa     1020
taccgtcatg tggaagaaga tgggttgatt tttgaaccga ctcaagtgat caaatcaaac     1080
gcttttgggt atgtggtgcc tcatggagat cattatcata ttatcccaag aagtcagtta     1140
tcacctcttg aaatggaatt agcagatcga tacttagctg ccaaactga ggacaatgac      1200 tcaggttcag agcactcaaa accatcagat aaagaagtga cacataccttt tcttggtcat    1260 cgcatcaaag cttacggaaa aggcttagat ggtaaaccat atgatacgag tgatgcttat     1320
gtttttagta aagaatccat tcattcagtg ataaatcag gagttacagc taaacacgga      1380
gatcatttcc actatatagg atttggagaa cttgaacaat atgagttgga tgaggtcgct     1440
aactgggtga agcaaaagg tcaagctgat gagcttgctg ctgctttgga tcaggaacaa      1500
ggcaaagaaa aaccactctt tgacactaaa aaagtgagtc gcaaagtaac aaaagatggt    1560
aaagtgggct atatgatgcc aaaagatggt aaggactatt tctatgctcg tgatcaactt    1620
gatttgactc agattgcctt tgccgaacaa gaactaatgc ttaaagataa gaagcattac    1680
cgttatgaca ttgttgacac aggtattgag ccacgacttg ctgtagatgt gtcaagtctg    1740
ccgatgcatg ctggtaatgc tacttacgat actggaagtt cgtttgttat cccacatatt    1800
gatcatatcc atgtcgttcc gtattcatgg ttgacgcgcg atcagattgc aacagtcaag    1860
tatgtgatgc aacaccccga agttcgtccg gatgtatggt ctaagccagg gcatgaagag    1920
tcaggttcgg tcattccaaa tgttacgcct cttgataaac gtgctggtat gccaaactgg    1980
caaattatcc attctgctga agaagttcaa aaagccctag cagaaggtcg ttttgcaaca    2040
ccagacggct atattttcga tccacgagat gttttggcca aagaaacttt tgtatggaaa    2100
gatggctcct ttagcatccc aagagcagat ggcagttcat tgagaaccat taataaatct   2160
gatctatccc aagctgagtg caacaagct caagagttat tggcaaagaa aaatactggt     2220
gatgctactg tatcggataa acccaaagaa agcaacagg cagataagag caatgaaaac     2280
caacagccaa gtgaagccag taaagaagaa aaagaatcag atgactttat agacagttta    2340
ccagactatg gtctagatag agcaacccta gaagatcata tcaatcaatt agcacaaaaa    2400
gctaatatcg atcctaagta tctcattttc caaccagaag gtgtccaatt ttataataaa    2460
aatggtgaat tggtaactta tgatatcaag acacttcaac aaataaaccc ttaaccaaaa    2520
gaagatctca ttgttaaagc actgctttgt caaagcaagt tacggtgatt ttgaagtcat    2580
tctatgtaac gagtagtgat aaaagttgga taatagcggt tttcttttgc aaagaaatgg    2640
tatccatgtt agaatagtaa aaaaagagga ggattcttgg actaatgtca aataagtaga    2700
cagaaaactg tgttatttta ttgcgttaaa ataattttct tctttctgat tagggggttag   2760 tcctagatta gccgtatgtg ggttgtaatt gttataaaaa ttctcaatgt attcaaagca    2820
gtctaattga acctgtttga tattttgata atgttttcgg ttgatttgtc tatgctttaa    2880
atacttgaaa aatgcttcag ttacggcatt atcataagga tatccaggat tagaaaaaga    2940
atgcatgata ttggcactgc accctaatag tgagacgcaa gaaaacact tttaggcaat     3000 cagttttctg tactgtacag gcgactggtc gtttaatctc tgttgaattc tagtttcatt    3060
ataaaatgta atgtaatttt taacaatatt tgttatacta tctttgttgt attttctcct    3120
```

-continued

```
attatggaaa taaaaggttt cagtctttag gacggtgtga aaccattcaa tacaggcatt      3180
atctgcaggt gttcctttc gagacattga gcggataatg tcttttccg tgcaagcctg       3240 gtagtaagcc atagaagtat acactgagcc ttggtcactg tgtaagattg ctcctttatt      3300
taggcaattt taactgatta agggtgtcta gtacaaaatc cgtgtcctga caatctgaga      3360
tagtgtaagc tataatttct cggttataga gattcataat tgatgagaga tacaatttac      3420
agttaccgaa atataggtag gtaatatctg ttacgagctt ttccttaggc ttatcggcat      3480
ggaaatcccg actcaattta ttatctgtta aataataagc tttacccaaa ttgggaactt      3540
tcttggtacg tgtccgacaa agccagccat tatttttcat gatacgatag actttctttg      3600
tattaacagt caatccgtgg atttttttga gcaatcgtgt aatggtacga tagccataaa      3660
taaagtgatt ctccatacag agctgttcaa ttaattcaat aaggtcatct ttttttgcgg      3720
cttctcatac tcctttttcc aacggtaata ggtcgaccgc ttgaccttaa aacagtctag      3780
aatgaaaact atcgggtagt tgttttata gtcttccaca agcttgataa gacttacttt      3840
atcgatttcc ttatcaagcc tcgatacttt tttaagaggt caacctgtaa ttgtaattgt      3900
tccacttcag acagatgttc caagccttta ccgtaggtat attgcttgcc aacaccttga      3960
tgaaaacgat aaagctcctc gttttcgtac catttcatcc aagtatagat ttgactatta      4020 ttttgatgc ctaaagtctc cataataact ctgttagact tgcctgcttt cttcatatcg       4080
atgcaagcca gcttagtttc ccatgaatat gcttttttaa ccataataaa acattcctgt      4140
ttctagttta ctaaatttca acaggagtgt ttttcttttg tctcattta gggattcagt       4200 gcctattgtt gtcatcaatt attttttctaa attccccgga cttaaattgt gacccttggt     4260
cggaatgaaa gagaagtgtt ccttcaatct ttctttatt aagtgaaaag gcaacacttt       4320
tctgtacaac atttataaag tgtttttcta ggcaattaat cttttagtca ttggtgtttg      4380
gtagttgaga ctaccatgaa tgcggtggta attccaccaa tgaacatagt ctttagtctt      4440
aagagctagt tcttccagca attgaaaggt ttcttgataa acaaattcaa ttttgaaagc      4500
acgatacgta ctttcagcta cggcattgtc ataaggataa ccagcctgac taagcgaacg      4560
tgtgattcca aaggcttcca atatttcatc aattaactga ttatcaaact ctttgccacg      4620
atctgaatgg aacatcttga ctttggtcag ggcgtaaggg atgctttgta tggcttgctt      4680
aacgagttca gcggtcttgt gccaaccaag agacaggccg atgatttcac ggttgtatag      4740
gtcaatgatg aggcaaacat aagcccaacg attgcctaca cgaacatagg ttaagtcagt      4800
gactaaggct tgtagtggtc tttcttgctt aaattgcctg tctaagtggt tgggaatagg      4860
ggcttcattc ttgcctctag aatgtggttt gaaggtggct ttctgataaa cagaaaccaa      4920
attgagtcgc ttcataatgc gtcgaatccg acgacgtgaa agtgtgatac cttcgttatt      4980
caagcatatt ttgattttc tggatccgta tctagactcg ctatcgagaa aaattctttt      5040
aatagtttct tcaaactccg tttcagatac tgactccacg gcttgatagt aataacttga      5100
gtgtggcata ttcagccagc gacacatctt tgaaatgctg tatttatcct tattagcagt      5160
gattatttcc cttttgtgc cataatcacc gctgcttgct ttaggatatc taatt            5215
```

<210> SEQ ID NO 14
<211> LENGTH: 40
<212> TYPE: PRT
<213> ORGANISM: Group B streptococcus -continued

```
<400> SEQUENCE: 14

Phe Gly Ser Ala Leu Ser Thr Val Glu Val Lys Glu Ile Ile Ser Glu
 1               5                  10                  15

Glu Asn Ile Trp Leu Tyr Arg Leu Ser Cys Cys His Phe Thr Ser Tyr
             20                  25                  30

Ser Tyr Trp Lys Leu Pro Thr Trp
         35                  40

<210> SEQ ID NO 15
<211> LENGTH: 793
<212> TYPE: PRT
<213> ORGANISM: Group B streptococcus

<400> SEQUENCE: 15

Met Gly Leu Ala Thr Lys Asp Asn Gln Ile Ala Tyr Ile Asp Asp Ser
 1               5                  10                  15

Lys Gly Lys Ala Lys Ala Pro Lys Thr Asn Lys Thr Met Asp Gln Ile
             20                  25                  30

Ser Ala Glu Glu Gly Ile Ser Ala Glu Gln Ile Val Val Lys Ile Thr
         35                  40                  45

Asp Gln Gly Tyr Val Thr Ser His Gly Asp His His Phe Tyr Asn
     50                  55                  60

Gly Lys Val Pro Tyr Asp Ala Ile Ile Ser Glu Glu Leu Leu Met Thr
65                  70                  75                  80

Asp Pro Asn Tyr Arg Phe Lys Gln Ser Asp Val Ile Asn Glu Ile Leu
                 85                  90                  95

Asp Gly Tyr Val Ile Lys Val Asn Gly Asn Tyr Tyr Val Tyr Leu Lys
            100                 105                 110

Pro Gly Ser Lys Arg Lys Asn Ile Arg Thr Lys Gln Gln Ile Ala Glu
            115                 120                 125

Gln Val Ala Lys Gly Thr Lys Glu Ala Lys Glu Lys Gly Leu Ala Gln
        130                 135                 140

Val Ala His Leu Ser Lys Glu Glu Val Ala Ala Val Asn Glu Ala Lys
145                 150                 155                 160

Arg Gln Gly Arg Tyr Thr Thr Asp Asp Gly Tyr Ile Phe Ser Pro Thr
                165                 170                 175

Asp Ile Ile Asp Asp Leu Gly Asp Ala Tyr Leu Val Pro His Gly Asn
            180                 185                 190

His Tyr His Tyr Ile Pro Lys Lys Asp Leu Ser Pro Glu Leu Ala
        195                 200                 205

Ala Ala Gln Ala Tyr Trp Ser Gln Lys Gln Gly Arg Gly Ala Arg Pro
    210                 215                 220

Ser Asp Tyr Arg Pro Thr Pro Ala Pro Gly Arg Arg Lys Ala Pro Ile
225                 230                 235                 240

Pro Asp Val Thr Pro Asn Pro Gly Gln Gly His Gln Pro Asp Asn Gly
                245                 250                 255

Gly Tyr His Pro Ala Pro Pro Arg Pro Asn Asp Ala Ser Gln Asn Lys
            260                 265                 270

His Gln Arg Asp Glu Phe Lys Gly Lys Thr Phe Lys Glu Leu Leu Asp
        275                 280                 285

Gln Leu His Arg Leu Asp Leu Lys Tyr Arg His Val Glu Glu Asp Gly
    290                 295                 300

Leu Ile Phe Glu Pro Thr Gln Val Ile Lys Ser Asn Ala Phe Gly Tyr
305                 310                 315                 320
```

```
Val Val Pro His Gly Asp His Tyr His Ile Pro Arg Ser Gln Leu
            325                 330                 335

Ser Pro Leu Glu Met Glu Leu Ala Asp Arg Tyr Leu Ala Gly Gln Thr
            340                 345                 350

Glu Asp Asn Asp Ser Gly Ser Glu His Ser Lys Pro Ser Asp Lys Glu
            355                 360                 365

Val Thr His Thr Phe Leu Gly His Arg Ile Lys Ala Tyr Gly Lys Gly
            370                 375                 380

Leu Asp Gly Lys Pro Tyr Asp Thr Ser Asp Ala Tyr Val Phe Ser Lys
385                 390                 395                 400

Glu Ser Ile His Ser Val Asp Lys Ser Gly Val Thr Ala Lys His Gly
            405                 410                 415

Asp His Phe His Tyr Ile Gly Phe Gly Glu Leu Glu Gln Tyr Glu Leu
            420                 425                 430

Asp Glu Val Ala Asn Trp Val Lys Ala Lys Gly Gln Ala Asp Glu Leu
            435                 440                 445

Ala Ala Ala Leu Asp Gln Glu Gln Gly Lys Glu Lys Pro Leu Phe Asp
450                 455                 460

Thr Lys Lys Val Ser Arg Lys Val Thr Lys Asp Gly Lys Val Gly Tyr
465                 470                 475                 480

Met Met Pro Lys Asp Gly Lys Asp Tyr Phe Tyr Ala Arg Asp Gln Leu
            485                 490                 495

Asp Leu Thr Gln Ile Ala Phe Ala Glu Gln Glu Leu Met Leu Lys Asp
            500                 505                 510

Lys Lys His Tyr Arg Tyr Asp Ile Val Asp Thr Gly Ile Glu Pro Arg
            515                 520                 525

Leu Ala Val Asp Val Ser Ser Leu Pro Met His Ala Gly Asn Ala Thr
530                 535                 540

Tyr Asp Thr Gly Ser Ser Phe Val Ile Pro His Ile Asp His Ile His
545                 550                 555                 560

Val Val Pro Tyr Ser Trp Leu Thr Arg Asp Gln Ile Ala Thr Val Lys
            565                 570                 575

Tyr Val Met Gln His Pro Glu Val Arg Pro Asp Val Trp Ser Lys Pro
            580                 585                 590

Gly His Glu Glu Ser Gly Ser Val Ile Pro Asn Val Thr Pro Leu Asp
            595                 600                 605

Lys Arg Ala Gly Met Pro Asn Trp Gln Ile Ile His Ser Ala Glu Glu
610                 615                 620

Val Gln Lys Ala Leu Ala Glu Gly Arg Phe Ala Thr Pro Asp Gly Tyr
625                 630                 635                 640

Ile Phe Asp Pro Arg Asp Val Leu Ala Lys Glu Thr Phe Val Trp Lys
            645                 650                 655

Asp Gly Ser Phe Ser Ile Pro Arg Ala Asp Gly Ser Ser Leu Arg Thr
            660                 665                 670

Ile Asn Lys Ser Asp Leu Ser Gln Ala Glu Trp Gln Ala Gln Glu
            675                 680                 685

Leu Leu Ala Lys Lys Asn Thr Gly Asp Ala Thr Asp Thr Asp Lys Pro
            690                 695                 700

Lys Glu Lys Gln Gln Ala Asp Lys Ser Asn Glu Asn Gln Pro Ser
705                 710                 715                 720

Glu Ala Ser Lys Glu Glu Lys Glu Ser Asp Asp Phe Ile Asp Ser Leu
            725                 730                 735

Pro Asp Tyr Gly Leu Asp Arg Ala Thr Leu Glu Asp His Ile Asn Gln
            740                 745                 750
```

```
Leu Ala Gln Lys Ala Asn Ile Asp Pro Lys Tyr Leu Ile Phe Gln Pro
        755                 760                 765

Glu Gly Val Gln Phe Tyr Asn Lys Asn Gly Leu Val Thr Tyr Asp
    770                 775                 780

Ile Lys Thr Leu Gln Gln Ile Asn Pro
785                 790

<210> SEQ ID NO 16
<211> LENGTH: 715
<212> TYPE: PRT
<213> ORGANISM: Group B streptococcus

<400> SEQUENCE: 16

Met Thr Asp Pro Asn Tyr Arg Phe Lys Gln Ser Asp Val Ile Asn Glu
1               5                   10                  15

Ile Leu Asp Gly Tyr Val Ile Lys Val Asn Gly Asn Tyr Tyr Val Tyr
            20                  25                  30

Leu Lys Pro Gly Ser Lys Arg Lys Asn Ile Arg Thr Lys Gln Gln Ile
        35                  40                  45

Ala Glu Gln Val Ala Lys Gly Thr Lys Glu Ala Lys Glu Lys Gly Leu
    50                  55                  60

Ala Gln Val Ala His Leu Ser Lys Glu Glu Val Ala Ala Val Asn Glu
65                  70                  75                  80

Ala Lys Arg Gln Gly Arg Tyr Thr Thr Asp Asp Gly Tyr Ile Phe Ser
                85                  90                  95

Pro Thr Asp Ile Ile Asp Asp Leu Gly Asp Ala Tyr Leu Val Pro His
            100                 105                 110

Gly Asn His Tyr His Tyr Ile Pro Lys Lys Asp Leu Ser Pro Ser Glu
        115                 120                 125

Leu Ala Ala Gln Ala Tyr Trp Ser Gln Lys Gln Gly Arg Gly Ala
    130                 135                 140

Arg Pro Ser Asp Tyr Arg Pro Thr Pro Ala Pro Gly Arg Arg Lys Ala
145                 150                 155                 160

Pro Ile Pro Asp Val Thr Pro Asn Pro Gly Gln Gly His Gln Pro Asp
                165                 170                 175

Asn Gly Gly Tyr His Pro Ala Pro Pro Arg Pro Asn Asp Ala Ser Gln
            180                 185                 190

Asn Lys His Gln Arg Asp Glu Phe Lys Gly Lys Thr Phe Lys Glu Leu
        195                 200                 205

Leu Asp Gln Leu His Arg Leu Asp Leu Lys Tyr Arg His Val Glu Glu
    210                 215                 220

Asp Gly Leu Ile Phe Glu Pro Thr Gln Val Ile Lys Ser Asn Ala Phe
225                 230                 235                 240

Gly Tyr Val Val Pro His Gly Asp His Tyr His Ile Ile Pro Arg Ser
                245                 250                 255

Gln Leu Ser Pro Leu Glu Met Glu Leu Ala Asp Arg Tyr Leu Ala Gly
            260                 265                 270

Gln Thr Glu Asp Asn Asp Ser Gly Ser Glu His Ser Lys Pro Ser Asp
        275                 280                 285

Lys Glu Val Thr His Thr Phe Leu Gly His Arg Ile Lys Ala Tyr Gly
    290                 295                 300

Lys Gly Leu Asp Gly Lys Pro Tyr Asp Thr Ser Asp Ala Tyr Val Phe
305                 310                 315                 320

Ser Lys Glu Ser Ile His Ser Val Asp Lys Ser Gly Val Thr Ala Lys
                325                 330                 335
```

-continued

```
His Gly Asp His Phe His Tyr Ile Gly Phe Gly Glu Leu Glu Gln Tyr
            340                 345                 350

Glu Leu Asp Glu Val Ala Asn Trp Val Lys Ala Lys Gly Gln Ala Asp
        355                 360                 365

Glu Leu Ala Ala Ala Leu Asp Gln Glu Gln Gly Lys Glu Lys Pro Leu
370                 375                 380

Phe Asp Thr Lys Lys Val Ser Arg Lys Val Thr Lys Asp Gly Lys Val
385                 390                 395                 400

Gly Tyr Met Met Pro Lys Asp Gly Lys Asp Tyr Phe Tyr Ala Arg Asp
                405                 410                 415

Gln Leu Asp Leu Thr Gln Ile Ala Phe Ala Gln Glu Leu Met Leu
            420                 425                 430

Lys Asp Lys Lys His Tyr Arg Tyr Asp Ile Val Asp Thr Gly Ile Glu
            435                 440                 445

Pro Arg Leu Ala Val Asp Val Ser Ser Leu Pro Met His Ala Gly Asn
        450                 455                 460

Ala Thr Tyr Asp Thr Gly Ser Ser Phe Val Ile Pro His Ile Asp His
465                 470                 475                 480

Ile His Val Val Pro Tyr Ser Trp Leu Thr Arg Asp Gln Ile Ala Thr
                485                 490                 495

Val Lys Tyr Val Met Gln His Pro Glu Val Arg Pro Asp Val Trp Ser
            500                 505                 510

Lys Pro Gly His Glu Gly Ser Gly Ser Val Ile Pro Asn Val Thr Pro
        515                 520                 525

Leu Asp Lys Arg Ala Gly Met Pro Asn Trp Gln Ile Ile His Ser Ala
530                 535                 540

Glu Glu Val Gln Lys Ala Leu Ala Glu Gly Arg Phe Ala Thr Pro Asp
545                 550                 555                 560

Gly Tyr Ile Phe Asp Pro Arg Asp Val Leu Ala Lys Glu Thr Phe Val
                565                 570                 575

Trp Lys Asp Gly Ser Phe Ser Ile Pro Arg Ala Asp Gly Ser Ser Leu
            580                 585                 590

Arg Thr Ile Asn Lys Ser Asp Leu Ser Gln Ala Glu Trp Gln Gln Ala
        595                 600                 605

Gln Glu Leu Leu Ala Lys Lys Asn Thr Gly Asp Ala Thr Asp Thr Asp
610                 615                 620

Lys Pro Lys Glu Lys Gln Ala Asp Lys Ser Asn Glu Asn Gln Gln
625                 630                 635                 640

Pro Ser Glu Ala Ser Lys Glu Glu Lys Glu Ser Asp Asp Phe Ile Asp
                645                 650                 655

Ser Leu Pro Asp Tyr Gly Leu Asp Arg Ala Thr Leu Glu Asp His Ile
            660                 665                 670

Asn Gln Leu Ala Gln Lys Ala Asn Ile Asp Pro Lys Tyr Leu Ile Phe
        675                 680                 685

Gln Pro Glu Gly Val Gln Phe Tyr Asn Lys Asn Gly Glu Leu Val Thr
690                 695                 700

Tyr Asp Ile Lys Thr Leu Gln Gln Ile Asn Pro
705                 710                 715
```

<210> SEQ ID NO 17
<211> LENGTH: 77
<212> TYPE: PRT
<213> ORGANISM: Group B streptococcus -continued

<400> SEQUENCE: 17

Met His Ser Phe Ser Asn Pro Gly Tyr Pro Tyr Asp Asn Ala Val Thr
1               5                   10                  15

Glu Ala Phe Phe Lys Tyr Leu Lys His Arg Gln Ile Asn Arg Lys His
            20                  25                  30

Tyr Gln Asn Ile Lys Gln Val Gln Leu Asp Cys Phe Glu Tyr Ile Glu
        35                  40                  45

Asn Phe Tyr Asn Tyr Asn Pro His Thr Ala Asn Leu Gly Leu Thr
    50                  55                  60

Pro Asn Gln Lys Glu Glu Asn Tyr Phe Asn Ala Ile Lys
65                  70                  75

<210> SEQ ID NO 18
<211> LENGTH: 86
<212> TYPE: PRT
<213> ORGANISM: Group B streptococcus

<400> SEQUENCE: 18

Met Ala Tyr Tyr Gln Ala Cys Thr Glu Lys Asp Ile Ile Arg Ser Met
1               5                   10                  15

Ser Arg Lys Gly Thr Pro Ala Asp Asn Ala Cys Ile Glu Trp Phe His
            20                  25                  30

Thr Val Leu Lys Thr Glu Thr Phe Tyr Phe His Asn Arg Arg Lys Tyr
        35                  40                  45

Asn Lys Asp Ser Ile Thr Asn Ile Val Lys Asn Tyr Ile Thr Phe Tyr
    50                  55                  60

Asn Glu Thr Arg Ile Gln Gln Arg Leu Asn Asp Gln Ser Pro Val Gln
65                  70                  75                  80

Tyr Arg Lys Leu Ile Ala
                85

<210> SEQ ID NO 19
<211> LENGTH: 126
<212> TYPE: PRT
<213> ORGANISM: Group B streptococcus

<400> SEQUENCE: 19

Met Glu Asn His Phe Ile Tyr Gly Tyr Arg Thr Ile Thr Arg Leu Leu
1               5                   10                  15

Lys Lys Ile His Gly Leu Thr Val Asn Thr Lys Lys Val Tyr Arg Ile
            20                  25                  30

Met Lys Asn Asn Gly Trp Leu Cys Arg Thr Arg Thr Lys Lys Val Pro
        35                  40                  45

Asn Leu Gly Lys Ala Tyr Tyr Leu Thr Asp Asn Lys Leu Ser Arg Asp
    50                  55                  60

Phe His Ala Asp Lys Pro Lys Glu Lys Leu Val Thr Asp Ile Thr Tyr
65                  70                  75                  80

Leu Tyr Phe Gly Asn Cys Lys Leu Tyr Leu Ser Ser Ile Met Asn Leu
                85                  90                  95

Tyr Asn Arg Glu Ile Ile Ala Tyr Thr Ile Ser Asp Cys Gln Asp Thr
            100                 105                 110

Asp Phe Val Leu Asp Thr Leu Asn Gln Leu Lys Leu Pro Lys
        115                 120                 125

<210> SEQ ID NO 20
<211> LENGTH: 96
<212> TYPE: PRT
<213> ORGANISM: Group B streptococcus

<400> SEQUENCE: 20

Met Val Lys Lys Ala Tyr Ser Trp Glu Thr Lys Leu Ala Cys Ile Asp
1               5                   10                  15

Met Lys Lys Ala Gly Lys Ser Asn Arg Val Ile Met Glu Thr Leu Gly
            20                  25                  30

Ile Lys Asn Asn Ser Gln Ile Tyr Thr Trp Met Lys Trp Tyr Glu Asn
        35                  40                  45

Glu Glu Leu Tyr Arg Phe His Gln Gly Val Gly Lys Gln Tyr Thr Tyr
    50                  55                  60

Gly Lys Gly Leu Glu His Leu Ser Glu Val Glu Gln Leu Gln Leu Gln
65                  70                  75                  80

Val Asp Leu Leu Lys Lys Tyr Arg Gly Leu Ile Arg Lys Ser Ile Lys
                85                  90                  95

<210> SEQ ID NO 21
<211> LENGTH: 288
<212> TYPE: PRT
<213> ORGANISM: Group B streptococcus

<400> SEQUENCE: 21

Ile Arg Tyr Pro Lys Ala Ser Ser Gly Asp Tyr Gly Thr Lys Arg Glu
1               5                   10                  15

Ile Ile Thr Ala Asn Lys Asp Lys Tyr Ser Ile Ser Lys Met Cys Arg
            20                  25                  30

Trp Leu Asn Met Pro His Ser Ser Tyr Tyr Gln Ala Val Glu Ser
        35                  40                  45

Val Ser Glu Thr Glu Phe Glu Glu Thr Ile Lys Arg Ile Phe Leu Asp
    50                  55                  60

Ser Glu Ser Arg Tyr Gly Ser Arg Lys Ile Lys Ile Cys Leu Asn Asn
65                  70                  75                  80

Glu Gly Ile Thr Leu Ser Arg Arg Ile Arg Arg Ile Met Lys Arg
                85                  90                  95

Leu Asn Leu Val Ser Val Tyr Gln Lys Ala Thr Phe Lys Pro His Ser
                100                 105                 110

Arg Gly Lys Asn Glu Ala Pro Ile Pro Asn His Leu Asp Arg Gln Phe
            115                 120                 125

Lys Gln Glu Arg Pro Leu Gln Ala Leu Val Thr Asp Leu Thr Tyr Val
    130                 135                 140

Arg Val Gly Asn Arg Trp Ala Tyr Val Cys Leu Ile Ile Asp Leu Tyr
145                 150                 155                 160

Asn Arg Glu Ile Ile Gly Leu Ser Leu Gly Trp His Lys Thr Ala Glu
                165                 170                 175

Leu Val Lys Gln Ala Ile Gln Ser Ile Pro Tyr Ala Leu Thr Lys Val
            180                 185                 190

Lys Met Phe His Ser Asp Arg Gly Lys Glu Phe Asp Asn Gln Leu Ile
    195                 200                 205

Asp Glu Ile Leu Glu Ala Phe Gly Ile Thr Arg Ser Leu Ser Gln Ala
210                 215                 220

Gly Tyr Pro Tyr Asp Asn Ala Val Ala Glu Ser Thr Tyr Arg Ala Phe
225                 230                 235                 240

Lys Ile Glu Phe Val Tyr Gln Glu Thr Phe Gln Leu Leu Glu Glu Leu
                245                 250                 255

```
Ala Leu Lys Thr Lys Asp Tyr Val His Trp Trp Asn Tyr His Arg Ile
            260                 265                 270

His Gly Ser Leu Asn Tyr Gln Thr Pro Met Thr Lys Arg Leu Ile Ala
    275                 280                 285

<210> SEQ ID NO 22
<211> LENGTH: 5058
<212> TYPE: DNA
<213> ORGANISM: Group B streptococcus

<400> SEQUENCE: 22
```

| | | | | | |
|---|---|---|---|---|---|
| aatttgaaag | cagaattatc | tgtagaagat | gagcaatata | cagcaacagt | ttatggtaaa | 60 |
| tctgctcatg | gttcaacacc | acaagaaggt | gttaatgggg | cgacttattt | agctctttat | 120 |
| ctaagtcaat | ttgattttga | aggtcctgct | cgtgctttct | tagatgttac | agccaacatt | 180 |
| attcacgaag | acttctcagg | tgaaaaactt | ggagtagctt | atgaagatga | ctgtatggga | 240 |
| ccattgagca | tgaatgcagg | tgtcttccag | tttgatgaaa | ctaatgatga | taatactatc | 300 |
| gctcttaatt | tccgttaccc | acaagggaca | gatgctaaaa | ctatccaaac | taagcttgag | 360 |
| aaacttaacg | gagttgaaaa | agtgactctt | tctgaccatg | aacacacacc | acactatgta | 420 |
| cctatggacg | atgaattagt | atcaaccttaa | ctagctgtct | atgaaaagca | aactggtctt | 480 |
| aaaggacatg | aacaggttat | tggtggtggg | acatttggtc | gcttacttga | acggggtgtt | 540 |
| gcatacggtg | ccatgttccc | aggagatgaa | acactatgc | atcaagctaa | tgagtacatg | 600 |
| cctttagaaa | atattttccg | ttcggctgct | atctacgcag | aagctatcta | tgaattaatc | 660 |
| aaataaaata | atccttaaac | taaatatgtg | atcaatgata | aagggtggtg | aagacatgaa | 720 |
| agtgtctttg | cctctttttca | taaggttaga | tttggagact | ttatgactga | cttggaaaaa | 780 |
| attattaaag | caataaaaag | tgattcacag | aatcaaaatt | atacagaaaa | tggtattgat | 840 |
| cctttgtttg | ctgctcctaa | aacagctagg | atcaatattg | ttggccaagc | acctggttta | 900 |
| aaaactcaag | aagcaagact | ctattggaaa | gataaatctg | gagatcgtct | acgccagtgg | 960 |
| cttggagttg | atgaagagac | attttaccat | tctggaaaat | ttgctgtttt | acctttagat | 1020 |
| ttttattacc | caggcaaagg | aaaatcagga | gatttacccc | ctagaaaagg | ttttgcggag | 1080 |
| aaatggcacc | ctcttatttt | aaaagaaatg | cctaatgttc | aattgaccct | gctagttggt | 1140 |
| cagtatgctc | agaaatatta | tcttggaagc | tccgcacata | aaaatctaac | agaaacagtt | 1200 |
| aaagcttaca | agactatct | acccgattat | ttaccctgg | ttcacccatc | accgcgaaat | 1260 |
| caaatttggc | taaagaagaa | tccatggttt | gaaaaagatc | taatcgttga | tttacaaaag | 1320 |
| atagtagcag | atatttaaa | agattaagga | taggagttgg | tatgagagat | aatcatctac | 1380 |
| acacgtattt | ttcctatgat | tgtcaaacgg | catttgagga | ctatattaat | ggttttacag | 1440 |
| gtgaatttat | cacgacagaa | cattttgatt | tatcaaatcc | ttacaccggt | caagacgatg | 1500 |
| ttcctgatta | tagtgcttat | tgtcaaaaaa | tagattatct | taatcagaaa | tatggaaatc | 1560 |
| gatttaaaaa | aggaattgaa | atcggttatt | ttaaagatag | ggaatcagat | attttagatt | 1620 |
| atttaaaaaa | taagaatttt | gatttaaaac | tattgtcaat | ccatcataat | ggtaggtatg | 1680 |
| attatctgca | agaagaagct | ctgaaagtac | caacaaaggg | agcttttagc | agattacttt | 1740 |
| aatcgtatgg | aatttgccat | aggccgtgtg | gaagcgcacg | ttttagctca | ctttgattat | 1800 |
| ggttttcgta | agtaaacttt | agatgtagaa | gatttaaaac | cgtttgaaac | gcaattgaag | 1860 |
| cgcattttca | taaagatgtt | atctaagggg | ttagcttttg | aactaaatac | caaatcccctt | 1920 |
| tatctatatg | ggaatgaaaa | actttatcgc | tatgctttag | agatactcaa | acagcttggt | 1980 |

```
tgtaaacaat actctatagg ctctgacggt catattcctg aacatttttg ttatgaattt      2040
gatagacttc aaggtctgct aaaggactat caaattgatg aaaatcattt gatatgagga      2100 aattttgat  aaaaaagcta ggcaatattg cttagctttt ttgtaatgct attgatagtt      2160
ttagtgaaaa tttcaaaaaa ataaagaaat catttacttg ttgcaagcgc ttgcgtaaat      2220
tgttatgatt ttattggtaa caattcatta aaaaggaga  atgatatgaa agaaaagac       2280 ttatttggtg ataaacaaac tcaatacacg attagaaagt taagtgttgg agtagcttca      2340
gttacaacag gggtatgtat ttttcttcat agtccacagg tatttgctga agaagtaagt      2400
gtttctcctg caactacagc gattgcagag tcgaatatta atcaggttga caaccaacaa      2460
tctactaatt taaagatga  cataaactca aactctgaga cggttgtgac accctcagat      2520
atgccggata ccaagcaatt agtatcagat gaaactgaca ctcaaaaggg agtgacagag      2580
ccggataagg cgacaagcct gcttgaagaa ataaaggtc  ctgtttcaga taaaaatacc      2640
ttagatttaa aagtagcacc atctacattg caaaatactc ccgacaaaac ttctcaagct      2700
ataggtgctc caagccctac cttgaaagta gctaatcaag ctccacggat tgaaaatggt      2760
tactttaggc tacatcttaa agaattgcct caaggtcatc ctgtagaaag cactggactt      2820
tggatatggg gagatgttga tcaaccgtct agtaattggc caaatggtgc tatccctatg      2880
actgatgcta agaagatga  ttacggttat tatgttgatt ttaaattatc tgaaaaacaa      2940
cgaaaacaaa tatctttttt aattaataac aaagcaggga caaatttaag cggcgatcat      3000
catattccat tattacgacc tgagatgaac caagtttgga ttgatgaaaa gtacggtata      3060
catacttatc aaccccctcaa agaagggtat gtccgtatta actatttgag ttcctctagt      3120
aactatgacc acttatcagc atggctcttt aaagatgttg caaccccytc aacaacttgg      3180
ccagatggta gtaattttgt gaatcaagga ctatatggaa ggtatattga tgtatcacta      3240
aaaactaacg ccaaagagat tggttttcta atcttagatg aaagtaagac aggagatgca      3300
gtgaaagttc aacccaacga ctatgttttt agagatttag ctaaccataa ccaaatttt      3360 gtaaaagata aggatccaaa ggtttataat aatccttatt acattgatca agtgcagcta      3420
aaggatgccc aacaaattga tttaacaagt attcaagcaa gttttacaac tctagatggg      3480
gtagataaaa ctgaaatttt aaaagaattg aaagtgactg ataaaaatca aaatgctata      3540
caaatttctg atatcactct cgatactagt aaatctcttt taataatcaa aggcgacttt      3600
aatcctaaac aaggtcattt caacatatct tataatggta acaatgtcat gacaaggcaa      3660
tcttgggaat ttaaagacca actttatgct tatagtggaa atttaggtgc agttctcaat      3720
caagatggtt caaaagttga agccagcctc tggtcaccga gtgctgatag tgtcactatg      3780
attatttatg acaaagataa ccaaaacagg gttgtagcga ctacccccct tgtgaaaaat      3840
aataaaggtg tttggcagac gatacttgat actaaattag gtattaaaaa ctatactggt      3900
tactattatc tttacgaaat aaaaagaggt aaggataagg ttaagatttt agatccttat      3960
gcaaagtcat tagcagagtg ggatagtaat actgttaatg atgatattaa aacggctaaa      4020
gcagcttttg taaatccaag tcaacttgga cctcaaaatt taagttttgc taaaattgct      4080
aattttaaag gaagacaaga tgctgttata tacgaagcac atgtaagaga cttcacttct      4140
gatcgatctt tggatggaaa attaaaaaat caatttggta cctttgcagc cttttcagag      4200
aaactagatt atttcagaa  attaggagtt acacacattc agcttttacc ggtattgagt      4260 tattttttatg ttaatgaaat ggataagtca cgctcaacag cttacacttc ctcagacaat      4320
aattacaatt ggggctatga cccacagagc tattttgctc tttctgggat gtattcagag      4380
```

```
aaaccaaaag atccatcagc acgtatcgcc gaattaaaac aattaataca tgatattcat    4440
aaacgtggca tggggttat  acttgatgtc gtctataatc acactgcaaa aacttatctc    4500
tttgaggata tagaacctaa ttattatcac tttatgaatg aagatggttc accaagagaa    4560
agttttggag ggggacgttt aggaaccact catgcaatga gtcgtcgtgt tttggttgat    4620
tccattaaat atcttacaag tgaatttaaa gttgatggtt ccgttttga tatgatggga     4680 gatcatgatg cggctgcgat tgaattagct tataaagaag ctaaagctat taatcctaat    4740
atgattatga ttggtgaggg ctggagaaca ttccaaggcg atcaaggtca gccggttaaa    4800
ccagctgacc aagattggat gaagtcaacc gatacagttg gcgtcttttc agatgatatt    4860
cgtaatagct tgaaatctgg ttttccaaat gaaggtactc cagctttcat cacaggtggc    4920
ccacaatctt tacaaggtat ttttaaaaat atcaaagcac aacctgggaa ttttgaagca    4980
gattcgccag gagatgtggt gcagtatatt gctgcacatg ataaccttac cttgcatgat    5040
gtgattgcaa aatcaatt                                                   5058
```

<210> SEQ ID NO 23
<211> LENGTH: 221
<212> TYPE: PRT
<213> ORGANISM: Group B streptococcus

<400> SEQUENCE: 23

```
Asn Leu Lys Ala Glu Leu Ser Val Glu Asp Glu Gln Tyr Thr Ala Thr
 1               5                  10                  15

Val Tyr Gly Lys Ser Ala His Gly Ser Thr Pro Gln Glu Gly Val Asn
            20                  25                  30

Gly Ala Thr Tyr Leu Ala Leu Tyr Leu Ser Gln Phe Asp Phe Glu Gly
        35                  40                  45

Pro Ala Arg Ala Phe Leu Asp Val Thr Ala Asn Ile Ile His Glu Asp
    50                  55                  60

Phe Ser Gly Glu Lys Leu Gly Val Ala Tyr Glu Asp Asp Cys Met Gly
65                  70                  75                  80

Pro Leu Ser Met Asn Ala Gly Val Phe Gln Phe Asp Glu Thr Asn Asp
                85                  90                  95

Asp Asn Thr Ile Ala Leu Asn Phe Arg Tyr Pro Gln Gly Thr Asp Ala
           100                 105                 110

Lys Thr Ile Gln Thr Lys Leu Glu Lys Leu Asn Gly Val Glu Lys Val
       115                 120                 125

Thr Leu Ser Asp His Glu His Thr Pro His Tyr Val Pro Met Asp Asp
   130                 135                 140

Glu Leu Val Ser Thr Leu Leu Ala Val Tyr Glu Lys Gln Thr Gly Leu
145                 150                 155                 160

Lys Gly His Glu Gln Val Ile Gly Gly Gly Thr Phe Gly Arg Leu Leu
                165                 170                 175

Glu Arg Gly Val Ala Tyr Gly Ala Met Phe Pro Gly Asp Glu Asn Thr
            180                 185                 190

Met His Gln Ala Asn Glu Tyr Met Pro Leu Glu Asn Ile Phe Arg Ser
        195                 200                 205

Ala Ala Ile Tyr Ala Glu Ala Ile Tyr Glu Leu Ile Lys
    210                 215                 220
```

<210> SEQ ID NO 24
<211> LENGTH: 194
<212> TYPE: PRT
<213> ORGANISM: Group B streptococcus -continued

```
<400> SEQUENCE: 24

Met Thr Asp Leu Glu Lys Ile Ile Lys Ala Ile Lys Ser Asp Ser Gln
 1               5                  10                  15

Asn Gln Asn Tyr Thr Glu Asn Gly Ile Asp Pro Leu Phe Ala Ala Pro
             20                  25                  30

Lys Thr Ala Arg Ile Asn Ile Val Gly Gln Ala Pro Gly Leu Lys Thr
         35                  40                  45

Gln Glu Ala Arg Leu Tyr Trp Lys Asp Lys Ser Gly Asp Arg Leu Arg
 50                  55                  60

Gln Trp Leu Gly Val Asp Glu Glu Thr Phe Tyr His Ser Gly Lys Phe
 65                  70                  75                  80

Ala Val Leu Pro Leu Asp Phe Tyr Pro Gly Lys Gly Lys Ser Gly
                 85                  90                  95

Asp Leu Pro Pro Arg Lys Gly Phe Ala Glu Lys Trp His Pro Leu Ile
                100                 105                 110

Leu Lys Glu Met Pro Asn Val Gln Leu Thr Leu Leu Val Gly Gln Tyr
            115                 120                 125

Ala Gln Lys Tyr Tyr Leu Gly Ser Ser Ala His Lys Asn Leu Thr Glu
        130                 135                 140

Thr Val Lys Ala Tyr Lys Asp Tyr Leu Pro Asp Tyr Leu Pro Leu Val
145                 150                 155                 160

His Pro Ser Pro Arg Asn Gln Ile Trp Leu Lys Lys Asn Pro Trp Phe
                165                 170                 175

Glu Lys Asp Leu Ile Val Asp Leu Gln Lys Ile Val Ala Asp Ile Leu
            180                 185                 190

Lys Asp

<210> SEQ ID NO 25
<211> LENGTH: 126
<212> TYPE: PRT
<213> ORGANISM: Group B streptococcus

<400> SEQUENCE: 25

Met Arg Asp Asn His Leu His Thr Tyr Phe Ser Tyr Asp Cys Gln Thr
 1               5                  10                  15

Ala Phe Glu Asp Tyr Ile Asn Gly Phe Thr Gly Glu Phe Ile Thr Thr
             20                  25                  30

Glu His Phe Asp Leu Ser Asn Pro Tyr Thr Gly Gln Asp Asp Val Pro
         35                  40                  45

Asp Tyr Ser Ala Tyr Cys Gln Lys Ile Asp Tyr Leu Asn Gln Lys Tyr
 50                  55                  60

Gly Asn Arg Phe Lys Lys Gly Ile Glu Ile Gly Tyr Phe Lys Asp Arg
 65                  70                  75                  80

Glu Ser Asp Ile Leu Asp Tyr Leu Lys Asn Lys Glu Phe Asp Leu Lys
                 85                  90                  95

Leu Leu Ser Ile His His Asn Gly Arg Tyr Asp Tyr Leu Gln Glu Glu
                100                 105                 110

Ala Leu Lys Val Pro Thr Lys Gly Ala Phe Ser Arg Leu Leu
            115                 120                 125

<210> SEQ ID NO 26
<211> LENGTH: 931
<212> TYPE: PRT
<213> ORGANISM: Group B streptococcus
```

-continued

```
<220> FEATURE:
<221> NAME/KEY: VARIANT
<222> LOCATION: 301
<223> OTHER INFORMATION: Xaa = Any Amino Acid

<400> SEQUENCE: 26

Met Lys Arg Lys Asp Leu Phe Gly Asp Lys Gln Thr Gln Tyr Thr Ile
 1               5                  10                  15

Arg Lys Leu Ser Val Gly Val Ala Ser Val Thr Thr Gly Val Cys Ile
            20                  25                  30

Phe Leu His Ser Pro Gln Val Phe Ala Glu Glu Val Ser Val Ser Pro
        35                  40                  45

Ala Thr Thr Ala Ile Ala Glu Ser Asn Ile Asn Gln Val Asp Asn Gln
    50                  55                  60

Gln Ser Thr Asn Leu Lys Asp Asp Ile Asn Ser Asn Ser Glu Thr Val
65                  70                  75                  80

Val Thr Pro Ser Asp Met Pro Asp Thr Lys Gln Leu Val Ser Asp Glu
                85                  90                  95

Thr Asp Thr Gln Lys Gly Val Thr Glu Pro Asp Lys Ala Thr Ser Leu
            100                 105                 110

Leu Glu Glu Asn Lys Gly Pro Val Ser Asp Lys Asn Thr Leu Asp Leu
        115                 120                 125

Lys Val Ala Pro Ser Thr Leu Gln Asn Thr Pro Asp Lys Thr Ser Gln
130                 135                 140

Ala Ile Gly Ala Pro Ser Pro Thr Leu Lys Val Ala Asn Gln Ala Pro
145                 150                 155                 160

Arg Ile Glu Asn Gly Tyr Phe Arg Leu His Leu Lys Glu Leu Pro Gln
                165                 170                 175

Gly His Pro Val Glu Ser Thr Gly Leu Trp Ile Trp Gly Asp Val Asp
            180                 185                 190

Gln Pro Ser Ser Asn Trp Pro Asn Gly Ala Ile Pro Met Thr Asp Ala
        195                 200                 205

Lys Lys Asp Asp Tyr Gly Tyr Tyr Val Asp Phe Lys Leu Ser Glu Lys
210                 215                 220

Gln Arg Lys Gln Ile Ser Phe Leu Ile Asn Asn Lys Ala Gly Thr Asn
225                 230                 235                 240

Leu Ser Gly Asp His His Ile Pro Leu Leu Arg Pro Glu Met Asn Gln
                245                 250                 255

Val Trp Ile Asp Glu Lys Tyr Gly Ile His Thr Tyr Gln Pro Leu Lys
            260                 265                 270

Glu Gly Tyr Val Arg Ile Asn Tyr Leu Ser Ser Ser Asn Tyr Asp
        275                 280                 285

His Leu Ser Ala Trp Leu Phe Lys Asp Val Ala Thr Xaa Ser Thr Thr
290                 295                 300

Trp Pro Asp Gly Ser Asn Phe Val Asn Gln Gly Leu Tyr Gly Arg Tyr
305                 310                 315                 320

Ile Asp Val Ser Leu Lys Thr Asn Ala Lys Glu Ile Gly Phe Leu Ile
                325                 330                 335

Leu Asp Glu Ser Lys Thr Gly Asp Ala Val Lys Val Gln Pro Asn Asp
            340                 345                 350

Tyr Val Phe Arg Asp Leu Ala Asn His Asn Gln Ile Phe Val Lys Asp
        355                 360                 365

Lys Asp Pro Lys Val Tyr Asn Asn Pro Tyr Tyr Ile Asp Gln Val Gln
370                 375                 380
```

```
Leu Lys Asp Ala Gln Gln Ile Asp Leu Thr Ser Ile Gln Ala Ser Phe
385                 390                 395                 400

Thr Thr Leu Asp Gly Val Asp Lys Thr Glu Ile Leu Lys Glu Leu Lys
                405                 410                 415

Val Thr Asp Lys Asn Gln Asn Ala Ile Gln Ile Ser Asp Ile Thr Leu
            420                 425                 430

Asp Thr Ser Lys Ser Leu Leu Ile Ile Lys Gly Asp Phe Asn Pro Lys
        435                 440                 445

Gln Gly His Phe Asn Ile Ser Tyr Asn Gly Asn Asn Val Met Thr Arg
    450                 455                 460

Gln Ser Trp Glu Phe Lys Asp Gln Leu Tyr Ala Tyr Ser Gly Asn Leu
465                 470                 475                 480

Gly Ala Val Leu Asn Gln Asp Gly Ser Lys Val Glu Ala Ser Leu Trp
                485                 490                 495

Ser Pro Ser Ala Asp Ser Val Thr Met Ile Ile Tyr Asp Lys Asp Asn
            500                 505                 510

Gln Asn Arg Val Val Ala Thr Thr Pro Leu Val Lys Asn Asn Lys Gly
        515                 520                 525

Val Trp Gln Thr Ile Leu Asp Thr Lys Leu Gly Ile Lys Asn Tyr Thr
    530                 535                 540

Gly Tyr Tyr Tyr Leu Tyr Glu Ile Lys Arg Gly Lys Asp Lys Val Lys
545                 550                 555                 560

Ile Leu Asp Pro Tyr Ala Lys Ser Leu Ala Glu Trp Asp Ser Asn Thr
                565                 570                 575

Val Asn Asp Asp Ile Lys Thr Ala Lys Ala Ala Phe Val Asn Pro Ser
            580                 585                 590

Gln Leu Gly Pro Gln Asn Leu Ser Phe Ala Lys Ile Ala Asn Phe Lys
        595                 600                 605

Gly Arg Gln Asp Ala Val Ile Tyr Glu Ala His Val Arg Asp Phe Thr
    610                 615                 620

Ser Asp Arg Ser Leu Asp Gly Lys Leu Lys Asn Gln Phe Gly Thr Phe
625                 630                 635                 640

Ala Ala Phe Ser Glu Lys Leu Asp Tyr Leu Gln Lys Leu Gly Val Thr
                645                 650                 655

His Ile Gln Leu Leu Pro Val Leu Ser Tyr Phe Tyr Val Asn Glu Met
            660                 665                 670

Asp Lys Ser Arg Ser Thr Ala Tyr Thr Ser Ser Asp Asn Asn Tyr Asn
        675                 680                 685

Trp Gly Tyr Asp Pro Gln Ser Tyr Phe Ala Leu Ser Gly Met Tyr Ser
    690                 695                 700

Glu Lys Pro Lys Asp Pro Ser Ala Arg Ile Ala Glu Leu Lys Gln Leu
705                 710                 715                 720

Ile His Asp Ile His Lys Arg Gly Met Gly Val Ile Leu Asp Val Val
                725                 730                 735

Tyr Asn His Thr Ala Lys Thr Tyr Leu Phe Glu Asp Ile Glu Pro Asn
            740                 745                 750

Tyr Tyr His Phe Met Asn Glu Asp Gly Ser Pro Arg Glu Ser Phe Gly
        755                 760                 765

Gly Gly Arg Leu Gly Thr Thr His Ala Met Ser Arg Arg Val Leu Val
    770                 775                 780

Asp Ser Ile Lys Tyr Leu Thr Ser Glu Phe Lys Val Asp Gly Phe Arg
785                 790                 795                 800

Phe Asp Met Met Gly Asp His Asp Ala Ala Ala Ile Glu Leu Ala Tyr
                805                 810                 815
```

```
Lys Glu Ala Lys Ala Ile Asn Pro Asn Met Ile Met Ile Gly Glu Gly
            820                 825                 830

Trp Arg Thr Phe Gln Gly Asp Gln Gly Gln Pro Val Lys Pro Ala Asp
            835                 840                 845

Gln Asp Trp Met Lys Ser Thr Asp Thr Val Gly Val Phe Ser Asp Asp
        850                 855                 860

Ile Arg Asn Ser Leu Lys Ser Gly Phe Pro Asn Glu Gly Thr Pro Ala
865                 870                 875                 880

Phe Ile Thr Gly Gly Pro Gln Ser Leu Gln Gly Ile Phe Lys Asn Ile
                885                 890                 895

Lys Ala Gln Pro Gly Asn Phe Glu Ala Asp Ser Pro Gly Asp Val Val
            900                 905                 910

Gln Tyr Ile Ala Ala His Asp Asn Leu Thr Leu His Asp Val Ile Ala
        915                 920                 925

Lys Ser Ile
        930

<210> SEQ ID NO 27
<211> LENGTH: 5607
<212> TYPE: DNA
<213> ORGANISM: Group B streptococcus

<400> SEQUENCE: 27
aattcaaagt tgacagaag gtcaacttcg ttctgatatc cctgagttcc gtgctggtga      60
tactgtacgt gttcacgcta aagttgttga aggtactcgc gaacgtattc agatctttga     120
aggtgttgtt atctcacgta aaggtcaagg aatctcagaa atgtacacag tacgtaaaat     180
ttctggtggt atcggtgtag agcgtacatt cccaattcac actcctcgtg ttgataaaat     240
cgaagttgtt cgttatggta agtacgtcg tgctaaactt tactacttac gcgcattgca     300
aggtaaagct gcacgtatta agaaatccg tcgttaattt tgatgatcag attttaaaaa     360
tgcttggttg tttgaggata gtaactatgt tttaaaactg acaaccaag acgtaaaaaa     420 tctgcctgtg ggcagttttt ttactaggtc cccttagttc aatggatata acaactccct     480
cctaaggagt aattgctggt tcgattccgg caggggacat attcattgca tgtaaatagc     540
ggtttagagc tattttgccc caaatttctc tgattaagtt tatcgttcct atcttttgt     600 tcttgtaatt gatgtgcgta aacttctaaa gtgatattta aattctcgtg atctaaaact     660
tgagagatgg aaattagata gcttgcaaat gtatgcctga gagtgcac tcgtacctcg     720 cgaccagtta ttttcggat agttttattg actgcattat ttgaaagttt gtcgaataat     780
ctgtcgtttt tatttttttgt aaattcatgc aaaaaaaata atgtatcatt gtcaattggt     840
atatttctga tactactttt gtttttttgtt ggcaggtatc tttggttgaa atgataatcc     900
caagttttat taattgataa atatttgtta gtgtaatcaa tatcattaac tgttaaacct     960
aaacattcag cgaagcgcat gccagtttta gcgatgaggt ataacgctgc atacgattga    1020
tgttgtgatt tttctttaca aatttttatc aagcgtaagt attcattggt ttcaagaaat    1080
tttatctcta tttacgcccc ttatttttttg ctttaacctt agtgaataaa caaaaatttt    1140
tttctatata tccctcgtga acagccatgg atacgcaggc ttttacatgt atgttaaaac    1200
gctttactgt atcttgcaca tgcgtttgac tataatgatt tatgacttgt tgatatttag    1260
tggaagtaat attgcaaagt aatatatttc ctattatatg tttatacgat attcgatatt    1320 cccaccccgtt gtcgcgttta cggaaatacg ccattgatat actccacatt agctaaagaa    1380
cagggtgttc aaggctacct tgatggaaaa ggctctctta gagatatttg taaatggtat    1440
```

```
gatatctcaa gtcgctctgt tctccaaaag tggataaaac ggtatactag tggtgaagac    1500
ttgaaagcca ctagtagagg atatagccgt atgaaacaag gaaggcaagc cacatttgaa    1560
gaacgtgtag agattgttaa ctacaccatt gcccatggga aagactatca agcagctatt    1620
gagaagtttg gtgtttccta ccaacaaatt tattcttggg tgcgtaagct tgagaagaat    1680
ggctcacaag gtttggttga tagacgtgtg aaagggttgg agagtaggcc tgatttaacc    1740
gagattgagc aactttaact caagattaaa caattggagg aacgtaatcg tctcttagaa    1800
atcgaggtta gtttactaaa aaagttagaa gacatcaaac gaggaaacag acggtaagac    1860
taggtaagca tttagcggag ttccaagtaa tcaagaatta ttacgatgag gaatctaatg    1920
tgcctattca ggccttatgc caactcttga aggggtctcg ttcaggctat tacaagtggc    1980
tcaatcgtca aaaacagat tttgagacaa aaaatacaaa gctaatggct aaaatcaagg     2040
aacttcgtag actctacaat ggtatcttag gttatcgccg tatgacaaca tttattaatc    2100
gtcaacttgg gacaacttaa aacaagaaac ggattcgttg attgatgaac attctgggga    2160
ttagttcagt cattcgtcgt gttagccatg cttgtacaaa agctggtgac agattttacg    2220
aagaaaatat tcttaatcgt gaatttacag ccacagctca taaccagaaa tggtgcacag    2280
atgtcaccta tcttcaatac ggtctgggag ctaaagctta tctcagtgcg attaaagacc    2340
tgtataacgg ttctattatc gcttatgaga ttagtcacaa caatgaaatc cacttgttat    2400
gaagaccatt aaaaagggc tagagctcaa tccaggagcc acacctatca tccatagcga    2460
ttgaggtagt caatatactt ccaaagaata ccgttatatc atacaacaag ctggtctgac    2520
cttatccatg tcccggattg gcaaatgtat tgataatgca ccaactgaaa gtttctttgg    2580
gttttccaag actgagtctt accaccttaa gaaatacaac tcttatgatg agttggtcaa    2640
tgatgtggca cgttatatcg aattctacaa cacacaacgt tatcaatcaa aattaaacaa    2700
cctgactcct ctagaattca ggaatcaggt tgcataactt atcttttatt atttgactgt    2760
ctacttgaca gggagccgtt cagattgctt aacctttcta aatttgctaa aatagctaca    2820
agaaaacgag ccatttaatg cttatttctt atactgtctt gcctcacgct ctcctcgacc    2880
aaaaattgag cgtgaggctt tttgtttcat taaacgatga tatttccata ttcatcagtt    2940
tgttttccga gagccatcaa agcttcgata aggtcgataa ttccaggaat aaaggtaata    3000
ctaaaaataa tatataaaaa aacctggcct attttcctg cgtaaaattt atgcgctcca     3060
atgccgccca aagaacgtt aataaaacat aaactactat gttagcataa gactttattt     3120
ttacaactga atttcatata aatggattag agtaagggat aaaagaaatt agcatagctc    3180
ttttgaaaat aaaaaaatta atataatatg gaaaaattt tatttcataa acgtttcata     3240
aaaggtatgt aatctagtat ttaggcaaca ctattttgtc actggtgtct agtaacttat    3300
agattgataa ttttactagt aaacgtaatt cttcgcttta agagttaaat gtctatttat    3360
tgtaagctaa attgggaggt gaacttatgt aaaattagat aggtactgtc aagtacggga    3420
tgattattga acagccagt atgcatcata aaatctgtat tgcttaataa ctatttcctt     3480
aaccagacat cagttcattg tttatcatcg ctaccctaag tctagttttt tcaatagagc    3540
attaggtagt ttttgataat aaaactatat aaacatgaga attagatttc gtattgcatt    3600
cttcataatg agttatttga gattttcctt tgaataaata gatacgaaat tcagtaactt    3660
catatataaa cggctctatc attgagatag tttgtcaaat gaagaaattt ttaatggaaa    3720
tagttttaaa acattagtt gtaggcgatg taaaaatatt aatccagtgg atgcaatagt     3780
tgcggagtaa aaatagagag gagtaattag gaagtgataa aaaatgctat agcatatatt    3840
```

```
accagaaaaa aaaatagaac acttattata tttgctattt taacaattgt tctttcttgc    3900
ttgtattcat gtttaacaat aatgaaatca agtaatgaaa tagaaaaggc tttatatgaa    3960
agttctaatt cttcaatatc aattacaaaa aaagatggta aatattttaa tattaatcaa    4020
tttaagaata ttgaaaaaat aaaagaggtt gaagaaaaaa tatttcaata tgatggatta    4080
gcaaaattga agatcttaa agtagttagt ggtgagcaaa gtataaatag agaagattta     4140
tctgacgaat ttaaaaatgt tgtttcacta gaagctacaa gtaatactaa aagaaatctt    4200
ttatttagta gtggagtatt tagttttaaa gaaggaaaaa atatagaaga aaatgataag    4260
aattcaattc ttgttcatga agaatttgct aaacaaaaca aactaaaatt gggtgatgaa    4320
attgatcttg aattactaga tacggaaaaa agtggaaaaa taaaagtca taaatttaaa     4380 attataggaa tcttttctgg taaaaaacag gaaacatata caggattatc atctgatttt    4440
agcgaaaata tggttttgt agattattca actagccaag aaatattaaa taaatcagag     4500
aataatagaa ttgcaaataa aattttaatg tattctggta gtttagaatc tacagagctt    4560
gccttaaaca aattgaaaga ctttaaaatt gataagtcaa agtattctat taagaaagat    4620
aataaagcat tcgaagagtc tttagagtca gtgagtggaa taaacatat aattaaaata     4680 atgacttatt cgattatgtt aggtggaata gttgttcttt cattaatctt gattctatgg    4740
ttaagagaaa gaatttatga aataggtata ttttatcta ttggaacaac taagatacaa     4800
attataaggc aatttatatt tgagttaata ttcatatcaa taccaagtat aatatcctcc    4860
ttatttttag ggaatctact attaaaagta attgtagaag gattatttaa ctcagagaac    4920
tcaatgattt tcggtggaag tttaataaat aaaagcagtt ttatgttaaa cataacaaca    4980
cttgcagaaa gttatttaat attaataagt attattgttt tatcagttgt aatggcctct    5040
tcattaatat tatttaagaa accacaagaa atattatcaa aaataagtta ggagcaaata    5100
atggatatat tagaaataaa gaatgtaaat tacagttacg caaattctaa agaaaaagtt    5160
ttgtcaggag taaatcaaaa atttgaactt ggaaagtttt atgcgatagt agggaagtca    5220
ggaacaggaa aatccacact tctttcctta cttgcaggac ttgataaagt tcaaacagga    5280
aaaatcttgt ttaagaatga agatatagaa aagaaaggat atagtaatca cagaaaaaat    5340
aatatatctt tggtatttca aaattataat ttaatagatt atttatcgcc gattgaaaat    5400
attagactag taaataaatc agtagatgag agtatcttgt tcgaattagg tttagataaa    5460
aaacaaataa aaagaaatgt tatgaaatta tctggtggtc agcaacaaag ggtagctatt    5520
gctagggcac tggtatcaga tgccccaata atactagctg atgagcctac cggtaaccta    5580
gacagtgtta ctgctggaga aataatt                                       5607
```

<210> SEQ ID NO 28
<211> LENGTH: 111
<212> TYPE: PRT
<213> ORGANISM: Group B streptococcus

<400> SEQUENCE: 28

```
Ile Gln Ser Leu Thr Glu Gly Gln Leu Arg Ser Asp Ile Pro Glu Phe
  1               5                  10                  15

Arg Ala Gly Asp Thr Val Arg Val His Ala Lys Val Val Glu Gly Thr
             20                  25                  30

Arg Glu Arg Ile Gln Ile Phe Glu Gly Val Val Ile Ser Arg Lys Gly
         35                  40                  45

Gln Gly Ile Ser Glu Met Tyr Thr Val Arg Lys Ile Ser Gly Gly Ile
     50                  55                  60
```

```
Gly Val Glu Arg Thr Phe Pro Ile His Thr Pro Arg Val Asp Lys Ile
 65                  70                  75                  80

Glu Val Val Arg Tyr Gly Lys Val Arg Ala Lys Leu Tyr Tyr Leu
                 85                  90                  95

Arg Ala Leu Gln Gly Lys Ala Arg Ile Lys Glu Ile Arg Arg
                100                 105                 110

<210> SEQ ID NO 29
<211> LENGTH: 173
<212> TYPE: PRT
<213> ORGANISM: Group B streptococcus

<400> SEQUENCE: 29

Met Arg Phe Ala Glu Cys Leu Gly Leu Thr Val Asn Asp Ile Asp Tyr
  1               5                  10                  15

Thr Asn Lys Tyr Leu Ser Ile Asn Lys Thr Trp Asp Tyr His Phe Asn
                 20                  25                  30

Gln Arg Tyr Leu Pro Thr Lys Asn Lys Ser Ser Ile Arg Asn Ile Pro
             35                  40                  45

Ile Asp Asn Asp Thr Leu Phe Phe Leu His Glu Phe Thr Lys Asn Lys
 50                  55                  60

Asn Asp Arg Leu Phe Asp Lys Leu Ser Asn Asn Ala Val Asn Lys Thr
 65                  70                  75                  80

Ile Arg Lys Ile Thr Gly Arg Glu Val Arg Val His Ser Leu Arg His
                 85                  90                  95

Thr Phe Ala Ser Tyr Leu Ile Ser Ile Ser Gln Val Leu Asp His Glu
                100                 105                 110

Asn Leu Asn Ile Thr Leu Glu Val Tyr Ala His Gln Leu Gln Glu Gln
            115                 120                 125

Lys Asp Arg Asn Asp Lys Leu Asn Gln Arg Asn Leu Gly Gln Asn Ser
130                 135                 140

Ser Lys Pro Leu Phe Thr Cys Asn Glu Tyr Val Pro Cys Arg Asn Arg
145                 150                 155                 160

Thr Ser Asn Tyr Ser Leu Gly Gly Ser Cys Tyr Ile His
                165                 170

<210> SEQ ID NO 30
<211> LENGTH: 389
<212> TYPE: PRT
<213> ORGANISM: Group B streptococcus

<400> SEQUENCE: 30

Met Lys Ser Ser Asn Glu Ile Glu Lys Ala Leu Tyr Glu Ser Ser Asn
  1               5                  10                  15

Ser Ser Ile Ser Ile Thr Lys Lys Asp Gly Lys Tyr Phe Asn Ile Asn
                 20                  25                  30

Gln Phe Lys Asn Ile Glu Lys Ile Lys Glu Val Glu Glu Lys Ile Phe
             35                  40                  45

Gln Tyr Asp Gly Leu Ala Lys Leu Lys Asp Leu Lys Val Val Ser Gly
 50                  55                  60

Glu Gln Ser Ile Asn Arg Glu Asp Leu Ser Asp Glu Phe Lys Asn Val
 65                  70                  75                  80

Val Ser Leu Glu Ala Thr Ser Asn Thr Lys Arg Asn Leu Leu Phe Ser
                 85                  90                  95

Ser Gly Val Phe Ser Phe Lys Glu Gly Lys Asn Ile Glu Glu Asn Asp
                100                 105                 110
```

```
Lys Asn Ser Ile Leu Val His Glu Glu Phe Ala Lys Gln Asn Lys Leu
        115                 120                 125

Lys Leu Gly Asp Glu Ile Asp Leu Glu Leu Leu Asp Thr Glu Lys Ser
        130                 135                 140

Gly Lys Ile Lys Ser His Lys Phe Lys Ile Ile Gly Ile Phe Ser Gly
145                 150                 155                 160

Lys Lys Gln Glu Thr Tyr Thr Gly Leu Ser Ser Asp Phe Ser Glu Asn
                165                 170                 175

Met Val Phe Val Asp Tyr Ser Thr Ser Gln Glu Ile Leu Asn Lys Ser
                180                 185                 190

Glu Asn Asn Arg Ile Ala Asn Lys Ile Leu Met Tyr Ser Gly Ser Leu
            195                 200                 205

Glu Ser Thr Glu Leu Ala Leu Asn Lys Leu Lys Asp Phe Lys Ile Asp
        210                 215                 220

Lys Ser Lys Tyr Ser Ile Lys Lys Asp Asn Lys Ala Phe Glu Glu Ser
225                 230                 235                 240

Leu Glu Ser Val Ser Gly Ile Lys His Ile Ile Lys Ile Met Thr Tyr
                245                 250                 255

Ser Ile Met Leu Gly Gly Ile Val Val Leu Ser Leu Ile Leu Ile Leu
            260                 265                 270

Trp Leu Arg Glu Arg Ile Tyr Glu Ile Gly Ile Phe Leu Ser Ile Gly
        275                 280                 285

Thr Thr Lys Ile Gln Ile Ile Arg Gln Phe Ile Phe Glu Leu Ile Phe
        290                 295                 300

Ile Ser Ile Pro Ser Ile Ile Ser Ser Leu Phe Leu Gly Asn Leu Leu
305                 310                 315                 320

Leu Lys Val Ile Val Glu Gly Phe Ile Asn Ser Glu Asn Ser Met Ile
                325                 330                 335

Phe Gly Gly Ser Leu Ile Asn Lys Ser Ser Phe Met Leu Asn Ile Thr
            340                 345                 350

Thr Leu Ala Glu Ser Tyr Leu Ile Leu Ile Ser Ile Ile Val Leu Ser
        355                 360                 365

Val Val Met Ala Ser Ser Leu Ile Leu Phe Lys Lys Pro Gln Glu Ile
370                 375                 380

Leu Ser Lys Ile Ser
385

<210> SEQ ID NO 31
<211> LENGTH: 169
<212> TYPE: PRT
<213> ORGANISM: Group B streptococcus

<400> SEQUENCE: 31

Met Asp Ile Leu Glu Ile Lys Asn Val Asn Tyr Ser Tyr Ala Asn Ser
  1               5                  10                  15

Lys Glu Lys Val Leu Ser Gly Val Asn Gln Lys Phe Glu Leu Gly Lys
                20                  25                  30

Phe Tyr Ala Ile Val Gly Lys Ser Gly Thr Gly Lys Ser Thr Leu Leu
            35                  40                  45

Ser Leu Leu Ala Gly Leu Asp Lys Val Gln Thr Gly Lys Ile Leu Phe
        50                  55                  60

Lys Asn Glu Asp Ile Glu Lys Lys Gly Tyr Ser Asn His Arg Lys Asn
65                  70                  75                  80

Asn Ile Ser Leu Val Phe Gln Asn Tyr Asn Leu Ile Asp Tyr Leu Ser
                85                  90                  95
```

| Pro | Ile | Glu | Asn | Ile | Arg | Leu | Val | Asn | Lys | Ser | Val | Asp | Glu | Ser | Ile |
|---|---|---|---|---|---|---|---|---|---|---|---|---|---|---|---|
| | | | 100 | | | | 105 | | | | 110 | | | | |

| Leu | Phe | Glu | Leu | Gly | Leu | Asp | Lys | Lys | Gln | Ile | Lys | Arg | Asn | Val | Met |
|---|---|---|---|---|---|---|---|---|---|---|---|---|---|---|---|
| | | 115 | | | | | 120 | | | | | 125 | | | |

| Lys | Leu | Ser | Gly | Gly | Gln | Gln | Gln | Arg | Val | Ala | Ile | Ala | Arg | Ala | Leu |
|---|---|---|---|---|---|---|---|---|---|---|---|---|---|---|---|
| 130 | | | | | 135 | | | | | 140 | | | | | |

| Val | Ser | Asp | Ala | Pro | Ile | Ile | Leu | Ala | Asp | Glu | Pro | Thr | Gly | Asn | Leu |
|---|---|---|---|---|---|---|---|---|---|---|---|---|---|---|---|
| 145 | | | | | 150 | | | | | 155 | | | | | 160 |

| Asp | Ser | Val | Thr | Ala | Gly | Glu | Ile | Ile |
|---|---|---|---|---|---|---|---|---|
| | | | | 165 | | | | |

<210> SEQ ID NO 32
<211> LENGTH: 4171
<212> TYPE: DNA
<213> ORGANISM: Group B streptococcus

<400> SEQUENCE: 32

| catatgacaa | tatttttcaa | agtctacatc | acttactcgc | ctgtcgtgga | aaatctggca | 60 |
|---|---|---|---|---|---|---|
| atacattaat | cgaccaatta | gttgctgatg | gtttacttca | tgcagataat | cactaccatt | 120 |
| ttttcaatgg | gaagtctctg | gccactttca | atactaacca | attgattcgc | gaagttgtct | 180 |
| atgttgaaat | atccttagat | actatgtcta | gtggtgaaca | tgatttagta | aaagttaaca | 240 |
| ttatcagacc | cactaccgag | catactatcc | ccacgatgat | gacagctagc | ccctatcatc | 300 |
| aaggtatcaa | tgatcctgcc | gcagaccaaa | aacataccca | aatggagggt | gcgctagcag | 360 |
| ttaaacagcc | taaacacata | caagttgaca | caaaaccatt | aaagaagaa | gtaaaacatc | 420 |
| cttcaaaatt | acccatcagc | cctgcaactg | aaagcttcac | acacattgac | agttatagtc | 480 |
| tcaatgacta | ttttctttct | cgtggttttg | ctaatatata | cgtttcaggt | gtgggtactg | 540 |
| ctggctctac | gggtttcatg | accagtgggg | attaccaaca | aatacaaagc | tttaaagcag | 600 |
| tcattgattg | gttaaatggt | aaggttactg | cattcacaag | tcataaacga | gataaacaag | 660 |
| tcaaggctga | ttggtcaaac | ggccttgtag | caaccacagg | taaatcttat | ctcggtacca | 720 |
| tgtcaactgg | tttagcaaca | actggcgttg | aggggctgaa | agtcattatc | gctgaagccg | 780 |
| caatctccac | atggtatgat | tattatcgag | aaaatgggct | tgtgtgtagt | ccaggcggct | 840 |
| accccggtga | agatttagac | gttttaacag | aattaacata | ctcacgaaac | ctcttagctg | 900 |
| gtgattacat | caaaaacaac | gattgctatc | aagcattgtt | aaatgaacaa | tcaaaagcaa | 960 |
| ttgaccgtca | aagtggggat | acaaccaat | actggcatga | ccgtaattac | ctaactcacg | 1020 |
| tcaataatgt | caaaagtcga | gtagtttaca | ctcatggact | acaggattgg | aatgttaagc | 1080 |
| caagacatgt | ctacaaagtt | ttcaatgcat | tgcctcaaac | catcaaaaaa | cacctttttt | 1140 |
| tacatcaagg | tcaacatgtg | tatatgcata | attggcagtc | gattgatttt | cgtgaaagca | 1200 |
| tgaatgcctt | actaagccaa | gaactacttg | gcattgacaa | tcatttccaa | ttagaagagg | 1260 |
| tcatttggca | agataatact | actgagcaaa | cttggcaagt | tttagatgct | ttcggaggaa | 1320 |
| accatcaaga | gcaaattggt | ttaggtgata | gtaaaaaact | tattgataac | cattatgaca | 1380 |
| aagaagcctt | tgatacttat | tgtaaagact | tcaatgtgtt | caaaaatgat | cttttcaagg | 1440 |
| gaaataataa | aaccaatcaa | atcactatta | atcttcctct | aaagaaaaat | tatctcctga | 1500 |
| atggacagtg | caaactccat | ctcgtgttta | aaactagtga | caaaaggcc | attttatcag | 1560 |
| cccaaatctt | agactatggt | cctaaaaaac | gattcaaaga | tacaccaacc | atcaaattct | 1620 |
| taaacagcct | tgataatggt | aaaaattttg | ccagagaagc | tttacgtgaa | ctcccgttta | 1680 |
| ctaaagatca | ttatcgtgtc | atcagtaaag | gtgtcttgaa | ccttcaaaat | cgtacagact | 1740 |

```
tacttacaat tgaggctatc gagccagaac aatggtttga tatcgagttt agcctccaac   1800
caagtatata tcaattgagt aaaggtgata atctaaggat tatcctttat acaactgatt   1860
ttgaacatac cattcgagat aatgctagtt actctataac agtagatttg agtcaatctt   1920
atttaactat cccaactaat caaggaaatt aacttatgaa acttcttact aaagaacggt   1980
ttgatgattc tcaacacttt tggtaccaga tcaatttatt acaagagagt aacttcggag   2040
cagtttttga ccatgataat aaaaacattc cacaggttgt tgcaactatt gttgatgatt   2100
tacaaggttc cggaagttcg aatcatttct ggtattttgg caatactact gatacttcca   2160
tccttatgat tgctcattta aatcgaaaat tctatattca ggttaattta aaggactttg   2220
actttgcact caatttaata gctataaata attggaagag tctcctccaa actcaacttg   2280
aagctctaaa cgatacccta gcaatatttc aataaataag gtagaatgga gtgacaaagc   2340
aacgcgaggg agactgatta atgtcatctt attggaataa ctatcctgaa cttaaaaaaa   2400
atattgatga aaccaatcaa ctaattcaag aaagaataca ggtcagaaat aaagatattg   2460
aagcggcgct aagccaactc acagctgcgg gaggaaaaca gctcagacca gcattctttt   2520 acctttttc tcaacttggt aataaggaga tcaagatac tcagcaacta aagaaaatcg   2580
ctgcttcttt agaaatcctt cacgttgcta cattaatcca tgatgatgtc attgatgact   2640
caccactaag acgtggaaat atgaccattc aaagcaagtt tggcaaagac atcgcagttt   2700
atactgggga tttacttttc acagtctttt tcgatcttat tttagaatct atgactgata   2760
caccatttat gaggattaat gcaaaatcta tgcgtaaaat tctcatggga gaattggacc   2820
agatgcacct tcgttacaat caacaacaag gtatccatca ctatttacgt gcgatttcag   2880
gtaagacagc cgaactcttt aaattagcta gcaaagaagg agcttacttt ggtggtgcag   2940
agaaggaggt tgttcgtcta gcaggccata tcggctttaa cattggtatg acattccaaa   3000
ttttggatga tatcctggat tatactgcag ataaaaaaac atttaataag cctgtcttag   3060
aggatttaac acaaggcgtt tacagccttc ctctacttct tgccattgaa gaaaatcctg   3120
atattttcaa acctatttta gataaaaaaa cagatatggc tactgaagac atggaaaaaa   3180
ttgcttatct cgtcgtttcc catagaggtg ttgacaaagc tcgccatcta gctcgtaaat   3240
ttactgagaa agctattagt gacataaata agctaccca gaactctgca aaaaaacagt   3300
tgctacaatt aactaattac cttttaaaac gcaaaattta aataataaaa aaacattcca   3360
caatgctaga aaagcagtta gggaatgttt ttttattatc atttatttat cgcacctatc   3420
aatcatcata gatcaccatc atcagcggct ttcagctgac ggtaacgttg actactttga   3480
gacaattctt gaggagaacc ttccaactct aattgcccat tttctataaa taagatacga   3540
tcagcatgtt caatacctttt aagtgatgt gtaatccaaa ctaaggtctt accttccaat   3600
tctttcataa ataccttag taaggcttgt tcagtaatag gatcaagtcc aacagttggc   3660
tcatctaaga taacaattgg gacatctttt agtaagattc tagccaaagc aattctatgc   3720
ctttcgccac ctgaaaacct aagtccagct tcatcaacca ttgtatagag accatctgat   3780
aaatcagtga ccatctcttt caatccaact cgttcaagaa ctttccatac atcttcttca   3840
ctagcatctt ggtttccaat gcgaatgtta tttagcaggg ttgtattaaa aaggtagggc   3900
gcttgttgta tcactccaat atagttagaa atgcaatcac caactattga acatcagca   3960 ccgcctaggg taatcttccc ttgacttgct ttcaagtcgc cacgaagtag actagctaag   4020
gtactcttgc cagaaccact ccgccctaaa atagcaattt tttctccttc tttaatatcc   4080
```

```
aaatctaaat gatgcaaaac ccatttctct tgtggcttat actgaaact taaattcttg    4140 acggaaaaat catatggctt attaggcaat t                                   4171
```

<210> SEQ ID NO 33
<211> LENGTH: 649
<212> TYPE: PRT
<213> ORGANISM: Group B streptococcus

<400> SEQUENCE: 33

| | | | | | | | | | | | | | | |
|---|---|---|---|---|---|---|---|---|---|---|---|---|---|---|
|Tyr|Asp|Asn|Ile|Phe|Gln|Ser|Leu|His|His|Leu|Leu|Ala|Cys|Arg|Gly|
|1| | | |5| | | | |10| | | | |15| |

Lys Ser Gly Asn Thr Leu Ile Asp Gln Leu Val Ala Asp Gly Leu Leu
           20                  25                  30

His Ala Asp Asn His Tyr His Phe Phe Asn Gly Lys Ser Leu Ala Thr
        35                  40                  45

Phe Asn Thr Asn Gln Leu Ile Arg Glu Val Val Tyr Val Glu Ile Ser
 50                  55                  60

Leu Asp Thr Met Ser Ser Gly Glu His Asp Leu Val Lys Val Asn Ile
65                  70                  75                  80

Ile Arg Pro Thr Thr Glu His Thr Ile Pro Thr Met Met Thr Ala Ser
                85                  90                  95

Pro Tyr His Gln Gly Ile Asn Asp Pro Ala Ala Asp Gln Lys Thr Tyr
            100                 105                 110

Gln Met Glu Gly Ala Leu Ala Val Lys Gln Pro Lys His Ile Gln Val
        115                 120                 125

Asp Thr Lys Pro Phe Lys Glu Val Lys His Pro Ser Lys Leu Pro
    130                 135                 140

Ile Ser Pro Ala Thr Glu Ser Phe Thr His Ile Asp Ser Tyr Ser Leu
145                 150                 155                 160

Asn Asp Tyr Phe Leu Ser Arg Gly Phe Ala Asn Ile Tyr Val Ser Gly
                165                 170                 175

Val Gly Thr Ala Gly Ser Thr Gly Phe Met Thr Ser Gly Asp Tyr Gln
            180                 185                 190

Gln Ile Gln Ser Phe Lys Ala Val Ile Asp Trp Leu Asn Gly Lys Val
        195                 200                 205

Thr Ala Phe Thr Ser His Lys Arg Asp Lys Gln Val Lys Ala Asp Trp
    210                 215                 220

Ser Asn Gly Leu Val Ala Thr Thr Gly Lys Ser Tyr Leu Gly Thr Met
225                 230                 235                 240

Ser Thr Gly Leu Ala Thr Thr Gly Val Glu Gly Leu Lys Val Ile Ile
                245                 250                 255

Ala Glu Ala Ala Ile Ser Thr Trp Tyr Asp Tyr Tyr Arg Glu Asn Gly
            260                 265                 270

Leu Val Cys Ser Pro Gly Gly Tyr Pro Gly Glu Asp Leu Asp Val Leu
        275                 280                 285

Thr Glu Leu Thr Tyr Ser Arg Asn Leu Leu Ala Gly Asp Tyr Ile Lys
    290                 295                 300

Asn Asn Asp Cys Tyr Gln Ala Leu Leu Asn Glu Gln Ser Lys Ala Ile
305                 310                 315                 320

Asp Arg Gln Ser Gly Asp Tyr Asn Gln Tyr Trp His Asp Arg Asn Tyr
                325                 330                 335

Leu Thr His Val Asn Asn Val Lys Ser Arg Val Val Tyr Thr His Gly
            340                 345                 350

Leu Gln Asp Trp Asn Val Lys Pro Arg His Val Tyr Lys Val Phe Asn
        355                 360                 365

-continued

Ala Leu Pro Gln Thr Ile Lys Lys His Leu Phe Leu His Gln Gly Gln
        370                 375                 380

His Val Tyr Met His Asn Trp Gln Ser Ile Asp Phe Arg Glu Ser Met
385                 390                 395                 400

Asn Ala Leu Leu Ser Gln Glu Leu Leu Gly Ile Asp Asn His Phe Gln
                405                 410                 415

Leu Glu Glu Val Ile Trp Gln Asp Asn Thr Thr Glu Gln Thr Trp Gln
            420                 425                 430

Val Leu Asp Ala Phe Gly Gly Asn His Gln Glu Gln Ile Gly Leu Gly
        435                 440                 445

Asp Ser Lys Lys Leu Ile Asp Asn His Tyr Asp Lys Glu Ala Phe Asp
    450                 455                 460

Thr Tyr Cys Lys Asp Phe Asn Val Phe Lys Asn Asp Leu Phe Lys Gly
465                 470                 475                 480

Asn Asn Lys Thr Asn Gln Ile Thr Ile Asn Leu Pro Leu Lys Lys Asn
                485                 490                 495

Tyr Leu Leu Asn Gly Gln Cys Lys Leu His Leu Arg Val Lys Thr Ser
            500                 505                 510

Asp Lys Lys Ala Ile Leu Ser Ala Gln Ile Leu Asp Tyr Gly Pro Lys
        515                 520                 525

Lys Arg Phe Lys Asp Thr Pro Thr Ile Lys Phe Leu Asn Ser Leu Asp
    530                 535                 540

Asn Gly Lys Asn Phe Ala Arg Glu Ala Leu Arg Glu Leu Pro Phe Thr
545                 550                 555                 560

Lys Asp His Tyr Arg Val Ile Ser Lys Gly Val Leu Asn Leu Gln Asn
                565                 570                 575

Arg Thr Asp Leu Leu Thr Ile Glu Ala Ile Glu Pro Glu Gln Trp Phe
            580                 585                 590

Asp Ile Glu Phe Ser Leu Gln Pro Ser Ile Tyr Gln Leu Ser Lys Gly
        595                 600                 605

Asp Asn Leu Arg Ile Ile Leu Tyr Thr Thr Asp Phe Glu His Thr Ile
    610                 615                 620

Arg Asp Asn Ala Ser Tyr Ser Ile Thr Val Asp Leu Ser Gln Ser Tyr
625                 630                 635                 640

Leu Thr Ile Pro Thr Asn Gln Gly Asn
                645

<210> SEQ ID NO 34
<211> LENGTH: 119
<212> TYPE: PRT
<213> ORGANISM: Group B streptococcus

<400> SEQUENCE: 34

Met Lys Leu Leu Thr Lys Glu Arg Phe Asp Asp Ser Gln His Phe Trp
1               5                   10                  15

Tyr Gln Ile Asn Leu Leu Gln Glu Ser Asn Phe Gly Ala Val Phe Asp
                20                  25                  30

His Asp Asn Lys Asn Ile Pro Gln Val Val Ala Thr Ile Val Asp Asp
            35                  40                  45

Leu Gln Gly Ser Gly Ser Ser Asn His Phe Trp Tyr Phe Gly Asn Thr
        50                  55                  60

Thr Asp Thr Ser Ile Leu Met Ile Ala His Leu Asn Arg Lys Phe Tyr
65                  70                  75                  80

Ile Gln Val Asn Leu Lys Asp Phe Asp Phe Ala Leu Asn Leu Ile Ala
                85                  90                  95

```
Ile Asn Asn Trp Lys Ser Leu Leu Gln Thr Gln Leu Glu Ala Leu Asn
                100                 105                 110

Asp Thr Leu Ala Ile Phe Gln
        115
```

<210> SEQ ID NO 35
<211> LENGTH: 326
<212> TYPE: PRT
<213> ORGANISM: Group B streptococcus

<400> SEQUENCE: 35

```
Met Ser Ser Tyr Trp Asn Asn Tyr Pro Glu Leu Lys Lys Asn Ile Asp
  1               5                  10                  15

Glu Thr Asn Gln Leu Ile Gln Glu Arg Ile Gln Val Arg Asn Lys Asp
                 20                  25                  30

Ile Glu Ala Ala Leu Ser Gln Leu Thr Ala Ala Gly Gly Lys Gln Leu
             35                  40                  45

Arg Pro Ala Phe Phe Tyr Leu Phe Ser Gln Leu Gly Asn Lys Glu Asn
 50                  55                  60

Gln Asp Thr Gln Leu Lys Lys Ile Ala Ala Ser Leu Glu Ile Leu
 65                  70                  75                  80

His Val Ala Thr Leu Ile His Asp Asp Val Ile Asp Asp Ser Pro Leu
                 85                  90                  95

Arg Arg Gly Asn Met Thr Ile Ser Lys Phe Gly Lys Asp Ile Ala
                100                 105                 110

Val Tyr Thr Gly Asp Leu Leu Phe Thr Val Phe Phe Asp Leu Ile Leu
            115                 120                 125

Glu Ser Met Thr Asp Thr Pro Phe Met Arg Ile Asn Ala Lys Ser Met
130                 135                 140

Arg Lys Ile Leu Met Gly Glu Leu Asp Gln Met His Leu Arg Tyr Asn
145                 150                 155                 160

Gln Gln Gln Gly Ile His His Tyr Leu Arg Ala Ile Ser Gly Lys Thr
                165                 170                 175

Ala Glu Leu Phe Lys Leu Ala Ser Lys Glu Gly Ala Tyr Phe Gly Gly
            180                 185                 190

Ala Glu Lys Glu Val Val Arg Leu Ala Gly His Ile Gly Phe Asn Ile
        195                 200                 205

Gly Met Thr Phe Gln Ile Leu Asp Asp Ile Leu Asp Tyr Thr Ala Asp
    210                 215                 220

Lys Lys Thr Phe Asn Lys Pro Val Leu Glu Asp Leu Thr Gln Gly Val
225                 230                 235                 240

Tyr Ser Leu Pro Leu Leu Leu Ala Ile Glu Glu Asn Pro Asp Ile Phe
                245                 250                 255

Lys Pro Ile Leu Asp Lys Lys Thr Asp Met Ala Thr Glu Asp Met Glu
            260                 265                 270

Lys Ile Ala Tyr Leu Val Val Ser His Arg Gly Val Asp Lys Ala Arg
        275                 280                 285

His Leu Ala Arg Lys Phe Thr Glu Lys Ala Ile Ser Asp Ile Asn Lys
    290                 295                 300

Leu Pro Gln Asn Ser Ala Lys Lys Gln Leu Leu Gln Leu Thr Asn Tyr
305                 310                 315                 320

Leu Leu Lys Arg Lys Ile
                325
```

```
<210> SEQ ID NO 36
<211> LENGTH: 247
<212> TYPE: PRT
<213> ORGANISM: Group B streptococcus

<400> SEQUENCE: 36

Leu Pro Asn Lys Pro Tyr Asp Phe Ser Val Lys Asn Leu Ser Phe Gln
  1               5                  10                  15

Tyr Lys Pro Gln Glu Lys Trp Val Leu His His Leu Asp Leu Asp Ile
             20                  25                  30

Lys Glu Gly Glu Lys Ile Ala Ile Leu Gly Arg Ser Gly Ser Gly Lys
         35                  40                  45

Ser Thr Leu Ala Ser Leu Leu Arg Gly Asp Leu Lys Ala Ser Gln Gly
     50                  55                  60

Lys Ile Thr Leu Gly Gly Ala Asp Val Ser Ile Val Gly Asp Cys Ile
 65                  70                  75                  80

Ser Asn Tyr Ile Gly Val Ile Gln Gln Ala Pro Tyr Leu Phe Asn Thr
                 85                  90                  95

Thr Leu Leu Asn Asn Ile Arg Ile Gly Asn Gln Asp Ala Ser Glu Glu
            100                 105                 110

Asp Val Trp Lys Val Leu Glu Arg Val Gly Leu Lys Glu Met Val Thr
        115                 120                 125

Asp Leu Ser Asp Gly Leu Tyr Thr Met Val Asp Glu Ala Gly Leu Arg
    130                 135                 140

Phe Ser Gly Gly Glu Arg His Arg Ile Ala Leu Ala Arg Ile Leu Leu
145                 150                 155                 160

Lys Asp Val Pro Ile Val Ile Leu Asp Glu Pro Thr Val Gly Leu Asp
                165                 170                 175

Pro Ile Thr Glu Gln Ala Leu Leu Arg Val Phe Met Lys Glu Leu Glu
            180                 185                 190

Gly Lys Thr Leu Val Trp Ile Thr His His Leu Lys Gly Ile Glu His
        195                 200                 205

Ala Asp Arg Ile Leu Phe Ile Glu Asn Gly Gln Leu Glu Leu Glu Gly
    210                 215                 220

Ser Pro Gln Glu Leu Ser Gln Ser Ser Gln Arg Tyr Arg Gln Leu Lys
225                 230                 235                 240

Ala Ala Asp Asp Gly Asp Leu
                245

<210> SEQ ID NO 37
<211> LENGTH: 3480
<212> TYPE: DNA
<213> ORGANISM: Group B streptococcus

<400> SEQUENCE: 37
aattctattt ggaggttttt cttgaataaa tggttagtta aggcaagttc cttagttgtt      60
ttaggtggta tggttttatc tgcgggttcc cgagttttag cggatactta tgtccgtcca     120
attgataatg gtagaattac aacaggtttc aatggttatc ctggacattg tggggtggat     180
tatgctgttc cgactggaac gattattagg gcagtggcag atggtactgt gaaatttgca     240
ggagctggag ccaacttttc ttggatgaca gacttagcag gaaattgtgt catgattcaa     300
catgcggatg gaatgcatag tggttacgct catatgtcac gtgtggtggc taggactggg     360
gaaaaagtca acaaggaga tatcatcggt tacgtaggag caactggtat ggcgacggga     420
cctcaccttc atttttgaatt tttaccagct aaccctaatt ttcaaaatgg tttccatgga     480
cgtatcaatc caacgtcact aattgctaac gttgcgacct ttagtggaaa aacgcaagca     540
```

```
tcagctccaa gcattaagcc attacaatca gctcctgtac agaatcaatc tagtaaatta      600
aaagtgtatc gagtagatga attacaaaag gttaatggtg tttggttagt caaaaataac      660
accctaacgc cgactgggtt tgattggaac gataatggta taccagcatc agaaattgat      720
gaggttgatg ctaatggtaa tttgacagct gaccaggttc ttcaaaaagg tggttacttt      780
atctttaatc ctaaaactct taagactgta gaaaaaccca tccaaggaac agctggttta      840
acttgggcta agacacgctt tgctaatggt agttcagttt ggcttcgcgt tgacaacagt      900
caagaactgc tttacaaata gtttgaggta ttgattcatt gttttaaatg acagttttgt      960
tactaactaa gtacaatttc tttaaaccgt ctgaaaataa ttttatagtc cagtaaagtg     1020
tgatattata gtctcggact aataaaaagg aaataggaat tgaagcaatg aaaatgaata     1080
aaaaggtact attgacatcg acaatggcag cttcgctatt atcagtcgca agtgttcaag     1140
cacaagaaac agatacgacg tggacagcac gtactgtttc agaggtaaag gctgatttgg     1200
taaagcaaga caataaatca tcatatactg tgaaatatgg tgatacacta agcgttattt     1260
cagaagcaat gtcaattgat atgaatgtct tagcaaaaat taataacatt gcagatatca     1320
atcttattta tcctgagaca acactgacag taacttacga tcagaagagt catactgcca     1380
cttcaatgaa aatagaaaca ccagcaacaa atgctgctgg tcaaacaaca gctactgtgg     1440
atttgaaaac caatcaagtt tctgttgcag accaaaaagt ttctctcaat acaatttcgg     1500
aaggtatgac accagaagca gcaacaacga ttgtttcgcc aatgaagaca tattcttctg     1560
cgccagcttt gaaatcaaaa gaagtattag cacaagagca agctgttagt caagcagcag     1620
ctaatgaaca ggtatcaaca gctcctgtga agtcgattac ttcagaagtt ccagcagcta     1680
aagaggaagt taaaccaact cagacgtcag tcagtcagtc aacaacagta tcaccagctt     1740
ctgttgccgc tgaaacacca gctccagtag ctaaagtagc accggtaaga actgtagcag     1800
cccctagagt ggcaagtgtt aaagtagtca ctcctaaagt agaaactggt gcatcaccag     1860
agcatgtatc agctccagca gttcctgtga ctacgacttc aacagctaca gacagtaagt     1920
tacaagcgac tgaagttaag agcgttccgg tagcacaaaa agctccaaca gcaacaccgg     1980
tagcacaacc agcttcaaca acaaatgcag tagctgcaca tcctgaaaat gcagggctcc     2040
aacctcatgt tgcagcttat aaagaaaaag tagcgtcaac ttatggagtt aatgaattca     2100
gtacataccg tgcaggtgat ccaggtgatc atggtaaagg tttagcagtc gactttattg     2160
taggtaaaaa ccaagcactt ggtaatgaag ttgcacagta ctctacacaa aatatggcag     2220
caaataacat ttcatatgtt atctggcaac aaaagtttta ctcaaataca aatagtattt     2280
atggacctgc taatacttgg aatgcaatgc cagatcgtgg tggcgttact gccaaccatt     2340
atgaccatgt tcacgtatca tttaacaaat aatataaaaa aggaagctat ttggcttctt     2400
ttttatatgc cttgaataga ctttcaaggt tcttatctaa ttttttattaa attgaggaga     2460 ttaagctata agtctgaaac tactttcacg ttaaccgtga ctaaatcaaa acgttaaaac     2520
taaaatctaa gtctgtaaag attattgaaa acgctttaaa aacagatata ataaggtttg     2580
tagatatcta aaattaaaaa agataaggaa gtgagaatat gccacatcta agtaaagaag     2640
cttttaaaaa gcaaataaaa aatggcatta ttgtgtcatg tcaagctttg cctggggagc     2700
ctctttatac tgaaagtgga ggtgttatgc ctcttttagc tttggcagct caagaagcag     2760
gagcggttgg tataagagcc aatagtgtcc gcgacattaa ggaaattcaa gaagttacta     2820
atttacctat catcggcatt attaaacgtg aatatcctcc acaagaacca tttatcactg     2880
ctacgatgac agaggtggat caattagcta gtttagatat tgcagtaata gccttagatt     2940
```

-continued

```
gtacacttag agagcgtcat gatggtttga gtgtagctga gtttattcaa aagataaaag      3000
ggaaatatcc tgaacagttg ctaatggctg atataagtac ttttgaagaa ggtaaaaatg      3060
cttttgaagc aggagttgat tttgtgggta caactctatc tggatacaca gattacagcc      3120
gccaagaaga aggaccggat atagaactcc ttaataagct tgtcaagcc  ggtatagatg      3180 tgattgcgga aggtaaaatt catactccta agcaagctaa tgaaattaat catataggtg      3240
ttgcaggaat gtagttggt  ggtgctatca ctagaccaaa agaaatagcg gagcgtttca      3300
tctcaggact tagttaaaag tgttactcaa aaatcaaaat caaaataaaa aaggggaata      3360
gttatgagta tcaaaaaaag tgtgattggt ttttgcctcg gagctgcagc attatcaatg      3420
tttgcttgtg tagacagtag tcaatctgtt atggctgccg agaaggataa agtcgaaatt      3480
```

<210> SEQ ID NO 38
<211> LENGTH: 306
<212> TYPE: PRT
<213> ORGANISM: Group B streptococcus

<400> SEQUENCE: 38

```
Asn Ser Ile Trp Arg Phe Phe Leu Asn Lys Trp Leu Val Lys Ala Ser
  1               5                  10                  15

Ser Leu Val Val Leu Gly Gly Met Val Leu Ser Ala Gly Ser Arg Val
             20                  25                  30

Leu Ala Asp Thr Tyr Val Arg Pro Ile Asp Asn Gly Arg Ile Thr Thr
         35                  40                  45

Gly Phe Asn Gly Tyr Pro Gly His Cys Gly Val Asp Tyr Ala Val Pro
     50                  55                  60

Thr Gly Thr Ile Ile Arg Ala Val Ala Asp Gly Thr Val Lys Phe Ala
 65                  70                  75                  80

Gly Ala Gly Ala Asn Phe Ser Trp Met Thr Asp Leu Ala Gly Asn Cys
                 85                  90                  95

Val Met Ile Gln His Ala Asp Gly Met His Ser Gly Tyr Ala His Met
            100                 105                 110

Ser Arg Val Val Ala Arg Thr Gly Glu Lys Val Lys Gln Gly Asp Ile
        115                 120                 125

Ile Gly Tyr Val Gly Ala Thr Gly Met Ala Thr Gly Pro His Leu His
    130                 135                 140

Phe Glu Phe Leu Pro Ala Asn Pro Asn Phe Gln Asn Gly Phe His Gly
145                 150                 155                 160

Arg Ile Asn Pro Thr Ser Leu Ile Ala Asn Val Ala Thr Phe Ser Gly
                165                 170                 175

Lys Thr Gln Ala Ser Ala Pro Ser Ile Lys Pro Leu Gln Ser Ala Pro
            180                 185                 190

Val Gln Asn Gln Ser Ser Lys Leu Lys Val Tyr Arg Val Asp Glu Leu
        195                 200                 205

Gln Lys Val Asn Gly Val Trp Leu Val Lys Asn Asn Thr Leu Thr Pro
    210                 215                 220

Thr Gly Phe Asp Trp Asn Asp Asn Gly Ile Pro Ala Ser Glu Ile Asp
225                 230                 235                 240

Glu Val Asp Ala Asn Gly Asn Leu Thr Ala Asp Gln Val Leu Gln Lys
                245                 250                 255

Gly Gly Tyr Phe Ile Phe Asn Pro Lys Thr Leu Lys Thr Val Glu Lys
            260                 265                 270

Pro Ile Gln Gly Thr Ala Gly Leu Thr Trp Ala Lys Thr Arg Phe Ala
        275                 280                 285
```

```
Asn Gly Ser Ser Val Trp Leu Arg Val Asp Asn Ser Gln Glu Leu Leu
            290                 295                 300

Tyr Lys
305

<210> SEQ ID NO 39
<211> LENGTH: 434
<212> TYPE: PRT
<213> ORGANISM: Group B streptococcus

<400> SEQUENCE: 39

Met Lys Met Asn Lys Lys Val Leu Leu Thr Ser Thr Met Ala Ala Ser
  1               5                  10                  15

Leu Leu Ser Val Ala Ser Val Gln Ala Gln Glu Thr Asp Thr Thr Trp
             20                  25                  30

Thr Ala Arg Thr Val Ser Glu Val Lys Ala Asp Leu Val Lys Gln Asp
         35                  40                  45

Asn Lys Ser Ser Tyr Thr Val Lys Tyr Gly Asp Thr Leu Ser Val Ile
 50                  55                  60

Ser Glu Ala Met Ser Ile Asp Met Asn Val Leu Ala Lys Ile Asn Asn
 65                  70                  75                  80

Ile Ala Asp Ile Asn Leu Ile Tyr Pro Glu Thr Thr Leu Thr Val Thr
                 85                  90                  95

Tyr Asp Gln Lys Ser His Thr Ala Thr Ser Met Lys Ile Glu Thr Pro
            100                 105                 110

Ala Thr Asn Ala Ala Gly Gln Thr Thr Ala Thr Val Asp Leu Lys Thr
        115                 120                 125

Asn Gln Val Ser Val Ala Asp Gln Lys Val Ser Leu Asn Thr Ile Ser
130                 135                 140

Glu Gly Met Thr Pro Glu Ala Ala Thr Thr Ile Val Ser Pro Met Lys
145                 150                 155                 160

Thr Tyr Ser Ser Ala Pro Ala Leu Lys Ser Lys Glu Val Leu Ala Gln
                165                 170                 175

Glu Gln Ala Val Ser Gln Ala Ala Asn Glu Gln Val Ser Thr Ala
            180                 185                 190

Pro Val Lys Ser Ile Thr Ser Glu Val Pro Ala Ala Lys Glu Glu Val
        195                 200                 205

Lys Pro Thr Gln Thr Ser Val Ser Gln Ser Thr Thr Val Ser Pro Ala
210                 215                 220

Ser Val Ala Ala Glu Thr Pro Ala Pro Val Ala Lys Val Ala Pro Val
225                 230                 235                 240

Arg Thr Val Ala Ala Pro Arg Val Ala Ser Val Lys Val Val Thr Pro
                245                 250                 255

Lys Val Glu Thr Gly Ala Ser Pro Glu His Val Ser Ala Pro Ala Val
            260                 265                 270

Pro Val Thr Thr Thr Ser Thr Ala Thr Asp Ser Lys Leu Gln Ala Thr
        275                 280                 285

Glu Val Lys Ser Val Pro Val Ala Gln Lys Ala Pro Thr Ala Thr Pro
290                 295                 300

Val Ala Gln Pro Ala Ser Thr Asn Ala Val Ala Ala His Pro Glu
305                 310                 315                 320

Asn Ala Gly Leu Gln Pro His Val Ala Ala Tyr Lys Glu Lys Val Ala
                325                 330                 335

Ser Thr Tyr Gly Val Asn Glu Phe Ser Thr Tyr Arg Ala Gly Asp Pro
            340                 345                 350
```

-continued

Gly Asp His Gly Lys Gly Leu Ala Val Asp Phe Ile Val Gly Lys Asn
              355                 360                 365

Gln Ala Leu Gly Asn Glu Val Ala Gln Tyr Ser Thr Gln Asn Met Ala
    370                 375                 380

Ala Asn Asn Ile Ser Tyr Val Ile Trp Gln Gln Lys Phe Tyr Ser Asn
385                 390                 395                 400

Thr Asn Ser Ile Tyr Gly Pro Ala Asn Thr Trp Asn Ala Met Pro Asp
                405                 410                 415

Arg Gly Gly Val Thr Ala Asn His Tyr Asp His Val His Val Ser Phe
                420                 425                 430

Asn Lys

<210> SEQ ID NO 40
<211> LENGTH: 232
<212> TYPE: PRT
<213> ORGANISM: Group B streptococcus
<220> FEATURE:
<221> NAME/KEY: VARIANT
<222> LOCATION: 167
<223> OTHER INFORMATION: Xaa = Any Amino Acid

<400> SEQUENCE: 40

Met Pro His Leu Ser Lys Glu Ala Phe Lys Lys Gln Ile Lys Asn Gly
1               5                   10                  15

Ile Ile Val Ser Cys Gln Ala Leu Pro Gly Glu Pro Leu Tyr Thr Glu
                20                  25                  30

Ser Gly Gly Val Met Pro Leu Leu Ala Leu Ala Ala Gln Glu Ala Gly
        35                  40                  45

Ala Val Gly Ile Arg Ala Asn Ser Val Arg Asp Ile Lys Glu Ile Gln
    50                  55                  60

Glu Val Thr Asn Leu Pro Ile Ile Gly Ile Ile Lys Arg Glu Tyr Pro
65                  70                  75                  80

Pro Gln Glu Pro Phe Ile Thr Ala Thr Met Thr Glu Val Asp Gln Leu
                85                  90                  95

Ala Ser Leu Asp Ile Ala Val Ile Ala Leu Asp Cys Thr Leu Arg Glu
                100                 105                 110

Arg His Asp Gly Leu Ser Val Ala Glu Phe Ile Gln Lys Ile Lys Gly
            115                 120                 125

Lys Tyr Pro Glu Gln Leu Leu Met Ala Asp Ile Ser Thr Phe Glu Glu
    130                 135                 140

Gly Lys Asn Ala Phe Glu Ala Gly Val Asp Phe Val Gly Thr Thr Leu
145                 150                 155                 160

Ser Gly Tyr Thr Asp Tyr Xaa Arg Gln Glu Glu Gly Pro Asp Ile Glu
                165                 170                 175

Leu Leu Asn Lys Leu Cys Gln Ala Gly Ile Asp Val Ile Ala Glu Gly
                180                 185                 190

Lys Ile His Thr Pro Lys Gln Ala Asn Glu Ile Asn His Ile Gly Val
            195                 200                 205

Ala Gly Ile Val Val Gly Gly Ala Ile Thr Arg Pro Lys Glu Ile Ala
    210                 215                 220

Glu Arg Phe Ile Ser Gly Leu Ser
225                 230

<210> SEQ ID NO 41
<211> LENGTH: 39
<212> TYPE: PRT
<213> ORGANISM: Group B streptococcus -continued

```
<400> SEQUENCE: 41

Met Ser Ile Lys Lys Ser Val Ile Gly Phe Cys Leu Gly Ala Ala Ala
 1               5                  10                  15

Leu Ser Met Phe Ala Cys Val Asp Ser Ser Gln Ser Val Met Ala Ala
            20                  25                  30

Glu Lys Asp Lys Val Glu Ile
            35

<210> SEQ ID NO 42
<211> LENGTH: 1305
<212> TYPE: DNA
<213> ORGANISM: Group B streptococcus

<400> SEQUENCE: 42
atgaaaatga ataaaaaggt actattgaca tcgacaatgg cagcttcgct attatcagtc      60
gcaagtgttc aagcacaaga acagatacg acgtggacag cacgtactgt ttcagaggta     120
aaggctgatt tggtaaagca agacaataaa tcatcatata ctgtgaaata tggtgataca     180
ctaagcgtta tttcagaagc aatgtcaatt gatatgaatg tcttagcaaa aattaataac     240
attgcagata tcaatcttat ttatcctgag acaacactga cagtaactta cgatcagaag     300
agtcatactg ccacttcaat gaaaatagaa acaccagcaa caaatgctgc tggtcaaaca     360
acagctactg tggatttgaa accaatcaa gtttctgttg cagaccaaaa agtttctctc      420
aatacaattt cggaaggtat gacaccagaa gcagcaacaa cgattgtttc gccaatgaag     480
acatattctt ctgcgccagc tttgaaatca aagaagtat tagcacaaga gcaagctgtt     540
agtcaagcag cagctaatga acaggtatca acagctcctg tgaagtcgat tacttcagaa     600
gttccagcag ctaaagagga agttaaacca actcagacgt cagtcagtca gtcaacaaca     660
gtatcaccag cttctgttgc cgctgaaaca ccagctccag tagctaaagt agcaccggta     720
agaactgtag cagcccctag agtggcaagt gttaaagtag tcactcctaa agtagaaact     780
ggtgcatcac cagagcatgt atcagctcca gcagttcctg tgactacgac ttcaacagct     840
acagacagta agttacaagc gactgaagtt aagagcgttc cggtagcaca aaaagctcca     900
acagcaacac cggtagcaca accagcttca acaacaaatg cagtagctgc acatcctgaa     960
aatgcagggc tccaacctca tgttgcagct tataaagaaa aagtagcgtc aacttatgga    1020
gttaatgaat tcagtacata ccgtgcaggt gatccaggtg atcatggtaa aggtttagca    1080
gtcgacttta ttgtaggtaa aaaccaagca cttggtaatg aagttgcaca gtactctaca    1140
caaaatatgg cagcaaataa catttcatat gttatctggc aacaaaagtt ttactcaaat    1200
acaaatagta tttatggacc tgctaatact tggaatgcaa tgccagatcg tggtggcgtt    1260
actgccaacc attatgacca tgttcacgta tcatttaaca aataa                    1305

<210> SEQ ID NO 43
<211> LENGTH: 1230
<212> TYPE: DNA
<213> ORGANISM: Group B streptococcus

<400> SEQUENCE: 43
caagaaacag atacgacgtg gacagcacgt actgtttcag aggtaaaggc tgatttggta      60
aagcaagaca taaatcatc atatactgtg aaatatggtg atacactaag cgttatttca     120
gaagcaatgt caattgatat gaatgtctta gcaaaaatta ataacattgc agatatcaat     180
cttatttatc ctgagacaac actgacagta acttacgatc agaagagtca tactgccact     240
tcaatgaaaa tagaaacacc agcaacaaat gctgctggtc aaacaacagc tactgtggat    300
```

-continued

```
ttgaaaacca atcaagtttc tgttgcagac caaaaagttt ctctcaatac aatttcggaa    360
ggtatgacac cagaagcagc aacaacgatt gtttcgccaa tgaagacata ttcttctgcg    420
ccagctttga aatcaaaaga agtattagca caagagcaag ctgttagtca agcagcagct    480
aatgaacagg tatcaacagc tcctgtgaag tcgattactt cagaagttcc agcagctaaa    540
gaggaagtta aaccaactca gacgtcagtc agtcagtcaa caacagtatc accagcttct    600
gttgccgctg aaacaccagc tccagtagct aaagtagcac cggtaagaac tgtagcagcc    660
cctagagtgg caagtgttaa agtagtcact cctaaagtag aaactggtgc atcaccagag    720
catgtatcag ctccagcagt tcctgtgact acgacttcaa cagctacaga cagtaagtta    780
caagcgactg aagttaagag cgttccggta gcacaaaaag ctccaacagc aacaccggta    840
gcacaaccag cttcaacaac aaatgcagta gctgcacatc ctgaaaatgc agggctccaa    900
cctcatgttg cagcttataa agaaaaagta gcgtcaactt atggagttaa tgaattcagt    960
acataccgtg caggtgatcc aggtgatcat ggtaaaggtt tagcagtcga ctttattgta   1020
ggtaaaaacc aagcacttgg taatgaagtt gcacagtact ctacacaaaa tatggcagca   1080
aataacattt catatgttat ctggcaacaa aagtttact caaatacaaa tagtattta   1140
ggacctgcta atacttggaa tgcaatgcca gatcgtggtg gcgttactgc caaccattat   1200
gaccatgttc acgtatcatt taacaaataa                                   1230
```

<210> SEQ ID NO 44
<211> LENGTH: 409
<212> TYPE: PRT
<213> ORGANISM: Group B streptococcus

<400> SEQUENCE: 44

```
Gln Glu Thr Asp Thr Thr Trp Thr Ala Arg Thr Val Ser Glu Val Lys
  1               5                  10                  15

Ala Asp Leu Val Lys Gln Asp Asn Lys Ser Ser Tyr Thr Val Lys Tyr
             20                  25                  30

Gly Asp Thr Leu Ser Val Ile Ser Glu Ala Met Ser Ile Asp Met Asn
         35                  40                  45

Val Leu Ala Lys Ile Asn Asn Ile Ala Asp Ile Asn Leu Ile Tyr Pro
     50                  55                  60

Glu Thr Thr Leu Thr Val Thr Tyr Asp Gln Lys Ser His Thr Ala Thr
 65                  70                  75                  80

Ser Met Lys Ile Glu Thr Pro Ala Thr Asn Ala Ala Gly Gln Thr Thr
                 85                  90                  95

Ala Thr Val Asp Leu Lys Thr Asn Gln Val Ser Val Ala Asp Gln Lys
            100                 105                 110

Val Ser Leu Asn Thr Ile Ser Glu Gly Met Thr Pro Glu Ala Ala Thr
        115                 120                 125

Thr Ile Val Ser Pro Met Lys Thr Tyr Ser Ser Ala Pro Ala Leu Lys
    130                 135                 140

Ser Lys Glu Val Leu Ala Gln Glu Gln Ala Val Ser Gln Ala Ala Ala
145                 150                 155                 160

Asn Glu Gln Val Ser Thr Ala Pro Val Lys Ser Ile Thr Ser Glu Val
                165                 170                 175

Pro Ala Ala Lys Glu Glu Val Lys Pro Thr Gln Thr Ser Val Ser Gln
            180                 185                 190

Ser Thr Thr Val Ser Pro Ala Ser Val Ala Ala Glu Thr Pro Ala Pro
        195                 200                 205
```

```
Val Ala Lys Val Ala Pro Val Arg Thr Val Ala Ala Pro Arg Val Ala
            210                 215                 220

Ser Val Lys Val Val Thr Pro Lys Val Glu Thr Gly Ala Ser Pro Glu
225                 230                 235                 240

His Val Ser Ala Pro Ala Val Pro Val Thr Thr Thr Ser Thr Ala Thr
                245                 250                 255

Asp Ser Lys Leu Gln Ala Thr Glu Val Lys Ser Val Pro Val Ala Gln
                260                 265                 270

Lys Ala Pro Thr Ala Thr Pro Val Ala Gln Pro Ala Ser Thr Thr Asn
                275                 280                 285

Ala Val Ala Ala His Pro Glu Asn Ala Gly Leu Gln Pro His Val Ala
            290                 295                 300

Ala Tyr Lys Glu Lys Val Ala Ser Thr Tyr Gly Val Asn Glu Phe Ser
305                 310                 315                 320

Thr Tyr Arg Ala Gly Asp Pro Gly Asp His Gly Lys Gly Leu Ala Val
                325                 330                 335

Asp Phe Ile Val Gly Lys Asn Gln Ala Leu Gly Asn Glu Val Ala Gln
                340                 345                 350

Tyr Ser Thr Gln Asn Met Ala Ala Asn Asn Ile Ser Tyr Val Ile Trp
            355                 360                 365

Gln Gln Lys Phe Tyr Ser Asn Thr Asn Ser Ile Tyr Gly Pro Ala Asn
370                 375                 380

Thr Trp Asn Ala Met Pro Asp Arg Gly Gly Val Thr Ala Asn His Tyr
385                 390                 395                 400

Asp His Val His Val Ser Phe Asn Lys
                405

<210> SEQ ID NO 45
<211> LENGTH: 21
<212> TYPE: DNA
<213> ORGANISM: Group B streptococcus

<400> SEQUENCE: 45
actaaggagg ttagatctat g                                      21

<210> SEQ ID NO 46
<211> LENGTH: 77
<212> TYPE: PRT
<213> ORGANISM: Group B streptococcus

<400> SEQUENCE: 46

Lys Ile Ala Asn Phe Tyr Asn Glu Glu Lys Gln Asn Pro Thr Leu Gly
1               5                   10                  15

Leu Asn Ala Thr His Pro Asn Tyr Asn Asn Tyr Phe Asn Glu Ile Tyr
            20                  25                  30

Glu Phe Cys Asp Leu Gln Val Gln Lys Ile Asn Gln Tyr His Lys Arg
        35                  40                  45

Asn Ile Gln Arg His Lys Leu Tyr Lys Phe Phe Ala Glu Thr Val Ala
50                  55                  60

Asn Asp Tyr Pro Tyr Gly Pro Asn Ser Phe Ser His Met
65                  70                  75

<210> SEQ ID NO 47
<211> LENGTH: 86
<212> TYPE: PRT
<213> ORGANISM: Group B streptococcus
```

```
<400> SEQUENCE: 47

Ala Ile Leu Lys Arg Tyr Gln Val Pro Ser Gln Asp Asn Leu Arg Gln
 1               5                  10                  15

Gln Ile Arg Thr Glu Asn Tyr Phe Thr Ile Tyr Asn Lys Val Ile Asn
             20                  25                  30

Thr Ile Ser Asp Lys Asn Tyr Lys Arg Arg Asn His Phe Tyr Phe Thr
         35                  40                  45

Glu Thr Lys Leu Val Thr His Phe Trp Glu Ile Cys Ala Asn Asp Ala
 50                  55                  60

Pro Thr Gly Lys Arg Ser Met Ser Arg Ile Ile Asp Lys Glu Thr Cys
 65                  70                  75                  80

Ala Gln Tyr Tyr Ala Met
                 85

<210> SEQ ID NO 48
<211> LENGTH: 126
<212> TYPE: PRT
<213> ORGANISM: Group B streptococcus

<400> SEQUENCE: 48

Lys Pro Leu Lys Leu Gln Asn Leu Thr Asp Leu Val Phe Asp Thr Asp
 1               5                  10                  15

Gln Cys Asp Ser Ile Thr Tyr Ala Ile Ile Glu Arg Asn Tyr Leu Asn
             20                  25                  30

Met Ile Ser Ser Leu Tyr Leu Lys Cys Asn Gly Phe Tyr Leu Tyr Thr
         35                  40                  45

Ile Asp Thr Val Leu Lys Glu Lys Pro Lys Asp Ala His Phe Asp Arg
 50                  55                  60

Ser Leu Lys Asn Asp Thr Leu Tyr Tyr Ala Lys Gly Leu Asn Pro Val
 65                  70                  75                  80

Lys Lys Thr Arg Thr Arg Cys Leu Trp Gly Asn Asn Lys Met Ile Arg
                 85                  90                  95

Tyr Val Lys Lys Thr Asn Val Thr Leu Gly His Ile Lys Lys Leu Leu
                100                 105                 110

Arg Thr Ile Thr Arg Tyr Gly Tyr Ile Phe His Asn Glu Met
                115                 120             125

<210> SEQ ID NO 49
<211> LENGTH: 96
<212> TYPE: PRT
<213> ORGANISM: Group B streptococcus

<400> SEQUENCE: 49

Lys Ile Ser Lys Arg Ile Leu Gly Arg Tyr Lys Lys Leu Leu Asp Val
 1               5                  10                  15

Gln Leu Gln Leu Gln Glu Val Glu Ser Leu His Glu Leu Gly Lys Gly
             20                  25                  30

Tyr Thr Tyr Gln Lys Gly Val Gly Gln His Phe Arg Tyr Leu Glu Glu
         35                  40                  45

Asn Glu Tyr Trp Lys Met Trp Thr Tyr Ile Gln Ser Asn Asn Lys Ile
 50                  55                  60

Gly Leu Thr Glu Met Ile Val Arg Asn Ser Lys Gly Ala Lys Lys Met
 65                  70                  75                  80

Asp Ile Cys Ala Leu Lys Thr Glu Trp Ser Tyr Ala Lys Lys Val Met
                 85                  90                  95
```

```
<210> SEQ ID NO 50
<211> LENGTH: 288
<212> TYPE: PRT
<213> ORGANISM: Group B streptococcus

<400> SEQUENCE: 50

Ala Ile Leu Arg Lys Thr Met Pro Thr Gln Tyr Asn Leu Ser Gly His
 1               5                  10                  15

Ile Arg His Tyr Asn Trp Trp His Val Tyr Asp Lys Thr Lys Leu Ala
            20                  25                  30

Leu Glu Glu Leu Leu Gln Phe Thr Glu Gln Tyr Val Phe Glu Ile Lys
        35                  40                  45

Phe Ala Arg Tyr Thr Ser Glu Ala Val Ala Asn Asp Tyr Pro Tyr Gly
50                  55                  60

Ala Gln Ser Leu Ser Arg Thr Ile Gly Phe Ala Glu Leu Ile Glu Asp
65                  70                  75                  80

Ile Leu Gln Asn Asp Phe Glu Lys Gly Arg Asp Ser His Phe Met Lys
                85                  90                  95

Val Lys Thr Leu Ala Tyr Pro Ile Ser Gln Ile Ala Gln Lys Val Leu
            100                 105                 110

Glu Ala Thr Lys His Trp Gly Leu Ser Leu Gly Ile Ile Glu Arg Asn
        115                 120                 125

Tyr Leu Asp Ile Ile Leu Cys Val Tyr Ala Trp Arg Asn Gly Val Arg
130                 135                 140

Val Tyr Thr Leu Asp Thr Val Leu Ala Gln Leu Pro Arg Glu Gln Lys
145                 150                 155                 160

Phe Gln Arg Asp Leu His Asn Pro Ile Pro Ala Glu Asn Lys Gly Arg
                165                 170                 175

Ser His Pro Lys Phe Thr Ala Lys Gln Tyr Val Ser Val Leu Asn Leu
            180                 185                 190

Arg Lys Met Ile Arg Arg Ile Arg Arg Ser Leu Thr Ile Gly Glu
        195                 200                 205

Asn Asn Leu Cys Ile Lys Ile Lys Arg Ser Gly Tyr Arg Ser Glu Ser
210                 215                 220

Asp Leu Phe Ile Arg Lys Ile Thr Glu Glu Phe Glu Thr Glu Ser Val
225                 230                 235                 240

Ser Glu Val Ala Gln Tyr Tyr Ser Ser His Pro Met Asn Leu Trp
                245                 250                 255

Arg Cys Met Lys Ser Ile Ser Tyr Lys Asp Lys Asn Ala Thr Ile Ile
            260                 265                 270

Glu Arg Lys Thr Gly Tyr Asp Gly Ser Ser Ala Lys Pro Tyr Arg Ile
        275                 280                 285

<210> SEQ ID NO 51
<211> LENGTH: 173
<212> TYPE: PRT
<213> ORGANISM: Group B streptococcus

<400> SEQUENCE: 51

His Ile Tyr Cys Ser Gly Gly Leu Ser Tyr Asn Ser Thr Arg Asn Arg
 1               5                  10                  15

Cys Pro Val Tyr Glu Asn Cys Thr Phe Leu Pro Lys Ser Ser Asn Gln
            20                  25                  30

Gly Leu Asn Arg Gln Asn Leu Lys Asp Asn Arg Asp Lys Gln Glu Gln
        35                  40                  45

Leu Gln His Ala Tyr Val Glu Leu Thr Ile Asn Leu Asn Glu His Asp
50                  55                  60
```

-continued

```
Leu Val Gln Ser Ile Ser Ile Leu Tyr Ser Ala Phe Thr His Arg Leu
65                  70              75                  80

Ser His Val Arg Val Glu Arg Gly Thr Ile Lys Arg Ile Thr Lys Asn
                85              90                  95

Val Ala Asn Asn Ser Leu Lys Asp Phe Leu Arg Asp Asn Lys Asn Lys
            100             105             110

Thr Phe Glu His Leu Phe Phe Leu Thr Asp Asn Asp Ile Pro Ile Asn
            115             120             125

Arg Ile Ser Ser Lys Asn Lys Thr Pro Leu Tyr Arg Gln Asn Phe His
        130             135             140

Tyr Asp Trp Thr Lys Asn Ile Ser Leu Tyr Lys Asn Thr Tyr Asp Ile
145             150             155             160

Asp Asn Val Thr Leu Gly Leu Cys Glu Ala Phe Arg Met
                165             170
```

We claim:

1. An isolated polypeptide comprising an amino acid sequence at least 95% identical to the amino acid sequence set forth in SEQ ID NO:44.

2. The isolated polypeptide of claim 1 comprising the amino acid sequence set forth in SEQ ID NO: 44.

3. An isolated polypeptide comprising an amino acid sequence at least 95% identical to the amino acid sequence set forth in SEQ ID NO:39.

4. The isolated polypeptide of claim 3 comprising the amino acid sequence set forth in SEQ ID NO:39.

5. An isolated polypeptide comprising (a) an amino acid sequence at least 95% identical to the amino acid sequence set forth in SEQ ID NO:39, and from which the N-terminal Met residue is deleted, or (b) the amino acid sequence set forth in SEQ ID NO:39, and from which the N-terminal Met residue is deleted.

6. An isolated polypeptide comprising (a) an amino acid sequence at least 95% identical to the amino acid sequence set forth in SEQ ID NO:39, and from which the secretory amino acid sequence is deleted, or (b) the amino acid sequence set forth in SEQ ID NO:39, and from which the secretory amino acid sequence is deleted.

7. An immunogenic composition comprising the isolated polypeptide according to either claim 1 or claim 2 and a pharmaceutically acceptable carrier or diluent.

8. An immunogenic composition comprising the isolated polypeptide according to any one of claims 3, 4, and 5, and a pharmaceutically acceptable carrier, diluent or adjuvant.

9. An immunogenic composition comprising the isolated polypeptide according to claim 6 and a pharmaceutically acceptable carrier, diluent or adjuvant.

10. A method for inducing an immune response in an animal susceptible to a group B streptococcus infection, said method comprising administering to said animal the composition according to claim 7.

11. A method for inducing an immune response in an animal susceptible to group B streptococcus infection, said method comprising administering to said animal the composition according to claim 8.

12. A method for inducing an immune response in an animal susceptible to group B streptococcus infection, said method comprising administering to said animal the composition according to claim 9.

13. The method according to claim 10, wherein said animal is a bovine.

14. The method according to claim 10, wherein said animal is a human.

15. The immunogenic composition according to claim 7 further comprising a pharmaceutically acceptable adjuvant.

* * * * *

UNITED STATES PATENT AND TRADEMARK OFFICE
CERTIFICATE OF CORRECTION

| | | |
|---|---|---|
| PATENT NO. | : 7,914,794 B2 | Page 1 of 1 |
| APPLICATION NO. | : 10/340792 | |
| DATED | : March 29, 2011 | |
| INVENTOR(S) | : Brodeur et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2243 days.

Signed and Sealed this
Twelfth Day of July, 2011

David J. Kappos
*Director of the United States Patent and Trademark Office*

UNITED STATES PATENT AND TRADEMARK OFFICE
CERTIFICATE OF CORRECTION

PATENT NO. : 7,914,794 B2
APPLICATION NO. : 10/340792
DATED : March 29, 2011
INVENTOR(S) : Bernard R. Brodeur et al.

Page 1 of 2

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2146 days.

Title Page
Item 63:
"(63) Continuation of application No. 09/252,088, filed on Feb. 18, 1999, now abandoned, which is a continuation of application No. 60/075,425, filed on Feb. 20, 1998." should read as, --(63) Continuation of application No. 09/252,088, filed on Feb. 18, 1999, now abandoned. (60) Provisional application No. 60/075,425, filed on Feb. 20, 1998.--.

Item 56:
"5,225,331 A 7/1993 Lacroix et al. 435/7.34" should read as, --5,225,331 A 7/1993 Jennings et al. 435/7.34--.

Col. 2, Line 53
Item 56:
"Linden, V., "Mouse-protective effect of rabbit anti-R-protein antibodies against group B *Streptococci* type II carrying R-protein. Lack of effect on type III carrying R-protein," *Acta Pathol. Microbial. Immunol. Scand.* [B] 91(2):145-51, Apr. 1983." should read as, --Linden, V., "Mouse-protective effect of rabbit anti-R-protein antibodies against group B streptococci type II carrying R-protein. Lack of effect on type III carrying R-protein," *Acta Pathol. Microbiol. Immunol. Scand.* [B] 91(2): 145-51, Apr. 1983.--.

Signed and Sealed this
Eighteenth Day of October, 2011

David J. Kappos
*Director of the United States Patent and Trademark Office*

Page 2, Col. 1, Line 32
Item 56:
"Kasper, D., et al., "Immune response to type III group B streptococcal polysaccharido-tetanus toxoid conjugate vaccine," *Journal of Clinical Investigation* 98(10):2308-14, Nov. 15, 1996." should read as, --Kasper, D., et al., "Immune response to type III group B streptococcal polysaccharide-tetanus toxoid conjugate vaccine," *Journal of Clinical Investigation* 98(10):2308-14, Nov. 15, 1996.--.